US012440549B2

(12) United States Patent
Xie et al.

(10) Patent No.: US 12,440,549 B2
(45) Date of Patent: Oct. 14, 2025

(54) POLYVALENT IMMUNOGENICITY COMPOSITION FOR HUMAN PAPILLOMAVIRUS

(71) Applicant: SinoCellTech Ltd., Beijing (CN)

(72) Inventors: Liangzhi Xie, Beijing (CN); Chunxia Luo, Beijing (CN); Wei Zhang, Beijing (CN); Xiaoyan Suo, Beijing (CN); Lin Pang, Beijing (CN); Ping Hu, Beijing (CN)

(73) Assignee: SinocellTech Ltd., Beijing (CN)

(*) Notice: Subject to any disclaimer, the term of this patent is extended or adjusted under 35 U.S.C. 154(b) by 789 days.

(21) Appl. No.: 17/579,459

(22) Filed: Jan. 19, 2022

(65) Prior Publication Data

US 2022/0370590 A1 Nov. 24, 2022

Related U.S. Application Data

(63) Continuation of application No. PCT/CN2020/102601, filed on Jul. 17, 2020.

(30) Foreign Application Priority Data

Jul. 19, 2019 (CN) ......................... 201910657255.8

(51) Int. Cl.
*A61K 39/12* (2006.01)
*A61K 39/39* (2006.01)
*A61K 39/00* (2006.01)

(52) U.S. Cl.
CPC .............. *A61K 39/12* (2013.01); *A61K 39/39* (2013.01); *A61K 2039/5258* (2013.01); *A61K 2039/55505* (2013.01)

(58) Field of Classification Search
CPC ............ A61K 2039/5258; A61K 39/12; A61K 2039/70; A61K 47/26; C12N 2710/20034; A61P 31/20; A61P 35/00; C07K 14/005
See application file for complete search history.

(56) References Cited

U.S. PATENT DOCUMENTS

| | | | |
|---|---|---|---|
| 5,821,087 | A | 10/1998 | Lowe et al. |
| 2005/0244432 | A1 | 11/2005 | Castillo et al. |

FOREIGN PATENT DOCUMENTS

| | | | |
|---|---|---|---|
| CN | 101518647 | A | 9/2009 |
| CN | 102268076 | A | 12/2011 |
| CN | 102747047 | A | 10/2012 |
| CN | 106795518 | A | 5/2017 |
| EP | 2154149 | A4 | 2/2010 |
| JP | 2005538938 | A | 12/2005 |
| JP | 2015-037430 | A | 2/2015 |
| RU | 2642287 | C2 | 1/2016 |
| WO | 01/97840 | A1 | 12/2001 |
| WO | 01097840 | A1 | 12/2001 |

OTHER PUBLICATIONS

Nuradi, Rani, Indonesian First Office Action, Patent Application No. P00202201350, 4 pages, Directorate General of Intellectual Property (DGIP) Ministry of Law and Human Rights, Jakarta Selatan.
Russian First Office Action, Patent Application No. RU2022102876, 5 pages, Federal Service for Intellectual Property (Rospatent), Moscow.
Russian Search Report, Patent Application No. RU2022102876, 2 pages, Federal Service for Intellectual Property (Rospatent), Moscow.
Ying, Sung Ying, Dr., Written Opinion, Patent Application No. 11202200504, 8 pages, Intellectual Property Office of Singapore, Singapore.
Luxembourg A. et al., Phase II studies to select the formulation of a multivalent HPV L1 virus-like particle (VLP) vaccine. Hum Vaccin Immunother, Apr. 27, 2015, vol. 11, No. 6, pp. 1313-1322.
Invitation to Respond to Written Opinion, Patent Application No. 11202200504, 2 pages, Intellectual Property Office of Singapore, Singapore.
Hua, Cassie, First Australian Office Action, Patent Application No. 2020317321, 4 pages, IP Australia, Woden ACT.
Qanbar, R., First Canadian Office Action, Patent Application No. 3,147,849, Feb. 22, 2023, 5 pages, Canadian Intellectual Property Office, Gatineau, Quebec.
Schulz, Regine, European Search Report, Patent Application No. 20843624.6, Feb. 14, 2023, 17 pages, European Patent Office, Munich, Germany,.
Zhang et al., Trivalent Human Papillomavirus (HPC) VLP vaccine covering HPV type 58 can elicit high level of humoral immunity but also induce immune interference among component types, 9 pages, Vaccine 28(2010) 3479-3487, doi:10.1016/j.vaccine.2010.02.057.
Christensen, et al., Hybrid Papillomavirus L1 Molecules Assemble into Virus-like Particles That Reconstitute Conformational Epitopes and Induce Neutralizing Antibodies to Distinct HPV Types, 11 pages, Virology 291, 324-334 (2001) doi: 10.1006/viro.2001.1220.
Wang, et al., Rational design of a multi-valent human papillomavirus vaccine by capsomere-hybrid co-assembly of virus-like particles, 15 pages, Nature Communications, 2020 11:2841.

(Continued)

*Primary Examiner* — Bao Q Li
(74) *Attorney, Agent, or Firm* — Smart & Biggar LP

(57) ABSTRACT

The present invention relates to a multivalent HPV immunogenic composition for preventing human papillomavirus (HPV) related diseases or infections and uses thereof. Said multivalent HPV immunogenic composition comprises: HPV virus-like particles assembled from L1 proteins of HPV Types 6, 11, 16, 18, 31, 33, 45, 52, and 58; and one or more HPV virus-like particles assembled from L1 proteins of other pathogenic HPV types. In one embodiment, said one or more other pathogenic HPV types are selected from HPV Types 35, 39, 51, 56 and 59. In one embodiment, at least one of said HPV virus-like particles is a chimeric HPV virus-like particle, and said chimeric HPV virus-like particle comprises one or more chimeric HPV L1 proteins.

7 Claims, 23 Drawing Sheets

Specification includes a Sequence Listing.

(56) References Cited

OTHER PUBLICATIONS

Boxus, et al., Broad Cross-Protection Is Induced in Preclinical Models by a Human Papillomavirus Vaccine Composed of L1/L2 Chimeric Virus-Like Particles, 12 pages, American Society for Microbiology—Journal of Virology, Jul. 2016, vol. 90, No. 14.
First Chinese Office Action, Patent Application No. 202080051322.2, 9 pages, China National Intellectual Property Administration (CNIPA), Beijing.
International Search Report and Written Opinion dated Nov. 18, 2020 in connection with International Application No. PCT/CN2020/102601, 9 pages.
Nishimura, Akiko, First Examiner's Report, JP 2022-503540, Jul. 31, 2024, Japan Patent Office (JPO), Tokyo, 3 pages.
Nishimura, Akiko, First Examiner's Report, JP 2022-503540, Jul. 31, 2024, Japan Patent Office (JPO), Tokyo, 5 pages.
Hum. Vaccine Immunother., 2015, vol. 11, No. 6, pp. 1313-1322.
Qanbar, R., Examiner's Report, CA 3147849, Aug. 15, 2024, Canadian Intellectual Property Office, Gatineau, Quebec, 4 pages.

POLYVALENT IMMUNOGENICITY COMPOSITION FOR HUMAN PAPILLOMAVIRUS

This application is a continuation of and claims priority to PCT Application No. PCT/CN2020/102601 filed Jul. 17, 2020, which itself claims priority to Chinese Patent Application No. 201910657255.8 filed Jul. 19, 2019. The contents from all of the above are hereby incorporated in their entirety by reference.

TECHNICAL FIELD

The present invention relates to a multivalent immunogenic composition for preventing human papillomavirus (HPV) related diseases or infections and uses thereof.

BACKGROUND

Papilloma virus (PV) belongs to the Papillomaviridae Family and causes papillomas in humans, cattle, dogs, and rabbits. One of its member, human papilloma virus (HPV), is a non-enveloped DNA virus. The genome of this virus is a double-stranded closed circular DNA, about 7.2-8 kb in size, with 8 open reading frames, which can be divided into three regions according to their functions: (1) early region (E), about 4.5 kb, encoding E1, E2, E4-E7, a total of 6 non-structural proteins related to viral replication, transcription and transformation; (2) late region (L), about 2.5 kb, encoding the major capsid protein L1 and the minor capsid protein L2; (3) long regulatory region (LCR), which is located between the end of the L region and the beginning of the E region, is about 800-900 bp long and does not encode any protein, serving as DNA replication and expression regulatory elements.

The L1 proteins and the L2 proteins are synthesized late in the HPV infection cycle. The L1 protein is the major capsid protein and has a molecular weight of 55-60 kDa. The L2 protein is the minor capsid protein. 72 L1 protein pentamers form the outer shell of the icosahedral HPV particle (45-55 nm in diameter), which encloses closed circular double-stranded DNA. The L2 protein is located on the inner side of the L1 protein (Structure of Small Virus-like Particles Assembled from the L1 Protein of Human Papillomavirus 16 Chen, X. S., R. L.Garcea, Mol. Cell. 5(3):557-567, 2000).

The ORF of the L1 protein, the most conserved gene in the PV genome, can be used to identify new PV types. A new PV type is identified if its complete genome is cloned and its L1 ORF DNA sequence differs from the closest known PV type by more than 10%. Homologies with differences between 2% and 10% are defined as different subtypes, and differences of less than 2% are defined as different variants of the same subtype (E.-M. de Villiers et al. /Virology 324 (2004) 17-27).

At late stages of HPV infection, newly synthesized L1 proteins in the cytoplasm are transported to the nucleus of terminally differentiated keratin where, together with L2 proteins, package the replicated HPV genomic DNA to form infectious viruses (Nelson, L. M., et al. 2002. Nuclear import strategies of high risk HPV16 L1 major capsid protein. J. Biol. Chem. 277: 23958-23964). This suggests that nuclear import of the L1 protein plays a very important role in HPV infection and production. The ability of the virus to enter the nucleus is determined by the nuclear localization signal (NLS) at the C-terminus of the HPV L1 protein, the NLS is characterized by its abundance of basic amino acids (Garcia-Bustos, J., et al. 1991. Nuclear protein localization. Biochimica et Biophysica Acta 1071: 83-101).

15 high-risk (HR) HPV types can lead to cancers of cervix, anus, penis, vagina, vulva and oropharynx, among which HPV-16 and HPV-18 are by far the most common causes of cancers, accounting for approximately 70% of cervical cancers, and the other HR-HPV types (Types 31, 33, 35, 39, 45, 51, 52, 56, 58, 59, 68, 73, and 82) cause the rest. HPV-16 accounts for approximately 95% of HPV-positive oropharyngeal cancers (OPCs). The persistent low-risk genotypes HPV-6 and HPV-11 cause most anogenital warts and respiratory papillomas, but are rarely associated with cancers (Human Papillomavirus in Cervical Cancer and Oropharyngeal Cancer: One Cause, Two Diseases Tara A. Bermanand John T. Schiller, PhD 2 Cancer 2017; 123:2219-29).

The L1 protein can be recombinantly expressed by poxvirus, baculovirus, or yeast systems and then self-assembles to form virus-like particles (VLP) containing approximately 72 L1 proteins, similar to the virus capsid. VLP has no indication. VLP induces neutralizing antibodies in inoculated animals and protects experimental animals from subsequent attack by infectious viruses. Thus, VLP appears to be an excellent candidate for papilloma virus vaccines (Structure of Small Virus-like Particles Assembled from the L1 Protein of Human Papillomavirus 16 Chen, X. S., R. L. Garcea, Mol. Cell. 5(3):557-567, 2000).

Glaxo's CERVARIX®, a bivalent recombinant HPV vaccine, contains HPV Type 16 recombinant L1 protein and HPV Type 18 recombinant L1 protein. The L1 protein is obtained by expression of a recombinant baculovirus expression vector system in insect cells of the nocturnal moth (*Trichoplusia ni*). The L1 protein self-assembles into virus-like particles for the prevention of cervical cancer, Grade 2 or 3 cervical intraepithelial neoplasia and adenocarcinoma in situ caused by HPV Types 16 and 18, and Grade 1 cervical intraepithelial neoplasia (oncogenic) in women aged 9-25 years (https://www.fda.gov/downloads/BiologicsBloodVaccines/Vaccines/ApprovedP roducts/UCM186981.pdf).

GARDASIL® is a human papilloma virus quadrivalent (Types 6, 11, 16 and 18) recombinant vaccine from Merck for the prevention of cervical cancer, genital warts (condyloma *acuminata*) and precancerous or proliferative abnormal lesions caused by HPV Types 6, 11, 16 and 18 in girls and women aged 9-26 years; and for the prevention of anal cancer, genital warts (condyloma *acuminatum*) and precancerous or abnormal developmental lesions caused by HPV Types 6, 11, 16, and 18 in boys and men aged 9-26 (https://www.fda.gov/vaccines-blood-biologics/vaccines/gardasil).

GARDASIL®9 is a nine-valent recombinant human papilloma virus vaccine from Merck that contains virus-like particles of L1 proteins of HPV Types 6, 11, 16, 18, 31, 33, 45, 52 and 58, the L1 protein is produced by fermentation of *Saccharomyces cerevisiae* and self-assembles into VLP. It is used in girls and women aged 9-45 years for the prevention of cervical cancer, vulvar cancer, vaginal cancer and anal cancer caused by HPV Types 16, 18, 31, 33, 45, 52 and 58, genital warts (condyloma *acuminata*) caused by HPV Types 6 and 11, and precancerous or proliferative abnormalities caused by HPV Types 6, 11, 16, 18, 31, 33, 45, 52 and 58; and in boys and men aged 9-45 years for the prevention of anal cancer caused by HPV Types 16, 18, 31, 33, 45, 52 and 58, genital warts (condyloma *acuminatum*) caused by HPV Types 6 and 11 and pre-cancerous or developmentally abnormal lesions caused by HPV Types 6, 11, 16, 18, 31, 33, 45, 52 and 58 (https://www.fda.gov/vaccines-blood-biologics/vaccines/gardasil-9).

The instruction for GARDASIL®9 announced that HPV Types 16 and 18 are the cause of about 70% of cervical cancers, with the remaining 20% of cases attributed to Types 31, 33, 45, 52 and 58, therefor GARDASIL®9 prevents 90% of cervical cancers (https://www.fda.gov/BiologicsBloodVaccines/Vaccines/ApprovedProducts/ucm426445.htm).

Industrial production of virus-like particles is critical to HPV vaccine development. The common systems for producing virus-like particles are mainly classified into the eukaryotic expression system and the prokaryotic expression system.

Commonly used eukaryotic expression systems include poxvirus expression systems, insect baculovirus expression systems, and yeast expression systems. The HPV L1 protein expressed in eukaryotic expression systems can be spontaneously assembled to virus-like particles as its natural conformation is less disrupted, but the yield thereof is low. The HPV L1 protein expressed in prokaryotic expression systems, mainly *E. coli* expression systems, is of high yields but mostly in the form of inclusion bodies, this form of protein cannot be easily purified thus makes the production process complicated.

Therefore, there is still a need to obtain high yields of HPV virus-like particles, so as to obtain HPV multivalent vaccines for broad-spectrum prevention of HPV-related diseases or infections, including those caused by the HPV types that are not currently covered by commercial available vaccines.

SUMMARY

In one aspect, the present invention provides a multivalent HPV immunogenic composition for the prevention of HPV-related disease or infection comprising: HPV virus-like particles assembled from L1 proteins of HPV types 6, 11, 16, 18, 31, 33, 45, 52 and 58; and one or more HPV virus-like particles assembled from L1 proteins of other pathogenic HPV types virus-like particles.

In another aspect, the present invention provides a method for preventing HPV-related disease or infection comprising: administering to a subject a multivalent HPV immunogenic composition.

In another aspect, the present invention provides the use of multivalent HPV immunogenic compositions in the preparation of vaccines or drugs for the prevention of HPV-related diseases or infections.

cell lysate; E-S: supernatant collected after centrifugation of the lysate.

Figure 1A:
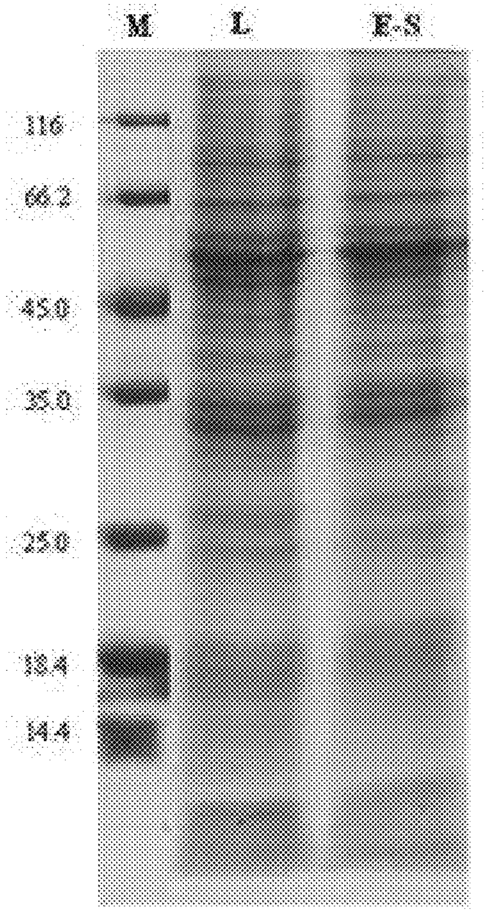
FIG. 1A: Expression of L1 protein of HPV 6 L1: 33C. M: Marker; L: cell lysate; E-S: supernatant collected after centrifugation of the lysate.
Figure 1B:
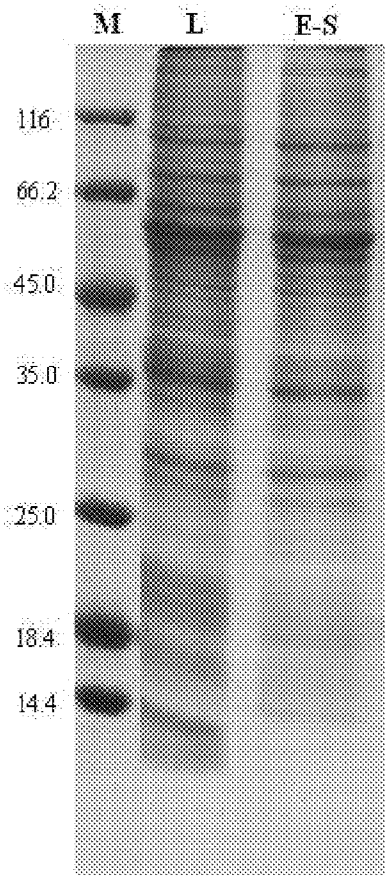
FIG. 1B: Expression of L1 protein of HPV 11 L1: 33C. M: Marker; L: cell lysate; E-S: supernatant collected after centrifugation of the lysate.
Figure 1C:
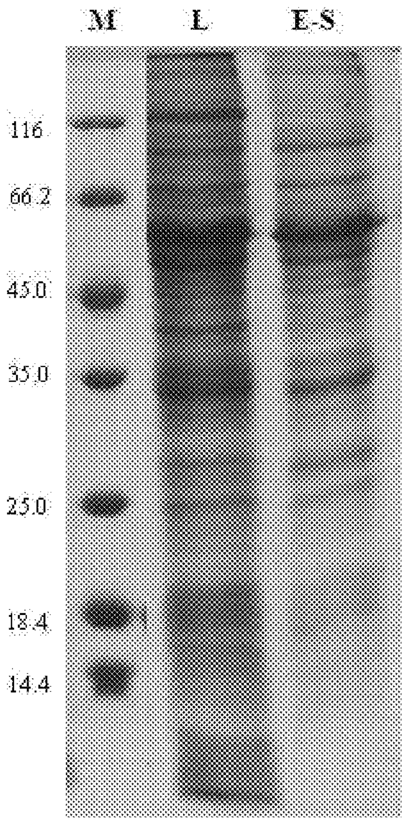
FIG. 1C: Expression of L1 protein of HPV 16 L1: 33C. M: Marker; L.
Figure 1D:
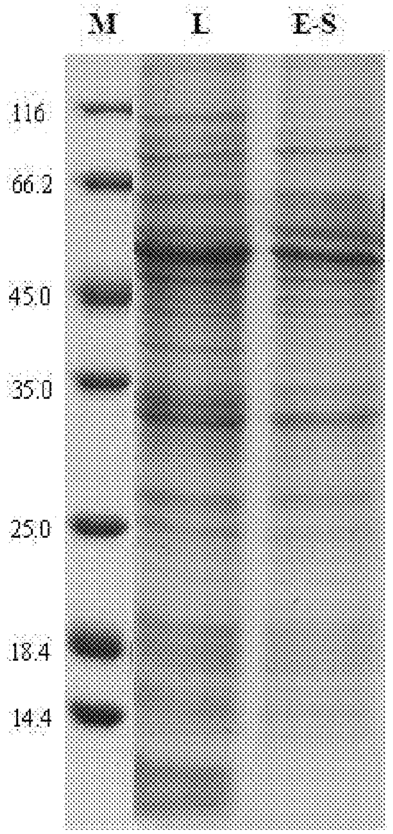

FIG. 1D: Expression of L1 protein of HPV 18 L1: 33C. M: Marker; L: cell lysate; E-S: supernatant collected after centrifugation of the lysate.

Figure 1E:
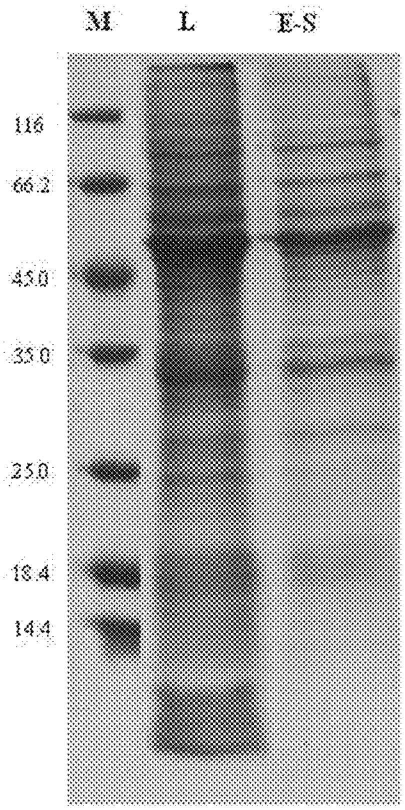

FIG. 1E: Expression of L1 protein of HPV 31 L1: 33C. M: Marker; L: cell lysate; E-S: supernatant collected after centrifugation of the lysate.

Figure 1F:
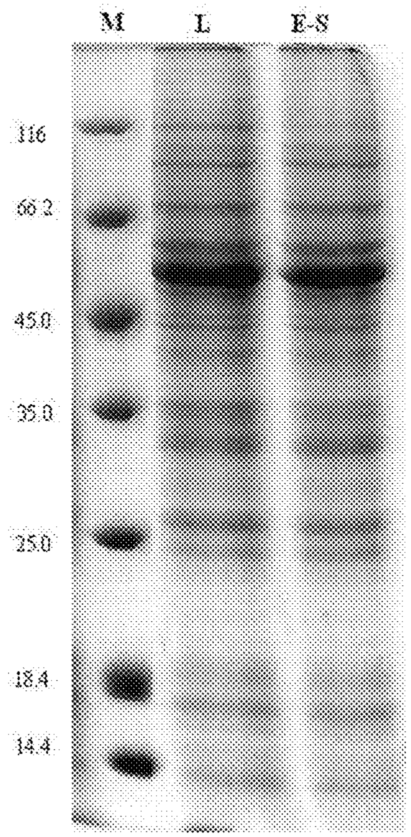

FIG. 1F: Expression of L1 protein of HPV 33 L1. M: Marker; L: cell lysate; E-S: supernatant collected after centrifugation of the lysate.

Figure 1G:
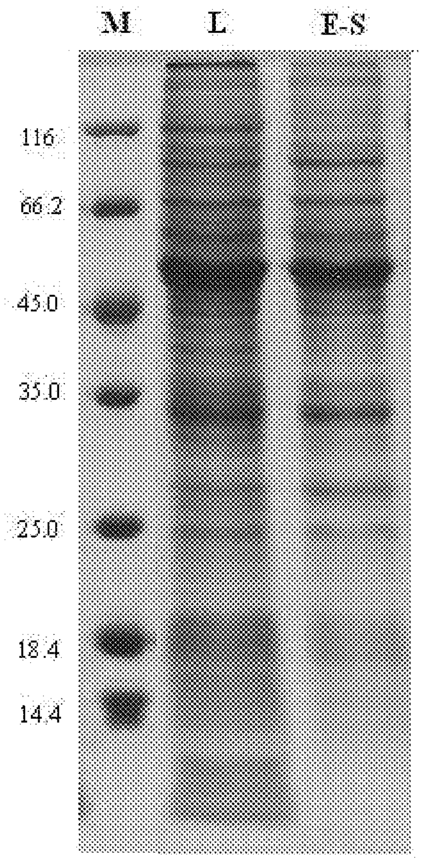

FIG. 1G: Expression of L1 protein of HPV 35 L1: 33C. M: Marker; L: cell lysate; E-S: supernatant collected after centrifugation of the lysate.

Figure 1H:
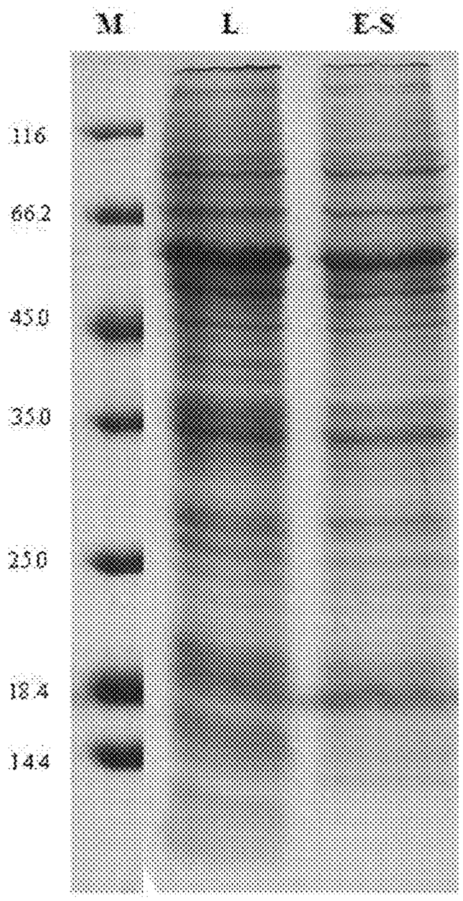

FIG. 1H: Expression of L1 protein of HPV 39 L1: 59C. M: Marker; L: cell lysate; E-S: supernatant collected after centrifugation of the lysate.

Figure 1I:
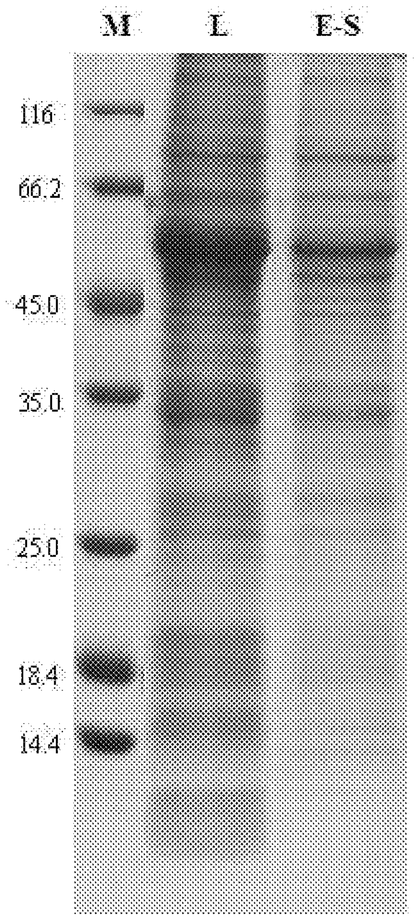

FIG. 1I: Expression of L1 protein of HPV 45 L1: 33C. M: Marker; L:

cell lysate; E-S: supernatant collected after centrifugation of the lysate.

Figure 1J:
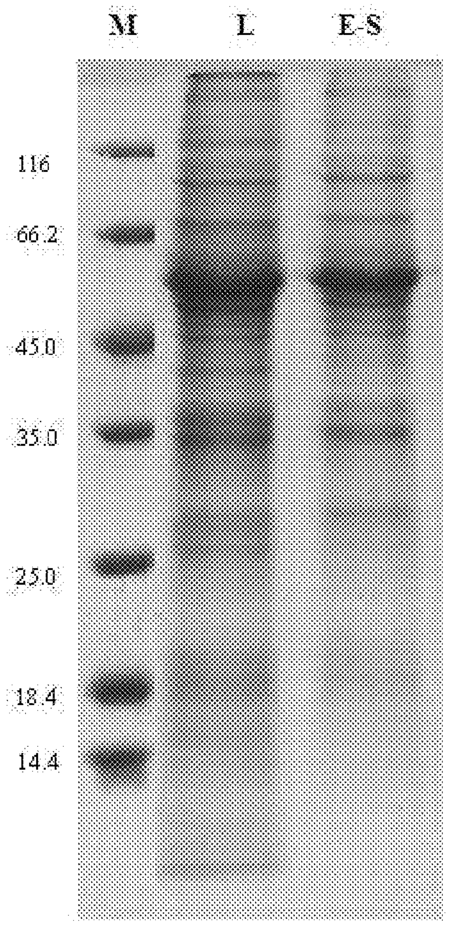

FIG. 1J: Expression of L1 protein of HPV 51 L1: 33C. M: Marker; L: cell lysate; E-S: supernatant collected after centrifugation of the lysate.

Figure 1K:
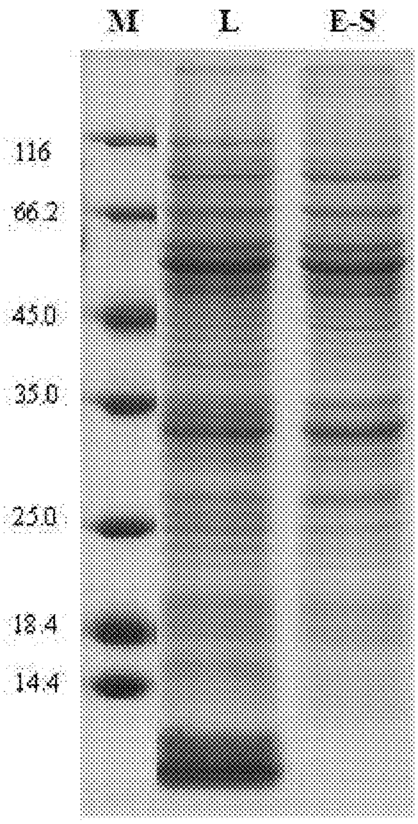

FIG. 1K: Expression of L1 protein of HPV 52 L1: 33C. M: Marker; L: cell lysate; E-S: supernatant collected after centrifugation of the lysate.

Figure 1L:
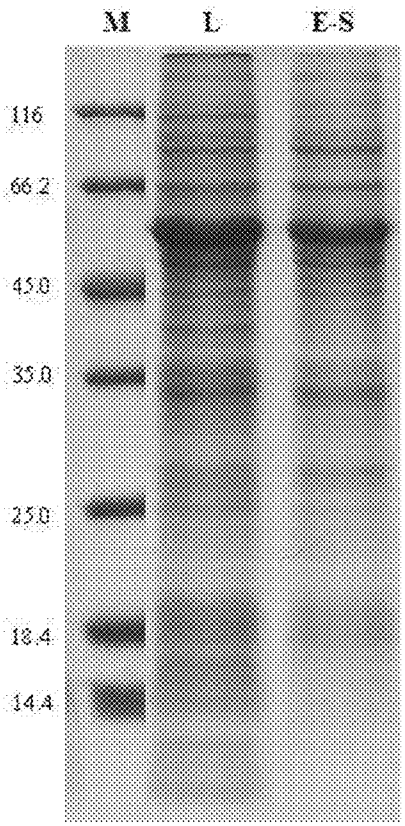

FIG. 1L: Expression of L1 protein of HPV 56 L1: 33C. M: Marker; L: cell lysate; E-S: supernatant collected after centrifugation of the lysate.

Figure 1M:
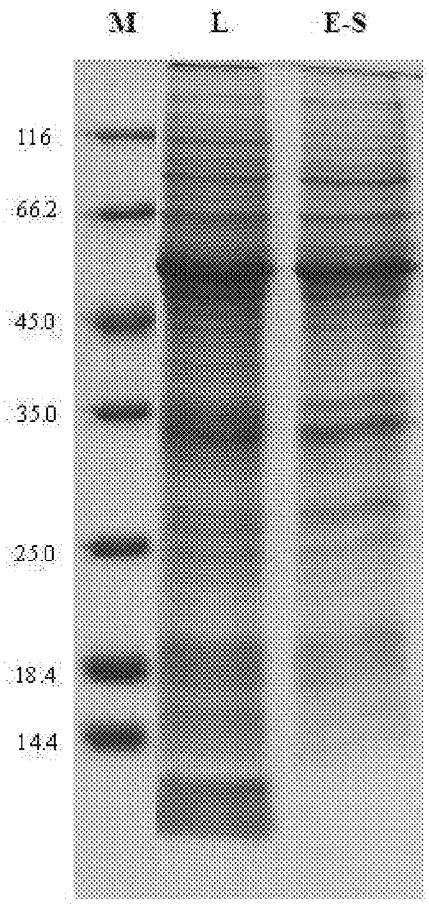

FIG. 1M: Expression of L1 protein of HPV 58 L1: 33C. M: Marker; L: cell lysate; E-S: supernatant collected after centrifugation of the lysate.

Figure 1N:
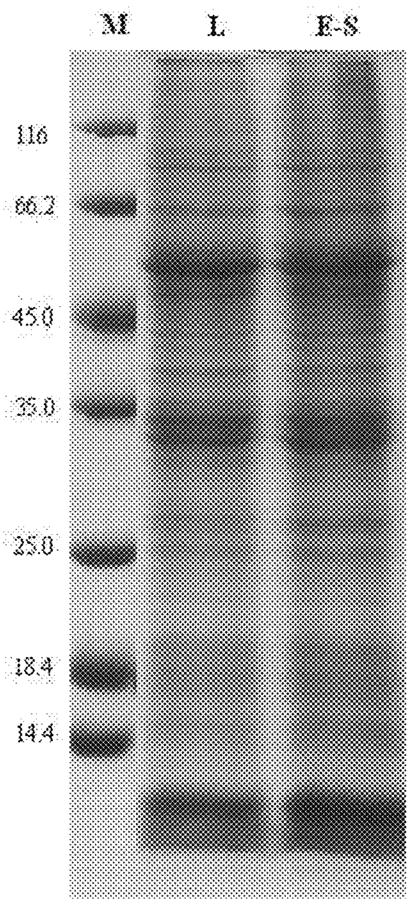

FIG. 1N: Expression of L1 protein of HPV 59 L1. M: Marker; L: cell lysate; E-S: supernatant collected after centrifugation of the lysate.

Figure 2A:
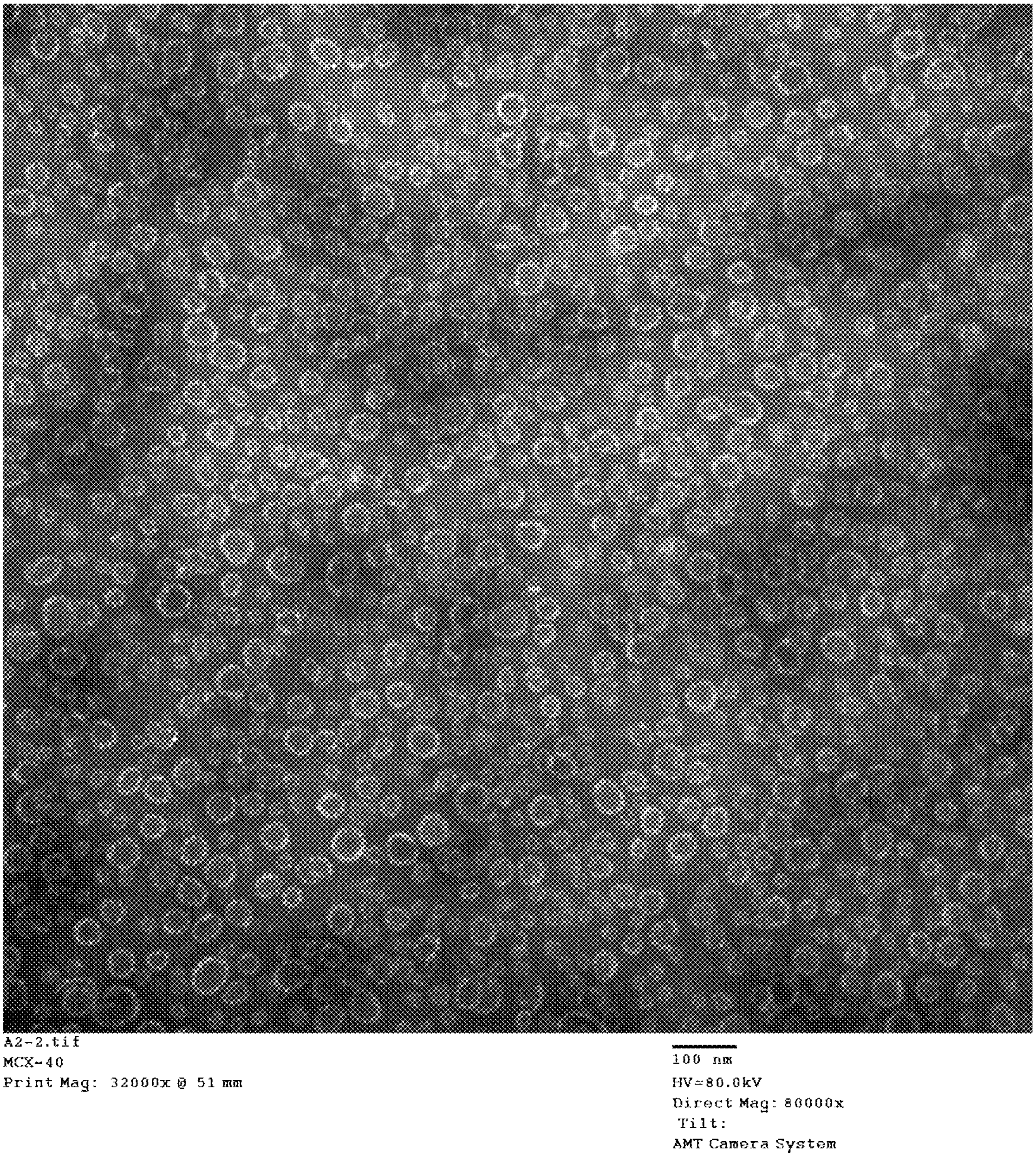

FIG. 2A: Transmission electron microscopy of HPV 6 L1: 33C virus-like particles.

Figure 2B:
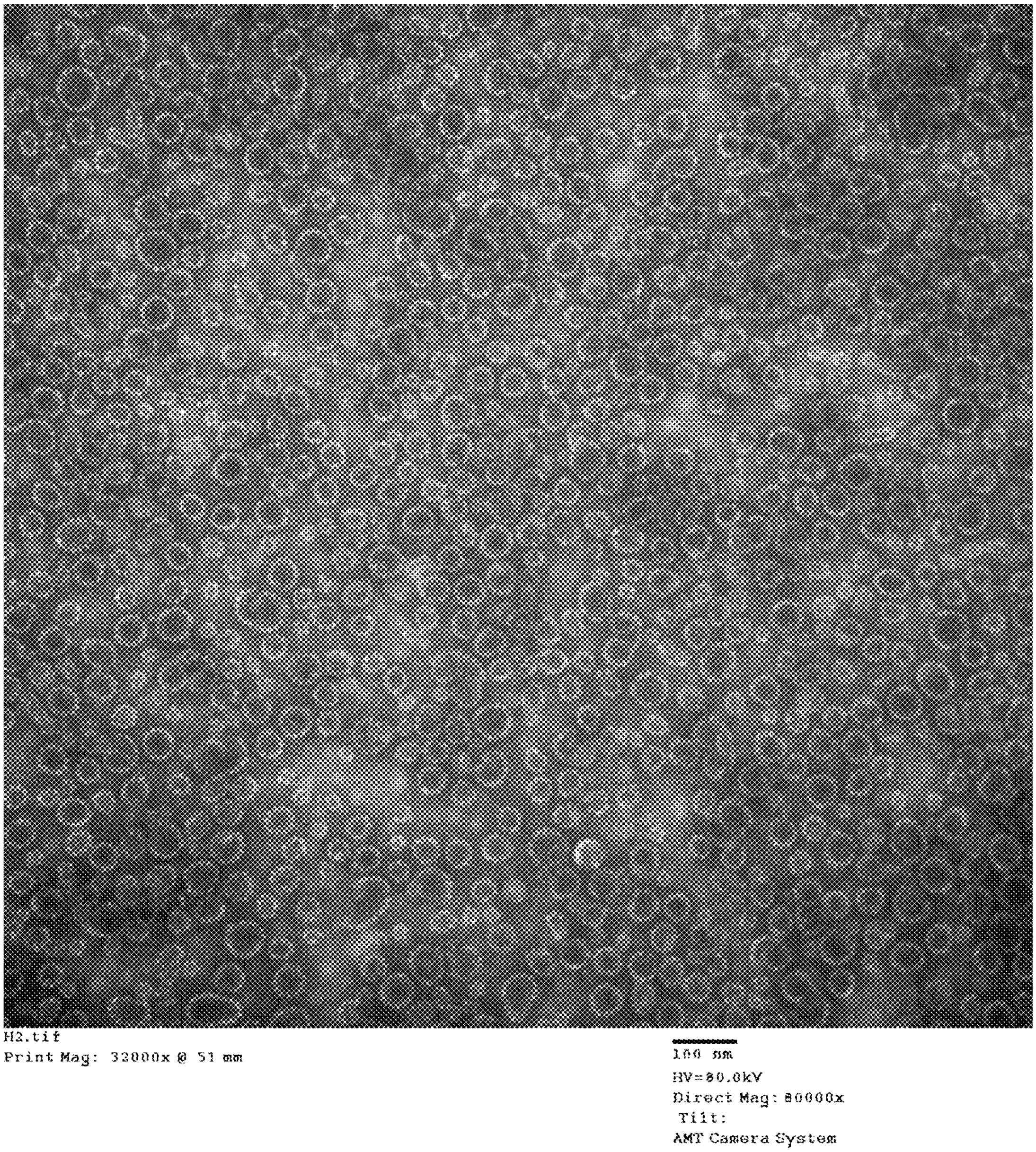

FIG. 2B: Transmission electron microscopy of HPV 11 L1: 33C virus-like particles.

Figure 2C:
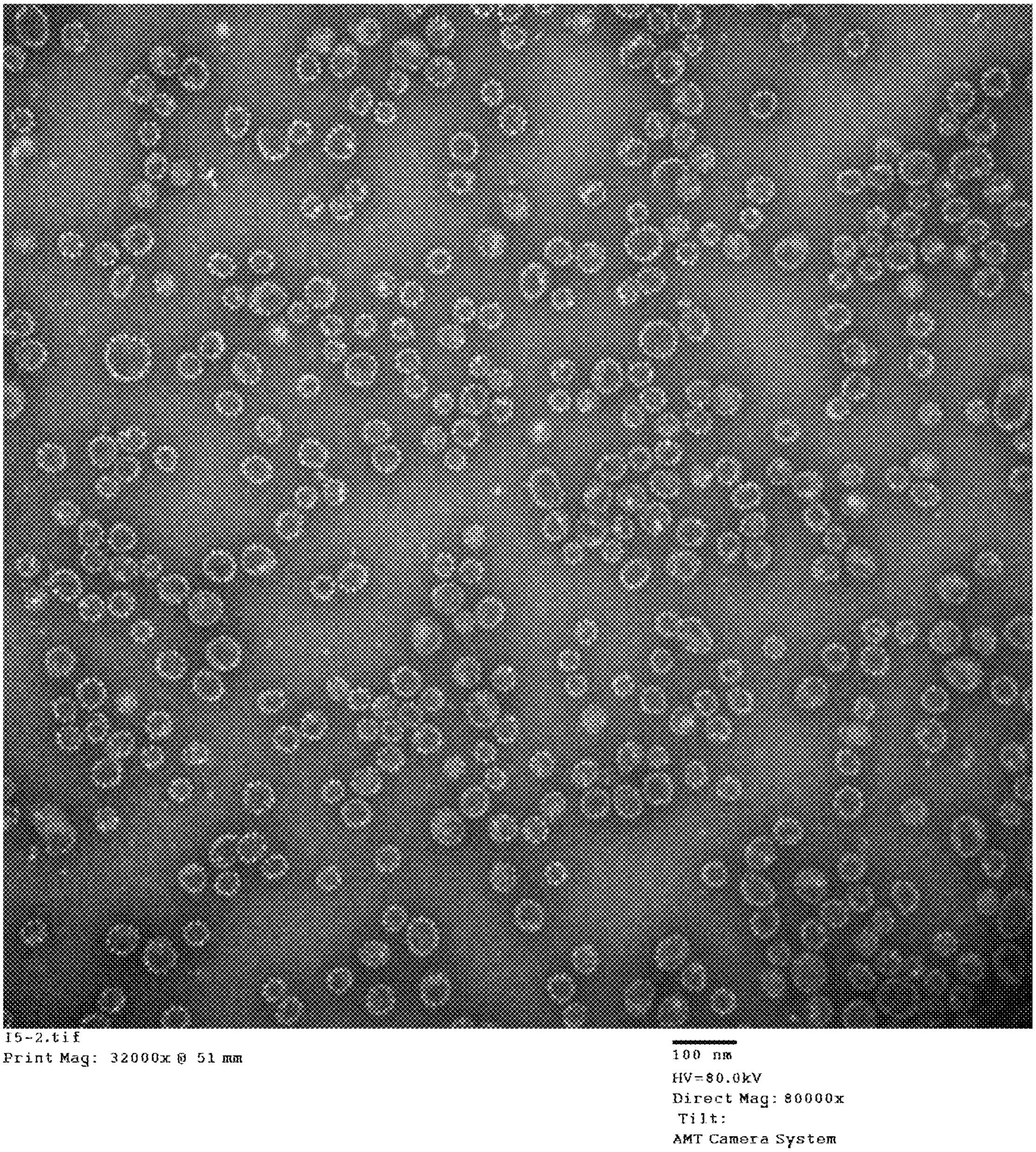

FIG. 2C: Transmission electron microscopy of HPV 16 L1: 33C virus-like particles.

Figure 2D:
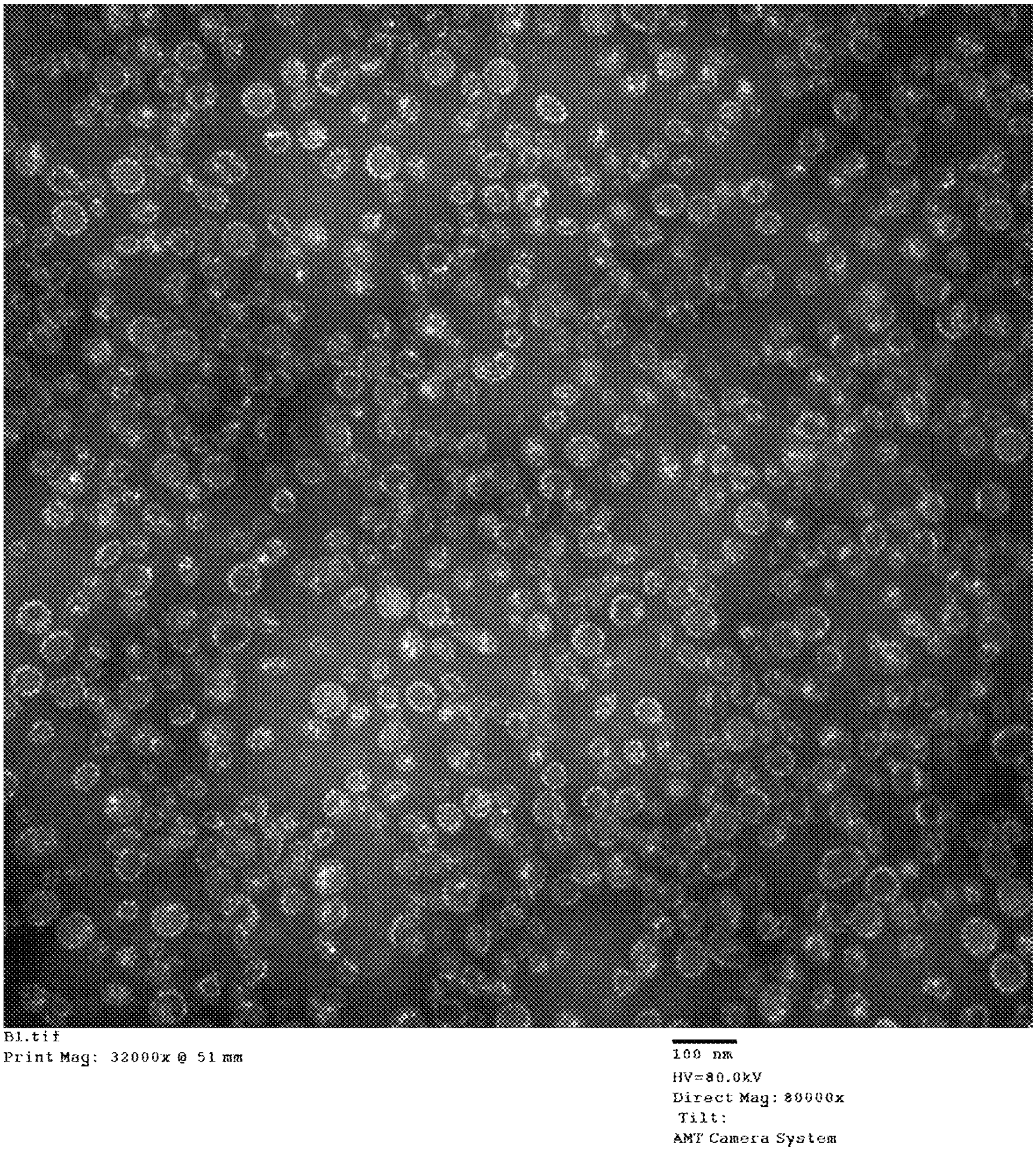

FIG. 2D: Transmission electron microscopy of HPV 18 L1: 33C virus-like particles.

Figure 2E:
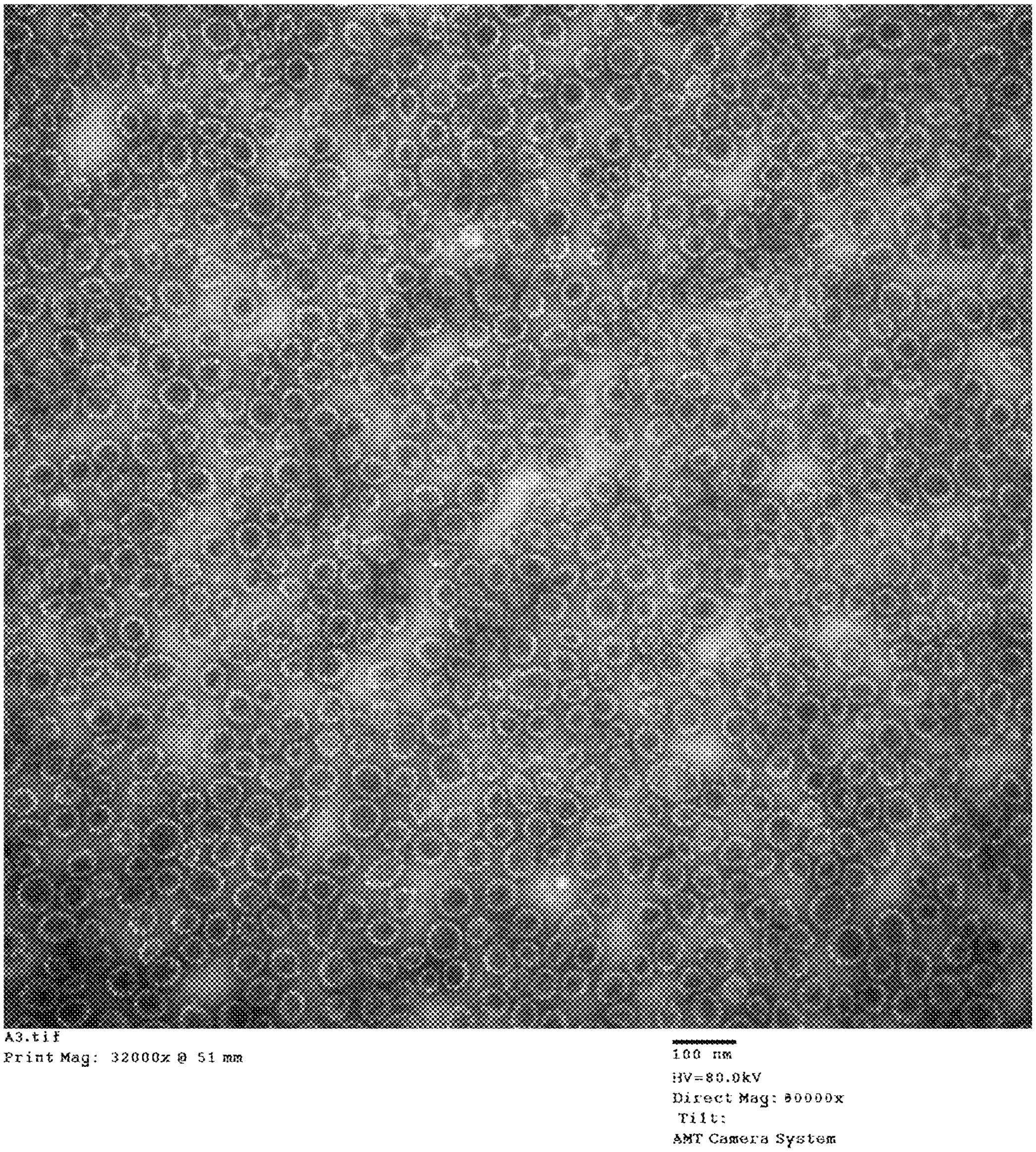

FIG. 2E: Transmission electron microscopy of HPV 31 L1: 33C virus-like particles.

Figure 2F:
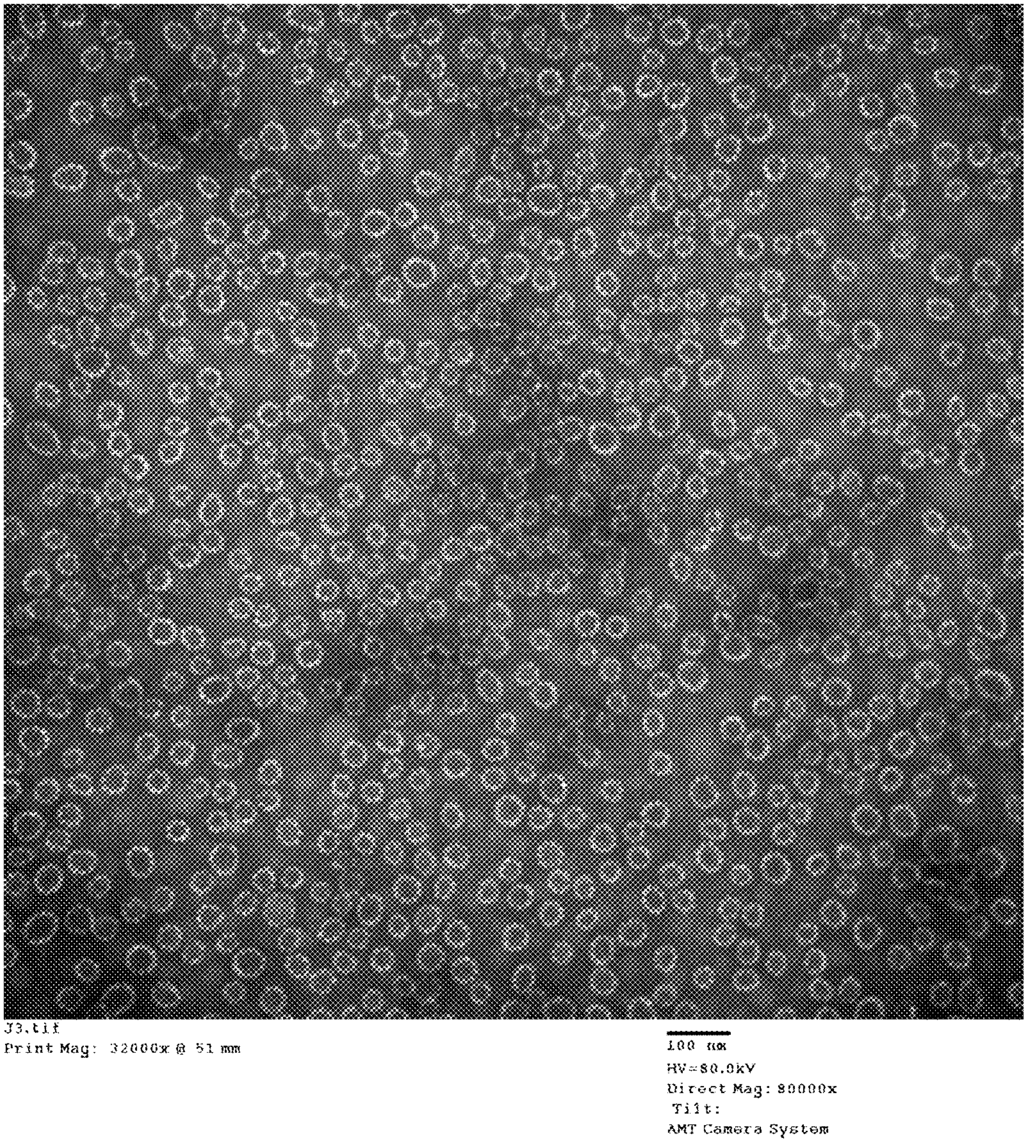

FIG. 2F: Transmission electron microscopy of HPV 33 L1 virus-like particles.

Figure 2G:
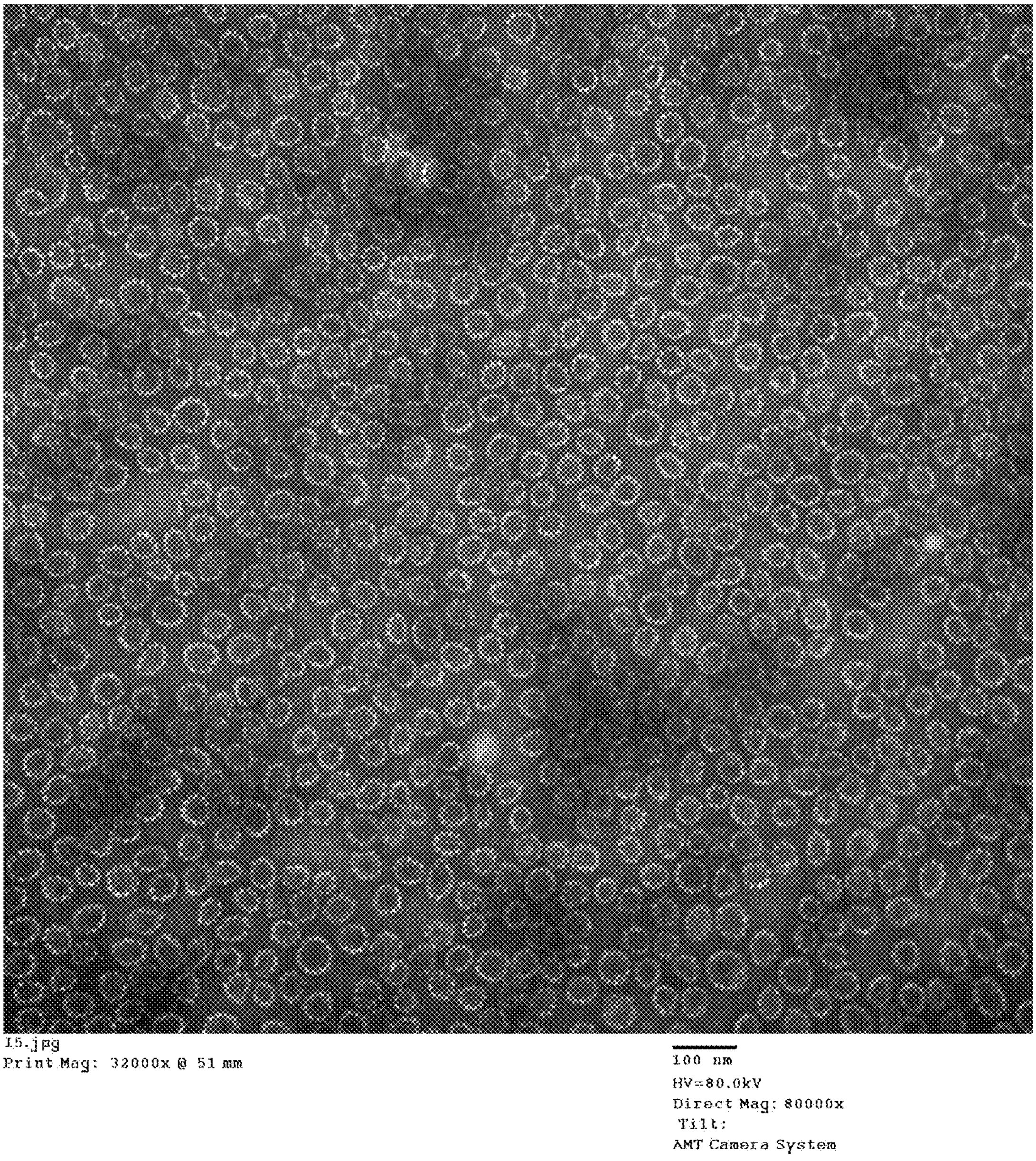

FIG. 2G: Transmission electron microscopy of HPV 35 L1: 33C virus-like particles.

Figure 2H:
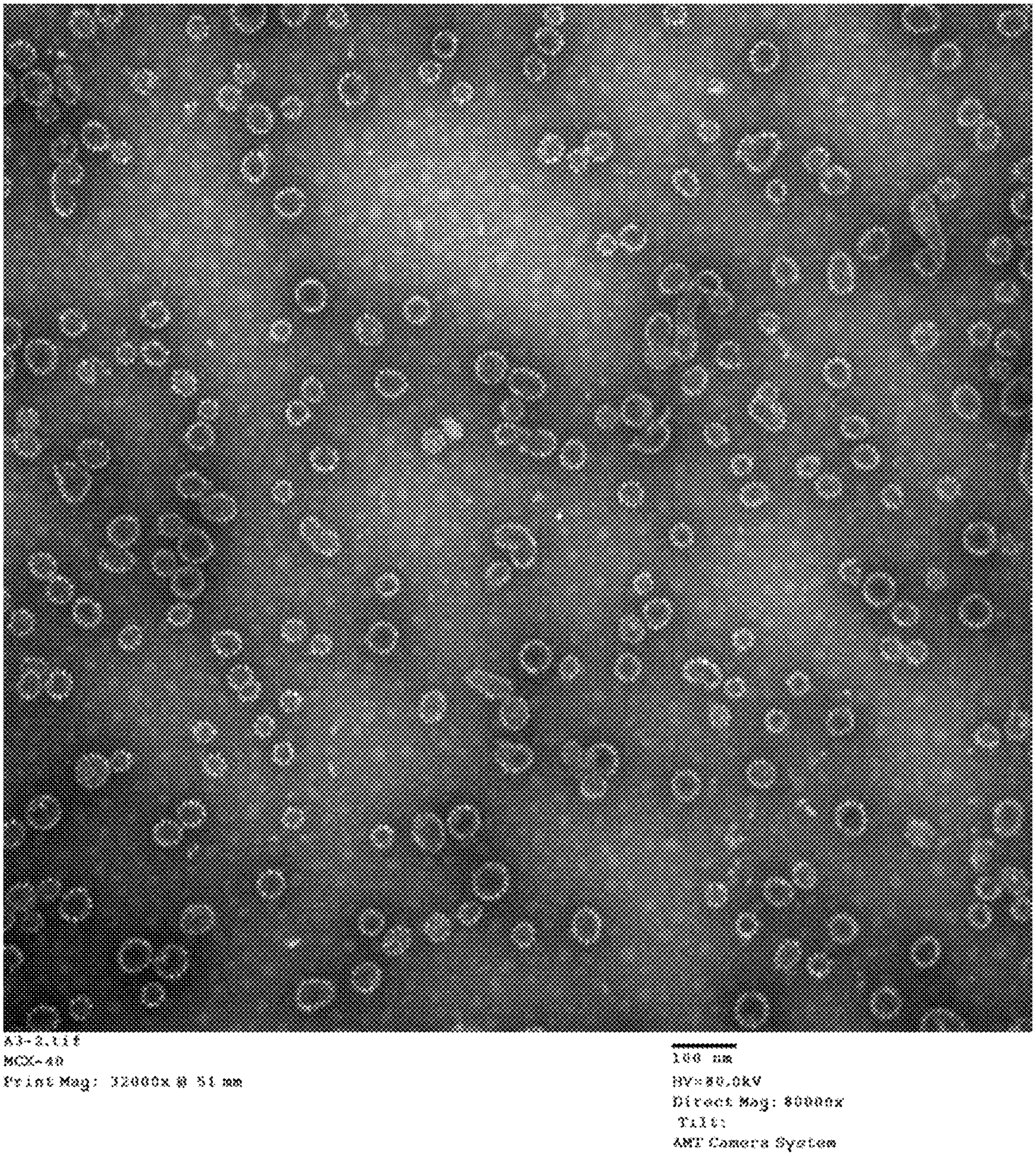

FIG. 2H: Transmission electron microscopy of HPV 39 L1: 59C virus-like particles.

Figure 2I:
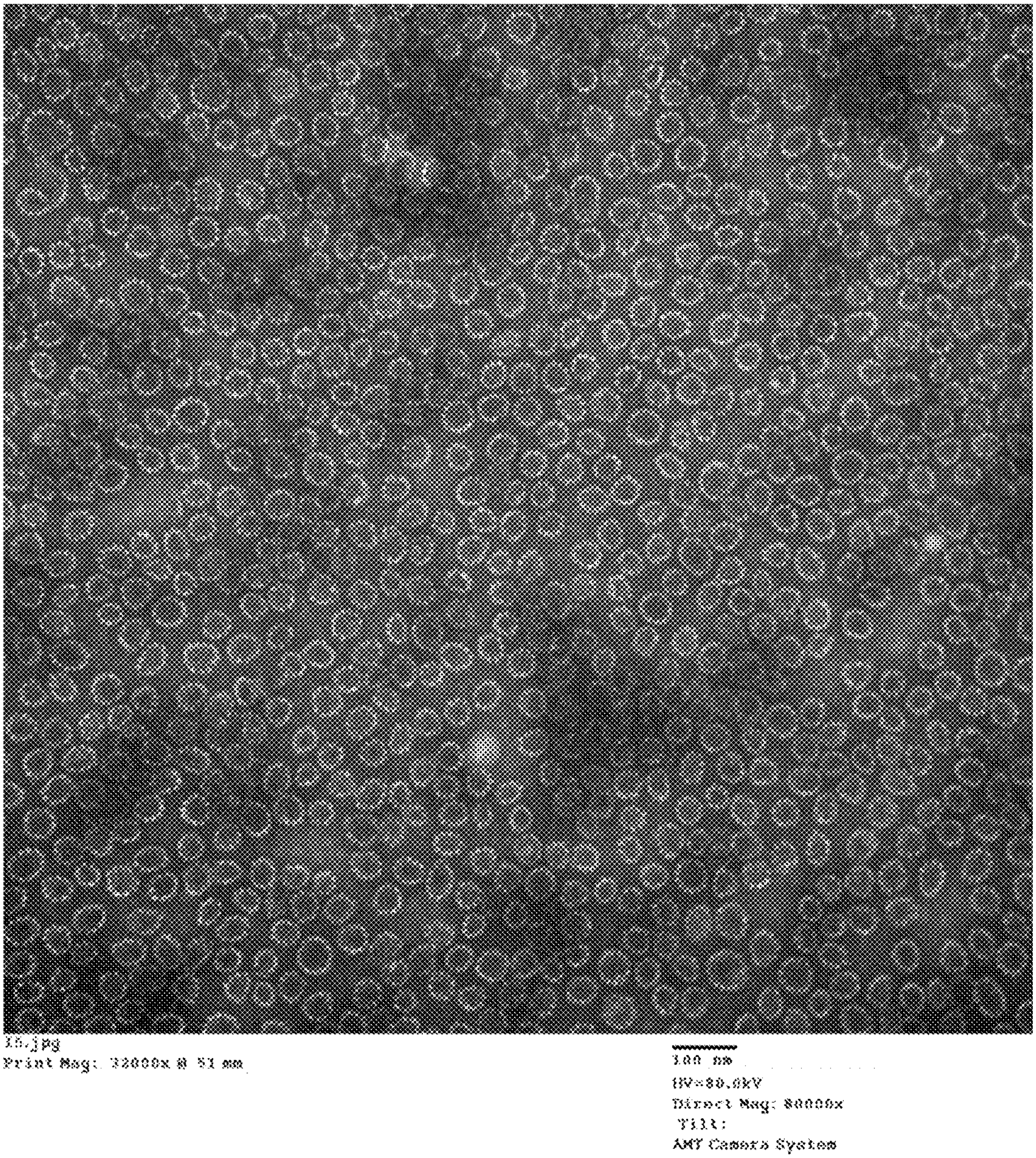

FIG. 2I: Transmission electron microscopy of HPV 45 L1: 33C virus-like particles.

Figure 2J:
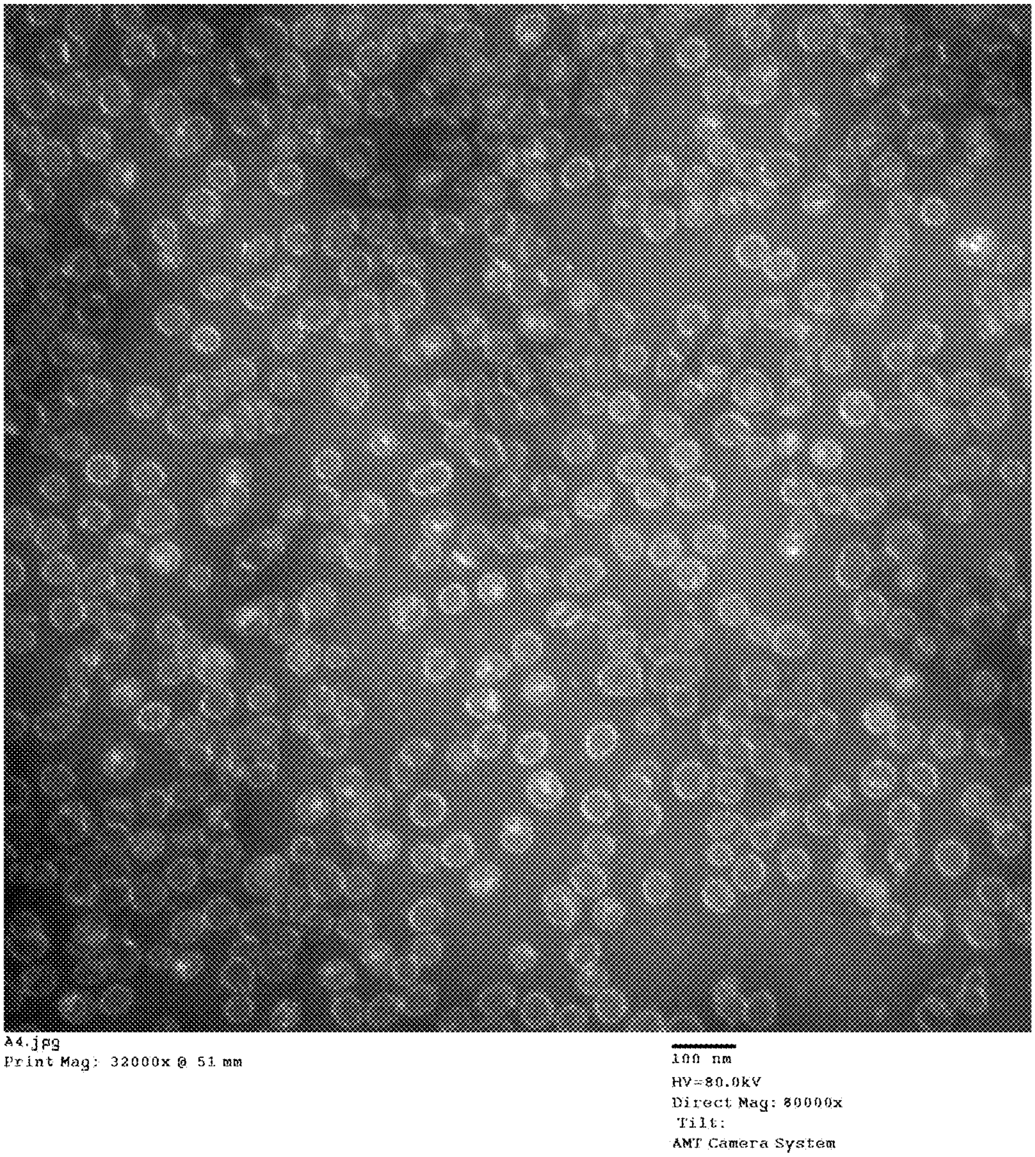

FIG. 2J: Transmission electron microscopy of HPV 51 L1: 33C virus-like particles.

Figure 2K:
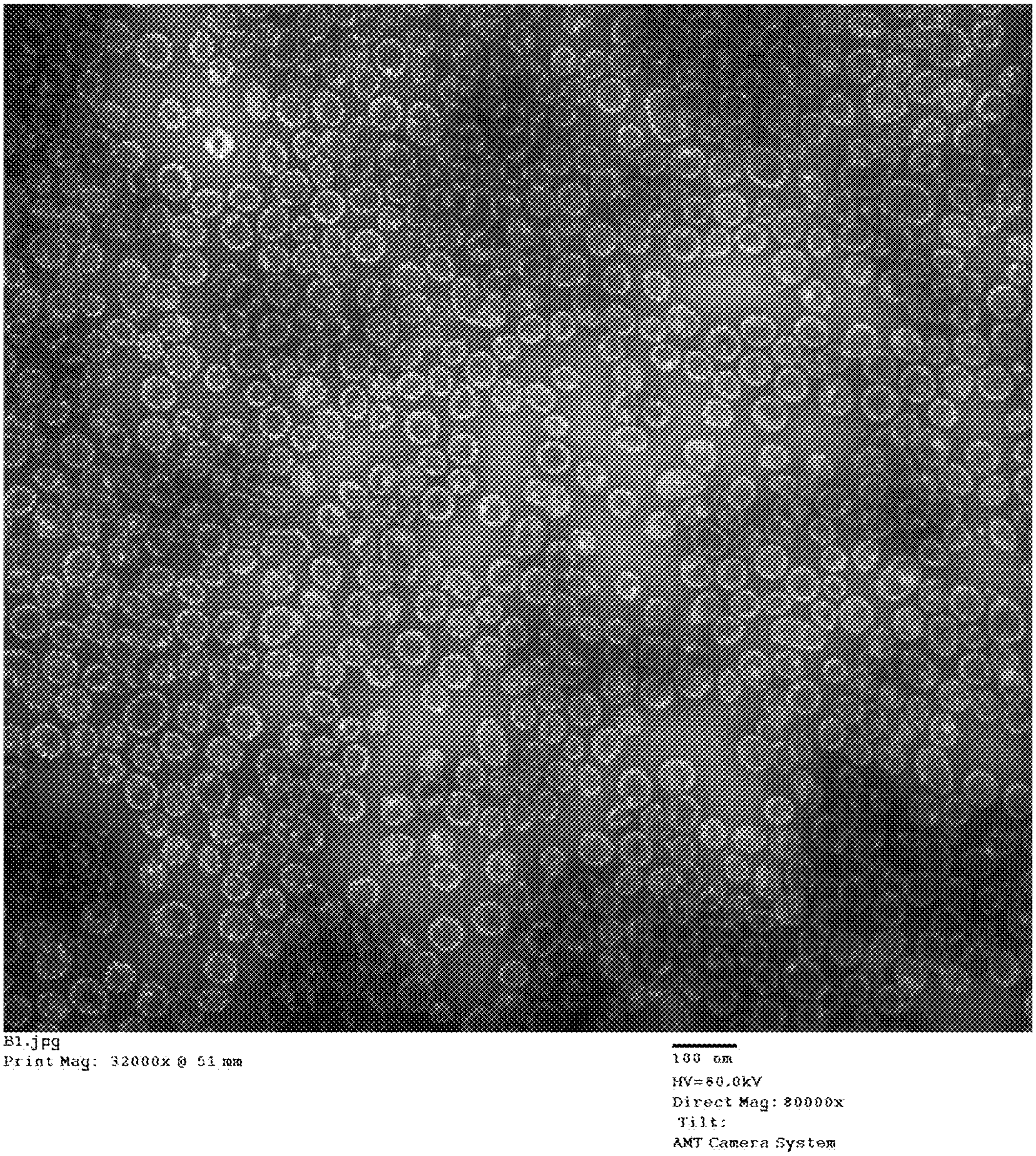

FIG. 2K: Transmission electron microscopy of HPV 52 L1: 33C virus-like particles.

Figure 2L:
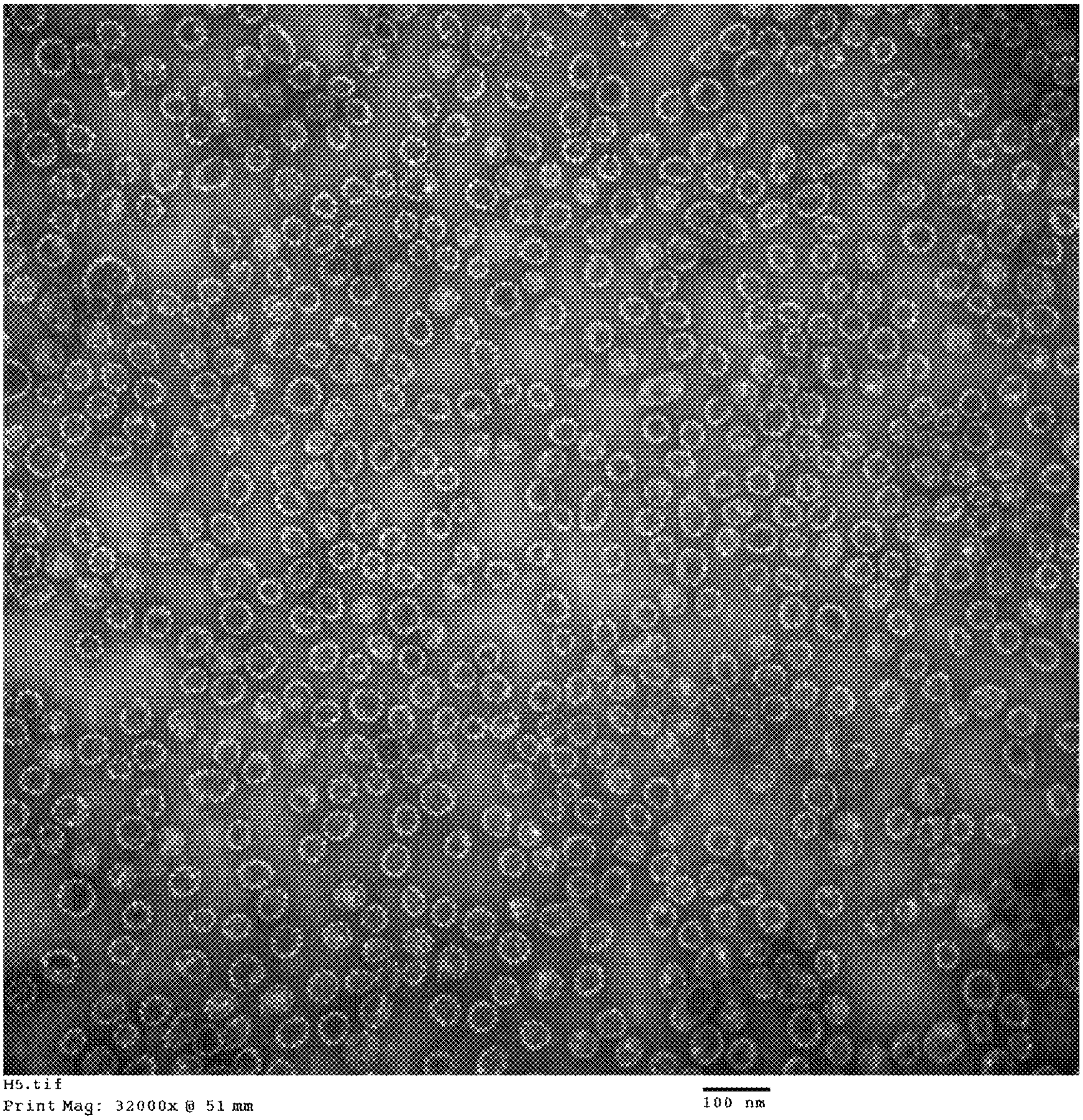

FIG. 2L: Transmission electron microscopy of HPV 56 L1: 33C virus-like particles.

Figure 2M:
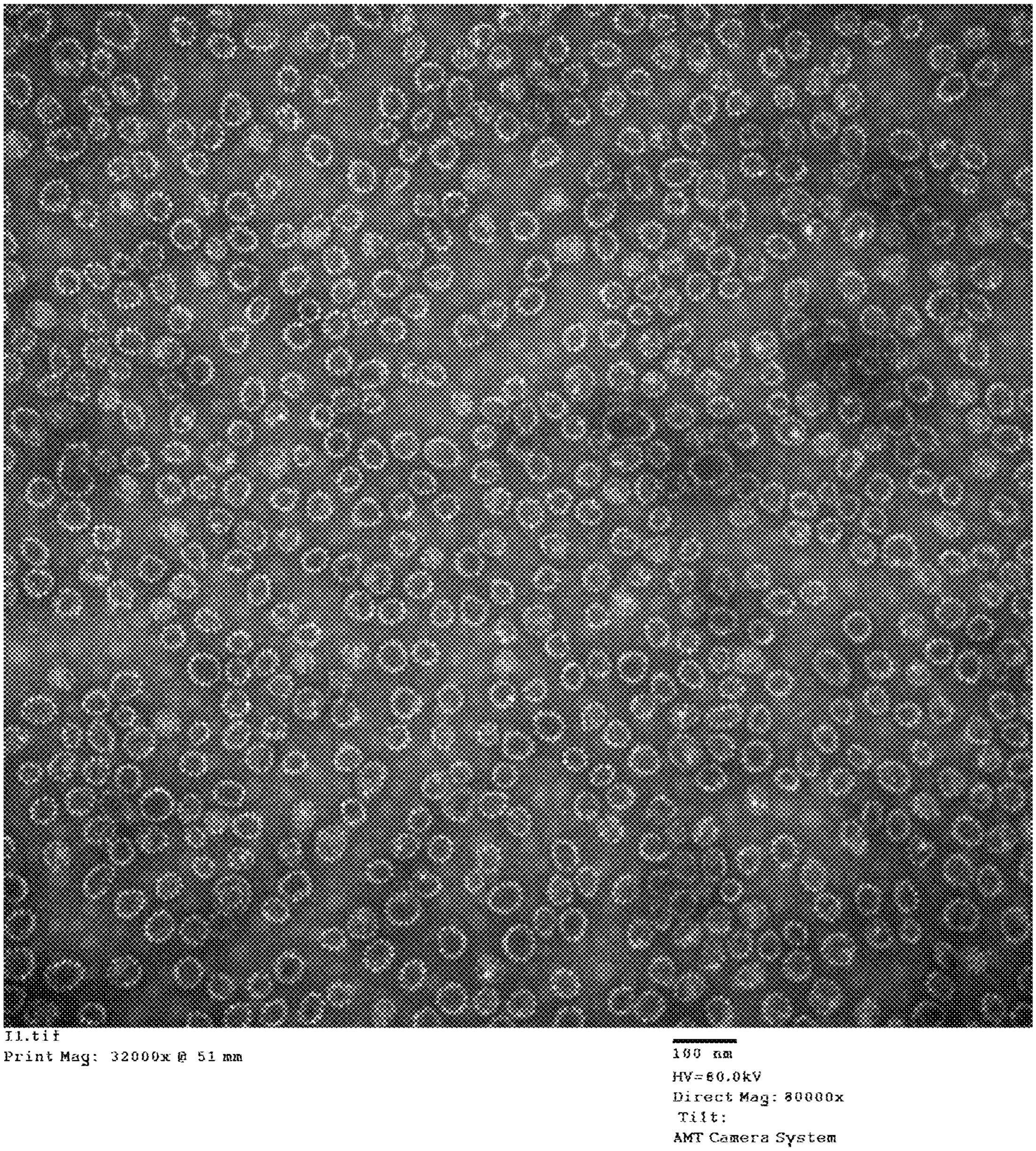

FIG. 2M: Transmission electron microscopy of HPV 58 L1: 33C virus-like particles.

Figure 2N:
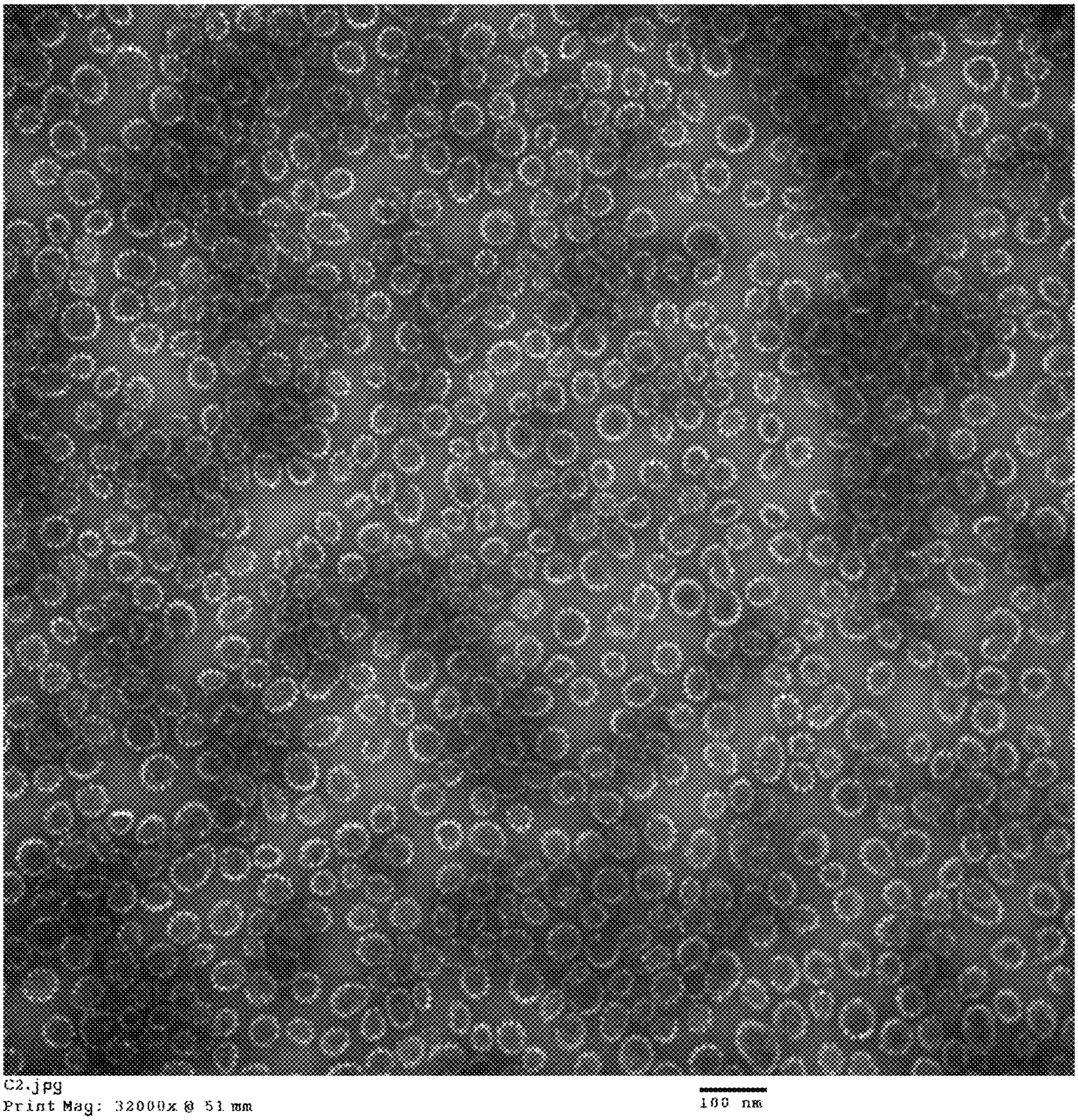

FIG. 2N: Transmission electron microscopy of HPV 59 L1 virus-like particles.

Figure 3:
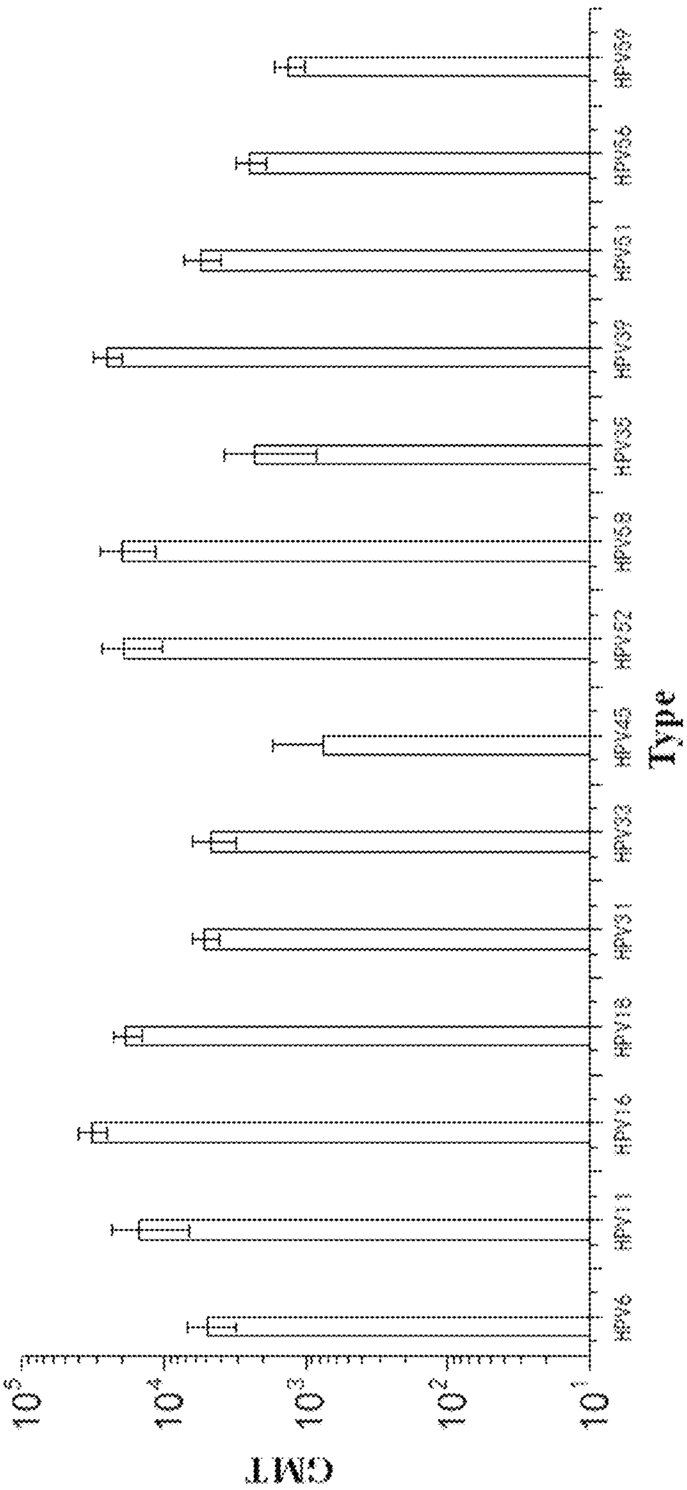

FIG. 3: The pseudovirus neutralizing titers in mice immunized with compositions of 14 HPV types of virus-like particles. Number of mice, N=10. GMT: Geometric Mean Titer.

Figure 4:
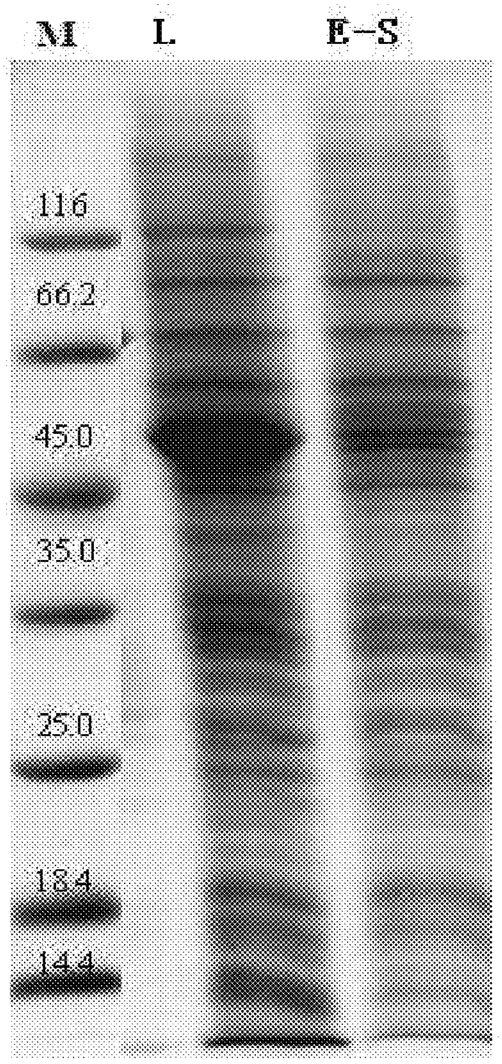

FIG. 4: Expression of C-terminal truncated HPV 16L1 (1-474). M: Marker; L: cell lysates; E-S: supernatant collected after centrifugation of the lysates.

DETAILED DESCRIPTION

In one aspect, the present invention provides a multivalent immunogenic composition for preventing papillomavirus-related diseases or infections. In one embodiment, the papillomavirus may be human papillomavirus. In another embodiment, the papillomavirus may be canine papillomavirus or rabbit papillomavirus.

In one aspect, the present invention provides a multivalent HPV immunogenic composition for preventing HPV-related diseases or infections, comprising: HPV virus-like particles assembled from L1 proteins of HPV Types 6, 11, 16, 18, 31, 33, 45, 52, and 58; and one or more HPV virus-like particles assembled from L1 proteins of other pathogenic HPV types.

In one embodiment, said L1 protein of each HPV type can be a naturally occurring L1 protein, or a non-naturally occurring L1 protein, or a chimeric HPV L1 protein. In one embodiment, said HPV virus-like particles can be assembled from a single type of HPV L1 protein to form monovalent HPV virus-like particles, or can be assembled from multiple types of HPV L1 proteins to form multivalent HPV virus-like particles.

In one embodiment, said one or more other pathogenic HPV types are selected from HPV Types 35, 39, 51, 56, and 59. In one embodiment, at least one of said HPV virus-like particle is a chimeric HPV virus-like particle, said chimeric HPV virus-like particle comprises one or more chimeric HPV L1 proteins; said chimeric HPV L1 protein comprises, from its N-terminus to C-terminus orientation: a. an N-terminal fragment derived from L1 protein of the first papilloma virus type, wherein said L1 protein of the first papilloma virus type is selected from HPV Types 6, 11, 16, 18, 31, 35, 39, 45, 51, 52, 56, or 58, said N-terminal fragment maintains the immunogenicity of the L1 protein of the corresponding HPV type; and b. a C-terminal fragment derived from the L1 protein of the second papilloma virus type, said L1 protein of the second papilloma virus type has a better expression level and solubility compared to L1 proteins of other types; wherein the chimeric L1 protein of HPV Types 6, 11, 16, 18, 31, 35, 39, 45, 51, 52, 56, or 58 has the immunogenicity of the L1 protein of the corresponding HPV type.

In one embodiment, said chimeric HPV virus-like particle may be assembled from a single type of chimeric HPV L1 proteins to form monovalent HPV virus-like particles, or may be assembled from multiple types of chimeric HPV L1 proteins to form multivalent HPV virus-like particles.

In one embodiment, said C-terminal fragment and N-terminal fragment may be freely combined as needed. In one embodiment, the chimeric HPV L1 protein may comprise one or plurality of C-terminal fragments. Said plurality of C-terminal fragments may be the same or different.

In one embodiment, said N-terminal fragment is a fragment obtained by truncating the C-terminus of the natural sequence of said L1 protein of the first papilloma virus type at any amino acid position within its α5 region, and a fragment having at least 98% identity therewith; said C-terminal fragment is a fragment obtained by truncating the N-terminus of the natural sequence of the L1 protein of the second papilloma virus type at any amino acid position within its α5 region and functional variants resulting from further mutations, deletions and/or additions to the fragment.

In another embodiment, said N-terminal fragment has at least 98.5%, 99%, 99.5% or 100% identity to a fragment obtained by truncating the C-terminus of the natural sequence of said L1 protein of the first papilloma virus type at any amino acid position within its α5 region.

In one embodiment, said C-terminal fragment comprises one or plurality of nuclear localization sequences.

In one embodiment, said L1 protein of the second papilloma virus type is selected from L1 proteins of HPV Types 1, 2, 3, 4, 6, 7, 10, 11, 13, 16, 18, 22, 26, 28, 31, 32, 33, 35, 39, 42, 44, 45, 51, 52, 53, 56, 58, 59, 60, 63, 66, 68, 73 or 82.

Preferably, said L1 protein of the second papilloma virus type is selected from L1 proteins of HPV Types 16, 28, 33, 59, or 68.

More preferably, said L1 protein of the second papilloma virus type is selected from L1 protein of HPV Type 33 or HPV Type 59.

In one embodiment, said L1 protein of the second papilloma virus type is an HPV Type 33 L1 protein, said C-terminal fragment is SEQ ID No: 2; or a fragment having a length of m1 amino acids, preferably a fragment covering amino acids 1-m1 position of SEQ ID No: 2; wherein m1 is an integer of 8-26; or said C-terminal fragment is SEQ ID No: 135; or a fragment having a length of m2 amino acids, preferably a fragment covering amino acids 1-m2 position of SEQ ID No: 135; wherein m2 is an integer of 13-31.

In one embodiment, the C-terminal fragment of the HPV Type 33 L1 protein has a nuclear localization sequence. In another embodiment, the C-terminal fragment of the HPV Type 33 L1 protein has two nuclear localization sequences. In one embodiment, the amino acid sequences with amino acid No: 7-8 (KR) and the amino acid sequences amino with amino acid No: 20-23 (KRKK) of SEQ ID No: 2 are nuclear localization sequences of the C-terminal fragments of the HPV Type 33 L1 protein.

In one embodiment, said L1 protein of the second papilloma virus type is the HPV Type 59 L1 protein, said C-terminal fragment is SEQ ID No: 13; or a fragment having a length of n amino acids, preferably covering amino acids 1-n position of SEQ ID No: 13; wherein n is an integer of 16-38.

In one embodiment, the C-terminal fragment of the HPV Type 59 L1 protein has a nuclear localization sequence. In another embodiment, the C-terminal fragment of the HPV Type 59 L1 protein has two nuclear localization sequences. In some embodiments, the chimeric HPV L1 protein comprises one or plurality of C-terminal fragments of the HPV Type 59 L1 protein. Said plurality of C-terminal fragments of the HPV Type 59 L1 protein may be the same or different.

In one embodiment, the amino acid sequence (RKR) of the $14^{th}$ to $16^{th}$ position of SEQ ID No: 13 and the amino acid sequence (KRVKRRK) of the $28^{th}$ to $34^{th}$ position of SEQ ID No: 13 are the nuclear localization sequences of the C-terminal fragment of the HPV Type 59 L1 protein.

In one embodiment, said chimeric HPV L1 protein comprises both a C-terminal fragment of the HPV Type 33 L1 protein and a C-terminal fragment of the HPV Type 59 L1 protein.

In one embodiment, said N-terminal fragment of said HPV Type 6 L1 protein has 98%, 98.5%, 99%, 99.5%, 99%, or 100% identity to the fragment obtained by truncating the C-terminus of the sequence shown in SEQ ID No: 1 at any amino acid site within its alpha 5 region.

Said N-terminal fragment of said HPV Type 11 L1 protein has 98%, 98.5%, 99%, 99.5%, 99% or 100% identity to the fragment obtained by truncating the C-terminus of the sequence shown in SEQ ID No: 14 at any amino acid site within its alpha 5 region.

Said N-terminal fragment of said HPV Type 16 L1 protein has 98%, 98.5%, 99%, 99.5%, 99% or 100% identity to the fragment obtained by truncating the C-terminus of the sequence shown in SEQ ID No: 27 at any amino acid site within its alpha 5 region.

Said N-terminal fragment of said HPV Type 18 L1 protein has 98%, 98.5%, 99%, 99.5%, 99% or 100% identity to the fragment obtained by truncating the C-terminus of the sequence shown in SEQ ID No: 40 at any amino acid site within its alpha 5 region.

Said N-terminal fragment of said HPV Type 31 L1 protein has 98%, 98.5%, 99%, 99.5%, 99% or 100% identity to the fragment obtained by truncating the C-terminus of the sequence shown in SEQ ID No: 53 at any amino acid site within its alpha 5 region.

Said N-terminal fragment of said HPV Type 35 L1 protein has 98%, 98.5%, 99%, 99.5%, 99% or 100% identity to the fragment obtained by truncating the C-terminus of the sequence shown in SEQ ID No: 69 at any amino acid site within its alpha 5 region.

Said N-terminal fragment of said HPV Type 39 L1 protein has 98%, 98.5%, 99%, 99.5%, 99% or 100% identity to the fragment obtained by truncating the C-terminus of the sequence shown in SEQ ID No: 82 at any amino acid site within its alpha 5 region.

Said N-terminal fragment of said HPV Type 45 L1 protein has 98%, 98.5%, 99%, 99.5%, 99% or 100% identity to the fragment obtained by truncating the C-terminus of the sequence shown in SEQ ID No: 95 at any amino acid site within its alpha 5 region.

Said N-terminal fragment of said HPV Type 51 L1 protein has 98%, 98.5%, 99%, 99.5%, 99% or 100% identity to the fragment obtained by truncating the C-terminus of the sequence shown in SEQ ID No: 108 at any amino acid site within its alpha 5 region.

Said N-terminal fragment of said HPV Type 52 L1 protein has 98%, 98.5%, 99%, 99.5%, 99% or 100% identity to the fragment obtained by truncating the C-terminus of the sequence shown in SEQ ID No: 121 at any amino acid site within its alpha 5 region.

Said N-terminal fragment of said HPV Type 56 L1 protein has 98%, 98.5%, 99%, 99.5%, 99% or 100% identity to the fragment obtained by truncating the C-terminus of the sequence shown in SEQ ID No: 134 at any amino acid site within its alpha 5 region; and Said N-terminal fragment of said HPV Type 58 L1 protein has 98%, 98.5%, 99%, 99.5%, 99% or 100% identity to the fragment obtained by truncating the C-terminus of the sequence shown in SEQ ID No: 147 at any amino acid site within its alpha 5 region.

In one embodiment, the C-terminus of said N-terminal fragment is connected to the N-terminus of said C-terminal fragment directly or via a linker.

The linker does not affect the immunogenicity of said N-terminal fragment and does not affect the expression level or solubility of the protein. In one embodiment, said N-terminal fragment and said C-terminal fragment are connected via a linker comprising 1, 2, 3, 4, 5, 6, 7, 8, 9 or 10 amino acids. In one embodiment, the linker is an artificial sequence. In another embodiment, the linker is a naturally occurring sequence in the HPV L1 protein. In another embodiment, the linker may be a partial sequence of the HPV Type 33 L1 protein. In another embodiment, the linker may be a partial sequence of the HPV Type 59 L1 protein.

In one embodiment, within the range of plus or minus 4 amino acid positions of the connection point when the C-terminus of said N-terminal fragment is connected to the N-terminus of said C-terminal fragment, there presents the following continuous amino acid sequence: RKFL (SEQ ID NO: 163); preferably, within the range of plus or minus 6 amino acid positions of the connection point, there presents the following continuous amino acid sequence: LGRKFL (SEQ ID NO: 164).

In some embodiments, said chimeric HPV L1 proteins of chimeric HPV Types 6, 11, 16, 18, 31, 35, 39, 45, 51, 52, 56, and 58 have 98%, 98.5%, 99%, 99.5% or 100% identity to SEQ ID No: 3, SEQ ID No: 16, SEQ ID No: 29, SEQ ID No: 42, SEQ ID No: 55, SEQ ID No: 71, SEQ ID No: 84, SEQ ID No: 97, SEQ ID No: 110, SEQ ID No: 123, SEQ ID No: 136 and SEQ ID No: 149, respectively; and the HPV Type 33 L1 protein and the HPV Type 59 L1 protein have 98%, 98.5%, 99%, 99.5%, or 100% identity to SEQ ID No: 66 and SEQ ID No: 160, respectively.

In one embodiment, at least one of said HPV virus-like particles is composed of a single type of chimeric HPV L1 protein, preferably is composed of said single type of chimeric HPV L1 protein having the same amino acid sequence.

In one embodiment, the chimeric HPV virus-like particle is the icosahedron comprising 72 pentamers of said chimeric HPV L1 protein. In one embodiment, the HPV virus-like particle has correctly formed disulfide bonds and thus has a good natural conformation. In one embodiment, the chimeric HPV virus-like particles self-assemble in an in vivo expression system.

In one embodiment, said multivalent HPV immunogenic composition further comprises a physiologically acceptable carrier and, optionally, an adjuvant. In one embodiment, the adjuvant comprises one or more of aluminum salt, lipid A derivative, and ISCOM.

In one embodiment, said adjuvant is an aluminum phosphate adjuvant. In one aspect, the present invention provides a method of preventing HPV-related diseases or infections, comprising: administering to a subject a multivalent HPV immunogenic composition. Said prevention may be considered as a treatment and they can be used interchangeably. In one embodiment, the subject is a human.

In one aspect, the present invention provides the use of the aforementioned multivalent HPV immunogenic compositions in the preparation of vaccines or drugs for preventing HPV-related diseases or infections.

Papillomavirus L1 proteins expressed by eukaryotic expression systems can spontaneously assemble to virus-like particles, but the low expression level make them not suitable for mass production.

The sequences of the L1 proteins of each HPV type can be easily obtained from https://www.uniprot.org. For a given HPV type, the L1 protein can be derived from different strains, thus the amino acid sequence thereof may have multiple versions, any version of the natural sequence can be used in the present invention. It is possible that the sequence of the HPV L1 protein of a given type used during the conception and design of the present invention may differ from the sequence used in the following examples, but such differences do not affect the decisions and conclusions of the inventors.

It is generally accepted by those of skill in the art that the C-terminus of the L1 protein does not contain major neutralizing antigenic epitope and therefore attempts have been made to increase expression by truncating the C-terminus of the HPV L1 protein, for example Glaxo's U.S. Pat. No. 6,361,778 B1, in which the C-terminus of the HPV16 L1 protein is truncated by 1-34 amino acids, preferably 26 amino acids, states that the yield of VLP is increased by many-fold, preferably at least by 10 folds, and in particular by about 10 to 100 folds. Inspired by this, the inventors attempted to truncate the C-terminus of HPV 16 L1 protein by 31 amino acids and named the truncated protein as HPV 16 L1 (1-474). The protein is in high expression level but poor solubility, and is difficult to be extract and purified (see Comparative Example).

The poor solubility of the protein due to this truncation may be caused by the deletion of the nuclear localization sequence located at the C-terminus, but the present invention is not binding to this speculation. During research and production, the inventor discovered that HPV Type 16 L1 protein, HPV Type 28 L1 protein, HPV Type 33 L1 protein, HPV Type 59 L1 protein and HPV Type 68 L1 protein have better expression levels and solubility than other HPV types L1 proteins. Inspired by the discovery, the inventors replaced the C-terminus of specific HPV types L1 proteins that are less extractable or less soluble with the C-terminus of specific HPV types L1 protein having better expression levels and solubility. That is, the inventors have constructed a chimeric protein: comprising, in the N-terminus to C-terminus orientation, an N-terminal fragment derived from the L1 protein of the first papilloma virus type (e.g., HPV L1 protein), which provides the immunogenicity of the first papilloma virus type (e.g., HPV), and a C-terminal fragment derived from the L1 protein of the second papilloma virus type (e.g., HPV L1 protein), which provides the features of better expression levels and solubility. These two fragments can be connected directly or via a linker.

The length of the N-terminal fragment of the HPV L1 protein appropriate for maintaining the immunogenicity of the L1 protein of the first type and ensuring the formation of VLP is determined. The following reports relate to epitope studies of common HPV types.

Sunanda Baidya et al. reported that the epitopes of the L1 protein 48EEYDLQFIFQLCKITLTA65 (SEQ ID NO: 165), 45RHGEEYDLQFIFQLCKITLTA65 (SEQ ID NO: 166), 63LPDPNKF69 SEQ ID NO: 167, 79PETQRLVWAC88 (SEQ ID NO: 168), 36PVPGQYDA43 (SEQ ID NO: 169), 77YNPETQRLVWAC88 (SEQ ID NO: 170), 188DTGYGAMD195 (SEQ ID NO: 171), 36PVPGQYDATK45 (SEQ ID NO: 172), 45KQDIPKVSAYQYRVFRV61 (SEQ ID NO: 173), 13ORDNVSVDYKQTQLCI144 (SEQ ID NO: 174) and 49YSRHVEEYDLQFIF62 (SEQ ID NO: 175) can be used as tools for designing HPV 16 and 18 vaccines (see Epitope design of L1 protein for vaccine production against Human Papilloma Virus types 16 and 18, Bioinformation 13(3): 86-93 March 2017, incorporated herein by reference in its entirety).

Katharina Slupetzky et al. reported that the regions near aa 282-286 and 351-355 of HPV-16 contribute to the neutralization epitopes and that the latter is the immunodominant site (see Chimeric papilloma virus-like particles expressing a foreign epitope on capsid surface loops, Journal of General Virology (2001), 82, 2799-2804, incorporated herein by reference in its entirety).

Brooke Bishop et al. prepared the following three variants of the HPV 11, 16, 18 and 35 L1 proteins: deletion of 9 amino acids at its N terminus, deletion of α4 (corresponding to amino acid residues 404-436 of HPV 16), and deletion of 31 amino acids at its C terminus respectively, and reported that the former two could not be assembled into VLP, but this phenomenon has not been reported in the latter one (Crystal Structures of Four Types of Human Papillomavirus L1 Capsid Proteins UNDERSTANDING THE SPECIFICITY OF NEUTRALIZING MONOCLONAL ANTIBODIES, The Journal of Biological Chemistry, 282, 31803-31811. incorporated herein by reference in its entirety). Each the α-helix, β-fold sheets and Loop Region of each type of HPV L1 protein can be conveniently determined by sequence analysis software commonly used in the field.

Wherein the α-helix regions contains the α1 Region, α2 Region, α3 Region, α4 Region and α5 Region.
(SEQ ID NOS: 176-179, respectively)

```
                ▼      ▼                             β-B1        β-B2          BC-loop          β-C
HPV16-L1  mslWlpseaTVYlPP-vpVskVVsTDeYVarTnIyYHAgtSRLLaVGhPYfpikkpnnnKilvPRVSglQYRVFrihLPDPNKFgfPDTS  89
HPV35-L1  mslWrsneaTVYlPP-vpVskVVsTDeYVtrTnIyYHAgsSRLLaVGhPYyaikkqdsnKiavPRVSglQYRVFrvkLPDPNKFgfPDTS  89
HPV11-L1  --mWrpsdsTVYvPPpnpVskVVaTDaYVkrtnIfYHAssSRLLaVGhPYysikkvn--HtvvPKVSgyQYRVFkvvLPDPNKFaLPDSS  86
HPV18-L1  mslWrpsdnTVYlPP-psVarVVnTDdYVtpTsIfYHAgsSRLLtVGnPYfrvpagggnKqdiPKVsayQYRVFrvqLPDPNKFglPDTS  89

                β-D                      DE-loop                              β-E          EF-
HPV16-L1  fynPdtQRLVWACvGvEvGRGQPLGVGiSGHPllNKlDDtEnasayaaNagvDnRecisnDYKQTQLCliGCkPpiGEHWgKGspCtnva  179
HPV35-L1  fynPasQRLVWACtGvEvGRGQPLGVGiSGHPllNKlDDtEnsnkyvgNsgtDnRecisnDYKQTQLCliGCrPpiGEHWgKGtpCnanq  179
HPV11-L1  lfdPttQRLVWACtGlEvGRGQPLGVGvSGHPllNKyDDvEnsggyggNpggDnRvnvgnDYKQTQLCnvGCAPplGEHWgKGtqCsnts  176
HPV18-L1  iynPetQRLVWACaGvEiGRGQPLGVGlSGHPllNKyDDtEsshaatsNvseDvRdnvsyDYKQTQLCilGCaPaiGEHWaKGtaCksrp  179

          loop                                                        α1        β-F          FG-
HPV16-L1  vnpGdCPPLELintViqDGDMVDTGFGAMdFttLQaNKseVPLDICtsiCKYPDYIkMvsePYGDslFFyLRrEQmFvRHlfNRAGavGe  269
HPV35-L1  vkaGeCPPLELintVlqDGDMVDTGFGAMdFttLQaNKsdVPLDICssiCKYPDYIkMvsePYGDnlFFyLRrEQmFvRHlfNRAGtvGe  269
HPV11-L1  vqnGdCPPLELitsViqDGDMVDTGFGAMnFadLQtNKsdVPLDICgtvCKYPDYLqMaadPYGDrlFFyLRkEQmFaRHlfNRAGtvGe  266
HPV18-L1  lsqGdCPPLELkntVleDGDMVDTGYGAMdFstLQdTKceVPLDICgsiCKYPDYLqMsadPYGDsnFFcLRrEQlFaRHfwNRAGtnGd  269

                 loop                     G1      G2                 β-H1       β-H2     HI-loop
HPV16-L1  nVPddLyiKGsgstanlaSsnYfptPSGSnVtSdaQiFNKPYWLqrAQGHNNGiCWgNgLFVTVVDTTrSTNnslCaaistse-ttYkny  358
HPV35-L1  tVPadLyiKG--ttgtlpStsYfptPSGSnVtSdaQiFNKPYWLqrAQGHNNGiCWsNqLFVTVVDTTrSTNnsvCsavsssd-stYknd  356
HPV11-L1  pVPddLlvKGgnnrssvaSsiYvhtPSGSlVsSeaQlFNKPYWLqkAQGHNNGiCWgNhLFVTVVDTTrSTNntlCasvsks--atYkns  354
HPV18-L1  tVPqsLyiKGtgmpaspgScvYspsPSGSiVtSdsQlFNKPYWLhkAQGHNNGvCWhNqLFVTVVDTTpSTNltiCastqspvPggYdat  359

                   β-1               α2        α3    ▼          α4                  ▼
HPV16-L1  nfKeYlRHgEEyDLQFIFQLCkITLtAdVMtYIHsNNstiLEDWNFGlqPPPggtLeDTYRfVtSqAiaCQKhtppapkeDPlkkytFWe  446
HPV35-L1  nfKeYlRHgEEyDLQFIFQLCkITLtAdVMtYIHsNNpsiLEDWNFGltPPPsgtLeDTYRfVtSqAvtCQKpsapkpkdDPlknytFWe  446
HPV11-L1  dyKeYnRHvEEfDLQFIFQLCsITLsAeVMaYIHtMNpsyLEDWNFGlsPPPngtLeDTYRyVqSqAitCQKptpekekqDPykdmsFWe  444
HPV18-L1  kfKqYsRHvEEyDLQFIFQLCtITLtAdVMsYIHsNNssiLEDWNFGvpPPPttsLvDTYRfVqSvAiatCQdaapaenkDPydklkFWn  449

          β-J         α5        ▼                                   ▼
HPV16-L1  VnLKEKFSadLDQfPLGRKFLlQaGlkakpkftlgkr-katpttsststtakRkkrkl  505
HPV35-L1  VdLKEKFSadLDQfPLGRKFLlQaGlkarpnfrlgkr-aapastskksstkrRkvks   502
HPV11-L1  VnLKEKFSseLDQfPLGRKFLlQsGyrgrtsartgik-rpavskpstapkrkRtktkk  501
HPV18-L1  VdLKEKFSldLDQyPLGRKFLvQaGlrrkptigprkrsapsattsskpakrvRvrark  507
```

The inventors performed sequence alignments of L1 proteins of 14 HPV types (Types 6, 11, 16, 18, 31, 33, 35, 39, 45, 51, 52, 56, 58, and 59) and then performed secondary structure prediction according to the literature cited above (Crystal Structures of Four Types of Human Papillomavirus L1 Capsid Proteins UNDERSTANDING THE SPECIFICITY OF NEUTRALIZING MONOCLONAL ANTIBODIES, The Journal of Biological Chemistry, 282, 31803-31811), the results of which are shown below, where the part between the downward-pointing arrows corresponds to the regions which had been deleted for preparing the variants in that literature.
(SEQ ID NOS: 180, 178, 181-184, 176-177, 185-188, 179 and 189, respectively)

```
            ▼      ▼                         β-B1      β-B2     BC-
HPV6-L1     --MWRPSDSTVVVPPPNPVSKVVATDAYVTRTNIFYHASSSRLLAVGHPYPSIKRA----      54
HPV11-L1    --MWRPSDSTVVVPPPNPVSKVVATDAYVTRTNIFYHASSSRLLAVGHPYYSIKKV----      54
HPV52-L1    MSVWRPSEATVYLP-PVPVSKVVSTDEVVSRTSIYYYAGSSRLLTVGHPYPSIKNTSSGN      54
HPV58-L1    MSVWRPSEATVYLP-PVPVSKVVSTDEVVSRTSIYYYAGSSRLLAVGHPYPSIKSP--NN      57
HPV33-L1    MSVWRPSEATVYLP-PVPVSKVVSTDEVVSRTSIYYYAGSSRLLAVGHPYPSIKNP--TN      57
HPV31-L1    MSLWRPSEATVYLP-PVPVSKVVSTDEVVSRTSIYYHAGSARLLTVGHPYYSIPKS--DN      57
HPV16-L1    MSLWRPSEATVYLP-PVPVSKVVSTDEVVSRTSIYYHAGTSRLLAVGHPYFPIKKP--NN      57
HPV35-L1    MSLWRSNEATVYLP-PVSVSKVVSTDEVVTRTNIYYHAGSSRLLAVGHPYYAIKKQ--DS      57
HPV51-L1    MALWRTNDSKVVLP-PAPVSRIVNTEEYITRTGIYYYAGSSRLITLGHPYFPIPK----T      55
HPV56-L1    MATWRPSENKVVLP-PTPVSKVVATDSVVKRTSIFYRAGSSRLLAVGHPYYSVTR----D      55
HPV39-L1    MAMWRSSDSMVYLP-PPSVAKVVNTDDVVTRTGIYYYAGSSRLLTVGHPYPKV-GM--NG      56
HPV59-L1    MALWRSSDNKVVLP-PPSVAKVVSTDEYVTRTSIFYHAGSSRLLTVGHPYPKV-PK--GG      56
HPV18-L1    MALWRPSDNTVVLP-PPSVAKVVNTDDVVTRTSIFYHAGSSRLLTVGNPYKRV-PA--GG      56
HPV45-L1    MALWRPSDSTVYLP-PPSVARVVNTDDVVSRTSIFYHAGSSRLLTVGNPYPRVVPS--GA      57
```

-continued

```
                  loop          β-C                         β-D
HPV6-L1    -NKTVVPKYSGYQYRVFKVVLPDPNKFALPDSSLFDPTTQRLVWACTGLEVGRGQPLCVG   113
HPV11-L1   -NKTVVPKVSGYQYRVFKVVLPDPNKFALPDSSLFDPTTQRLVWACTGLEVGRGQPLGVG   113
HPV52-L1   GKKVLVPKVSGLQYRVFRIKLPDPSKFGFPDTSFYNPETQRLVWACTGLETGRGQPLGVG   119
HPV58-L1   NKKVLVPKVSGLQYRVFRVRLPDPNKFGFPDTSFYNPDTQRLVWACVGLETGRGQPLGVG   117
HPV33-L1   AKKLLVPKVSGLQYRVFRVRLPDPNKFGFPDTSFYNPDTQRLVWACVGLEIGNGQPLGVG   117
HPV31-L1   PDDIVVPKVSGLQYRVFRVRLPDPNKPGFPDTSFYNPETQRLVWACVGLEVGRGQPLGVG   117
HPV16-L1   -NKILVPKVSGLGYRVFRIHLPDPNKFSFPDTSFYNPDTQRLVWACVGVEVGRGQPLGVG   116
HPV35-L1   -NKIAVPKVSGLQYRVFRVKLPDPNKFGFPDTSFYDPASQRLVWACTGVEVGRGQPLGVG   116
HPV51-L1   STRAAIPKVSAFQYRVFRVQLPDPNKFGLPDPNLYNPDTDRLVWGCVGVEVGRGQPLGVG   115
HPV56-L1   NTKTNTPKVSAVQYRVFRVRLPDPNKFGLPDTNIYNPDQERLVWACVGLEVGRGQPLGAG   115
HPV39-L1   GRKQDIPKVSAYQYRVFRVTLPDPNKFSTPDASLYNPETQRLVWACVGVEVGRGQPLGVG   116
HPV59-L1   NGRQDVPKYSAYGYRVFRVKLPDPNKPGLPDNTVYDPNSQRLVWACVGVETGRGQPLGVG   116
HPV18-L1   GNKQDTPKVSAVQYRVFRVQLPDPNKFGLPDTSIYNPETQRLVWACAGVELGRGQPLGVG   116
HPV45-L1   GNKQAVPKVSAYQYRVFRVALPDPNKFGLPDATIYNPETQRLVWACVGMETGRGQPLGIG   117

                         DE-loop                    β-E        EF-
HPV6-L1    VSGHPFLNKYDDVENSG-SGGNPGQDNRVNVGMDYKQTQLCMVGCAPPLGEHWGKGKQCI   172
HPV11-L1   VSGHPLLNKYDDVENSGGYGGNPGQDNRVNVGNDYKQTQLCMVGCAPPLGEHWGKGTQCS   173
HPV52-L1   ISGHPLLNKFDDTETSNKYAGKPGIDNNECLSMDYKQTQLCTLGCKPPLGEHWGKGTPCN   179
HPV58-L1   VSCHPYLNKFDDTETSNRYPAQPGSDNRECLSMDYKQTQLCLIGCKPPTGEHWGKGYACN   177
HPV33-L1   ISGHPLLNKFDDTETGNKYPGQPGADNRECLSMDYKQTQLCLLGCKPPTGEHWGKGVACT   177
HPV31-L1   ISGHPLLNKFDDTENSNRYAGGPGTDNRECISMDYKQTQLCLLGCKPPIGEHWGKGSPCS   177
HPV16-L1   ISGHPLLNKLDDTENASAYAANAGVDNRECTSMDYKQTQLCLIGCKPPIGEHWGKGSPCI   176
HPV35-L1   ISGHPLLNKLDDTENSNKVVGNSGTDNRRCISMDYKQTQLCLIGCRPPIGEHWGKGTPCN   176
HPV51-L1   LSGHPLFNKYDDTENSRIANGNAQQDVRDNTSVDNKQTQLCIIGCAPPIGFHWGIGTTCK   175
HPV56-L1   LSGHPLFNRLDDTESSNLANNNVIEDSRDNISVDGKQTQLCIVGCIPAMGEHWTKGAVCK   175
HPV39-L1   LSGHPLYNRQDDTENSPPS-STTNKDSRDNVSVDYKQTQLCTIGCVPAIGEHWGKGKACK   175
HPV59-L1   LSGHPLYNKLDDTENSHVASAVDIKDTRDNVSVDYKQTQLCIIGCVPAIGEHWTKGTACK   176
HPV18-L1   LSGHPFYNKLDDTESSHAATSNVSEDVRDNVSVDYKQTQLCILGCAPAIGEHWAKGTACK   176
HPV45-L1   LSGHPFYNKLDDTESAHAATAVITQDVRDNVSVDVKQTQLCILGCVPAIGEHWAKGTLCK   177

                  loop
HPV6-L1    NTPVQAGDCPPLELITSYIQDGDNVDTGFGAMNFADLQTNKSDVPIDICGTTCKYPDYLQ   232
HPV11-L1   NTSVQNGDCPPLELITSVIQDGDMVDTGFGAMNFADLQTNKSDVPLDICGTVCKYPDYLQ   233
HPV52-L1   NNSGNPGDCPPLQLINSVIQDGDMVDIGFGCMDFNTLQASKSDVPIDICSSVCKYPDYLQ   239
HPV58-L1   NNA-AATDCPPLELFNSIIEDGDMVDTGFGCMDFGTLQANKSDVPIDICNSTCKYPDYLK   236
HPV33-L1   NNA-PANDCPPLELINTIIEDGDMVDTGFGCMDFNTLQANKSDVPIDICGSTCKYPDYLK   236
HPV31-L1   NNAITPGDCPPLELKNSVIQDGDMVDIGFGAMDFTALQDTKSNVPLDICNSICKYPDYLK   237
HPV16-L1   NVAVNPGDCPPLKLINIVIQDGDMVDTGFGAMDFTTLQANKSEVPLDICTSICKYPDYIK   236
HPV35-L1   ANQVKAGECPPLELLNTVLQDGDMVDTGFGAMDFTTLQANKSDVPLDICSSICKYPDYLK   236
HPV51-L1   NTPVPPGDCPPLELVSSVIQDGDMIDTGFGAMDFAALQATKSDVPLDISQSVCKYPDYLK   235
HPV56-L1   STQVTTGDCPPLALINTPIEDGDMIDTGFGAMDFKVLQESKAEVPLDIVQSTCKYPDYLK   235
HPV39-L1   PNNVSTGDCPPLELVNTPIEDGDMIDTGYGAMDFGALQETKSEVPLDICQSICKYPDYLQ   235
HPV59-L1   PTTVVQGDCPPLELINTPIEDGDMVDTGYGAMDFKLLQDNKSEVPLDICQSICKYPDYLQ   236
HPV18-L1   SRPLSQGDCPPLELKNIVLEDGDMVDTGYGAMDFSTLQDTKCEVPLDICQSICKYPDYLQ   236
HPV45-L1   PAQLQPGDCPPLELKNTIIEDGDMVDTGYGAMDFSTLQDTKCEVPLDICQSICKYPDYLQ   237

           α1       β-F                     FG-loop
HPV6-L1    MAADPYGDRLFFFLRKEQMFARHFFNRAGEVGEPVPDTLIIKGS--GNRTSVGSSIYVNT   290
HPV11-L1   MAADPYGDRLFFYLRNEQMFARHFFNRAGIVGEPVPDDLLVNGG--NNRSSVASSIYVHT   291
HPV52-L1   MASEPYGDSLFFFLRREQMFVRHFFNRAGTLGDPVPGDLYIQGSNSGNTATVQSSAFFPT   299
HPV58-L1   MASEPYGDSLFFFLRREQMFVRHFFNRAGKLGEQVPDDLYIKGS--GNTAVIQSSAFFPT   294
HPV33-L1   MTSEPYGDSLFFFLRREQMFVRHFFNRAGILGFAVPDDLYIKGS--GTAASTQSSAFFPT   294
HPV31-L1   MVAEPYGDILFFYLRREQMFVRHFFNRSGTVGESVPTDLYIKGS--GSTATLANSTYFPT   295
HPV16-L1   MVSEPYGDSLFFYLRREQMFVRHLFNRAGAVGENVPDDLYINGS--GSTANLASSNYPPI   294
HPV35-L1   MVSEPYGDMLFFYLRREQNFVNHLFNRAGTVGETVPADLYIKGI--T--GILPSTSYFPT   292
HPV51-L1   MSADIYGNSMFFHLRREQIFARHYYNKLVGVGEDIPNDYYIKGSG-NGRDPTESYTYSAT   294
HPV56-L1   MSADAYGDSMWFYLRREQLFARHYFNRAGKVGETIPAELYLKGS--NGREFPPSSVYVAT   293
HPV39-L1   MSADVYGDSMFFCLRREQLFARHFWNRGGMWGDAIPAQLYIKGT--DTRANPGSSVYCPS   293
HPV59-L1   MSADAYGDSMFFCLRREQVFARHFWNRSGIMGDQLPESLYINGT--DIRANPGSYLYSPS   294
HPV18-L1   MSADPYGDSMFFCLRREQLFARHFWNRAGTMGDTVPQSLYIKGT--GMRASPGSCVVSPS   294
HPV45-L1   MSADPYGDSMFFCLRREQLFARHFWNRAGVMCDTVPTDLYIKGTSANMRETPGSCVYSPS   297

                G1         G2                   β-H1      β-H2   HI-
HPV6-L1    PSGSLVSSEAQLFNKPYWLQKAQGHNNGICWGNQLFVTVVDTTRSTNMTLCASVT--TSS   348
HPV11-L1   PSGSLVSSEAQLFNKPYWLGKAQGHNNGICWGNHLFVTVVDTTRSTNMTLCASVS--KSA   349
HPV52-L1   PSGSMVTSESQLFNRPYWLQRAQGHNNGICWGNQLFVTVVDTTRSTNMTLCAEVK--KES   357
HPV58-L1   MASEPYGDSLFFFLRREQMFVRHFFNRAGKLGEQVPDDLYIKGSSTNMTLCTEVT--KEG   352
HPV33-L1   PSGSMVTSESQLFNKPYWLGRAQGHNNGICWGNQVFVTVVDTTRSTNMTLCTQVT--SDS   352
HPV31-L1   PSGSMVTSDAQIFNKPYWMQRAQGHNNGICWGNQLFVTVVDTTRSTNMSVCAAIAN-SDT   354
HPV16-L1   PSGSMVTSDAQIFNKPYWLGRAQGHNNGICWGNQLFVTVVDTTRSTNMSLCAAIST-SET   353
HPV35-L1   PSGSMVTSDAQTFNKPYWLQRAQGHNNGICWSNQLFVTVVDTTRSTNMSVCSAVSS-SOS   351
HPV51-L1   PSGSMITSDSQIFNKPYWLHRAQGHNNGICWNNGLFITCVDTTRSTNLTISTATAA-VSP   353
HPV56-L1   PSGSMITSEAQLFNKPYWLQRAQGHNNGICWGNQLFVTVVDTTRSTNMTISTATE--QLS   351
HPV39-L1   PSGSMVTSDSQLFNKPYWLHKAQGHNNGICWHNQLFLTVVDTTRSTNFTLSTSTESSLPS   353
HPV59-L1   PSGSVVTSDSQLFNKPYWLHKAQGLNNGICWHNQLFLTVVDTTRSTNLSVCASTTSSTPN   354
HPV18-L1   PSGSIVTSDSQLFNKPYWLHKAQGHNNGVCWHNQLFVTVVDTTRSTNLTICASTQSPVPG   354
HPV45-L1   PSGSTTTSDSQLFNKPYWLHKAQGHNNGTCWHNQLFVTVVDTTRSTNLTLCASTQNPVPN   357
```

-continued

```
                loop        β-I                    α2        α3     ▼     _
HPV6-L1    TYTNSDYKEYMRHVEEYDLQFIFQLCSITLSAEVMAYIHTMNPSVLEDWNFGLSPPPNGT   408
HPV11-L1   TYTNSDYKEYMRHVEEFDLGFIFQLCSITLSAEVMAYIHTMNPSVLEDWNFGLSPPPNGT   409
HPV52-L1   TYKNENFKEYLRHGEEFDLQFIFQLCKITLTADVMTYIHKMDATILEDWQFGLTPPPSAS   417
HPV58-L1   TYKNDNFKEYVRHVEEYDLQFVFQLCKITLTAEIMTYIHTMDSNTLEDWQFGLTPPPSAS   412
HPV33-L1   TYKNENFKEYIRHVEEYDLGFVFQLCKVTLTAEVMTYIHAMNPDTLEDWQFGLTPPPSAS   412
HPV31-L1   TFKSSNFKEYLRHGEEFDLQFIFQLCKITLSADIMTYIHSMNPAILEDWNFGLTTPPSGS   414
HPV16-L1   TYKNTNFKEYLRHGEEYDLQFIFQLCKITLTADVMTYIHSMNSTTLEDWNFGLQPPPGGT   413
HPV35-L1   TYKNDNFKEYLRHGEEYDLQFIFQLCKITLTADVMTYIHSMNPSILEDWNFGLTPPPSGT   411
HPV51-L1   TFTPSNFKQYIRHGEEYELQFIFQLCKITLTTEVMAYLHTMDPTILEQWNFGLTLPPSAS   413
HPV56-L1   KYDARKINQYLRHVEEYELQFVFQLCKITLSAEVMAYLHNMNANLLEDWNTGLSPPVATS   411
HPV39-L1   TYDPSKFKEYTRHVEEYDLQFIFQLCIVTLTTDVMSYIHTMNSSILDNWNFAVAPPPSAS   413
HPV59-L1   VYTPTSFKEYARHVEEFDLQFIFQLCKITLTTEVMSYIHNMNTTILEDWNFGVTPPPTAS   414
HPV18-L1   QYDATKFKQYSRHVEEYDLGFLFQLCTITLTADVMSYIHSMNSSILEDWNFGVPPPPTTS   414
HPV45-L1   TYDPTKFNHYSRHVEEYDLQFIFQLCTITLTAEVMSYIHSMNSSILENWNFGVPPPPTTS   417

                 α4              ▼         β-J            α5
HPV6-L1    LEDTYRYVQSQAITCQKPTPEKEKPDPYKNLSFWEVNLKEKFSSELDQYPLGRKFLLQSG   468
HPV11-L1   LEDTYRYYQSQAITCQKPTPEKEKQDPYKDMSFWEVNLKEKFSSELDQFPLGRKFLLQSG   469
HPV52-L1   LEDTYRFVTSTAITCQKNTPPKGKEDPLKDYMFWEVDLKEKFSADLDQFPLGRKFLLQAG   477
HPV58-L1   LQDTYRFVTSQAITCQKTAPPKEKEDPLNKYTFWEVNLKEKFSADLDQFPLGRKFLLQSG   472
HPV33-L1   LQDTYRFVTSQAITCQKTVPPKEKEDPLGKYTPWEVDLKEKFSADLDQFPLGRKFLLQAG   472
HPV31-L1   LEDTYRFVTSQAITCQKSAPQKPKEDPFKDYVFWEVNLKEKFSADLDQFPLGRKFLLQAG   474
HPV16-L1   LEDTYRFVTSQAIACQKHTPPAPKEDPLKKYTFWEVNLKEKFSADLDQFPLGRKFLLQAG   473
HPV35-L1   LEDTYRYVTSQAVTCQKPSAPKPKDDPLKNYTFWEVDLKEKFSADLDQFPLGRKFLLQAG   471
HPV51-L1   LEDAYRFVRNAATSCQKDTPPQAKPDPLAKYKFWDYDLKEKFSLDLDQFALGRKFLLQVG   473
HPV56-L1   LEDKYRYVRSTAITCQREQPPTEKQDPLAKYKFWDVNLQDSFSTDLDQFPLGRKFLMQLG   471
HPV39-L1   LVDTYRVLQSAAITCQKDAPAPEKKDPYDGLKFWNVDLREKFSLELDQFPLGRKFLLQAR   473
HPV59-L1   LVDTTRFVQSAAVTCQKDTAPPVKQDPYDKLKFWPVDLKERFSADLDQFPLGRKFLLQLG   474
HPV18-L1   LVDTYRFYQSVAITCQRDAAPAENKDPVDKLKFWNVDLKENFSLDLDQYPLGRKFLVQAG   474
HPV45-L1   LVDTYRFVQSVAVTCQKDTTPPEKQDPYDKLKFWTVDLKEKFSSDLDQVPLGRKFLVQAG   477

            ▼                         ▼
HPV6-L1    YRGRSSIRTGVKRPAVSKASAAPKRKRAKTKR--      500
HPV11-L1   YRGRTSARTGIKRPAVSKPSTAPKRKRTKIKK--      501
HPV52-L1   LQARPKLKRPASSAPRIST----KKK-KVKR---      503
HPV58-L1   LKAKPRLNRSAPTTRAP-ST---KRK-KVKK---      498
HPV33-L1   LKAKPKLKRAAPTSTRTSSA---KRK-KVKK---      499
HPV31-L1   YRARPKFKAGKRSAPSASTTTPAKRKKTKK----      504
HPV16-L1   LKAKPKFTLGKRKATPTTSSTSTTAKRKKRKL--      505
HPV35-L1   LKARPNFRLGKRAAPASTSKKSSTKRRKVKS---      502
HPV51-L1   VQRKPRPGLKRPASSASSSSSSSAKRKRVKK---      504
HPV56-L1   TRSKPAVATSKKRSAPTSTS-TPAKRKRR-----      499
HPV39-L1   VRRRPTIGPRKRPAASTSSSSATKHKRKRVSK--      505
HPV59-L1   ARPKPTIGPRKRAAPAPTSTPSPKRVNRRKSSRK      508
HPV18-L1   LRRKPTIGPRKRSAPSATTSSKPAKRVRVRARK-      507
HPV45-L1   LRRRPTIGPRKRPAASTSTASRPAKKVRIRSKK-      510
```

In addition to the methods used by the inventors for sequence alignments, protein secondary structure prediction software that can be used for prediction includes, but is not limited to:

1. JPred: http://www.compbio.dundee.ac.uk/jpred/index.html
2. ProtPredicct: http://predictprotein.org
3. PsiPred: http://bioinf.cs.ucl.ac.uk/psipred
4. SCRATCH-1D: http://download.igb.uci.edu
5. Nnpredict: http://www.cmpharm.ucsf.edu/~nomi/nnpredict
6. Predictprotein: http://www.embl-heidelberg.de/predictprotein/SOPMA http://www.ibcp.fr/predict.html
7. SSPRED: http://www.embl-heidelberg.de/sspred/ssprd_info.html.

In one embodiment of the present invention, the inventors determine the length of the N-terminal fragment derived from the L1 protein of the first HPV type in the following manner: the natural sequence of the L1 protein is truncated within its α5 region and nearby regions thereof, with the sequence from its N-terminus to the newly generated C-terminus within the α5 region retained. Such a truncated sequence ensures that it has the immunogenicity of the first type and is capable of forming VLP.

The N-terminal fragment of the HPV L1 protein derived from the first type can be further modified as long as it retains the immunogenicity of the first type and is capable of forming VLP.

The length of the C-terminal fragment of the HPV L1 protein derived from the second type is determined in the following manner: The natural sequence of the L1 protein is truncated within its α5 region and nearby regions thereof, then the sequence from the newly generated N-terminus within its α5 region to the C-terminus is retained. Such a truncated sequence does not have the major neutralizing antigenic epitope so that does not interfere with the immunogenicity of the resulting chimeric protein.

The C-terminal fragment of the HPV L1 protein derived from the second type can be further mutated, deleted and/or added, preferably retaining at least one of its nuclear localization sequences. Yang et al. predicted the nuclear localization sequences of 107 HPV subtypes (Yang et al. Predicting the nuclear localization signals of 107 types of HPV L1 proteins by bioinformatic analysis. Geno. Prot. Bioinfo. Vol. 4 No. 1 2006, incorporated herein by reference in its entirety). The nuclear localization sequences of each type of HPV L1 protein can be conveniently determined by sequence analysis software commonly used in the field.

The above-described connection of the N-terminal fragment to the C-terminal fragment occurs at the newly generated C-terminus of the former and at the newly generated N-terminus of the latter. This can be a direct connection or a connection via a linker. The site where the connection occurs is defined as the origin coordinate, the N-terminal side of the origin is regarded as minus while the C-terminal side as plus.

The following shows the sequence of amino acids 453-469 of the HPV6 L1 protein and the corresponding sequences of L1 proteins of other HPV types. These sequences overlap with their α5 region respectively. It can be seen these sequences are highly similar. The numbers in brackets indicate the positions of the last amino acid residue of the listed sequences, where for HPV Type 45, an additional 26 amino acids are present at the N-terminus of the L1 protein of some HPV Type 45 strains, while at the N-terminus of the L1 protein of other HPV Type 45 strains, the said additional 26 amino acids are not present, therefore the number is indicated as (478)+26.

HPV6 ELDQYPLGRKFLLQSGY (469) (SEQ ID NO: 190)

HPV11 ELDQFPLGRKFLLQSGY (470) (SEQ ID NO: 191)

HPV16 DLDQFPLGRKFLLQAGL (474) (SEQ ID NO: 1912

HPV18 DLDQYPLGRKFLVQAGL (475) (SEQ ID NO: 193)

HPV31 DLDQFPLGRKFLLQAGY (475) (SEQ ID NO: 194)

HPV35 DLDQFPLGRKFLLQAGL (472) (SEQ ID NO: 195)

HPV39 ELDQFPLGRKFLLQARV (474) (SEQ ID NO: 196)

HPV45 DLDQYPLGRKFLVQAGL (478)+26 (SEQ ID NO: 197)

HPV51 DLDQFALGRKFLLQVGV (474) (SEQ ID NO: 198)

HPV52 DLDQFPLGRKFLLQAGL (478) (SEQ ID NO: 199)

HPV56 DLDQFPLGRKFLMQLGTRS (474) (SEQ ID NO: 200)

HPV58 DLDQFPLGRKFLLQSGL (473) (SEQ ID NO: 201)

HPV33 DLDQFPLGRKFLLQAGL (473)KAKPKLKRAAPTSTRTSSAKRKKVKK (SEQ ID NO: 202) wherein KR at positions 480-481 and KRKK (SEQ ID NO: 203) at positions 493-496 are nuclear localization sequences.

HPV59 DLDQFPLGRKFLLQLGA (475)RPKPTIGPRKRAAPAPTSTPSPKRVKRRK SSRK (SEQ ID NO: 204), wherein RKR at positions 484-486 and KRVKRRK (SEQ ID NO: 205) at positions 498-504 are nuclear localization sequences.

In one embodiment of the present invention, the inventors have completed C-terminus substitutions of L1 proteins between different HPV types by taking advantage of sequence similarity of the α5 region and nearby regions between the HPV types.

In the most preferred embodiment of the present invention, the inventors have noted that L1 protein of each HPV type has a tetrapeptide RKFL (SEQ ID NO: 163) or, more advantageously, a hexapeptide LGRKFL (SEQ ID NO: 164), at a similar position. The inventors have skillfully exploited this highly conserved sequence to locate the chimeric protein connection point at any amino acid position within this oligopeptide. On one hand, the sequence starting from the N-terminus of the chimeric protein to RKFL (SEQ ID NO: 163) or LGRKFL (SEQ ID NO: 164) is identical to the sequence of the N-terminal fragment derived from the L1 protein of the first type, while on the other hand, the sequence starting from RKFL (SEQ ID NO: 163) or LGRKFL (SEQ ID NO: 164) to the C-terminus of the chimeric protein is identical to the sequence of the C-terminal fragment derived from the L1 protein of the second type.

The chimeric protein thus produced maintains a high degree of similarity to the natural HPV L1 protein, and it can be expected to perform well in production and even in medical or prophylactic procedures thereafter.

It will be understandable for those skilled in the art that there are different strains with different natural sequences of a given HPV type, chimeric proteins constructed using different strains also fall within the scope of the present invention.

It will be understandable for those skilled in the art that because of the high degree of similarity between L1 protein of different HPV types, if, during the construction of the chimeric proteins, the N-terminal fragment derived from the L1 protein of the first type is extended by more amino acid residues towards the C-terminus, or the C-terminal fragment derived from L1 protein of the second HPV virus type is extended by more amino acid residues towards the N-terminus, it is also possible to form chimeric proteins that are structurally identical to the present invention due to identical or similar amino acids at the corresponding sites. The chimeric proteins thus formed also fall within the scope of the present invention.

It will be understandable for those skilled in the art that on the basis of the chimeric proteins of the above described embodiments, variants of the chimeric proteins may be formed by mutations, deletions and/or additions of amino acid residues. These variants are likely to have the immunogenicity of the L1 protein of the first type, can form VLP, and have a good yield and solubility. The chimeric proteins such formed also fall within the scope of the present invention.

The Beneficial Effects of the Invention

The expression systems commonly used for producing virus-like particles are classified into eukaryotic expression systems and prokaryotic expression systems. The papilloma virus L proteins expressed by the eukaryotic expression systems can spontaneously assemble into viral-like particles, but have the disadvantage of low expression level thus are not suitable for mass production. The papilloma virus L protein expressed by the prokaryotic expression system requires in vitro processing to obtain virus-like particles because of often-destroyed natural conformation, and has low yield, being difficult to be used in industrialization.

The present invention modifies the C-terminus of the L protein of the papilloma virus (e.g., human papilloma virus), for example by replacing it with the C-terminal fragment of HPV Type 16 L1 protein, HPV Type 28 L1 protein, HPV Type 33 L1 protein, HPV Type 59 L1 protein or HPV Type 68 L1 protein, thus can be used in expression systems (e.g., host cells, e.g., insect cells) to improve the expression level and the solubility of the papilloma virus L protein in expression systems (for example, host cells, e.g., insect cells). This can be used for the mass production of vaccines such as HPV vaccines.

The inventors found that the HPV Type 16 L1 protein, the HPV Type 28 L1 protein, the HPV Type 33 L1 protein, the HPV Type 59 L1 protein and the HPV Type 68 L1 protein have increased expression level and increased solubility compared to L1 proteins of other HPV types, and that said increased protein expression level and increased solubility was found to be depend on the C-terminal sequence of said HPV L1 protein. Among 107 HPV Type L1 proteins, most of them have nuclear localization sequences at the C-termini, and the C-terminal sequences have some similarities.

For papilloma virus L proteins that are currently inexpressible, very low in expression level or insoluble after expression, replacement of their C-terminal fragments with C-terminal fragments of the HPV Type 16 L1 protein, HPV Type 28 L1 protein, HPV Type 33 L1 protein, HPV Type 59 L1 protein or HPV Type 68 L1 protein makes it possible for soluble expression and subsequent purification. This strategy can be used for the mass production of polyvalent vaccines (e.g., HPV vaccines), making it possible to provide more comprehensive protection against a wide range of papilloma virus infections, especially HPV.

There needs to increase the expression level and the solubility of the HPV L1 protein in insect cells for mass production purpose. In addition, the virus-like particles assembled by the HPV L protein lack good conformation in yeast cells due to failure to form correct disulphide bonds.

For the HPV L1 proteins that are poorly expressed and insoluble in insect cells, a significant increase in expression level and solubility can be resulted after the modification of its C-terminal fragment into the C-terminal fragment of the HPV Type 33 or 59 L1 protein, thus they could be used for mass production of HPV vaccines.

For HPV L1 proteins that are better expressed and better soluble in insect cells compared to L1 proteins of other HPV types, such as HPV Type 16 protein, HPV Type 28 L1 protein, HPV Type 68 L1 protein, etc., there are needs to further improve the expression level and the solubility in order to achieve mass production of vaccines. In the present invention, for example, after modifying the C-terminal fragment of the HPV Type 16 L1 protein to the C-terminal fragment of the HPV Type 33 L1 protein, the expression level and the solubility of the modified chimeric HPV Type 16 protein are improved, which is conducive to the mass production of HPV vaccines.

To sum up, the chimeric HPV L1 proteins showed much higher expression level and solubility in insect cells compared to the unmodified HPV L1 protein. It can be used for the mass production of HPV vaccines. In addition, the chimeric HPV L1 proteins can correctly form disulfide bonds thus be assembled into HPV virus-like particles with good conformations in insect cells. This can improve the immunogenicity of HPV virus-like particles and trigger better immune responses.

The multivalent vaccine of the present invention can be used to prevent diseases or infections related with a wide range of HPV, including those HPV types that are not currently preventable.

Definition

Unless otherwise stated, all technical and scientific terms used herein have the meanings normally understood by a person of ordinary skill in the art to which the invention belongs. For the convenience of understanding the present invention, the following terms are cited below for their ordinary meaning.

When used herein and in the attached claims, the singular forms "a/an", "another" and "said/the" include the plural designations of the objects unless the context clearly indicates otherwise. Unless otherwise expressly stated, the terms "include/comprise/have", "for example", etc. are intended to convey inclusion rather than limitation.

The term "immunogenicity" refers to the ability of a substance, for example a protein or a peptide, to trigger an immune response, i.e. the ability to trigger the production of antibodies, in particular the ability to trigger humoral- or cell-mediated response.

The term "antibody" refers to an immunoglobulin molecule that binds an antigen. Antibodies may be polyclonal mixtures or monoclonal. Antibodies may be intact immunoglobulins of natural origin or of recombinant origin or may be immunoreactive portions of intact immunoglobulins. Antibodies may be present in a variety of forms including, for example, Fv, Fab', F(ab')2 and as single chains.

The term "antigenicity" refers to the ability of a substance, for example a protein or a peptide, to trigger the production of antibodies that bind specifically to it.

The term "epitope" includes any protein determinant cluster that specifically binds to an antibody or T-cell receptor. Epitope determinants typically consist of chemically active surface groups (e.g., amino acids or sugar side chains, or combinations thereof) of the molecule and typically have specific three-dimensional structural characteristics as well as specific charge characteristics.

The terms "subtype" or "type" are used interchangeably herein to refer to genetic variant of virus that allows it can be recognized by the immune system as distinct antigen from type to type. For example, HPV 16 is immunologically distinguishable from HPV 33.

The term "HPV L1 protein", as used herein, the term "HPV" and "human papilloma virus" refer to envelope-free double-stranded DNA viruses of the Papillomavirus family. Their genomes are circular and approximately 8 kilobase pairs in size. Most HPVs encode eight major proteins, six in the "early" region (E1-E2) and two in the "late" region (L1 (major capsid protein) and L2 (minor capsid protein)). Over 120 HPV types have been identified and they are labelled by numbers (e.g., HPV-16, HPV-18, etc.).

The term "HPV" or "HPV virus" refers to papilloma viruses of the Papillomaviridae Family, which are envelope-free DNA viruses with a double-stranded closed circular DNA genome of approximately 8 kb in size that is usually classified into three regions: (i) the early region (E), which contains six open reading frames E1, E2, E4-E7, encoding non-structural proteins related to viral replication, transcription and transformation, as well as open reading frames E3 and E8; (ii) the late region (L), which contains reading frames encoding the major capsid protein L1 and the minor capsid protein L2; and (iii) the long regulatory region (LCR), which does not encode any proteins but has the origin of replication and multiple transcription factor binding sites.

The terms "HPV L1 protein" and "HPV L2 protein" refer to proteins encoded by the late region (L) of the HPV gene and synthesized late in the HPV infection cycle. The L2 protein is the minor capsid protein. 72 L1 pentamers form the outer shell of the icosahedral HPV particles, which encloses the closed circular double-stranded DNA minichromosome.

The term "virus-like particle" refers to a hollow particle containing one or plurality of structural proteins of a virus, without viral nucleic acids.

"HPV pseudovirus" is an ideal model for in vitro neutralization of HPV, by taking advantages of the non-specific nucleic acid encapsulation property of HPV VLP, HPV pseudovirus is formed by wrapping free DNA or introducing an exogenous plasmid into a VLP composed of intracellularly-expressed HPV L1 and L2.

The "pseudovirus neutralization assay" is a method for evaluating the neutralizing activity of antibodies. After incubation of immunized animal serum with a certain amount of pseudovirus and then infection of the cells, the amount of the cells decreases when serum-neutralizing antibodies increases, showing a linear negative correlation in a certain range. The neutralizing activity of antibodies in serum can therefore be assessed by measuring changes in the amounts of cells.

The term "fragment thereof" or "variant thereof" refers to a deletion, insertion and/or substitution of nucleotides or amino acids sequence of the present invention. Preferably, the fragment or variant of the polypeptide provided by the present invention is capable of triggering the humoral- and/or the cellular-immune response in animals or humans.

The term "chimeric" means that sequences of polypeptides or nucleotides derived from different parental molecules are connected together by —CO—NH— or 3', 5'-phosphodiester bonds, respectively. Preferably, they are not spaced by additional linker sequences, but are directly adjacent to each other.

The term "truncation" refers to the removal of one or plurality of amino acids from the N- and/or C-terminus of a polypeptide or the deletion of one or plurality of amino acids from the interior of a polypeptide.

The term "nuclear localization sequence" refers to an amino acid sequence that directs the protein into the nucleus. In some HPV L1 proteins, two tight clusters of basic residues (i.e. nuclear localization sequences) (e.g., one is KRKR (SEQ ID NO: 206), KRKK (SEQ ID NO: 203), KRKRK (SEQ ID NO: 207), KRKKRK (SEQ ID NO: 208), KRVKRRK (SEQ ID NO: 205), etc. and the other is KR, RKR, KRK, etc.) have a spacer region of 10-14 amino acids between them. The above clusters of basic residues belong to nuclear localization sequences. In some other HPV L1 proteins, the nuclear localization sequence is a tight cluster of basic residues formed by arginines and/or lysines. Nuclear localization sequences include, but are not limited to, examples of clusters of basic residues as described above. See Jun Yang et al, Predicting the Nuclear Localization Signals of 107 Types of HPV L1 Proteins by Bioinformatic Analysis, Genomics, Proteomics & Bioinformatics Volume 4, Issue 1, 2006, Pages 34-41, the entire contents of which are incorporated herein by reference.

The term "functional variant" refers to a version of a polypeptide or a protein that retains the desired activities or characteristics after truncation, mutation, deletion and/or addition.

"Sequence identity" between two sequences of polypeptides or nucleic acids indicates the number of identical residues between said sequences as a percentage of the total number of residues, and is calculated based on the size of the smaller one of the compared molecules. When calculating the percentage identity, the sequences being compared are matched in such a way as to produce the maximum match between the sequences, with the vacant positions (if present) in the match being resolved by a specific algorithm. Preferred computer program methods for determining identity between two sequences include, but are not limited to, GCG program packages including GAP, BLASTP, BLASTN and FASTA (Altschul et al., 1990, J. Mol. Biol. 215: 403-410). The above programs are publicly available from the National Center of Biotechnology Information (NCBI) and other sources. The well-known Smith Waterman Algorithm can also be used to determine the identity.

Non-critical amino acids can be conservatively substituted without affecting the normal function of the protein. Conservative substitution means replacing amino acids with chemically or functionally similar amino acids. Tables for conservative substitutions that provide similar amino acids are well known in the art. By way of example, in some embodiments, the groups of amino acids provided in Tables 1-3 are considered to be conservative substitutions for each other.

TABLE 1

| In some embodiments, the selected groups of amino acids that are considered to be conservative substitutions for each other | |
|---|---|
| Acid residues | D and E |
| Basic residues | K, R and H |
| Hydrophilic uncharged residues | S, T, N and Q |
| Aliphatic uncharged residues | G, A, V, L and I |
| Non-polar uncharged residues | C, M and P |
| Aromatic residues | F, Y and W |

TABLE 2

| In some embodiments, other selected groups of amino acids considered to be conservative substitutions for each other | |
|---|---|
| Group 1 | A, S and T |
| Group 2 | D and E |
| Group 3 | N and Q |
| Group 4 | R and K |
| Group 5 | I, L and M |
| Group 6 | F, Y and W |

TABLE 3

| In some embodiments, other selected groups of amino acids considered to be conservative substitutions for each other | |
|---|---|
| Group A | A and G |
| Group B | D and E |
| Group C | N and Q |
| Group D | R, K and H |
| Group E | I, L, M and V |
| Group F | F, Y and W |
| Group G | S and T |
| Group H | C and M |

The term "amino acids" refers to the twenty common naturally occurring amino acids. Naturally occurring amino acids include alanine (Ala; A), arginine (Arg; R), asparagine (Asn; N), aspartic acid (Asp; D), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y) and valine (Val; V).

As used herein, a "physiologically acceptable carrier" is non-toxic to cells or mammals at the dose and concentration used. Usually it is a pH buffered aqueous solution, non-limiting examples of which include buffers; antioxidants; oligopeptides; proteins; hydrophilic polymers; amino acids; monosaccharides, disaccharides and other carbohydrates; chelating agents; sugar alcohols; salt-forming counterions such as sodium; and/or nonionic surface active agents.

The term "adjuvant" refers to a compound or mixture that enhances immune responses. In particular, a vaccine may comprise an adjuvant. Adjuvants for use in the present invention may include, but are not limited to, one or plurality of the following: mineral-containing adjuvant compositions, oil-emulsion adjuvants, saponin adjuvant formulations, derivatives of bacteria or microbes.

The term "vector" refers to a nucleic acid molecule capable of proliferating another nucleic acid connected to it.

The term includes vectors as self-replicating nucleic acid structures and as vectors integrated into the genome of host cells, into which the vector has been introduced. Certain vectors are capable of directing the expression of nucleic acids to which such vectors are operatively connected.

The term "host cell" refers to a cell into which an exogenous nucleic acid has been introduced, as well as to the progeny of such a cell. Host cells include "transformants" (or "transformed cells"), "transfectants" (or "transfected cells") or "infectants" (or "infected cells"), each of which includes primary transformed, transfected or infected cells and the progeny derived from them. Such progeny may not be identical to the parental cells in terms of nucleic acid content and may contain mutations.

The administration amount is preferably a "prophylactically effective amount" (herein the prophylaxis may be considered as treatment and the two may be used interchangeably), which is sufficient to show benefit to the individual.

EXAMPLES

Example 1 Construction of Chimeric Genes

Example 1.1: Construction of a Chimeric Gene with the C-Terminus of HPV6 L1 Substituted with the C-Terminus of HPV33 L1

1.1.1 Construction of pFB-HPV6 L1 as the Template

The HPV6 L1 gene with the KpnI and XbaI cleavage sites at both ends of the synthesized sequences was synthesized by Thermo Fisher [formerly Invitrogen (Shanghai) Trading Co.], its sequence is shown in SEQ ID NO: 5. The plasmid pcDNA3-HPV6-L1 comprising the nucleotide sequence encoding amino acid 1-500 of HPV6 L1 was obtained by ligating the synthesized gene fragment with pcDNA3 vector (distributor: Thermo Fisher) at KpnI and XbaI cleavage sites.

The obtained pcDNA3-HPV6-L1 plasmid was subjected to double enzyme digestion with KpnI and XbaI to obtain a gene fragment of HPV6 L1 (1-500). The fragment was then ligated with the KpnI/XbaI double digested pFastBac™1 vector (distributor: Thermo Fisher) to obtain a rod vector containing the HPV6 L1 (1-500) gene fragment, named as pFB-HPV6 L1.

1.1.2 Construction of pFB-HPV33 L1 as the Template

The HPV33 L1 gene with the KpnI and XbaI cleavage sites at both ends of the synthesized sequences was synthesized by Thermo Fisher [formerly Invitrogen (Shanghai) Trading Co.), its sequence is shown as SEQ ID NO: 6. The plasmid pcDNA3-HPV33-L1 comprising the nucleotide sequence encoding amino acids 1-499 of HPV33 L1 was obtained by ligating the synthesized gene fragment with pcDNA3 vector (distributor: Thermo Fisher) at Kpn I and XbaI cleavage sites.

The pcDNA3-HPV33-L1 plasmid was subjected to double enzyme digestion with KpnI and XbaI to obtain a fragment of the HPV33 L1 (1-499) gene. The fragment was then ligated to the KpnI and XbaI double digested pFastBac™1 vector (distributor: Thermo Fisher) to obtain a rod vector containing the HPV33 L1 (1-499) gene fragment, named as pFB-HPV33 L1.

1.1.3 Construction of pFB-HPV6 L1: 33C

Chimeric gene with HPV6 L1 C-terminus substituted with HPV33 L1 C-terminus: the constructed recombinant plasmid pFB-HPV6 L1 was used as the gene template to amplify a 1426 bp gene fragment using primers F1 and R1, the primer sequence F1 is shown in SEQ ID No: 7 and R1 is shown in SEQ ID No: 8.

This gene fragment contains a fragment encoding amino acids 1-469 of HPV6 L1, 10 bases overlapping with the gene fragment encoding amino acids 474-499 of HPV33 L1, and a fragment of the KpnI digest site (GGTAC^C), the amplified sequence is shown in SEQ ID No: 9.

PCR amplification parameters: pre-denaturation at 94° C. for 5 min; denaturation at 98° C. for 10 s, annealing at 69° C. for 15 s, 1 kb/1 min at 72° C., for 30 cycles; extension at 72° C. for 5 min; end at 16° C.

The recombinant plasmid pFB-HPV33 L1 was used as the gene template to amplify a gene fragment of 101 bp in length using primers F2 and R2, the primer sequence of F2 is shown in SEQ ID No: 10 and the primer sequence of R2 is shown in SEQ ID No: 11.

This gene fragment contains a gene fragment encoding 26 C-terminal amino acids (474-499) of HPV33 L1, a 10 bp base overlapping with the gene fragment encoding the C-terminus of amino acids 1-469 of HPV6 L1 and the XbaI (T^CTAGA) digest site, the amplified sequence is shown in SEQ ID No: 12.

PCR amplification parameters: pre-denaturation at 94° C. for 5 min; denaturation at 98° C. for 10 s, annealing at 69° C. for 15 s, 1 kb/1 min at 72° C., for 30 cycles; extension at 72° C. for 5 min; end at 16° C.

PCR Ligating Sequences

The ligating primers were F1 and R2, and the fragments amplified using the above primers (amplified fragments of F1 and R1, amplified fragments of F2 and R2) were used as templates.

PCR ligating parameters: pre-denaturation at 94° C. for 5 min; denaturation at 98° C. for 10 s, annealing at 52° C. for 15 s, 72° C. for 1 kb/1 min, for 5 cycles; denaturation at 98° C. for 10 s, annealing at 68° C. for 15 s, 72° C. for 1 kb/1 min, for 25 cycles; extension at 72° C. for 5 min; end at 16° C.

The final result was SEQ ID NO: 4, a nucleotide sequence encoding amino acids 1-469 of HPV6 L1 and 26 C-terminal amino acids of HPV33 L1(aa 474-499), with KpnI and XbaI cleavage sites at both ends (hereafter referred to as the ligating sequence).

The recombinant plasmid pFB-HPV6 L1: 33C was obtained by double digesting the pFastBac™1 vector and the ligating sequence fragment with KpnI+XbaI enzymes and cloning the ligating sequence into the pFastBac™1 vector to obtain pFB-HPV6 L1: 33C, which is a chimeric gene with the C-terminus of HPV6 L1 substituted by the C-terminus of HPV33 L1.

Example 1.2 Construction of Chimeric Gene with the C-Terminus of HPV11 L1 Substituted by the C-Terminus of HPV33 L1

The experimental methods and procedures were the same as in Example 1.1, see Appendix 2 for relevant sequences.

Example 1.3 Construction of a Chimeric Gene with the C-Terminus of HPV16 L1 Substituted by the C-Terminus of HPV33 L1

The experimental method and procedure were the same as in Example 1.1, see Appendix 3 for relevant sequences.

Example 1.4 Construction of a Chimeric Gene with the C-Terminus of HPV18 L1 Substituted by the C-Terminus of HPV33 L1

The experimental method and procedure were the same as in Example 1.1, see Appendix 4 for relevant sequences.

Example 1.5 Construction of a Chimeric Gene with the C-Terminus of HPV31 L1 Substituted by the C-Terminus of HPV33 L1

The experimental method and procedure were the same as in Example 1.1, see Appendix 5 for relevant sequences.

Example 1.6 Construction of HPV33 L1 Gene 1.6.1 Preparation of PFB-HPV33L1 Gene

The HPV33L1 gene with the KpnI and XbaI cleavage sites at both ends of the synthesized sequences was synthesized by Thermo Fisher [formerly Invitrogen (Shanghai) Trading Co.], its sequence is shown in SEQ ID No: 68. The plasmid pcDNA3-HPV33-L1 comprising the nucleotide sequence encoding amino acid 1-499 of HPV33 L1 was obtained by ligating the synthesized gene fragment with pcDNA3 vector (distributor: Thermo Fisher) at KpnI and XbaI cleavage sites.

The obtained pcDNA3-HPV33-L1 plasmid was subjected to double enzyme digestion with KpnI and XbaI to obtain a gene fragment of HPV33 L1 (1-499). The fragment was then ligated with the KpnI/XbaI double digested pFastBac™1 vector (distributor: Thermo Fisher) to obtain a rod vector containing the HPV33 L1 (1-499) gene fragment, named as pFB-HPV33 L1.

Example 1.7 Construction of a Chimeric Gene with the C-Terminus of HPV35 L1 Substituted by the C-Terminus of HPV33 L1

The experimental methods and procedures were the same as in Example 1.1, see Appendix 7 for relevant sequences.

Example 1.8 Construction of Chimeric Gene with the C-Terminus of HPV39 L1 Substituted by the C-Terminus of HPV59 L1

1.8.1 Construction of pFB-HPV39 L1 Used as the Template

The HPV39 L1 gene with the KpnI and XbaI cleavage sites at both ends of the synthesized sequences was synthesized by Thermo Fisher [formerly Invitrogen (Shanghai) Trading Co.), its sequence is shown as SEQ ID NO: 86. The plasmid pcDNA3-HPV39-L1 containing a nucleotide sequence encoding amino acids 1-505 of HPV39 L1 was obtained by ligating the synthesized gene fragment with pcDNA3 vector (distributor: Thermo Fisher) at KpnI and XbaI cleavage sites.

The pcDNA3-HPV39-L1 plasmid was subjected to double digestion with KpnI and XbaI to obtain a fragment of the HPV39 L1 (1-505) gene. The fragment was then ligated to the KpnI and XbaI double digested pFastBac™1 vector (distributor: Thermo Fisher) to obtain a rod vector containing the HPV39 L1 (1-505) gene fragment, named as pFB-HPV39 L1.

1.8.2 Construction of pFB-HPV59 L1 as the Template

The HPV59 L1 gene with the KpnI and XbaI cleavage sites at both ends of the synthesized sequences was synthesized by Thermo Fisher [formerly Invitrogen (Shanghai) Trading Co.), its sequence is shown as SEQ ID NO: 87. The plasmid pcDNA3-HPV59-L1 containing a nucleotide sequence encoding amino acids 1-508 of HPV59 L1 was obtained by ligating the synthesized gene fragment with pcDNA3 vector (distributor: Thermo Fisher) at KpnI and XbaI cleavage sites.

The pcDNA3-HPV59-L1 plasmid was subjected to double digestion with KpnI and XbaI to obtain a fragment of the HPV59 L1 (1-508) gene. The fragment was then ligated to the KpnI and XbaI double digested pFastBac™1 vector (distributor: Thermo Fisher) to obtain a rod vector containing the HPV59 L1 (1-508) gene fragment, named as pFB-HPV59 L1.

1.8.3 Construction of pFB-HPV39 L1: 59C

Chimeric gene with HPV39 L1 C-terminus substituted with HPV59 L1 C-terminus: The constructed recombinant plasmid pFB-HPV39 L1 was used as the gene template to amplify a 1428 bp gene fragment using primers F1 and R1, the primer sequence F1 is shown in SEQ ID No: 88 and the primer sequence R1 is shown in SEQ ID No: 89.

This fragment contains a fragment encoding amino acids 1-469 of HPV39 L1, a 12-base overlapping with a fragment encoding amino acids 471-508 of HPV59 L1 and a segment of the KpnI digest site (GGTACAC), the amplified sequence is shown in SEQ ID No: 90.

PCR amplification parameters: pre-denaturation at 94° C. for 5 min; denaturation at 98° C. for 10 s, annealing at 69° C. for 15 s, 1 kb/1 min at 72° C., for 30 cycles; extension at 72° C. for 5 min; end at 16° C.

The recombinant plasmid pFB-HPV59 L1 was used as the gene template to amplify a gene fragment of 139 bp in length using primers F2 and R2. The primer sequence F2 is shown in SEQ ID No: 91 and R2 is shown in SEQ ID No: 92.

This gene fragment contains a gene fragment encoding 38 C-terminal amino acids of the HPV59 L1(aa471-508), a 12 bp base overlapping with the gene fragment encoding amino acids 1-469 of HPV39 L1 and the XbaI (T^CTAGA) digest site, and the amplified sequence is shown in SEQ ID No: 93.

PCR amplification parameters: pre-denaturation at 94° C. for 5 min; denaturation at 98° C. for 10 s, annealing at 69° C. for 15 s, 1 kb/1 min at 72° C. for 30 cycles; extension at 72° C. for 5 min; end at 16° C.

PCR Ligating Sequence

The ligating primers were F1 and R2, and the fragments amplified by using the above primers (F1 and R1 amplified fragments, F2 and R2 amplified fragments) were used as templates.

PCR ligating parameters: pre-denaturation at 94° C. for 5 min; denaturation at 98° C. for 10 s, annealing at 52° C. for 15 s, 72° C. for 1 kb/1 min, for 5 cycles; denaturation at 98°

C. for 10 s, annealing at 68° C. for 15 s, 72° C. for 1 kb/1 min, for 25 cycles; extension at 72° C. for 5 min; end at 16° C.

The final result was SEQ ID NO: 85, a nucleotide sequence encoding amino acids 1-469 of HPV39 L1 and 38 C-terminal amino acids of HPV59 L1(471-508) with KpnI and XbaI enzyme cleavage sites at both ends (hereafter referred to as the ligating sequence).

The recombinant plasmid pFB-HPV39 L1: 59C was obtained by double digesting the pFastBac™1 vector and the ligating sequence fragment with KpnI+XbaI enzymes and the ligating sequence was cloned into the pFastBac™1 vector o obtain pFB-HPV39 L1: 59C, which is a chimeric gene with the C-terminus of HPV39 L1 substituted by the C-terminus of HPV59 L1.

Example 1.9 Construction of Chimeric Gene with the C-Terminus of HPV45 L1 Substituted by the C-Terminus of HPV33 L1

The experimental methods and procedures were the same as in Example 1.1, see Appendix 9 for relevant sequences.

Example 1.10 Construction of a Chimeric Gene with the C-Terminus of HPV51 L1 Substituted by the C-Terminus of HPV33 L1

The experimental methods and procedures were the same as in Example 1.1, see Appendix 10 for relevant sequences.

Example 1.11 Construction of a Chimeric Gene with the C-Terminus of HPV52 L1 Substituted by the C-Terminus of HPV33 L1

The experimental methods and procedures were the same as in Example 1.1, see Appendix 11 for relevant sequences.

Example 1.12 Construction of a Chimeric Gene with the C-Terminus of HPV56 L1 Substituted by the C-Terminus of HPV33 L1

The experimental methods and procedures were the same as in Example 1.1, see Appendix 12 for relevant sequences.

Example 1.13 Construction of a Chimeric Gene with the C-Terminus of HPV58 L1 Substituted by the C-Terminus of HPV33 L1

The experimental methods and procedures were the same as in Example 1.1, see Appendix 13 for relevant sequences.

Example 1.14 Construction of HPV59 L1 Gene

Example 1.14.1 Preparation of pFB-HPV59 L1 Gene

The HPV59 L1 gene with the KpnI and XbaI cleavage sites at both ends of the synthesized sequences was synthesized by Thermo Fisher [formerly Invitrogen (Shanghai) Trading Co.], its sequence is shown in SEQ ID No: 162. The plasmid pcDNA3-HPV59-L1 comprising the nucleotide sequence encoding amino acid 1-508 of HPV59 L1 was obtained by ligating the synthesized gene fragment with pcDNA3 vector (distributor: Thermo Fisher) at KpnI and XbaI cleavage sites.

The obtained pcDNA3-HPV59-L1 plasmid was subjected to double enzyme digestion with KpnI and XbaI to obtain a gene fragment of HPV59 L1 (1-508). The fragment was then ligated with the KpnI/XbaI double digested pFastBac™1 vector (distributor: Thermo Fisher) to obtain a rod vector containing the HPV59 L1 (1-508) gene fragment, named as pFB-HPV59 L1.

Example 2 Recombinant Baculovirus Packaging

Example 2.1: HPV6 L1: 33C Recombinant Baculovirus Packaging

The recombinant plasmid of pFB-HPV6 L1: 33C constructed in Example 1 was identified and sequenced to be correct, and was transformed into DH10Bac bacteria competent cells (Bac-to-Bac® kit, purchased from Thermo Fisher), incubated at 37° C. for proliferation, and incubated in a flat dish for streak culture. White colonies was selected, incubated overnight. The bacterial culture was collected and the recombinant baculovirus DNA was extracted using alkaline lysis method.

The recombinant baculovirus DNA was transfected into insect cells SF9 using a cationic transfection reagent (purchased from Sino Biological) to package the recombinant baculovirus virulent strains. The procedure was as follows:

a. SF9 cells at log phase were inoculated in dishes at a density of $0.6\times10^6$ cell/dish. The dish inoculated with SF9 cells were left at room temperature for 2 hrs. for the cell's adhering to the dish wall.
b. 20 μL of extracted plasmid Bacmid DNA was added to 200 μL Grace's Medium (no serum, no additives, purchased from Gibico) and mixed and inverted 5 times.
c. 25 μL of 0.2×TF1 (transfection reagent, purchased from Sino Biological) was added dropwise to 200 μL of Grace's Medium and mixed gently.
d. Mixed b and c. Incubated at room temperature for 15-45 min.
e. During the incubation of DNA with cellfectin (purchased from Sino Biologial), the cell supernatant was discarded and 0.8 mL of Grace Medium(serum additive free) was added into the dish.
f. The incubated mixture of DNA and transfection reagent of d was added to the dish dropwise.
g. Incubated at 27° C. for 2 hr.
h. Cell culture medium was discarded and 2.5 mL complete growth media/dish (SCD6 SF+10% FBS) (SCD6 SF was purchased from Sino Biological, FBS was purchased from Gibico) was added.
i. Culture was performed at 27° C. for 7 days and whether the viral infection occurred was observed.

Virus supernatant was collected after visible lesions were observed in the transfected cells, typically after 7-11 days of culturing. The viral supernatant, i.e., the P1 generation virus strain of HPV6 L1: 33C is collected aseptically with a pipette. SF9 cells, at a density of $2\times10^6$ cells/mL, were infected using P1 generation virus strain of HPV6 L1: 33C at a ratio of 1:50 (V/V), cultured at 27° C. for 3 days, and centrifuged at 1000 g±200 g for 10 min at room temperature. The collected virus supernatant was the P2 generation virus and could be used for infecting the host cells and production.

Example 2.2: Packaging of HPV11 L1: 33C Recombinant Baculovirus

The experimental methods and procedures were the same as in Example 2.1.

Example 2.3: Packaging of HPV 16L1: 33C Recombinant Baculovirus

The experimental methods and procedures are the same as those of Example 2.1.

Example 2.4: Packaging of HPV18 L1: 33C Recombinant Baculovirus

The experimental methods and procedures are the same as those of Example 2.1.

Example 2.5: Packaging of HPV31 L1: 33C Recombinant Baculovirus

The experimental methods and procedures are the same as those of Example 2.1.

Example 2.6: Packaging of HPV33 L1 Recombinant Baculovirus

The experimental methods and procedures are the same as those of Example 2.1.

Example 2.7: Packaging of HPV35 L1: 33C Recombinant Baculovirus

The experimental methods and procedures are the same as those of Example 2.1.

Example 2.8: Packaging of HPV39 L1: 59C Recombinant Baculovirus

The experimental methods and procedures are the same as those of Example 2.1.

Example 2.9: Packaging of HPV45 L1: 33C Recombinant Baculovirus

The experimental methods and procedures are the same as those of Example 2.1.

Example 2.10: Packaging of HPV51 L1: 33C Recombinant Baculovirus

The experimental methods and procedures are the same as those of Example 2.1.

Example 2.11: Packaging of HPV52 L1: 33C Recombinant Baculovirus

The experimental methods and procedures are the same as those of Example 2.1.

Example 2.12: Packaging of HPV56 L1: 33C Recombinant Baculovirus

The experimental methods and procedures are the same as those of Example 2.1.

Example 2.13: Packaging of HPV58 L1: 33C Recombinant Baculovirus

The experimental methods and procedures were the same as those of Example 2.1.

Example 2.14: Packaging of HPV59 L1 Recombinant Baculovirus

The experimental methods and procedures were the same as those of Example 2.1.

Example 3 Expression of Chimeric Proteins or Proteins

Example 3.1: Expression of HPV6 L1: 33C

High Five cells were infected with baculovirus containing the HPV6 L1: 33C recombinant gene obtained in Example 2 at a ratio of 1:200 (V/V), and the cell precipitate was collected by centrifugation at 1000 g±100 g at room temperature. The cells were broken up by sonication at low temperature for 3 min, centrifuged at >10,000 g for 10 min and the supernatant was collected for SDS-PAGE. Lane 1: Marker (The marker is a mixture of 7 purified proteins with molecular weights ranging from 14.4 kDa to 116 kDa, produced by Thermo Scientific); Lane 2: cell lysate; Lane 3: supernatant of the lysate collected by centrifugation.

The result is shown in FIG. 1A. The HPV6 L1: 33C L1 protein prepared by this method has a yield of >100 mg/L and a protein size of approximate 56 KD, which can be used for mass production.

Example 3.2: Expression and Production of HPV11 L1: 33C

The experimental methods and procedures were the same as in Example 3.1.

The result is shown in FIG. 1B. The HPV11 L1: 33C L1 protein prepared by this method has a yield of >100 mg/L and a protein size of approximate 56 KD, which can be used for mass production.

Example 3.3: Expression and Production of HPV 16L1: 33C

The experimental methods and procedures were the same as in Example 3.1.

The result is shown in FIG. 1C. The HPV 16L1: 33C L1 protein prepared by this method has a yield of >100 mg/L and a protein size of approximate 56 KD, which can be used for mass production.

Example 3.4: Expression and Production of HPV18 L1: 33C

The experimental methods and procedures were the same as in Example 3.1.

The result is shown in FIG. 1D. The HPV18 L1: 33C L1 protein prepared method has a yield of >100 mg/L and a protein size of approximate 56 KD, which can be used for mass production.

Example 3.5: Expression and Production of HPV31 L1: 33C

The experimental methods and procedures were the same as in Example 3.1.

The result is shown in FIG. 1E. The HPV31 L1: 33C L1 protein prepared by this method has a yield of >100 mg/L and a protein size of approximate 56 KD, which can be used for mass production.

Example 3.6: Expression and Production of HPV33 L1

The experimental methods and procedures were the same as in Example 3.1.

The result is shown in FIG. 1F. The HPV33 L1 protein prepared by this method has a yield of >100 mg/L and a protein size of approximate 56 KD, which can be used for mass production.

Example 3.7: Expression and Production of HPV35 L1: 33C

The experimental methods and procedures were the same as in Example 3.1. The result is shown in FIG. 1G. The HPV35 L1: 33C L1 protein prepared by this method has a yield of >100 mg/L and a protein size of approximate 56 KD, which can be used for mass production.

Example 3.8: Expression and Production of HPV39 L1: 59C

The experimental methods and procedures were the same as in Example 3.1. The result is shown in FIG. 1H. The HPV39 L1: 59C L1 protein prepared by this method has a yield of >100 mg/L and a protein size of approximate 56 KD, which can be used for mass production.

Example 3.9: Expression and Production of HPV45 L1: 33C

The experimental methods and procedures were the same as in Example 3.1. The result is shown in Figure 1I. The HPV45 L1: 33C L1 protein prepared by this method has a yield of >100 mg/L and a protein size of approximate 56 KD, which can be used for mass production.

Example 3.10: Expression and Production of HPV51 L1: 33C

The experimental methods and procedures were the same as in Example 3.1. The result is shown in FIG. 1J. The HPV51 L1: 33C L1 protein prepared by this method has a yield of >100 mg/L and a protein size of approximate 56 KD, which can be used for mass production.

Example 3.11: Expression and Production of HPV52 L1: 33C

The experimental methods and procedures were the same as in Example 3.1. The result is shown in FIG. 1K. The HPV52 L1: 33C L1 protein prepared by this method has a yield of >100 mg/L and a protein size of approximate 56 KD, which can be used for mass production.

Example 3.12: Expression and Production of HPV56 L1: 33C

The experimental methods and procedures were the same as in Example 3.1. The result is shown in FIG. 1L. The HPV56 L1: 33C L1 protein prepared by this method has a yield of >100 mg/L and a protein size of approximate 56 KD, which can be used for mass production.

Example 3.13: Expression and Production of HPV58 L1: 33C

The experimental methods and procedures were the same as in Example 3.1. The result is shown in FIG. 1M. The HPV58 L1: 33C L1 protein prepared by this method has a yield of >100 mg/L and a protein size of approximate 56 KD, which can be used for mass production.

Example 3.14: Expression and Production of HPV59 L1

The experimental methods and procedures were the same as in Example 3.1. The result is shown in FIG. 1N. The HPV59 L1 protein prepared by this method has a yield of >100 mg/L and a protein size of approximate 56 KD, which can be used for mass production.

Example 4 Preparation of Purified Virus-Like Particles

Example 4.1: Preparation of Purified HPV6 L1: 33C Virus-Like Particles

The HPV6 L1: 33C virus-like particles were purified by a two-step chromatography method, i.e. HS-MMA method, the supernatant collected in Example 3 was purified, and finally, high purity virus-like particles were obtained.

First step chromatography: Medium: POROS® 50 HS strong cation exchange media produced by Thermo Fisher was used.

Medium volume: 150 mL of media volume, 30 mL/min of linear flow rate. Chromatography conditions: equilibration buffer (pH 6.2, the salt concentration is 50 mM phosphate, 0.5 M NaCl); wash buffer (the salt concentration is 50 mM phosphate, 0.75 M NaCl, pH 6.2).

The chromatography column was first equilibrated with 5 CV of equilibration buffer and then the sample was loaded. After loading, the column was then eluted with 5 CV of equilibration buffer and wash buffer, respectively, to remove the protein impurities.

Elution conditions: a 50 mM phosphate buffer containing 50 mM arginine hydrochloride, pH 6.2, with an elution salt concentration being of 1.25 M NaCl, was used.

Second step chromatography.

Medium: MMA ion exchange media produced by Bestchrom (Shanghai) Biosciences Co., Ltd was used.

Medium volume: media volume is 150 mL, while linear flow rate is 30 mL/min.

Chromatography conditions: equilibration buffer: 50 mM PB, 1.25 M NaCl, pH 6.2. The chromatography column was first equilibrated with 4 CV equilibration buffer and then the sample was loaded. After loading, protein impurities were rinsed off with 5 CV equilibration buffer and then the target protein was eluted with elution buffer and collected.

Elution conditions: 100 mM NaAC, 150 mM NaCl, 0.01% Tween 80, pH 4.5.

Example 4.2: Preparation of Purified HPV11 L1: 33C Virus-Like Particles

The experimental methods and procedures were the same as in Example 4.1.

Example 4.3: Purification and Preparation of HPV 16L1: 33C Virus-Like Particles

The experimental methods and procedures were the same as in Example 4.1.

Example 4.4: Purification and Preparation of HPV18 L1: 33C Virus-Like Particles

The experimental methods and procedures were the same as in Example 4.1.

Example 4.5: Purification and Preparation of HPV31 L1: 33C Virus-Like Particles

The experimental methods and procedures were the same as in Example 4.1.

Example 4.6: Preparation of Purified HPV33 L1 Virus-Like Particles

The experimental methods and procedures were the same as in Example 4.1.

Example 4.7: Preparation of Purified HPV35 L1: 33C Virus-Like Particles

The experimental methods and procedures were the same as in Example 4.1.

Example 4.8: Preparation of Purified HPV39 L1: 59C Virus-Like Particles

The experimental methods and procedures were the same as in Example 4.1.

Example 4.9: Preparation of Purified HPV45 L1: 33C Virus-Like Particles

The experimental methods and procedures were the same as in Example 4.1.

Example 4.10: Preparation of Purified HPV51 L1: 33C Virus-Like Particles

The experimental methods and procedures were the same as in Example 4.1.

Example 4.11: Preparation of Purified HPV52 L1: 33C Virus-Like Particles

The experimental methods and procedures were the same as in Example 4.1.

Example 4.12: Preparation of Purified HPV56 L1: 33C Virus-Like Particles

The experimental methods and procedures were the same as in Example 4.1.

Example 4.13: Preparation of Purified HPV58 L1: 33C Virus-Like Particles

The experimental methods and procedures were the same as in Example 4.1.

Example 4.14: Preparation of Purified HPV59 L1 Virus-Like Particles

The experimental methods and procedures were the same as in Example 4.1.

Example 5 Morphological Observation of Virus-Like Particles

Example 5.1: Morphological Observation of HPV6 L1: 33C Virus-Like Particles

10 μL sample was taken for transmission electron microscopy. The sample was fixed onto a carbon coated copper grid for 2 min, the rest liquid was absorbed off with filter paper, and then stained twice with phosphotungstic acid (Beijing Electron Microscopy China Technology Co., Ltd., concentration 2%, pH 6.5) for 30 seconds each time, the rest staining solution was absorbed off with filter paper, left the sample for drying, then performed transmission electron microscopy observation. The transmission electron microscope (Brand: Hitachi, Model No.: H-7650) was 80 KV with a magnification of 80,000×.

The electron microscopy observation is shown in FIG. 2A. As can be seen in FIG. 2A, the C-terminal-modified HPV6 L1: 33C can form uniform-sized virus-like particles with an average diameter of approximate 60 nm.

Example 5.2: Morphological Observation of HPV11 L1: 33C Virus-Like Particles

The experimental methods and procedures were the same as in Example 5.1. The electron microscopy observation is shown in FIG. 2B. As can be seen in FIG. 2B, the C-terminal-modified HPV11 L1: 33C can form uniform-sized virus-like particles, with an average diameter of approximate 60 nm.

Example 5.3: Morphological Observation of HPV 16L1: 33C Virus-Like Particles

The experimental methods and procedures were the same as in Example 5.1. The electron microscopy observation is shown in FIG. 2C. As can be seen in FIG. 2C, the C-terminal-modified HPV 16L1: 33C can form uniform-sized virus-like particles with an average diameter of approximate 60 nm.

Example 5.4: Morphological Observation of HPV18 L1: 33C Virus-Like Particles

The experimental methods and procedures were the same as in Example 5.1. The electron microscopy observation is shown in FIG. 2D. As can be seen in FIG. 2D, the C-terminal-modified HPV18 L1: 33C can form uniform-sized virus-like particles with an average diameter of approximate 60 nm.

Example 5.5: Morphological Observation of HPV31 L1: 33C Virus-Like Particles

The experimental methods and procedures were the same as in Example 5.1. The electron microscopy observation is shown in FIG. 2E. As can be seen in FIG. 2E, the C-terminal-modified HPV31 L1: 33C can form uniform-sized virus-like particles with an average diameter of approximate 60 nm.

Example 5.6: Morphological Observation of HPV33 L1 Virus-Like Particles

The experimental methods and procedures were the same as in Example 5.1. The electron microscopy observation is shown in FIG. 2F. As can be seen in FIG. 2F, the C-terminally modified HPV33 L1 can form uniform-sized virus-like particles with an average diameter of approximate 60 nm.

Example 5.7: Morphological Observation of HPV35 L1: 33C Virus-Like Particles

The experimental methods and procedures were the same as in Example 5.1. The electron microscopy observation is shown in FIG. 2G. As can be seen in FIG. 2G, the C-terminally modified HPV35 L1: 33C can form uniform-sized virus-like particles with an average diameter of approximate 60 nm.

Example 5.8: Morphological Observation of HPV39 L1: 59C Virus-Like Particles

The experimental methods and procedures were the same as in Example 5.1. The electron microscopy observation is shown in FIG. 2H. As can be seen in FIG. 2H, the C-terminal-modified HPV39 L1: 59C can form uniform-sized virus-like particles with an average diameter of approximate 60 nm.

Example 5.9: Morphological Observation of HPV45 L1: 33C Virus-Like Particles

The experimental methods and procedures were the same as in Example 5.1. The electron microscopy observation is shown in FIG. 2I. As can be seen in FIG. 2I, the C-terminal-modified HPV45 L1: 33C can form uniform-sized virus-like particles with an average diameter of approximate 60 nm.

Example 5.10: Morphological Observation of HPV51 L1: 33C Virus-Like Particles

The experimental methods and procedures were the same as in Example 5.1. The electron microscopy observation is shown in FIG. 2J. As can be seen in FIG. 2J, the C-terminal-modified HPV51 L1: 33C can form uniform-sized virus-like particles with an average diameter of approximate 60 nm.

Example 5.11: Morphological Observation of HPV52 L1: 33C Virus-Like Particles

The experimental methods and procedures were the same as in Example 5.1. The electron microscopy observation is shown in FIG. 2K. As can be seen in FIG. 2K, the C-terminal-modified HPV52 L1: 33C can form uniform-sized virus-like particles with an average diameter of approximate 60 nm.

Example 5.12: Morphological Observation of HPV56 L1: 33C Virus-Like Particles

The experimental methods and procedures were the same as in Example 5.1. The electron microscopy observation is shown in FIG. 2L. As can be seen in FIG. 2L, the C-terminal-modified HPV56 L1: 33C can form uniform-sized virus-like particles with an average diameter of approximate 60 nm.

Example 5.13: Morphological Observation of HPV58 L1: 33C Virus-Like Particles

The experimental methods and procedures were the same as in Example 5.1. The electron microscopy observation is shown in FIG. 2M. As can be seen in FIG. 2M, the C-terminal-modified HPV58 L1: 33C can form uniform-sized virus-like particles with an average diameter of approximate 60 nm.

Example 5.14: Morphological Observation of HPV59 L1 Virus-Like Particles

The experimental methods and procedures were the same as in Example 5.1. The electron microscopy observation is shown in FIG. 2N. As can be seen in FIG. 2N, the C-terminal-modified HPV59 L1: 33C can form uniform-sized virus-like particles with an average diameter of approximate 60 nm.

Example 6 Immunogenicity Evaluation of Virus-Like Particles in Animals

Example 6.1: Immunogenicity Evaluation of HPV6 L1: 33C Virus-Like Particles in Animals 6.1.1 Modeling of pseudovirus-neutralizing cells. As HPV is difficult to be cultured in vitro and has a strong host specificity, it is difficult to be reproduced in organisms other than humans, thus there is a lack of suitable animal models. Therefore, there is a need to establish suitable and effective in vitro neutralization experimental models for the evaluation of vaccine immunoprotectivity.

HPV pseudovirus is an ideal model for HPV in vitro neutralization: Thanks to the HPV VLP's characteristic of non-specifically encapsulating nucleic acids, HPV pseudovirus can be formed from the VLP's, composed of HPV L1 and L2 expressed in cells, by encapsulating free DNA or introducing exogenous plasmid.

The immunogenicity of immunized animal serum samples was analyzed by pseudovirus neutralization assay. The animal immunized with HPV6 virus-like particles can produce neutralizing antibodies against HPV6, which can neutralize HPV6 pseudovirus. When the immunized animal serum is incubated with a certain amount of pseudovirus and then infects cells, the number of cells capable of expressing GFP fluorescence decreases when neutralization antibodies in the serum increases, showing a linear negative correlation in a certain range, so the neutralizing activity of antibodies in the serum can be evaluated by detecting the change in the number of cells expressing GFP.

Construction method of pseudovirus: The HPV6 pCMV3-3-HPV6 L1+L2 (L1 sequence was from Uniprot P69898, L2 sequence was from Uniprot Q84297) plasmid (purchased from Sino Biological) and the fluorescent plasmid (PSEU-GFP Spark, purchased from Sino Biological) were co-transfected into 293FT adherent cells (purchased from Thermo Fisher). The specific methods refer to the published literature (Pastrana D V, Buck C B, Pang Y S, Thompson C D, Castle P E, FitzGerald P C, Kjaer S K, Lowy D R, Schiller J T. Reactivity of human sera in a sensitive, high-throughput pseudovirus-based papilloma virus neutralization assay for HPV16 and HPV18. [J] Virology 2004,321:205-216.). The pseudovirus supernatant was collected and aliquoted, and stored in a −80° C. refrigerator for stock.

6.1.2 Immunoprotective Evaluation of HPV6 L1: 33C Virus-Like Particles in Animals Immunization procedures in mice: HPV6 L1: 33C virus-like particles were absorbed onto aluminum phosphate adjuvant, mixed, and used to immunize mice at a dose of 0.15

μg/200 μL per mouse, 10 mice in total. The mice were immunized with the diluted samples on Days 0, 7 and 21, with control mice immunized with blank serum. Blood was collected from the eyes of the mice on Day 28 and the sera were isolated for pseudovirus neutralization titers assay.

EC50 assay of mice: the murine serum was inactivated at 56° C. for 30 minutes, centrifuged at 6000 g, 5 mins, and the supernatant was collected for assaying. 4-8 hours prior to the assay, 293FT cells were inoculated at a density of 15,000 cells/well into 96-well plates and incubated at 37° C. in a $CO_2$ incubator with 5% $CO_2$. The post-immune murine serum and blank control serum were serial diluted with neutralizing media respectively, then mixed with the HPV6 pseudovirus prepared in 6.1 at a volume ratio of 1:1, incubated at 2-8° C. for 1 hrs., then 100 μL/well of the mixture were added to 293FT cells, which had been inoculated for 4-8 hrs in advance. Each sample was in replicate, and blank serum control group, pseudovirus positive control group and pseudovirus negative control group were used. The cells infected by pseudovirus were incubated at 37° C. in a $CO_2$ incubator with 5% $CO_2$ for 62-96 hrs, fluorescence scanning photographed and counted in an ELISPOT analyser (Model No.: S6 Universal-V Analyzer, Manufacturer: CTL). Based on the neutralization inhibition of each murine serum sample, the maximum dilution of the serum at 50% neutralization inhibition was calculated for each murine serum sample according to the Reed-Muench method, i.e. the half efficacy dilution EC50.

The results of the HPV6 serum pseudovirus neutralization titer assay are detailed in Table 4.

TABLE 4

| EC50 of Serum Neutralization Titer Assay in Mice (GMT ± SEM) | |
|---|---|
| HPV Type | $EC_{50}$ Value |
| Type 6 | 4948 ± 1831 |

Notes:
1. number of animals, N = 10.
2. GMT (Geometric Mean Titer): geometric mean titer.
3. SEM (Standard Error of Mean): standard error.

The above evaluation results show that the HPV6 L1: 33C virus-like particles prepared by the present invention have good immunogenicity and can produce neutralizing antibodies with high titers in animals, which can be used to prepare into a vaccine for preventing HPV infections.

Example 6.2: Evaluation of Immunogenicity of HPV11 L1: 33C Virus-Like Particles in Animals The experimental methods and procedures were the same as in Example 6.1. The L1 sequence was from Uniprot P04012 and the L2 sequence was from Uniprot P04013.

The results of HPV11 serum pseudovirus neutralization titer assay are detailed in Table 5.

TABLE 5

| EC50 of Serum Neutralization Titer Assay in Mice (GMT ± SEM) | |
|---|---|
| HPV Type | $EC_{50}$ Value |
| Type 11 | 15024 ± 8400 |

The above evaluation results show that the HPV11 L1: 33C virus-like particles prepared by the present invention have good immunogenicity, can produce high titers of neutralizing antibodies in animals, and can be used to prepare into a vaccine for the prevention of HPV infection.

Example 6.3: Evaluation of Immunogenicity of HPV 16L1: 33C Virus-Like Particles in Animals The experimental methods and procedures were the same as in Example 6.1. The L1 sequence was from Uniprot P03101 and the L2 sequence was from Uniprot P03107. The results of HPV16 serum pseudovirus neutralization titer assay are detailed in Table 6.

TABLE 6

| EC50 of Serum Neutralization Titer Assay in Mice (GMT ± SEM) | |
|---|---|
| HPV Type | $EC_{50}$ Value |
| Type 16 | 32449 ± 7224 |

The above evaluation results show that the HPV 16L1: 33C virus-like particles prepared by the present invention have good immunogenicity and can produce high titers of neutralizing antibodies in animals, which can be used to prepare into a vaccine for the prevention of HPV infection.

Example 6.4: Evaluation of Immunogenicity of HPV18 L1: 33C Virus-Like Particles in Animals The experimental methods and procedures were the same as in Example 6.1. The L1 sequence was from Uniprot Q80B70 and the L2 sequence was from Uniprot P06793. The results of HPV18 serum pseudovirus neutralization titer assay are detailed in Table 7.

TABLE 7

| EC50 of Serum Neutralization Titer Assay in Mice (GMT ± SEM) | |
|---|---|
| HPV Type | $EC_{50}$ Value |
| Type 18 | 18480 ± 4051 |

The above evaluation results show that the HPV18 L1: 33C virus-like particles prepared by the present invention have good immunogenicity, can produce high titers of neutralizing antibodies in animals, and can be used to prepare into a vaccine for preventing HPV infection.

Example 6.5: Evaluation of Immunogenicity of HPV31 L1: 33C Virus-Like Particles in Animals The experimental methods and procedures were the same as in Example 6.1. The L1 sequence was from Uniprot P17388 and the L2 sequence was from Uniprot P17389. The results of HPV31 serum pseudovirus neutralization titer assay are detailed in Table 8.

TABLE 8

| EC50 of Serum Neutralization Titer Assay in Mice (GMT ± SEM) | |
|---|---|
| HPV Type | $EC_{50}$ Value |
| Type 31 | 5210 ± 1147 |

The above evaluation results show that the HPV31 L1: 33C virus-like particles prepared by the present invention have good immunogenicity, can produce high titers of neutralizing antibodies in animals, and can be used to prepare into a vaccine for preventing HPV infection.

Example 6.6: Evaluation of Immunogenicity of HPV33 L1 Virus-Like Particles in Animals The experimental methods and procedures were the same as in Example 6.1. The L1 sequence was from Uniprot P06416 and the L2 sequence was from Uniprot P06418. The results of HPV33 serum pseudovirus neutralization titer assay are detailed in Table 9.

TABLE 9

| EC50 of Serum Neutralization Titer Assay in Mice (GMT ± SEM) | |
|---|---|
| HPV Type | $EC_{50}$ Value |
| Type 33 | 4666 ± 1555 |

The above evaluation results show that the HPV33 L1 virus-like particles prepared by the present invention have good immunogenicity, can produce high titers of neutralizing antibodies in animals, and can be used to prepare into a vaccine for preventing HPV infection.

Example 6.7: Evaluation of Immunogenicity of HPV35 L1: 33C Virus-Like Particles in Animals The experimental methods and procedures were the same as in Example 6.1. The L1 sequence was from Uniprot P27232 and the L2 sequence was from Uniprot P27234. The results of HPV35 serum pseudovirus neutralization titer assay are detailed in Table 10.

TABLE 10

| EC50 of Serum Neutralization Titer Assay in Mice (GMT ± SEM) | |
|---|---|
| HPV Type | $EC_{50}$ Value |
| Type 35 | 2293 ± 1448 |

The above evaluation results show that the HPV35 L1: 33C virus-like particles prepared by the present invention have good immunogenicity, can produce high titers of neutralizing antibodies in animals, and can be used to prepare into a vaccine for preventing HPV infection.

Example 6.8: Immunogenicity Evaluation of HPV39 L1: 59C Virus-Like Particles in Animals The experimental methods and procedures were the same as in Example 6.1. The L1 sequence was from Uniprot P24838 and the L2 sequence was from Uniprot P24839.

The results of HPV39 serum pseudovirus neutralization titer assay are detailed in Table 11.

TABLE 11

| EC50 of Serum Neutralization Titer Assay in Mice (GMT ± SEM) | |
|---|---|
| HPV Type | $EC_{50}$ Value |
| Type 39 | 25526 ± 5857 |

The above evaluation results show that the HPV39 L1: 59C virus-like particles prepared by the present invention have good immunogenicity, can produce high titers of neutralizing antibodies in animals, and can be used to prepare into a vaccine for preventing HPV infection.

Example 6.9: Immunogenicity Evaluation of HPV45 L1: 33C Virus-Like Particles in Animals The experimental methods and procedures were the same as in Example 6.1. The L1 sequence was from Uniprot P36741 and the L2 sequence was from Uniprot P36761. The results of HPV45 serum pseudovirus neutralization titer assay are detailed in Table 12.

TABLE 12

| EC50 of Serum Neutralization Titer Assay in Mice (GMT ± SEM) | |
|---|---|
| HPV Type | $EC_{50}$ Value |
| Type 45 | 755 ± 935 |

The above evaluation results show that the HPV45 L1: 33C virus-like particles prepared by the present invention have good immunogenicity, can produce high titers of neutralizing antibodies in animals, and can be used to prepare into a vaccine for preventing HPV infection.

Example 6.10: Evaluation of Immunogenicity of HPV51 L1: 33C Virus-Like Particles in Animals The experimental methods and procedures were the same as in Example 6.1. The L1 sequence was from Uniprot P26536 and the L2 sequence was from Uniprot P26539.

The results of HPV51 serum pseudovirus neutralization titer assay are detailed in Table 13.

TABLE 13

| EC50 of Serum Neutralization Titer Assay in Mice (GMT ± SEM) | |
|---|---|
| HPV Type | $EC_{50}$ Value |
| Type 51 | 5528 ± 1572 |

The above evaluation results show that the HPV51 L1: 33C virus-like particles prepared by the present invention have good immunogenicity, can produce high titers of neutralizing antibodies in animals, and can be used to prepare into a vaccine for preventing HPV infection.

Example 6.11: Evaluation of Immunogenicity of HPV52 L1: 33C Virus-Like Particles in Animals The experimental methods and procedures were the same as in Example 6.1. The L1 sequence was from Uniprot Q05138 and the L2 sequence was from Uniprot F8S4U2. The results of HPV52 serum pseudovirus neutralization titer assay are detailed in Table 14.

TABLE 14

| EC50 of Serum Neutralization Titer Assay in Mice (GMT ± SEM) | |
|---|---|
| HPV Type | $EC_{50}$ Value |
| Type 52 | 19019 ± 8604 |

The above evaluation results show that the HPV52 L1: 33C virus-like particles prepared by the present invention have good immunogenicity, can produce high titers of neutralizing antibodies in animals, and can be used to prepare into a vaccine for preventing HPV infection.

Example 6.12: Evaluation of Immunogenicity of HPV56 L1: 33C Virus-Like Particles in Animals The experimental methods and procedures were the same as in Example 6.1. The L1 sequence was from Uniprot P36743 and the L2 sequence was from Uniprot P36765. The results of HPV56 serum pseudovirus neutralization titer assay are detailed in Table 15.

TABLE 15

| EC50 of Serum Neutralization Titer Assay in Mice (GMT ± SEM) | |
|---|---|
| HPV Type | $EC_{50}$ Value |
| Type 56 | 2497 ± 612 |

The above evaluation results show that the HPV56 L1: 33C virus-like particles prepared by the present invention have good immunogenicity, can produce high titers of neutralizing antibodies in animals, and can be used to prepare into a vaccine for preventing HPV infection.

Example 6.13: Evaluation of Immunogenicity of HPV58 L1: 33C Virus-Like Particles in Animals The experimental methods and procedures were the same as in Example 6.1. The L1 sequence was from Uniprot P26535 and the L2 sequence was from Uniprot B6ZB12. The results of HPV58 serum pseudovirus neutralization titer assay are detailed in Table 16.

TABLE 16

| EC50 of Serum Neutralization Titer Assay in Mice (GMT ± SEM) | |
|---|---|
| HPV Type | $EC_{50}$ Value |
| Type 58 | 19939 ± 8459 |

The above evaluation results show that the HPV58 L1: 33C virus-like particles prepared by the present invention have good immunogenicity, can produce high titers of neutralizing antibodies in animals, and can be used to prepare into a vaccine for the prevention of HPV infection.

Example 6.14: Evaluation of Immunogenicity of HPV59 L1 Virus-Like Particles in Animals The experimental methods and procedures were the same as in Example 6.1. The L1 sequence was from Uniprot Q81971 and the L2 sequence was from Uniprot Q81970. The results of HPV59 serum pseudovirus neutralization titer assay are detailed in Table 17.

TABLE 17

| EC50 of Serum Neutralization Titer Assay in Mice (GMT ± SEM) | |
|---|---|
| HPV Type | $EC_{50}$ Value |
| Type 59 | 1344 ± 335 |

The above evaluation results show that the HPV59 L1 virus-like particles prepared by the present invention have good immunogenicity, can produce high titers of neutralizing antibodies in animals, and can be used to prepare into a vaccine for the prevention of HPV infection.

Example 6.15: Immunogenicity Evaluation of 14-Valent Immunogenic Composition of Virus-Like Particles in Mice Immunization procedures in mice: a sample consisted of the aforementioned virus-like particles of 14 types (HPV Types 6, 11, 16, 18, 31, 33, 35, 39, 45, 51, 52, 56, 58, and 59) were diluted with aluminum phosphate adjuvant sterilely (for example, the HPV types which were of 20 μg in the sample, were diluted 80-fold to 0.5 μg/mL, the concentration of other HPV types in the samples being of different ration varied accordingly), 200 μL of the diluted virus-like particle sample was used to immunize each mouse, and the doses are shown in Table 18. SPF-grade female Bal b/c mice aged 6-8 weeks were divided into groups of 10 mice in each group (experimental group and control group), and were immunized with the diluted samples on Day 0, 7 and 21 respectively, with control mice immunized with blank serum. Blood was collected from the eyes of mice on Day 28, and the sera were isolated for pseudovirus neutralization titers assay.

TABLE 18

| Doses of Each HPV Types in the Immunogenic Composition for Immunization in Each Mouse (μg) | | | | | | | | | | | | | | |
|---|---|---|---|---|---|---|---|---|---|---|---|---|---|---|
| HPV Type | 6 | 11 | 16 | 18 | 31 | 33 | 45 | 52 | 58 | 35 | 39 | 51 | 56 | 59 |
| Dose | 0.15 | 0.2 | 0.3 | 0.2 | 0.1 | 0.1 | 0.1 | 0.1 | 0.1 | 0.1 | 0.1 | 0.1 | 0.1 | 0.1 |

Serum neutralization titer assay in immunized mice by pseudovirus neutralization assay: the murine serum was inactivated at 56° C. for 30 minutes, centrifuged at 6000 g, 5 mins, and the supernatant was collected for assaying. 4-8 hours prior to the assay, 293FT cells were inoculated at a density of 15,000 cells/well into 96-well plates and incubated at 37° C. in a $CO_2$ incubator with 5% $CO_2$. The immunized murine serum and blank control serum were serial diluted with neutralizing media respectively, then mixed with the diluted 14 types of pseudovirus samples (the 14 types of HPV pseudovirus are those of HPV types 6, 11, 16, 18, 31, 33, 35, 39, 45, 51, 52, 56, 58 and 59, prepared in Examples 6.1-6.14) at a volume ratio of 1:1, incubated at 2-8° C. for 1 h, then 100 μL/well of the mixture were added to 293FT cells, which had been inoculated for 4-8 h in advance. Each sample was in replicate; and blank serum control group, pseudovirus positive control group and pseudovirus negative control group were used. The cells infected by pseudovirus were incubated at 37° C. in a $CO_2$ incubator with 5% $CO_2$ for 62-96 h, fluorescence scanning photographed and counted in an ELISPOT analyzer (Model No.: S6 Universal-V Analyzer, Manufacturer: CTL). On the basis of the neutralization inhibition of each murine serum sample, the maximum dilution of the serum at 50% neutralization inhibition was calculated for each murine serum sample according to the Reed-Muench method, i.e. the half efficacy dilution EC50. The results are shown in FIG. 3.

As demonstrated FIG. 3, the 14-valent immunogenic composition of virus-like particles can produce high titers of neutralizing antibodies in animals, and can be used to prepare a vaccine for the prevention of HPV infection.

Comparative Example 1: Expression of C-Terminal Truncated HPV16 L1 (aa 1-474)

The inventors attempted to truncate the C-terminus of HPV16 L1 by 31 amino acids and named it HPV16 L1 (1-474) (SEQ ID NO: 27). However, it was found in the study that the truncated HPV16 L1 (1-474) protein was highly expressed but has very poor solubility, and is difficult to extract and purify, the detailed results of expression and extraction are shown in FIG. 4.

Although the present invention has been described in detail by way of illustration and embodiments in the foregoing, it is intended to facilitate understanding. It is obvious to those skilled in the art that various modifications and improvements can be made to the technical solutions of the present invention are apparently possible for those of ordinary skill in the art without deviating from the spirit or scope of the attached claims.

What is claimed is:

1. A multivalent HPV immunogenic composition for preventing HPV-related diseases or infections, wherein the composition comprises:

HPV virus-like particles assembled from the chimeric L1 protein of HPV Types 6, 11, 16, 18, 31, 35, 39, 45, 51, 52, 56, 58 and L1 protein of HPV Types 33 and 59;

wherein the chimeric L1 protein of HPV Type 6 comprises, from its N-terminus to C-terminus orientation, (a) an N-terminal fragment which is SEQ ID No: 1; and (b) a C-terminal fragment which is SEQ ID No: 2;

wherein the chimeric L1 protein of HPV Type 11 comprises, from its N-terminus to C-terminus orientation, (a) an N-terminal fragment which is SEQ ID No: 14; and (b) a C-terminal fragment which is SEQ ID No: 15;

wherein the chimeric L1 protein of HPV Type 16 comprises, from its N-terminus to C-terminus orientation, (a) an N-terminal fragment which is SEQ ID No: 27; and (b) a C-terminal fragment which is SEQ ID No: 28;

wherein the chimeric L1 protein of HPV Type 18 comprises, from its N-terminus to C-terminus orientation, (a) an N-terminal fragment which is SEQ ID No: 40; and (b) a C-terminal fragment which is SEQ ID No: 41;

wherein the chimeric L1 protein of HPV Type 31 comprises, from its N-terminus to C-terminus orientation, (a) an N-terminal fragment which is SEQ ID No: 53; and (b) a C-terminal fragment which is SEQ ID No: 54;

wherein the chimeric L1 protein of HPV Type 35 comprises, from its N-terminus to C-terminus orientation, (a) an N-terminal fragment which is SEQ ID No: 69; and (b) a C-terminal fragment which is SEQ ID No: 70;

wherein the chimeric L1 protein of HPV Type 39 comprises, from its N-terminus to C-terminus orientation, (a) an N-terminal fragment which is SEQ ID No: 82; and (b) a C-terminal fragment which is SEQ ID No: 83;

wherein the chimeric L1 protein of HPV Type 45 comprises, from its N-terminus to C-terminus orientation, (a) an N-terminal fragment which is SEQ ID No: 95; and (b) a C-terminal fragment which is SEQ ID No: 96;

wherein the chimeric L1 protein of HPV Type 51 comprises, from its N-terminus to C-terminus orientation, (a) an N-terminal fragment which is SEQ ID No: 108; and (b) a C-terminal fragment which is SEQ ID No: 109;

wherein the chimeric L1 protein of HPV Type 52 comprises, from its N-terminus to C-terminus orientation, (a) an N-terminal fragment which is SEQ ID No: 121; and (b) a C-terminal fragment which is SEQ ID No: 122;

wherein the chimeric L1 protein of HPV Type 56 comprises, from its N-terminus to C-terminus orientation, (a) an N-terminal fragment which is SEQ ID No: 134 and (b) a C-terminal fragment which is SEQ ID No: 135;

wherein the chimeric L1 protein of HPV Type 58 comprises, from its N-terminus to C-terminus orientation, (a) an N-terminal fragment which is SEQ ID No: 147; and (b) a C-terminal fragment which is SEQ ID No: 148;

wherein the HPV Type 33 L1 protein is SEQ ID No: 66 and wherein the HPV Type 59 L1 protein is SEQ ID No: 160.

2. The multivalent HPV immunogenic composition according to claim 1, wherein:

the amino acid sequences of said chimeric HPV L1 protein of HPV Types 6, 11, 16, 18, 31, 35, 39, 45, 51, 52, 56, and 58 is SEQ ID No: 3, SEQ ID No: 16, SEQ ID No: 29, SEQ ID No: 42, SEQ ID No: 55, SEQ ID No: 71, SEQ ID No: 84, SEQ ID No: 97, SEQ ID No: 110, SEQ ID No: 123, SEQ ID No: 136 and SEQ ID No: 149, respectively.

3. The multivalent HPV immunogenic composition according to claim 1, wherein said multivalent HPV immunogenic composition further comprises at least one of a physiologically acceptable carrier and an adjuvant.

4. The multivalent HPV immunogenic composition according to claim 3, wherein said adjuvant is an aluminum phosphate adjuvant.

5. A method of preventing HPV related disease or infection, the method comprising:

administering to a subject a multivalent HPV immunogenic composition of claim 1; and at least one HPV virus-like particles assembled from L1 proteins of other pathogenic HPV types.

6. A method of preparing one of a vaccine and a drug for preventing HPV-related diseases, the method comprising combining a carrier with a multivalent HPV immunogenic composition of claim 1; and at least one HPV virus-like particles assembled from L1 proteins of other pathogenic HPV types.

7. A multivalent HPV immunogenic composition for preventing HPV-related diseases or infections, wherein the composition comprises:

HPV virus-like particles assembled from the chimeric L1 protein of HPV Types 6, 11, 16, 18, 31, 35, 39, 45, 51, 52, 56, 58 and L1 protein of HPV Types 33 and 59;

wherein said chimeric HPV L1 protein of HPV Types 6 is encoded by SEQ ID No: 4, wherein said chimeric HPV L1 protein of HPV Types 11 is encoded by SEQ ID No: 17, wherein said chimeric HPV L1 protein of HPV Types 16 is encoded by SEQ ID No: 30, wherein said chimeric HPV L1 protein of HPV Types 18 is encoded by SEQ ID No: 43, wherein said chimeric HPV L1 protein of HPV Types 31 is encoded by SEQ ID No: 56, wherein said chimeric HPV L1 protein of HPV Types 35 is encoded by SEQ ID No: 72, wherein said chimeric HPV L1 protein of HPV Types 39 is encoded by SEQ ID No: 85, wherein said chimeric HPV L1 protein of HPV Types 45 is encoded by SEQ ID No: 98, wherein said chimeric HPV L1 protein of HPV Types 51 is encoded by SEQ ID No: 111, wherein said chimeric HPV L1 protein of HPV Types 52 is encoded by SEQ ID No: 124, wherein said chimeric HPV L1 protein of HPV Types 56 is encoded by SEQ ID No: 137, wherein said chimeric HPV L1 protein of HPV Types 58 is encoded by SEQ ID No: 150, wherein said HPV L1 protein of HPV Types 33 is encoded by SEQ ID No: 67, and/or wherein said HPV L1 protein of HPV Types 59 is encoded by SEQ ID No: 161.

* * * * *

SEQUENCE LISTING

```
<160> NUMBER OF SEQ ID NOS: 208

<210> SEQ ID NO 1
<211> LENGTH: 469
<212> TYPE: PRT
<213> ORGANISM: Homo sapiens
<220> FEATURE:
<221> NAME/KEY: misc_feature
<223> OTHER INFORMATION: 0601 Amino acid sequence of HPV type 6 L1
      protein aa 1-469

<400> SEQUENCE: 1

Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
```

```
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser Gly Tyr
465


<210> SEQ ID NO 2
<211> LENGTH: 26
<212> TYPE: PRT
<213> ORGANISM: Homo sapiens
<220> FEATURE:
<221> NAME/KEY: misc_feature
<223> OTHER INFORMATION: 0602 Amino acid sequence of HPV type 33 L1
      protein aa 474-499

<400> SEQUENCE: 2

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25


<210> SEQ ID NO 3
<211> LENGTH: 495
<212> TYPE: PRT
<213> ORGANISM: Artificial sequence
<220> FEATURE:
<223> OTHER INFORMATION: 0603 Amino acid sequence of chimeric HPV type 6
      L1 protein

<400> SEQUENCE: 3

Met Trp Arg Pro Ser Asp Ser Thr Val Tyr Val Pro Pro Pro Asn Pro
1               5                   10                  15
```

-continued

```
Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
```

```
        435                 440                 445

Lys Phe Ser Ser Glu Leu Asp Gln Tyr Pro Leu Gly Arg Lys Phe Leu
    450                 455                 460

Leu Gln Ser Gly Tyr Lys Ala Lys Pro Lys Leu Lys Arg Ala Ala Pro
465                 470                 475                 480

Thr Ser Thr Arg Thr Ser Ser Ala Lys Arg Lys Lys Val Lys Lys
                485                 490                 495


<210> SEQ ID NO 4
<211> LENGTH: 1488
<212> TYPE: DNA
<213> ORGANISM: Artificial sequence
<220> FEATURE:
<223> OTHER INFORMATION: 0604 Nucleotide sequence of chimeric HPV type 6
      L1 protein

<400> SEQUENCE: 4

atgtggagac catctgacag cacagtctat gtgcctcctc caaaccctgt gagcaaggtg     60

gtggctacag atgcctatgt gaccaggacc aacatcttct accatgcctc ctccagcaga    120

ctgctggctg tgggacaccc atacttcagc atcaagaggg ctaacaagac agtggtgcca    180

aaggtgtctg gctaccaata cagggtgttc aaggtggtgc tgcctgaccc aaacaagttt    240

gccctgcctg actcctccct gtttgaccca accacccaga gactggtgtg ggcttgtact    300

ggattggagg tgggcagggg acaaccactg ggagtgggag tgtctggaca cccattcctg    360

aacaaatatg atgatgtgga gaactctggc tctggaggca accctggaca agacaacagg    420

gtgaatgtgg ggatggacta caagcagacc caactttgta tggtgggctg tgcccctcca    480

ctgggagaac actggggcaa gggcaagcag tgtaccaaca cacctgtcca ggctggagac    540

tgtcctccat tggaactgat tacctctgtg attcaggatg gagatatggt ggacacaggc    600

tttggagcta tgaactttgc tgacctccaa accaacaagt ctgatgtgcc aattgacatc    660

tgtggcacca cttgtaaata ccctgactac ctccaaatgg ctgctgaccc atatggagac    720

agactgttct tcttcctgag gaaggaacag atgtttgcca gacacttctt caacagggct    780

ggagaggtgg gagaacctgt gcctgacacc ctgattatca agggctctgg caacaggacc    840

tctgtgggct ccagcatcta tgtgaacaca ccatctggct ccctggtgtc ctctgaggct    900

caacttttca acaagccata ctggctccaa aaggctcaag gacacaacaa tggcatctgt    960

tggggcaacc aactttttgt gacagtggtg gacaccacca ggagcaccaa tatgaccctg   1020

tgtgcctctg tgaccacctc cagcacctac accaactctg actacaagga atatatgagg   1080

catgtggagg aatatgacct ccaattcatc ttccaacttt gtagcatcac cctgtctgct   1140

gaggtgatgg cttacatcca cacaatgaac ccatctgtgt tggaggactg gaactttgga   1200

ctgagccctc ctccaaatgg caccttggag gacacctaca gatatgtcca gagccaggct   1260

atcacttgtc agaagccaac acctgagaag gagaagcctg acccatacaa gaacctgtcc   1320

ttctgggagg tgaacctgaa agagaagttc tcctctgaac tggaccaata cccactgggc   1380

aggaagttcc tgctccaatc tggctacaaa gccaagccaa aactgaaaag ggctgcccca   1440

accagcacca ggacctcctc tgccaagagg aagaaggtga agaagtaa                1488


<210> SEQ ID NO 5
<211> LENGTH: 1522
<212> TYPE: DNA
<213> ORGANISM: Artificial sequence
<220> FEATURE:
<223> OTHER INFORMATION: 0605 Synthetic HPV6 L1 gene
```

<400> SEQUENCE: 5
ctgggtacca tgtggagacc atctgacagc acagtctatg tgcctcctcc aaaccctgtg 60
agcaaggtgg tggctacaga tgcctatgtg accaggacca acatcttcta ccatgcctcc 120
tccagcagac tgctggctgt gggacaccca tacttcagca tcaagagggc taacaagaca 180
gtggtgccaa aggtgtctgg ctaccaatac agggtgttca aggtggtgct gcctgaccca 240
aacaagtttg ccctgcctga ctcctccctg tttgacccaa ccacccagag actggtgtgg 300
gcttgtactg gattggaggt gggcagggga caaccactgg gagtgggagt gtctggacac 360
ccattcctga acaaatatga tgatgtggag aactctggct ctggaggcaa ccctggacaa 420
gacaacaggg tgaatgtggg gatggactac aagcagaccc aactttgtat ggtgggctgt 480
gcccctccac tgggagaaca ctggggcaag ggcaagcagt gtaccaacac acctgtccag 540
gctggagact gtcctccatt ggaactgatt acctctgtga ttcaggatgg agatatggtg 600
gacacaggct ttggagctat gaactttgct gacctccaaa ccaacaagtc tgatgtgcca 660
attgacatct gtggcaccac ttgtaaatac cctgactacc tccaaatggc tgctgaccca 720
tatggagaca gactgttctt cttcctgagg aaggaacaga tgtttgccag acacttcttc 780
aacagggctg gagaggtggg agaacctgtg cctgacaccc tgattatcaa gggctctggc 840
aacaggacct ctgtgggctc cagcatctat gtgaacacac catctggctc cctggtgtcc 900
tctgaggctc aacttttcaa caagccatac tggctccaaa aggctcaagg acacaacaat 960
ggcatctgtt ggggcaacca actttttgtg acagtggtgg acaccaccag gagcaccaat 1020
atgaccctgt gtgcctctgt gaccacctcc agcacctaca ccaactctga ctacaaggaa 1080
tatatgaggc atgtggagga atatgacctc caattcatct tccaactttg tagcatcacc 1140
ctgtctgctg aggtgatggc ttacatccac acaatgaacc catctgtgtt ggaggactgg 1200
aactttggac tgagccctcc tccaaatggc accttggagg acacctacag atatgtccag 1260
agccaggcta tcacttgtca gaagccaaca cctgagaagg agaagcctga cccatacaag 1320
aacctgtcct tctgggaggt gaacctgaaa gagaagttct cctctgaact ggaccaatac 1380
ccactgggca ggaagttcct gctccaatct ggctacaggg gcaggtccag catcaggaca 1440
ggagtgaaga gacctgctgt gagcaaggca tctgctgccc caaagaggaa gagggctaag 1500
accaagaggt aaactcgagc tc 1522

<210> SEQ ID NO 6
<211> LENGTH: 1519
<212> TYPE: DNA
<213> ORGANISM: Artificial sequence
<220> FEATURE:
<223> OTHER INFORMATION: 0606 Synthetic HPV33 L1 gene

<400> SEQUENCE: 6
ctgggtacca tgagtgtgtg gagaccatct gaggctacag tctacctgcc tcctgtgcct 60
gtgagcaagg tggtgagcac agatgaatat gtgagcagga ccagcatcta ctactatgct 120
ggctccagca gactgctggc tgtgggacac ccatacttca gcatcaagaa cccaaccaat 180
gccaagaaac tgctggtgcc aaaggtgtct ggactccaat acagggtgtt cagggtgaga 240
ctgcctgacc caaacaagtt tggctttcct gacacctcct tctacaaccc tgacacccag 300
agactggtgt gggcttgtgt gggattggag attggcaggg gacaaccact gggagtgggc 360
atctctggac acccactgct gaacaagttt gatgacacag agacaggcaa caaataccct 420

-continued

```
ggacaacctg gagcagacaa cagggagtgt ctgagtatgg actacaagca gacccaactt    480

tgtctgctgg gctgtaagcc tccaacagga gaacactggg gcaagggagt ggcttgtacc    540

aatgctgccc ctgccaatga ctgtcctcca ttggaactga taaacaccat cattgaggat    600

ggagatatgg tggacacagg ctttggctgt atggacttca agaccctcca agccaacaag    660

tctgatgtgc caattgacat ctgtggcagc acttgtaaat accctgacta cctgaaaatg    720

acctctgaac catatggaga ctccctgttc ttcttcctga ggagggaaca gatgtttgtg    780

agacacttct tcaacagggc tggcaccctg ggagaggctg tgcctgatga cctctacatc    840

aagggctctg gcaccacagc cagcatccag tcctctgcct tctttccaac accatctggc    900

agtatggtga cctctgagag ccaacttttc aacaagccat actggctcca aagggctcaa    960

ggacacaaca atggcatctg ttggggcaac caggtgtttg tgacagtggt ggacaccacc   1020

aggagcacca atatgaccct gtgtacccag gtgacctctg acagcaccta caagaatgag   1080

aacttcaagg aatacatcag gcatgtggag gaatatgacc tccaatttgt gttccaactt   1140

tgtaaggtga ccctgacagc agaggtgatg acctacatcc atgctatgaa ccctgacatc   1200

ttggaggact ggcagtttgg actgacacct cctccatctg cctccctcca agacacctac   1260

aggtttgtga ccagccaggc tatcacttgt cagaagacag tgcctccaaa ggagaaggag   1320

gacccactgg gcaaatacac cttctgggag gtggacctga aagagaagtt ctctgctgac   1380

ctggaccagt ttccactggg caggaagttc ctgctccaag caggactgaa agccaagcca   1440

aaactgaaaa gggctgcccc aaccagcacc aggacctcct ctgccaagag gaagaaggtg   1500

aagaagtaaa ctcgagctc                                                1519


<210> SEQ ID NO 7
<211> LENGTH: 35
<212> TYPE: DNA
<213> ORGANISM: Artificial sequence
<220> FEATURE:
<223> OTHER INFORMATION: 0607 HPV6L1 F1

<400> SEQUENCE: 7

cttggtacca tgtggagacc atctgacagc acagt                                35


<210> SEQ ID NO 8
<211> LENGTH: 36
<212> TYPE: DNA
<213> ORGANISM: Artificial sequence
<220> FEATURE:
<223> OTHER INFORMATION: 0608 HPV6L1 R1

<400> SEQUENCE: 8

gcttggcttt gtagccagat tggagcagga acttcc                               36


<210> SEQ ID NO 9
<211> LENGTH: 1426
<212> TYPE: DNA
<213> ORGANISM: Artificial sequence
<220> FEATURE:
<223> OTHER INFORMATION: 0609 HPV6L1 amplified sequence 1

<400> SEQUENCE: 9

cttggtacca tgtggagacc atctgacagc acagtctatg tgcctcctcc aaaccctgtg     60

agcaaggtgg tggctacaga tgcctatgtg accaggacca acatcttcta ccatgcctcc    120

tccagcagac tgctggctgt gggacaccca tacttcagca tcaagagggc taacaagaca    180

gtggtgccaa aggtgtctgg ctaccaatac agggtgttca aggtggtgct gcctgaccca    240
```

-continued

```
aacaagtttg ccctgcctga ctcctccctg tttgacccaa ccacccagag actggtgtgg    300

gcttgtactg gattggaggt gggcagggga caaccactgg gagtgggagt gtctggacac    360

ccattcctga acaaatatga tgatgtggag aactctggct ctggaggcaa ccctggacaa    420

gacaacaggg tgaatgtggg gatggactac aagcagaccc aactttgtat ggtgggctgt    480

gcccctccac tgggagaaca ctggggcaag ggcaagcagt gtaccaacac acctgtccag    540

gctggagact gtcctccatt ggaactgatt acctctgtga ttcaggatgg agatatggtg    600

gacacaggct ttggagctat gaactttgct gacctccaaa ccaacaagtc tgatgtgcca    660

attgacatct gtggcaccac ttgtaaatac cctgactacc tccaaatggc tgctgaccca    720

tatggagaca gactgttctt cttcctgagg aaggaacaga tgtttgccag acacttcttc    780

aacagggctg gagaggtggg agaacctgtg cctgacaccc tgattatcaa gggctctggc    840

aacaggacct ctgtgggctc cagcatctat gtgaacacac catctggctc cctggtgtcc    900

tctgaggctc aacttttcaa caagccatac tggctccaaa aggctcaagg acacaacaat    960

ggcatctgtt ggggcaacca actttttgtg acagtggtgg acaccaccag gagcaccaat   1020

atgaccctgt gtgcctctgt gaccacctcc agcacctaca ccaactctga ctacaaggaa   1080

tatatgaggc atgtggagga atatgacctc caattcatct tccaactttg tagcatcacc   1140

ctgtctgctg aggtgatggc ttacatccac acaatgaacc catctgtgtt ggaggactgg   1200

aactttggac tgagccctcc tccaaatggc accttggagg acacctacag atatgtccag   1260

agccaggcta tcacttgtca gaagccaaca cctgagaagg agaagcctga cccatacaag   1320

aacctgtcct tctgggaggt gaacctgaaa gagaagttct cctctgaact ggaccaatac   1380

ccactgggca ggaagttcct gctccaatct ggctacaaag ccaagc                  1426

<210> SEQ ID NO 10
<211> LENGTH: 35
<212> TYPE: DNA
<213> ORGANISM: Artificial sequence
<220> FEATURE:
<223> OTHER INFORMATION: 0610 HPV6L1 F2

<400> SEQUENCE: 10

atctggctac aaagccaagc caaaactgaa aaggg                                35


<210> SEQ ID NO 11
<211> LENGTH: 37
<212> TYPE: DNA
<213> ORGANISM: Artificial sequence
<220> FEATURE:
<223> OTHER INFORMATION: 0611 HPV6L1 R2

<400> SEQUENCE: 11

ctgtctagat ttacttcttc accttcttcc tcttggc                              37


<210> SEQ ID NO 12
<211> LENGTH: 101
<212> TYPE: DNA
<213> ORGANISM: Artificial sequence
<220> FEATURE:
<223> OTHER INFORMATION: 0612 HPV6L1 amplified sequence 2

<400> SEQUENCE: 12

atctggctac aaagccaagc caaaactgaa aagggctgcc ccaaccagca ccaggacctc     60

ctctgccaag aggaagaagg tgaagaagta aatctagaca g                        101
```

```
<210> SEQ ID NO 13
<211> LENGTH: 38
<212> TYPE: PRT
<213> ORGANISM: Homo sapiens
<220> FEATURE:
<221> NAME/KEY: misc_feature
<223> OTHER INFORMATION: 0613 Amino acid sequence of HPV type 59 L1
      protein aa 471-508

<400> SEQUENCE: 13

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35


<210> SEQ ID NO 14
<211> LENGTH: 470
<212> TYPE: PRT
<213> ORGANISM: Homo sapiens
<220> FEATURE:
<221> NAME/KEY: misc_feature
<223> OTHER INFORMATION: 1101 Amino acid sequence of HPV type 11 L1
      protein aa 1-470

<400> SEQUENCE: 14

Met Trp Arg Pro Ser Asp Ser Thr Val Tyr Val Pro Pro Pro Asn Pro
1               5                   10                  15

Val Ser Lys Val Val Ala Thr Asp Ala Tyr Val Lys Arg Thr Asn Ile
            20                  25                  30

Phe Tyr His Ala Ser Ser Ser Arg Leu Leu Ala Val Gly His Pro Tyr
        35                  40                  45

Tyr Ser Ile Lys Lys Val Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
        115                 120                 125

Ser Gly Gly Tyr Gly Gly Asn Pro Gly Gln Asp Asn Arg Val Asn Val
    130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
        195                 200                 205

Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
```

-continued

```
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
        275                 280                 285

Val His Thr Pro Ser Gly Ser Leu Val Ser Ser Glu Ala Gln Leu Phe
    290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
            340                 345                 350

Asn Ser Asp Tyr Lys Glu Tyr Met Arg His Val Glu Glu Phe Asp Leu
        355                 360                 365

Gln Phe Ile Phe Gln Leu Cys Ser Ile Thr Leu Ser Ala Glu Val Met
    370                 375                 380

Ala Tyr Ile His Thr Met Asn Pro Ser Val Leu Glu Asp Trp Asn Phe
385                 390                 395                 400

Gly Leu Ser Pro Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
        435                 440                 445

Glu Lys Phe Ser Ser Glu Leu Asp Gln Phe Pro Leu Gly Arg Lys Phe
    450                 455                 460

Leu Leu Gln Ser Gly Tyr
465                 470


<210> SEQ ID NO 15
<211> LENGTH: 26
<212> TYPE: PRT
<213> ORGANISM: Homo sapiens
<220> FEATURE:
<221> NAME/KEY: misc_feature
<223> OTHER INFORMATION: 1102 Amino acid sequence of HPV type 33 L1
      protein aa 474-499

<400> SEQUENCE: 15

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25


<210> SEQ ID NO 16
<211> LENGTH: 496
<212> TYPE: PRT
<213> ORGANISM: Artificial sequence
<220> FEATURE:
<223> OTHER INFORMATION: 1103 Amino acid sequence of chimeric HPV type
      11 L1 protein

<400> SEQUENCE: 16

Met Trp Arg Pro Ser Asp Ser Thr Val Tyr Val Pro Pro Pro Asn Pro
1               5                   10                  15

Val Ser Lys Val Val Ala Thr Asp Ala Tyr Val Lys Arg Thr Asn Ile
            20                  25                  30
```

-continued

```
Phe Tyr His Ala Ser Ser Ser Arg Leu Leu Ala Val Gly His Pro Tyr
        35                  40                  45

Tyr Ser Ile Lys Lys Val Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
        115                 120                 125

Ser Gly Gly Tyr Gly Gly Asn Pro Gly Gln Asp Asn Arg Val Asn Val
    130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
        195                 200                 205

Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
        275                 280                 285

Val His Thr Pro Ser Gly Ser Leu Val Ser Ser Glu Ala Gln Leu Phe
    290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
            340                 345                 350

Asn Ser Asp Tyr Lys Glu Tyr Met Arg His Val Glu Glu Phe Asp Leu
        355                 360                 365

Gln Phe Ile Phe Gln Leu Cys Ser Ile Thr Leu Ser Ala Glu Val Met
    370                 375                 380

Ala Tyr Ile His Thr Met Asn Pro Ser Val Leu Glu Asp Trp Asn Phe
385                 390                 395                 400

Gly Leu Ser Pro Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
        435                 440                 445

Glu Lys Phe Ser Ser Glu Leu Asp Gln Phe Pro Leu Gly Arg Lys Phe
```

-continued

```
    450                 455                 460

Leu Leu Gln Ser Gly Tyr Lys Ala Lys Pro Lys Leu Lys Arg Ala Ala
465                 470                 475                 480

Pro Thr Ser Thr Arg Thr Ser Ser Ala Lys Arg Lys Lys Val Lys Lys
                485                 490                 495


<210> SEQ ID NO 17
<211> LENGTH: 1492
<212> TYPE: DNA
<213> ORGANISM: Artificial sequence
<220> FEATURE:
<223> OTHER INFORMATION: 1104 Nucleotide sequence of chimeric HPV type
      11 L1 protein

<400> SEQUENCE: 17

atgtggagac catctgacag cacagtctat gtgcctcctc caaaccctgt gagcaaggtg      60

gtggctacag atgcctatgt gaagaggacc aacatcttct accatgcctc ctccagcaga     120

ctgctggctg tgggacaccc atactacagc atcaagaagg tgaacaagac agtggtgcca     180

aaggtgtctg gctaccaata cagggtgttc aaggtggtgc tgcctgaccc aaacaagttt     240

gccctgcctg actcctccct gtttgaccca accacccaga gactggtgtg ggcttgtact     300

ggattggagg tgggcagggg acaaccactg ggagtgggag tgtctggaca cccactgctg     360

aacaaatatg atgatgtgga gaactctgga ggctatggag gcaaccctgg acaagacaac     420

agggtgaatg tggggatgga ctacaagcag acccaacttt gtatggtggg ctgtgcccct     480

ccactgggag aacactgggg caagggcacc cagtgtagca acacctctgt ccagaatgga     540

gactgtcctc cattggaact gattacctct gtgattcagg atggagatat ggtggacaca     600

ggctttggag ctatgaactt tgctgacctc caaaccaaca agtctgatgt gccactggac     660

atctgtggca cagtgtgtaa ataccctgac tacctccaaa tggctgctga cccatatgga     720

gacagactgt tcttctacct gaggaaggaa cagatgtttg ccagacactt cttcaacagg     780

gctggcacag tgggagaacc tgtgcctgat gacctgctgg tgaagggagg caacaacagg     840

tcctctgtgg catccagcat ctatgtgcat acaccatctg gctccctggt gtcctctgag     900

gctcaacttt tcaacaagcc atactggctc caaaaggctc aaggacacaa caatggcatc     960

tgttggggca accacctgtt tgtgacagtg gtggacacca ccaggagcac caatatgacc    1020

ctgtgtgcct ctgtgagcaa gtctgccacc tacaccaact ctgactacaa ggaatatatg    1080

aggcatgtgg aggagtttga cctccaattc atcttccaac tttgtagcat caccctgtct    1140

gctgaggtga tggcttacat ccacacaatg aacccatctg tgttggagga ctggaacttt    1200

ggactgagcc ctcctccaaa tggcaccttg gaggacacct acagatatgt ccagagccag    1260

gctatcactt gtcagaagcc aacacctgag aaggagaagc aggacccata caaggatatg    1320

agtttctggg aggtgaacct gaaagagaag ttctcctctg aactggacca gtttccactg    1380

ggcaggaagt tcctgctcca atctggctac aaagccaagc caaaactgaa aagggctgcc    1440

ccaaccagca ccaggacctc ctctgccaag aggaagaagg tgaagaagta aa            1492


<210> SEQ ID NO 18
<211> LENGTH: 1525
<212> TYPE: DNA
<213> ORGANISM: Artificial sequence
<220> FEATURE:
<223> OTHER INFORMATION: 1105 Synthetic HPV11 L1 gene

<400> SEQUENCE: 18
```

-continued

```
ctgggtacca tgtggagacc atctgacagc acagtctatg tgcctcctcc aaaccctgtg      60
agcaaggtgg tggctacaga tgcctatgtg aagaggacca acatcttcta ccatgcctcc     120
tccagcagac tgctggctgt gggacaccca tactacagca tcaagaaggt gaacaagaca     180
gtggtgccaa aggtgtctgg ctaccaatac agggtgttca aggtggtgct gcctgaccca     240
aacaagtttg ccctgcctga ctcctccctg tttgacccaa ccacccagag actggtgtgg     300
gcttgtactg gattggaggt gggcagggga caaccactgg gagtgggagt gtctggacac     360
ccactgctga acaaatatga tgatgtggag aactctggag gctatggagg caaccctgga     420
caagacaaca gggtgaatgt ggggatggac tacaagcaga cccaactttg tatggtgggc     480
tgtgcccctc cactgggaga acactggggc aagggcaccc agtgtagcaa cacctctgtc     540
cagaatggag actgtcctcc attggaactg attacctctg tgattcagga tggagatatg     600
gtggacacag gctttggagc tatgaacttt gctgacctcc aaaccaacaa gtctgatgtg     660
ccactggaca tctgtggcac agtgtgtaaa taccctgact acctccaaat ggctgctgac     720
ccatatggag acagactgtt cttctacctg aggaaggaac agatgtttgc cagacacttc     780
ttcaacaggg ctggcacagt gggagaacct gtgcctgatg acctgctggt gaagggaggc     840
aacaacaggt cctctgtggc atccagcatc tatgtgcata caccatctgg ctccctggtg     900
tcctctgagg ctcaactttt caacaagcca tactggctcc aaaaggctca aggacacaac     960
aatggcatct gttggggcaa ccacctgttt gtgacagtgg tggacaccac caggagcacc    1020
aatatgaccc tgtgtgcctc tgtgagcaag tctgccacct acaccaactc tgactacaag    1080
gaatatatga ggcatgtgga ggagtttgac ctccaattca tcttccaact ttgtagcatc    1140
accctgtctg ctgaggtgat ggcttacatc cacacaatga acccatctgt gttggaggac    1200
tggaactttg gactgagccc tcctccaaat ggcaccttgg aggacaccta cagatatgtc    1260
cagagccagg ctatcacttg tcagaagcca acacctgaga aggagaagca ggacccatac    1320
aaggatatga gtttctggga ggtgaacctg aaagagaagt tctcctctga actggaccag    1380
tttccactgg gcaggaagtt cctgctccaa tctggctaca ggggcaggac ctctgccagg    1440
acaggcatca agagacctgc tgtgagcaag ccaagcacag ccccaaagag gaagaggacc    1500
aagaccaaga agtaaactcg agctc                                          1525
```

<210> SEQ ID NO 19
<211> LENGTH: 1519
<212> TYPE: DNA
<213> ORGANISM: Artificial sequence
<220> FEATURE:
<223> OTHER INFORMATION: 1106 Synthetic HPV33 L1 gene

<400> SEQUENCE: 19

```
ctgggtacca tgagtgtgtg gagaccatct gaggctacag tctacctgcc tcctgtgcct      60
gtgagcaagg tggtgagcac agatgaatat gtgagcagga ccagcatcta ctactatgct     120
ggctccagca gactgctggc tgtgggacac ccatacttca gcatcaagaa cccaaccaat     180
gccaagaaac tgctggtgcc aaaggtgtct ggactccaat acagggtgtt cagggtgaga     240
ctgcctgacc caaacaagtt tggctttcct gacacctcct tctacaaccc tgacacccag     300
agactggtgt gggcttgtgt gggattggag attggcaggg gacaaccact gggagtgggc     360
atctctggac acccactgct gaacaagttt gatgacacag agacaggcaa caaataccct     420
ggacaacctg gagcagacaa cagggagtgt ctgagtatgg actacaagca gacccaactt     480
tgtctgctgg gctgtaagcc tccaacagga gaacactggg gcaagggagt ggcttgtacc     540
```

```
aatgctgccc ctgccaatga ctgtcctcca ttggaactga taaacaccat cattgaggat    600

ggagatatgg tggacacagg ctttggctgt atggacttca agaccctcca agccaacaag    660

tctgatgtgc caattgacat ctgtggcagc acttgtaaat accctgacta cctgaaaatg    720

acctctgaac catatggaga ctccctgttc ttcttcctga ggagggaaca gatgtttgtg    780

agacacttct tcaacagggc tggcaccctg ggagaggctg tgcctgatga cctctacatc    840

aagggctctg gcaccacagc cagcatccag tcctctgcct tctttccaac accatctggc    900

agtatggtga cctctgagag ccaacttttc aacaagccat actggctcca aagggctcaa    960

ggacacaaca atggcatctg ttggggcaac caggtgtttg tgacagtggt ggacaccacc   1020

aggagcacca atatgaccct gtgtacccag gtgacctctg acagcaccta caagaatgag   1080

aacttcaagg aatacatcag gcatgtggag gaatatgacc tccaatttgt gttccaactt   1140

tgtaaggtga ccctgacagc agaggtgatg acctacatcc atgctatgaa ccctgacatc   1200

ttggaggact ggcagtttgg actgacacct cctccatctg cctccctcca agacacctac   1260

aggtttgtga ccagccaggc tatcacttgt cagaagacag tgcctccaaa ggagaaggag   1320

gacccactgg gcaaatacac cttctgggag gtggacctga aagagaagtt ctctgctgac   1380

ctggaccagt ttccactggg caggaagttc ctgctccaag caggactgaa agccaagcca   1440

aaactgaaaa gggctgcccc aaccagcacc aggacctcct ctgccaagag gaagaaggtg   1500

aagaagtaaa ctcgagctc                                                1519


<210> SEQ ID NO 20
<211> LENGTH: 35
<212> TYPE: DNA
<213> ORGANISM: Artificial sequence
<220> FEATURE:
<223> OTHER INFORMATION: 1107 HPV11L1 F1

<400> SEQUENCE: 20

cttggtacca tgtggagacc atctgacagc acagt                                35


<210> SEQ ID NO 21
<211> LENGTH: 36
<212> TYPE: DNA
<213> ORGANISM: Artificial sequence
<220> FEATURE:
<223> OTHER INFORMATION: 1108 HPV11L1 R1

<400> SEQUENCE: 21

gcttggcttt gtagccagat tggagcagga acttcc                               36


<210> SEQ ID NO 22
<211> LENGTH: 1429
<212> TYPE: DNA
<213> ORGANISM: Artificial sequence
<220> FEATURE:
<223> OTHER INFORMATION: 1109 HPV11L1 amplified sequence 1

<400> SEQUENCE: 22

cttggtacca tgtggagacc atctgacagc acagtctatg tgcctcctcc aaaccctgtg     60

agcaaggtgg tggctacaga tgcctatgtg aagaggacca acatcttcta ccatgcctcc    120

tccagcagac tgctggctgt gggacaccca tactacagca tcaagaaggt gaacaagaca    180

gtggtgccaa aggtgtctgg ctaccaatac agggtgttca aggtggtgct gcctgaccca    240

aacaagtttg ccctgcctga ctcctccctg tttgacccaa ccacccagag actggtgtgg    300
```

-continued

```
gcttgtactg gattggaggt gggcagggga caaccactgg gagtgggagt gtctggacac    360

ccactgctga acaaatatga tgatgtggag aactctggag gctatggagg caaccctgga    420

caagacaaca gggtgaatgt ggggatggac tacaagcaga cccaactttg tatggtgggc    480

tgtgcccctc cactgggaga acactggggc aagggcaccc agtgtagcaa cacctctgtc    540

cagaatggag actgtcctcc attggaactg attacctctg tgattcagga tggagatatg    600

gtggacacag gctttggagc tatgaacttt gctgacctcc aaaccaacaa gtctgatgtg    660

ccactggaca tctgtggcac agtgtgtaaa taccctgact acctccaaat ggctgctgac    720

ccatatggag acagactgtt cttctacctg aggaaggaac agatgtttgc cagacacttc    780

ttcaacaggg ctggcacagt gggagaacct gtgcctgatg acctgctggt gaagggaggc    840

aacaacaggt cctctgtggc atccagcatc tatgtgcata caccatctgg ctccctggtg    900

tcctctgagg ctcaactttt caacaagcca tactggctcc aaaaggctca aggacacaac    960

aatggcatct gttggggcaa ccacctgttt gtgacagtgg tggacaccac caggagcacc   1020

aatatgaccc tgtgtgcctc tgtgagcaag tctgccacct acaccaactc tgactacaag   1080

gaatatatga ggcatgtgga ggagtttgac ctccaattca tcttccaact ttgtagcatc   1140

accctgtctg ctgaggtgat ggcttacatc cacacaatga acccatctgt gttggaggac   1200

tggaactttg gactgagccc tcctccaaat ggcaccttgg aggacaccta cagatatgtc   1260

cagagccagg ctatcacttg tcagaagcca acacctgaga aggagaagca ggacccatac   1320

aaggatatga gtttctggga ggtgaacctg aaagagaagt tctcctctga actggaccag   1380

tttccactgg gcaggaagtt cctgctccaa tctggctaca aagccaagc               1429
```

<210> SEQ ID NO 23
<211> LENGTH: 35
<212> TYPE: DNA
<213> ORGANISM: Artificial sequence
<220> FEATURE:
<223> OTHER INFORMATION: 1110 HPV11L1 F2

<400> SEQUENCE: 23

```
atctggctac aaagccaagc caaaactgaa aaggg                                35
```

<210> SEQ ID NO 24
<211> LENGTH: 37
<212> TYPE: DNA
<213> ORGANISM: Artificial sequence
<220> FEATURE:
<223> OTHER INFORMATION: 1111 HPV11L1 R2

<400> SEQUENCE: 24

```
ctgtctagat ttacttcttc accttcttcc tcttggc                              37
```

<210> SEQ ID NO 25
<211> LENGTH: 101
<212> TYPE: DNA
<213> ORGANISM: Artificial sequence
<220> FEATURE:
<223> OTHER INFORMATION: 1112 HPV11L1 amplified sequence 2

<400> SEQUENCE: 25

```
atctggctac aaagccaagc caaaactgaa aagggctgcc ccaaccagca ccaggacctc     60

ctctgccaag aggaagaagg tgaagaagta aatctagaca g                        101
```

<210> SEQ ID NO 26
<211> LENGTH: 38

```
<212> TYPE: PRT
<213> ORGANISM: Homo sapiens
<220> FEATURE:
<221> NAME/KEY: misc_feature
<223> OTHER INFORMATION: 1113 Amino acid sequence of HPV type 59 L1
      protein aa 471-508

<400> SEQUENCE: 26

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35


<210> SEQ ID NO 27
<211> LENGTH: 474
<212> TYPE: PRT
<213> ORGANISM: Homo sapiens
<220> FEATURE:
<221> NAME/KEY: misc_feature
<223> OTHER INFORMATION: 1601 Amino acid sequence of HPV type 16 L1
      protein aa 1-474

<400> SEQUENCE: 27

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
```

```
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
                405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu
465                 470
```

<210> SEQ ID NO 28
<211> LENGTH: 26
<212> TYPE: PRT
<213> ORGANISM: Homo sapiens
<220> FEATURE:
<221> NAME/KEY: misc_feature
<223> OTHER INFORMATION: 1602 Amino acid sequence of HPV type 33 L1 protein aa 474-499

<400> SEQUENCE: 28

```
Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25
```

<210> SEQ ID NO 29
<211> LENGTH: 500
<212> TYPE: PRT
<213> ORGANISM: Artificial sequence
<220> FEATURE:
<223> OTHER INFORMATION: 1603 Amino acid sequence of chimeric HPV type 16 L1 protein

<400> SEQUENCE: 29

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45
```

-continued

```
Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
                405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Leu
```

```
465                 470                 475                 480

Lys Arg Ala Ala Pro Thr Ser Thr Arg Thr Ser Ser Ala Lys Arg Lys
                485                 490                 495

Lys Val Lys Lys
            500


<210> SEQ ID NO 30
<211> LENGTH: 1504
<212> TYPE: DNA
<213> ORGANISM: Artificial sequence
<220> FEATURE:
<223> OTHER INFORMATION: 1604 Nucleotide sequence of chimeric HPV type
      16 L1 protein

<400> SEQUENCE: 30

atgagtctgt ggctgccatc tgaggctaca gtctacctgc ctcctgtgcc tgtgagcaag     60

gtggtgagca cagatgaata tgtggcaagg accaacatct actaccatgc tggcaccagc    120

agactgctgg ctgtgggaca cccatacttt ccaatcaaga agccaaacaa caacaagatt    180

ctggtgccaa aggtgtctgg actccaatac agggtgttca ggattcacct gcctgaccca    240

aacaagtttg gctttcctga cacctccttc tacaaccctg acacccagag actggtgtgg    300

gcttgtgtgg gagtggaggt gggcagggga caaccactgg gagtgggcat ctctggacac    360

ccactgctga acaaactgga tgacacagag aatgcctctg cctatgctgc caatgctgga    420

gtggacaaca gggagtgtat cagtatggac tacaagcaga cccaactttg tctgattggc    480

tgtaagcctc caattggaga acactggggc aagggcagcc catgtaccaa tgtggctgtg    540

aaccctggag actgtcctcc attggaactg ataaacacag tgattcagga tggagatatg    600

gtggacacag gctttggagc tatggacttc accaccctcc aagccaacaa gtctgaggtg    660

ccactggaca tctgtaccag catctgtaaa taccctgact acatcaagat ggtgtctgaa    720

ccatatggag actccctgtt cttctacctg aggagggaac agatgtttgt gagacacctg    780

ttcaacaggg ctggagcagt gggagagaat gtgcctgatg acctctacat caagggctct    840

ggcagcacag ccaacctggc atccagcaac tactttccaa caccatctgg cagtatggtg    900

acctctgatg cccagatttt caacaagcca tactggctcc aaagggctca aggacacaac    960

aatggcatct gttggggcaa ccaacttttt gtgacagtgg tggacaccac caggagcacc   1020

aatatgagtc tgtgtgctgc catcagcacc tctgagacca cctacaagaa caccaacttc   1080

aaggaatacc tgagacatgg agaggaatat gacctccaat tcatcttcca actttgtaag   1140

attaccctga cagcagatgt gatgacctac atccacagta tgaacagcac catcttggag   1200

gactggaact ttggactcca acctcctcct ggaggcacct tggaggacac ctacaggttt   1260

gtgaccagcc aggctattgc ctgtcagaaa cacacacctc ctgccccaaa ggaggaccca   1320

ctgaaaaaat acaccttctg ggaggtgaac ctgaaagaga agttctctgc tgacctggac   1380

cagtttccac tgggcaggaa gttcctgctc caagcaggac tgaaagccaa gccaaaactg   1440

aaaagggctg ccccaaccag caccaggacc tcctctgcca agaggaagaa ggtgaagaag   1500

taaa                                                                1504


<210> SEQ ID NO 31
<211> LENGTH: 1537
<212> TYPE: DNA
<213> ORGANISM: Artificial sequence
<220> FEATURE:
<223> OTHER INFORMATION: 1605 Synthetic HPV16 L1 gene
```

<400> SEQUENCE: 31
ctgggtacca tgagtctgtg gctgccatct gaggctacag tctacctgcc tcctgtgcct 60
gtgagcaagg tggtgagcac agatgaatat gtggcaagga ccaacatcta ctaccatgct 120
ggcaccagca gactgctggc tgtgggacac ccatactttc caatcaagaa gccaaacaac 180
aacaagattc tggtgccaaa ggtgtctgga ctccaataca gggtgttcag gattcacctg 240
cctgacccaa acaagtttgg ctttcctgac acctccttct acaaccctga cacccagaga 300
ctggtgtggg cttgtgtggg agtggaggtg ggcaggggac aaccactggg agtgggcatc 360
tctggacacc cactgctgaa caaactggat gacacagaga atgcctctgc ctatgctgcc 420
aatgctggag tggacaacag ggagtgtatc agtatggact acaagcagac ccaactttgt 480
ctgattggct gtaagcctcc aattggagaa cactggggca agggcagccc atgtaccaat 540
gtggctgtga accctggaga ctgtcctcca ttggaactga taaacacagt gattcaggat 600
ggagatatgg tggacacagg ctttggagct atggacttca ccaccctcca agccaacaag 660
tctgaggtgc cactggacat ctgtaccagc atctgtaaat accctgacta catcaagatg 720
gtgtctgaac catatggaga ctccctgttc ttctacctga ggagggaaca gatgtttgtg 780
agacacctgt tcaacagggc tggagcagtg ggagagaatg tgcctgatga cctctacatc 840
aagggctctg gcagcacagc caacctggca tccagcaact actttccaac accatctggc 900
agtatggtga cctctgatgc ccagattttc aacaagccat actggctcca aagggctcaa 960
ggacacaaca atggcatctg ttggggcaac caactttttg tgacagtggt ggacaccacc 1020
aggagcacca atatgagtct gtgtgctgcc atcagcacct ctgagaccac ctacaagaac 1080
accaacttca aggaatacct gagacatgga gaggaatatg acctccaatt catcttccaa 1140
ctttgtaaga ttaccctgac agcagatgtg atgacctaca tccacagtat gaacagcacc 1200
atcttggagg actggaactt tggactccaa cctcctcctg gaggcacctt ggaggacacc 1260
tacaggtttg tgaccagcca ggctattgcc tgtcagaaac acacacctcc tgccccaaag 1320
gaggacccac tgaaaaaata caccttctgg gaggtgaacc tgaaagagaa gttctctgct 1380
gacctggacc agtttccact gggcaggaag ttcctgctcc aagcaggact gaaagccaag 1440
ccaaagttca ccctgggcaa gaggaaggct acaccaacca cctccagcac cagcaccaca 1500
gccaagagga agaagaggaa actgtaaact cgagctc 1537

<210> SEQ ID NO 32
<211> LENGTH: 1519
<212> TYPE: DNA
<213> ORGANISM: Artificial sequence
<220> FEATURE:
<223> OTHER INFORMATION: 1606 Synthetic HPV33 L1 gene

<400> SEQUENCE: 32
ctgggtacca tgagtgtgtg gagaccatct gaggctacag tctacctgcc tcctgtgcct 60
gtgagcaagg tggtgagcac agatgaatat gtgagcagga ccagcatcta ctactatgct 120
ggctccagca gactgctggc tgtgggacac ccatacttca gcatcaagaa cccaaccaat 180
gccaagaaac tgctggtgcc aaaggtgtct ggactccaat acagggtgtt cagggtgaga 240
ctgcctgacc caaacaagtt tggctttcct gacacctcct tctacaaccc tgacacccag 300
agactggtgt gggcttgtgt gggattggag attggcaggg gacaaccact gggagtgggc 360
atctctggac acccactgct gaacaagttt gatgacacag agacaggcaa caaataccct 420
ggacaacctg gagcagacaa cagggagtgt ctgagtatgg actacaagca gacccaactt 480
tgtctgctgg gctgtaagcc tccaacagga gaacactggg gcaagggagt ggcttgtacc 540
aatgctgccc ctgccaatga ctgtcctcca ttggaactga taaacaccat cattgaggat 600
ggagatatgg tggacacagg ctttggctgt atggacttca agaccctcca agccaacaag 660
tctgatgtgc caattgacat ctgtggcagc acttgtaaat accctgacta cctgaaaatg 720
acctctgaac catatggaga ctccctgttc ttcttcctga ggagggaaca gatgtttgtg 780
agacacttct tcaacagggc tggcaccctg ggagaggctg tgcctgatga cctctacatc 840
aagggctctg gcaccacagc cagcatccag tcctctgcct tctttccaac accatctggc 900
agtatggtga cctctgagag ccaacttttc aacaagccat actggctcca aagggctcaa 960
ggacacaaca atggcatctg ttggggcaac caggtgtttg tgacagtggt ggacaccacc 1020
aggagcacca atatgaccct gtgtacccag gtgacctctg acagcaccta caagaatgag 1080
aacttcaagg aatacatcag gcatgtggag gaatatgacc tccaatttgt gttccaactt 1140
tgtaaggtga ccctgacagc agaggtgatg acctacatcc atgctatgaa ccctgacatc 1200
ttggaggact ggcagtttgg actgacacct cctccatctg cctccctcca agacacctac 1260
aggtttgtga ccagccaggc tatcacttgt cagaagacag tgcctccaaa ggagaaggag 1320
gacccactgg gcaaatacac cttctgggag gtggacctga aagagaagtt ctctgctgac 1380
ctggaccagt ttccactggg caggaagttc ctgctccaag caggactgaa agccaagcca 1440
aaactgaaaa gggctgcccc aaccagcacc aggacctcct ctgccaagag gaagaaggtg 1500
aagaagtaaa ctcgagctc 1519

<210> SEQ ID NO 33
<211> LENGTH: 34
<212> TYPE: DNA
<213> ORGANISM: Artificial sequence
<220> FEATURE:
<223> OTHER INFORMATION: 1607 HPV16L1 F1

<400> SEQUENCE: 33
cttggtacca tgagtctgtg gctgccatct gagg 34

<210> SEQ ID NO 34
<211> LENGTH: 36
<212> TYPE: DNA
<213> ORGANISM: Artificial sequence
<220> FEATURE:
<223> OTHER INFORMATION: 1608 HPV16L1 R1

<400> SEQUENCE: 34
gcttggcttt cagtcctgct tggagcagga acttcc 36

<210> SEQ ID NO 35
<211> LENGTH: 1441
<212> TYPE: DNA
<213> ORGANISM: Artificial sequence
<220> FEATURE:
<223> OTHER INFORMATION: 1609 HPV16L1 amplified sequence 1

<400> SEQUENCE: 35
cttggtacca tgagtctgtg gctgccatct gaggctacag tctacctgcc tcctgtgcct 60
gtgagcaagg tggtgagcac agatgaatat gtggcaagga ccaacatcta ctaccatgct 120
ggcaccagca gactgctggc tgtgggacac ccatactttc caatcaagaa gccaaacaac 180
aacaagattc tggtgccaaa ggtgtctgga ctccaataca gggtgttcag gattcacctg 240

-continued

```
cctgacccaa acaagtttgg ctttcctgac acctccttct acaaccctga cacccagaga    300
ctggtgtggg cttgtgtggg agtggaggtg ggcaggggac aaccactggg agtgggcatc    360
tctggacacc cactgctgaa caaactggat gacacagaga atgcctctgc ctatgctgcc    420
aatgctggag tggacaacag ggagtgtatc agtatggact acaagcagac ccaactttgt    480
ctgattggct gtaagcctcc aattggagaa cactggggca agggcagccc atgtaccaat    540
gtggctgtga accctggaga ctgtcctcca ttggaactga taaacacagt gattcaggat    600
ggagatatgg tggacacagg ctttggagct atggacttca ccaccctcca agccaacaag    660
tctgaggtgc cactggacat ctgtaccagc atctgtaaat accctgacta catcaagatg    720
gtgtctgaac catatggaga ctccctgttc ttctacctga ggagggaaca gatgtttgtg    780
agacacctgt tcaacagggc tggagcagtg ggagagaatg tgcctgatga cctctacatc    840
aagggctctg gcagcacagc caacctggca tccagcaact actttccaac accatctggc    900
agtatggtga cctctgatgc ccagattttc aacaagccat actggctcca aagggctcaa    960
ggacacaaca atggcatctg ttggggcaac caactttttg tgacagtggt ggacaccacc   1020
aggagcacca atatgagtct gtgtgctgcc atcagcacct ctgagaccac ctacaagaac   1080
accaacttca aggaatacct gagacatgga gaggaatatg acctccaatt catcttccaa   1140
ctttgtaaga ttaccctgac agcagatgtg atgacctaca tccacagtat gaacagcacc   1200
atcttggagg actggaactt tggactccaa cctcctcctg gaggcacctt ggaggacacc   1260
tacaggtttg tgaccagcca ggctattgcc tgtcagaaac acacacctcc tgccccaaag   1320
gaggacccac tgaaaaaata caccttctgg gaggtgaacc tgaaagagaa gttctctgct   1380
gacctggacc agtttccact gggcaggaag ttcctgctcc aagcaggact gaaagccaag   1440
c                                                                   1441
```

```
<210> SEQ ID NO 36
<211> LENGTH: 35
<212> TYPE: DNA
<213> ORGANISM: Artificial sequence
<220> FEATURE:
<223> OTHER INFORMATION: 1610 HPV16L1 F2

<400> SEQUENCE: 36

agcaggactg aaagccaagc caaaactgaa aaggg                                35


<210> SEQ ID NO 37
<211> LENGTH: 36
<212> TYPE: DNA
<213> ORGANISM: Artificial sequence
<220> FEATURE:
<223> OTHER INFORMATION: 1611 HPV16L1 R2

<400> SEQUENCE: 37

ctgtctagat ttacttcttc accttcttcc tcttgg                               36


<210> SEQ ID NO 38
<211> LENGTH: 101
<212> TYPE: DNA
<213> ORGANISM: Artificial sequence
<220> FEATURE:
<223> OTHER INFORMATION: 1612 HPV16L1 amplified sequence 2

<400> SEQUENCE: 38

agcaggactg aaagccaagc caaaactgaa aagggctgcc ccaaccagca ccaggacctc     60
ctctgccaag aggaagaagg tgaagaagta aatctagaca g                        101
```

<210> SEQ ID NO 39
<211> LENGTH: 38
<212> TYPE: PRT
<213> ORGANISM: Homo sapiens
<220> FEATURE:
<221> NAME/KEY: misc_feature
<223> OTHER INFORMATION: 1613 Amino acid sequence of HPV type 59 L1
protein aa 471-508

<400> SEQUENCE: 39

Leu Gln Leu Gly Ala Arg Pro Lys Pro Thr Ile Gly Pro Arg Lys Arg
1 5 10 15

Ala Ala Pro Ala Pro Thr Ser Thr Pro Ser Pro Lys Arg Val Lys Arg
20 25 30

Arg Lys Ser Ser Arg Lys
35

<210> SEQ ID NO 40
<211> LENGTH: 470
<212> TYPE: PRT
<213> ORGANISM: Homo sapiens
<220> FEATURE:
<221> NAME/KEY: misc_feature
<223> OTHER INFORMATION: 1801 Amino acid sequence of HPV type 18 L1
protein aa 1-470

<400> SEQUENCE: 40

Met Ala Leu Trp Arg Pro Ser Asp Asn Thr Val Tyr Leu Pro Pro Pro
1 5 10 15

Ser Val Ala Arg Val Val Asn Thr Asp Asp Tyr Val Thr Arg Thr Ser
20 25 30

Ile Phe Tyr His Ala Gly Ser Ser Arg Leu Leu Thr Val Gly Asn Pro
35 40 45

Tyr Phe Arg Val Pro Ala Gly Gly Gly Asn Lys Gln Asp Ile Pro Lys
50 55 60

Val Ser Ala Tyr Gln Tyr Arg Val Phe Arg Val Gln Leu Pro Asp Pro
65 70 75 80

Asn Lys Phe Gly Leu Pro Asp Thr Ser Ile Tyr Asn Pro Glu Thr Gln
85 90 95

Arg Leu Val Trp Ala Cys Ala Gly Val Glu Ile Gly Arg Gly Gln Pro
100 105 110

Leu Gly Val Gly Leu Ser Gly His Pro Phe Tyr Asn Lys Leu Asp Asp
115 120 125

Thr Glu Ser Ser His Ala Ala Thr Ser Asn Val Ser Glu Asp Val Arg
130 135 140

Asp Asn Val Ser Val Asp Tyr Lys Gln Thr Gln Leu Cys Ile Leu Gly
145 150 155 160

Cys Ala Pro Ala Ile Gly Glu His Trp Ala Lys Gly Thr Ala Cys Lys
165 170 175

Ser Arg Pro Leu Ser Gln Gly Asp Cys Pro Pro Leu Glu Leu Lys Asn
180 185 190

Thr Val Leu Glu Asp Gly Asp Met Val Asp Thr Gly Tyr Gly Ala Met
195 200 205

Asp Phe Ser Thr Leu Gln Asp Thr Lys Cys Glu Val Pro Leu Asp Ile
210 215 220

Cys Gln Ser Ile Cys Lys Tyr Pro Asp Tyr Leu Gln Met Ser Ala Asp
225 230 235 240

```
Pro Tyr Gly Asp Ser Met Phe Phe Cys Leu Arg Arg Glu Gln Leu Phe
                245                 250                 255

Ala Arg His Phe Trp Asn Arg Ala Gly Thr Met Gly Asp Thr Val Pro
            260                 265                 270

Gln Ser Leu Tyr Ile Lys Gly Thr Gly Met Arg Ala Ser Pro Gly Ser
        275                 280                 285

Cys Val Tyr Ser Pro Ser Pro Ser Gly Ser Ile Val Thr Ser Asp Ser
    290                 295                 300

Gln Leu Phe Asn Lys Pro Tyr Trp Leu His Lys Ala Gln Gly His Asn
305                 310                 315                 320

Asn Gly Val Cys Trp His Asn Gln Leu Phe Val Thr Val Val Asp Thr
                325                 330                 335

Thr Arg Ser Thr Asn Leu Thr Ile Cys Ala Ser Thr Gln Ser Pro Val
            340                 345                 350

Pro Gly Gln Tyr Asp Ala Thr Lys Phe Lys Gln Tyr Ser Arg His Val
        355                 360                 365

Glu Glu Tyr Asp Leu Gln Phe Ile Phe Gln Leu Cys Thr Ile Thr Leu
    370                 375                 380

Thr Ala Asp Val Met Ser Tyr Ile His Ser Met Asn Ser Ser Ile Leu
385                 390                 395                 400

Glu Asp Trp Asn Phe Gly Val Pro Pro Pro Pro Thr Thr Ser Leu Val
                405                 410                 415

Asp Thr Tyr Arg Phe Val Gln Ser Val Ala Ile Thr Cys Gln Lys Asp
            420                 425                 430

Ala Ala Pro Ala Glu Asn Lys Asp Pro Tyr Asp Lys Leu Lys Phe Trp
        435                 440                 445

Asn Val Asp Leu Lys Glu Lys Phe Ser Leu Asp Leu Asp Gln Tyr Pro
    450                 455                 460

Leu Gly Arg Lys Phe Leu
465                 470


<210> SEQ ID NO 41
<211> LENGTH: 26
<212> TYPE: PRT
<213> ORGANISM: Homo sapiens
<220> FEATURE:
<221> NAME/KEY: misc_feature
<223> OTHER INFORMATION: 1802 Amino acid sequence of HPV type 33 L1
      protein aa 474-499

<400> SEQUENCE: 41

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25


<210> SEQ ID NO 42
<211> LENGTH: 496
<212> TYPE: PRT
<213> ORGANISM: Artificial sequence
<220> FEATURE:
<223> OTHER INFORMATION: 1803 Amino acid sequence of chimeric HPV type
      18 L1 protein

<400> SEQUENCE: 42

Met Ala Leu Trp Arg Pro Ser Asp Asn Thr Val Tyr Leu Pro Pro Pro
1               5                   10                  15

Ser Val Ala Arg Val Val Asn Thr Asp Asp Tyr Val Thr Arg Thr Ser
            20                  25                  30
```

-continued

```
Ile Phe Tyr His Ala Gly Ser Ser Arg Leu Leu Thr Val Gly Asn Pro
        35                  40                  45

Tyr Phe Arg Val Pro Ala Gly Gly Gly Asn Lys Gln Asp Ile Pro Lys
    50                  55                  60

Val Ser Ala Tyr Gln Tyr Arg Val Phe Arg Val Gln Leu Pro Asp Pro
65                  70                  75                  80

Asn Lys Phe Gly Leu Pro Asp Thr Ser Ile Tyr Asn Pro Glu Thr Gln
                85                  90                  95

Arg Leu Val Trp Ala Cys Ala Gly Val Glu Ile Gly Arg Gly Gln Pro
            100                 105                 110

Leu Gly Val Gly Leu Ser Gly His Pro Phe Tyr Asn Lys Leu Asp Asp
        115                 120                 125

Thr Glu Ser Ser His Ala Ala Thr Ser Asn Val Ser Glu Asp Val Arg
    130                 135                 140

Asp Asn Val Ser Val Asp Tyr Lys Gln Thr Gln Leu Cys Ile Leu Gly
145                 150                 155                 160

Cys Ala Pro Ala Ile Gly Glu His Trp Ala Lys Gly Thr Ala Cys Lys
                165                 170                 175

Ser Arg Pro Leu Ser Gln Gly Asp Cys Pro Pro Leu Glu Leu Lys Asn
            180                 185                 190

Thr Val Leu Glu Asp Gly Asp Met Val Asp Thr Gly Tyr Gly Ala Met
        195                 200                 205

Asp Phe Ser Thr Leu Gln Asp Thr Lys Cys Glu Val Pro Leu Asp Ile
    210                 215                 220

Cys Gln Ser Ile Cys Lys Tyr Pro Asp Tyr Leu Gln Met Ser Ala Asp
225                 230                 235                 240

Pro Tyr Gly Asp Ser Met Phe Phe Cys Leu Arg Arg Glu Gln Leu Phe
                245                 250                 255

Ala Arg His Phe Trp Asn Arg Ala Gly Thr Met Gly Asp Thr Val Pro
            260                 265                 270

Gln Ser Leu Tyr Ile Lys Gly Thr Gly Met Arg Ala Ser Pro Gly Ser
        275                 280                 285

Cys Val Tyr Ser Pro Ser Pro Ser Gly Ser Ile Val Thr Ser Asp Ser
    290                 295                 300

Gln Leu Phe Asn Lys Pro Tyr Trp Leu His Lys Ala Gln Gly His Asn
305                 310                 315                 320

Asn Gly Val Cys Trp His Asn Gln Leu Phe Val Thr Val Val Asp Thr
                325                 330                 335

Thr Arg Ser Thr Asn Leu Thr Ile Cys Ala Ser Thr Gln Ser Pro Val
            340                 345                 350

Pro Gly Gln Tyr Asp Ala Thr Lys Phe Lys Gln Tyr Ser Arg His Val
        355                 360                 365

Glu Glu Tyr Asp Leu Gln Phe Ile Phe Gln Leu Cys Thr Ile Thr Leu
    370                 375                 380

Thr Ala Asp Val Met Ser Tyr Ile His Ser Met Asn Ser Ser Ile Leu
385                 390                 395                 400

Glu Asp Trp Asn Phe Gly Val Pro Pro Pro Pro Thr Thr Ser Leu Val
                405                 410                 415

Asp Thr Tyr Arg Phe Val Gln Ser Val Ala Ile Thr Cys Gln Lys Asp
            420                 425                 430

Ala Ala Pro Ala Glu Asn Lys Asp Pro Tyr Asp Lys Leu Lys Phe Trp
        435                 440                 445
```

-continued

```
Asn Val Asp Leu Lys Glu Lys Phe Ser Leu Asp Leu Asp Gln Tyr Pro
    450                 455                 460

Leu Gly Arg Lys Phe Leu Lys Ala Lys Pro Lys Leu Lys Arg Ala Ala
465                 470                 475                 480

Pro Thr Ser Thr Arg Thr Ser Ser Ala Lys Arg Lys Lys Val Lys Lys
                485                 490                 495
```

<210> SEQ ID NO 43
<211> LENGTH: 1492
<212> TYPE: DNA
<213> ORGANISM: Artificial sequence
<220> FEATURE:
<223> OTHER INFORMATION: 1804 Nucleotide sequence of chimeric HPV type 18 L1 protein

<400> SEQUENCE: 43

```
atggccctct ggagaccatc cgataacaca gtgtacttgc ccccacccag cgtcgcccgg      60

gtggtgaaca cagacgacta cgtcaccaga acctcaatct tctaccacgc cgggtccagc     120

cggctgctga ccgtgggcaa cccctacttc cgcgtgcccg ccggcggcgg aaacaaacaa     180

gacatcccca aagtcagcgc ctatcagtac cgggtgttcc gcgtccaact gcccgatccc     240

aacaagttcg gcctgcccga cacctccatc tacaaccccg agacccagag gctggtctgg     300

gcttgcgccg gcgtcgagat cgggaggggc caacccctgg gcgtggggtt gtccggccac     360

cccttctaca acaagctgga cgataccgag tccagccacg cagcaaccag caacgtctcc     420

gaagatgtgc gcgataacgt cagcgtggac tacaaacaaa cccaactgtg catcctggga     480

tgcgcacccg ccatcggcga gcattgggcc aaggggaccg cctgcaagag caggcccctg     540

agccaagggg actgtccacc cctggagttg aagaataccg tgctcgagga cggcgacatg     600

gtggacaccg gctacggcgc tatggatttc tccaccctcc aggacaccaa gtgcgaagtg     660

cccctcgaca tctgccaaag catctgcaag taccccgact acctccagat gagcgccgac     720

ccctacggcg acagcatgtt cttctgtctc agaagggaac aattgttcgc ccgccacttc     780

tggaaccggg ccggcacaat gggagataca gtcccccaga gcctgtacat caaggggacc     840

ggaatgaggg ccagccccgg gtcctgcgtc tacagcccaa gcccctccgg gagcatcgtc     900

acaagcgata gccaactctt caacaagccc tactggctcc acaaagccca aggccacaat     960

aacggggtgt gttggcacaa ccagctgttc gtgaccgtcg tggacacaac caggtccaca    1020

aacctgacca tctgcgccag cacccaaagc cccgtgcccg gccagtacga cgccacaaag    1080

ttcaaacaat actctcggca cgtggaagag tacgacctcc aattcatctt ccaactctgc    1140

accatcaccc tcaccgccga cgtgatgagc tacatccact ccatgaactc ctccatcctg    1200

gaagactgga atttcggcgt gccaccaccc cctaccacct ccctcgtcga cacctacaga    1260

ttcgtgcaga gcgtggccat cacatgccag aaagacgccg cccccgccga gaacaaagac    1320

ccatacgaca aactgaaatt ctggaacgtc gacctgaaag agaaattcag cctggatctg    1380

gaccagtacc cattgggcag gaagttcctc aaagccaagc caaaactgaa aagggctgcc    1440

ccaaccagca ccaggacctc ctctgccaag aggaagaagg tgaagaagta aa            1492
```

<210> SEQ ID NO 44
<211> LENGTH: 1543
<212> TYPE: DNA
<213> ORGANISM: Artificial sequence
<220> FEATURE:
<223> OTHER INFORMATION: 1805 Synthetic HPV18 L1 gene

<400> SEQUENCE: 44

```
ctgggtacca tggccctctg gagaccatcc gataacacag tgtacttgcc cccacccagc     60

gtcgcccggg tggtgaacac agacgactac gtcaccagaa cctcaatctt ctaccacgcc    120

gggtccagcc ggctgctgac cgtgggcaac ccctacttcc gcgtgcccgc cggcggcgga    180

aacaaacaag acatccccaa agtcagcgcc tatcagtacc gggtgttccg cgtccaactg    240

cccgatccca acaagttcgg cctgcccgac acctccatct acaaccccga gacccagagg    300

ctggtctggg cttgcgccgg cgtcgagatc gggaggggcc aacccctggg cgtggggttg    360

tccggccacc ccttctacaa caagctggac gataccgagt ccagccacgc agcaaccagc    420

aacgtctccg aagatgtgcg cgataacgtc agcgtggact acaaacaaac ccaactgtgc    480

atcctgggat gcgcacccgc catcggcgag cattgggcca aggggaccgc ctgcaagagc    540

aggcccctga gccaagggga ctgtccaccc ctggagttga agaataccgt gctcgaggac    600

ggcgacatgg tggacaccgg ctacggcgct atggatttct ccaccctcca ggacaccaag    660

tgcgaagtgc ccctcgacat ctgccaaagc atctgcaagt accccgacta cctccagatg    720

agcgccgacc cctacggcga cagcatgttc ttctgtctca gaagggaaca attgttcgcc    780

cgccacttct ggaaccgggc cggcacaatg ggagatacag tcccccagag cctgtacatc    840

aaggggaccg gaatgagggc cagcccccggg tcctgcgtct acagcccaag cccctccggg    900

agcatcgtca caagcgatag ccaactcttc aacaagccct actggctcca caaagcccaa    960

ggccacaata acggggtgtg ttggcacaac cagctgttcg tgaccgtcgt ggacacaacc   1020

aggtccacaa acctgaccat ctgcgccagc acccaaagcc ccgtgcccgg ccagtacgac   1080

gccacaaagt tcaaacaata ctctcggcac gtggaagagt acgacctcca attcatcttc   1140

caactctgca ccatcaccct caccgccgac gtgatgagct acatccactc catgaactcc   1200

tccatcctgg aagactggaa tttcggcgtg ccaccacccc ctaccacctc cctcgtcgac   1260

acctacagat tcgtgcagag cgtggccatc acatgccaga aagacgccgc ccccgccgag   1320

aacaaagacc catacgacaa actgaaattc tggaacgtcg acctgaaaga gaaattcagc   1380

ctggatctgg accagtaccc attgggcagg aagttcctcg tgcaagccgg cctcaggaga   1440

aaaccaacaa tcgggcccag gaagaggagc gcccccagcg caaccaccag cagcaagccc   1500

gcaaaaaggg tcagagtgag ggcacgcaaa taaactcgag ctc                     1543
```

```
<210> SEQ ID NO 45
<211> LENGTH: 1519
<212> TYPE: DNA
<213> ORGANISM: Artificial sequence
<220> FEATURE:
<223> OTHER INFORMATION: 1806 Synthetic HPV33 L1 gene

<400> SEQUENCE: 45

ctgggtacca tgagtgtgtg gagaccatct gaggctacag tctacctgcc tcctgtgcct     60

gtgagcaagg tggtgagcac agatgaatat gtgagcagga ccagcatcta ctactatgct    120

ggctccagca gactgctggc tgtgggacac ccatacttca gcatcaagaa cccaaccaat    180

gccaagaaac tgctggtgcc aaaggtgtct ggactccaat acagggtgtt cagggtgaga    240

ctgcctgacc caaacaagtt tggctttcct gacacctcct tctacaaccc tgacacccag    300

agactggtgt gggcttgtgt gggattggag attggcaggg gacaaccact gggagtgggc    360

atctctggac acccactgct gaacaagttt gatgacacag agacaggcaa caaataccct    420

ggacaacctg gagcagacaa cagggagtgt ctgagtatgg actacaagca gacccaactt    480
```

-continued

```
tgtctgctgg gctgtaagcc tccaacagga gaacactggg gcaagggagt ggcttgtacc    540

aatgctgccc ctgccaatga ctgtcctcca ttggaactga taaacaccat cattgaggat    600

ggagatatgg tggacacagg ctttggctgt atggacttca agaccctcca agccaacaag    660

tctgatgtgc caattgacat ctgtggcagc acttgtaaat accctgacta cctgaaaatg    720

acctctgaac catatggaga ctccctgttc ttcttcctga ggagggaaca gatgtttgtg    780

agacacttct tcaacagggc tggcaccctg ggagaggctg tgcctgatga cctctacatc    840

aagggctctg gcaccacagc cagcatccag tcctctgcct tctttccaac accatctggc    900

agtatggtga cctctgagag ccaacttttc aacaagccat actggctcca aagggctcaa    960

ggacacaaca atggcatctg ttggggcaac caggtgtttg tgacagtggt ggacaccacc   1020

aggagcacca atatgaccct gtgtacccag gtgacctctg acagcaccta caagaatgag   1080

aacttcaagg aatacatcag gcatgtggag gaatatgacc tccaatttgt gttccaactt   1140

tgtaaggtga ccctgacagc agaggtgatg acctacatcc atgctatgaa ccctgacatc   1200

ttggaggact ggcagtttgg actgacacct cctccatctg cctccctcca agacacctac   1260

aggtttgtga ccagccaggc tatcacttgt cagaagacag tgcctccaaa ggagaaggag   1320

gacccactgg gcaaatacac cttctgggag gtggacctga aagagaagtt ctctgctgac   1380

ctggaccagt ttccactggg caggaagttc ctgctccaag caggactgaa agccaagcca   1440

aaactgaaaa gggctgcccc aaccagcacc aggacctcct ctgccaagag gaagaaggtg   1500

aagaagtaaa ctcgagctc                                                1519
```

```
<210> SEQ ID NO 46
<211> LENGTH: 34
<212> TYPE: DNA
<213> ORGANISM: Artificial sequence
<220> FEATURE:
<223> OTHER INFORMATION: 1807 HPV18L1 F1

<400> SEQUENCE: 46

cttggtacca tggccctctg gagaccatcc gata                                 34


<210> SEQ ID NO 47
<211> LENGTH: 35
<212> TYPE: DNA
<213> ORGANISM: Artificial sequence
<220> FEATURE:
<223> OTHER INFORMATION: 1808 HPV18L1 R1

<400> SEQUENCE: 47

gcttggcttt gaggaacttc ctgcccaatg ggtac                                35


<210> SEQ ID NO 48
<211> LENGTH: 1429
<212> TYPE: DNA
<213> ORGANISM: Artificial sequence
<220> FEATURE:
<223> OTHER INFORMATION: 1809 HPV18L1 amplified sequence 1

<400> SEQUENCE: 48

cttggtacca tggccctctg gagaccatcc gataacacag tgtacttgcc cccacccagc     60

gtcgcccggg tggtgaacac agacgactac gtcaccagaa cctcaatctt ctaccacgcc    120

gggtccagcc ggctgctgac cgtgggcaac ccctacttcc gcgtgcccgc cggcggcgga    180

aacaaacaag acatccccaa agtcagcgcc tatcagtacc gggtgttccg cgtccaactg    240

cccgatccca acaagttcgg cctgcccgac acctccatct acaaccccga gacccagagg    300
```

-continued ctggtctggg cttgcgccgg cgtcgagatc gggaggggcc aacccctggg cgtggggttg 360
tccggccacc ccttctacaa caagctggac gataccgagt ccagccacgc agcaaccagc 420
aacgtctccg aagatgtgcg cgataacgtc agcgtggact acaaacaaac ccaactgtgc 480
atcctgggat gcgcacccgc catcggcgag cattgggcca aggggaccgc ctgcaagagc 540
aggcccctga gccaagggga ctgtccaccc ctggagttga agaataccgt gctcgaggac 600
ggcgacatgg tggacaccgg ctacggcgct atggatttct ccaccctcca ggacaccaag 660
tgcgaagtgc ccctcgacat ctgccaaagc atctgcaagt accccgacta cctccagatg 720
agcgccgacc cctacggcga cagcatgttc ttctgtctca gaagggaaca attgttcgcc 780
cgccacttct ggaaccgggc cggcacaatg ggagatacag tcccccagag cctgtacatc 840
aaggggaccg gaatgagggc cagcccccggg tcctgcgtct acagcccaag cccctccggg 900
agcatcgtca caagcgatag ccaactcttc aacaagccct actggctcca caaagcccaa 960
ggccacaata acggggtgtg ttggcacaac cagctgttcg tgaccgtcgt ggacacaacc 1020
aggtccacaa acctgaccat ctgcgccagc acccaaagcc ccgtgcccgg ccagtacgac 1080
gccacaaagt tcaaacaata ctctcggcac gtggaagagt acgacctcca attcatcttc 1140
caactctgca ccatcaccct caccgccgac gtgatgagct acatccactc catgaactcc 1200
tccatcctgg aagactggaa tttcggcgtg ccaccacccc ctaccacctc cctcgtcgac 1260
acctacagat tcgtgcagag cgtggccatc acatgccaga aagacgccgc ccccgccgag 1320
aacaaagacc catacgacaa actgaaattc tggaacgtcg acctgaaaga gaaattcagc 1380
ctggatctgg accagtaccc attgggcagg aagttcctca aagccaagc 1429

<210> SEQ ID NO 49
<211> LENGTH: 35
<212> TYPE: DNA
<213> ORGANISM: Artificial sequence
<220> FEATURE:
<223> OTHER INFORMATION: 1810 HPV18L1 F2

<400> SEQUENCE: 49
gaagttcctc aaagccaagc caaaactgaa aaggg 35

<210> SEQ ID NO 50
<211> LENGTH: 36
<212> TYPE: DNA
<213> ORGANISM: Artificial sequence
<220> FEATURE:
<223> OTHER INFORMATION: 1811 HPV18L1 R2

<400> SEQUENCE: 50
ctgtctagat ttacttcttc accttcttcc tcttgg 36

<210> SEQ ID NO 51
<211> LENGTH: 101
<212> TYPE: DNA
<213> ORGANISM: Artificial sequence
<220> FEATURE:
<223> OTHER INFORMATION: 1812 HPV18L1 amplified sequence 2

<400> SEQUENCE: 51
gaagttcctc aaagccaagc caaaactgaa aagggctgcc ccaaccagca ccaggacctc 60
ctctgccaag aggaagaagg tgaagaagta aatctagaca g 101

<210> SEQ ID NO 52

<211> LENGTH: 38
<212> TYPE: PRT
<213> ORGANISM: Homo sapiens
<220> FEATURE:
<221> NAME/KEY: misc_feature
<223> OTHER INFORMATION: 1813 Amino acid sequence of HPV type 59 L1
protein aa 471-508

<400> SEQUENCE: 52

```
Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35
```

<210> SEQ ID NO 53
<211> LENGTH: 475
<212> TYPE: PRT
<213> ORGANISM: Homo sapiens
<220> FEATURE:
<221> NAME/KEY: misc_feature
<223> OTHER INFORMATION: 3101 Amino acid sequence of HPV type 31 L1
protein aa 1-475

<400> SEQUENCE: 53

```
Met Ser Leu Trp Arg Pro Ser Glu Ala Thr Val Tyr Leu Pro Pro Val
1               5                   10                  15

Pro Val Ser Lys Val Val Ser Thr Asp Glu Tyr Val Thr Arg Thr Asn
            20                  25                  30

Ile Tyr Tyr His Ala Gly Ser Ala Arg Leu Leu Thr Val Gly His Pro
        35                  40                  45

Tyr Tyr Ser Ile Pro Lys Ser Asp Asn Pro Lys Lys Ile Val Val Pro
    50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Glu Thr
                85                  90                  95

Gln Arg Leu Val Trp Ala Cys Val Gly Leu Glu Val Gly Arg Gly Gln
            100                 105                 110

Pro Leu Gly Val Gly Ile Ser Gly His Pro Leu Leu Asn Lys Phe Asp
        115                 120                 125

Asp Thr Glu Asn Ser Asn Arg Tyr Ala Gly Gly Pro Gly Thr Asp Asn
    130                 135                 140

Arg Glu Cys Ile Ser Met Asp Tyr Lys Gln Thr Gln Leu Cys Leu Leu
145                 150                 155                 160

Gly Cys Lys Pro Pro Ile Gly Glu His Trp Gly Lys Gly Ser Pro Cys
                165                 170                 175

Ser Asn Asn Ala Ile Thr Pro Gly Asp Cys Pro Pro Leu Glu Leu Lys
            180                 185                 190

Asn Ser Val Ile Gln Asp Gly Asp Met Val Asp Thr Gly Phe Gly Ala
        195                 200                 205

Met Asp Phe Thr Ala Leu Gln Asp Thr Lys Ser Asn Val Pro Leu Asp
    210                 215                 220

Ile Cys Asn Ser Ile Cys Lys Tyr Pro Asp Tyr Leu Lys Met Val Ala
225                 230                 235                 240

Glu Pro Tyr Gly Asp Thr Leu Phe Phe Tyr Leu Arg Arg Glu Gln Met
                245                 250                 255
```

```
Phe Val Arg His Phe Phe Asn Arg Ser Gly Thr Val Gly Glu Ser Val
            260                 265                 270

Pro Thr Asp Leu Tyr Ile Lys Gly Ser Gly Ser Thr Ala Thr Leu Ala
        275                 280                 285

Asn Ser Thr Tyr Phe Pro Thr Pro Ser Gly Ser Met Val Thr Ser Asp
    290                 295                 300

Ala Gln Ile Phe Asn Lys Pro Tyr Trp Met Gln Arg Ala Gln Gly His
305                 310                 315                 320

Asn Asn Gly Ile Cys Trp Gly Asn Gln Leu Phe Val Thr Val Val Asp
                325                 330                 335

Thr Thr Arg Ser Thr Asn Met Ser Val Cys Ala Ala Ile Ala Asn Ser
            340                 345                 350

Asp Thr Thr Phe Lys Ser Ser Asn Phe Lys Glu Tyr Leu Arg His Gly
        355                 360                 365

Glu Glu Phe Asp Leu Gln Phe Ile Phe Gln Leu Cys Lys Ile Thr Leu
    370                 375                 380

Ser Ala Asp Ile Met Thr Tyr Ile His Ser Met Asn Pro Ala Ile Leu
385                 390                 395                 400

Glu Asp Trp Asn Phe Gly Leu Thr Thr Pro Pro Ser Gly Ser Leu Glu
                405                 410                 415

Asp Thr Tyr Arg Phe Val Thr Ser Gln Ala Ile Thr Cys Gln Lys Ser
            420                 425                 430

Ala Pro Gln Lys Pro Lys Glu Asp Pro Phe Lys Asp Tyr Val Phe Trp
        435                 440                 445

Glu Val Asn Leu Lys Glu Lys Phe Ser Ala Asp Leu Asp Gln Phe Pro
    450                 455                 460

Leu Gly Arg Lys Phe Leu Leu Gln Ala Gly Tyr
465                 470                 475
```

<210> SEQ ID NO 54
<211> LENGTH: 26
<212> TYPE: PRT
<213> ORGANISM: Homo sapiens
<220> FEATURE:
<221> NAME/KEY: misc_feature
<223> OTHER INFORMATION: 3102 Amino acid sequence of HPV type 33 L1 protein aa 474-499

<400> SEQUENCE: 54

```
Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25
```

<210> SEQ ID NO 55
<211> LENGTH: 501
<212> TYPE: PRT
<213> ORGANISM: Artificial sequence
<220> FEATURE:
<223> OTHER INFORMATION: 3103 Amino acid sequence of chimeric HPV type 31 L1 protein

<400> SEQUENCE: 55

```
Met Ser Leu Trp Arg Pro Ser Glu Ala Thr Val Tyr Leu Pro Pro Val
1               5                   10                  15

Pro Val Ser Lys Val Val Ser Thr Asp Glu Tyr Val Thr Arg Thr Asn
            20                  25                  30

Ile Tyr Tyr His Ala Gly Ser Ala Arg Leu Leu Thr Val Gly His Pro
        35                  40                  45
```

-continued

```
Tyr Tyr Ser Ile Pro Lys Ser Asp Asn Pro Lys Lys Ile Val Val Pro
    50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Glu Thr
                85                  90                  95

Gln Arg Leu Val Trp Ala Cys Val Gly Leu Glu Val Gly Arg Gly Gln
            100                 105                 110

Pro Leu Gly Val Gly Ile Ser Gly His Pro Leu Leu Asn Lys Phe Asp
        115                 120                 125

Asp Thr Glu Asn Ser Asn Arg Tyr Ala Gly Gly Pro Gly Thr Asp Asn
    130                 135                 140

Arg Glu Cys Ile Ser Met Asp Tyr Lys Gln Thr Gln Leu Cys Leu Leu
145                 150                 155                 160

Gly Cys Lys Pro Pro Ile Gly Glu His Trp Gly Lys Gly Ser Pro Cys
                165                 170                 175

Ser Asn Asn Ala Ile Thr Pro Gly Asp Cys Pro Pro Leu Glu Leu Lys
            180                 185                 190

Asn Ser Val Ile Gln Asp Gly Asp Met Val Asp Thr Gly Phe Gly Ala
        195                 200                 205

Met Asp Phe Thr Ala Leu Gln Asp Thr Lys Ser Asn Val Pro Leu Asp
    210                 215                 220

Ile Cys Asn Ser Ile Cys Lys Tyr Pro Asp Tyr Leu Lys Met Val Ala
225                 230                 235                 240

Glu Pro Tyr Gly Asp Thr Leu Phe Phe Tyr Leu Arg Arg Glu Gln Met
                245                 250                 255

Phe Val Arg His Phe Phe Asn Arg Ser Gly Thr Val Gly Glu Ser Val
            260                 265                 270

Pro Thr Asp Leu Tyr Ile Lys Gly Ser Gly Ser Thr Ala Thr Leu Ala
        275                 280                 285

Asn Ser Thr Tyr Phe Pro Thr Pro Ser Gly Ser Met Val Thr Ser Asp
    290                 295                 300

Ala Gln Ile Phe Asn Lys Pro Tyr Trp Met Gln Arg Ala Gln Gly His
305                 310                 315                 320

Asn Asn Gly Ile Cys Trp Gly Asn Gln Leu Phe Val Thr Val Val Asp
                325                 330                 335

Thr Thr Arg Ser Thr Asn Met Ser Val Cys Ala Ala Ile Ala Asn Ser
            340                 345                 350

Asp Thr Thr Phe Lys Ser Ser Asn Phe Lys Glu Tyr Leu Arg His Gly
        355                 360                 365

Glu Glu Phe Asp Leu Gln Phe Ile Phe Gln Leu Cys Lys Ile Thr Leu
    370                 375                 380

Ser Ala Asp Ile Met Thr Tyr Ile His Ser Met Asn Pro Ala Ile Leu
385                 390                 395                 400

Glu Asp Trp Asn Phe Gly Leu Thr Thr Pro Pro Ser Gly Ser Leu Glu
                405                 410                 415

Asp Thr Tyr Arg Phe Val Thr Ser Gln Ala Ile Thr Cys Gln Lys Ser
            420                 425                 430

Ala Pro Gln Lys Pro Lys Glu Asp Pro Phe Lys Asp Tyr Val Phe Trp
        435                 440                 445

Glu Val Asn Leu Lys Glu Lys Phe Ser Ala Asp Leu Asp Gln Phe Pro
    450                 455                 460
```

```
Leu Gly Arg Lys Phe Leu Leu Gln Ala Gly Tyr Lys Ala Lys Pro Lys
465                 470                 475                 480

Leu Lys Arg Ala Ala Pro Thr Ser Thr Arg Thr Ser Ser Ala Lys Arg
                485                 490                 495

Lys Lys Val Lys Lys
            500


<210> SEQ ID NO 56
<211> LENGTH: 1507
<212> TYPE: DNA
<213> ORGANISM: Artificial sequence
<220> FEATURE:
<223> OTHER INFORMATION: 3104 Nucleotide sequence of chimeric HPV type
      31 L1 protein

<400> SEQUENCE: 56

atgagcctgt ggaggcccag cgaggccacc gtgtacctgc cccccgtgcc cgtgagcaag      60

gtggtgagca ccgacgagta cgtgaccagg accaacatct actaccacgc cggcagcgcc     120

aggctgctga ccgtgggcca cccctactac agcatcccca agagcgacaa ccccaagaag     180

atcgtggtgc ccaaggtgag cggcctgcag tacagggtgt tcagggtgag gctgcccgac     240

cccaacaagt tcggcttccc cgacaccagc ttctacaacc ccgagaccca gaggctggtg     300

tgggcctgcg tgggcctgga ggtgggcagg ggccagcccc tgggcgtggg catcagcggc     360

cacccccctgc tgaacaagtt cgacgacacc gagaacagca acaggtacgc cggcggcccc     420

ggcaccgaca acagggagtg catcagcatg gactacaagc agacccagct gtgcctgctg     480

ggctgcaagc cccccatcgg cgagcactgg ggcaagggca gcccctgcag caacaacgcc     540

atcacccccg gcgactgccc ccccctggag ctgaagaaca gcgtgatcca ggacggcgac     600

atggtggaca ccggcttcgg cgccatggac ttcaccgccc tgcaggacac caagagcaac     660

gtgcccctgg acatctgcaa cagcatctgc aagtaccccg actacctgaa gatggtggcc     720

gagccctacg gcgacaccct gttcttctac ctgaggaggg agcagatgtt cgtgaggcac     780

ttcttcaaca ggagcggcac cgtgggcgag agcgtgccca ccgacctgta catcaagggc     840

agcggcagca ccgccaccct ggccaacagc acctacttcc ccacccccag cggcagcatg     900

gtgaccagcg acgcccagat cttcaacaag ccctactgga tgcagagggc ccagggccac     960

aacaacggca tctgctgggg caaccagctg ttcgtgaccg tggtggacac caccaggagc    1020

accaacatga gcgtgtgcgc cgccatcgcc aacagcgaca ccaccttcaa gagcagcaac    1080

ttcaaggagt acctgaggca cggcgaggag ttcgacctgc agttcatctt ccagctgtgc    1140

aagatcaccc tgagcgccga catcatgacc tacatccaca gcatgaaccc cgccatcctg    1200

gaggactgga acttcggcct gaccaccccc cccagcggca gcctggagga cacctacagg    1260

ttcgtgacca gccaggccat cacctgccag aagtccgccc cccagaagcc caaggaggac    1320

cccttcaagg actacgtgtt ctgggaggtg aacctgaagg agaagttcag cgccgacctg    1380

gaccagttcc ccctgggcag gaagttcctg ctgcaggccg gctacaaagc caagccaaaa    1440

ctgaaaaggg ctgccccaac cagcaccagg acctcctctg ccaagaggaa gaaggtgaag    1500

aagtaaa                                                              1507


<210> SEQ ID NO 57
<211> LENGTH: 1534
<212> TYPE: DNA
<213> ORGANISM: Artificial sequence
<220> FEATURE:
<223> OTHER INFORMATION: 3105 Synthetic HPV31 L1 gene
```

<400> SEQUENCE: 57
ctgggtacca tgagcctgtg gaggcccagc gaggccaccg tgtacctgcc ccccgtgccc 60
gtgagcaagg tggtgagcac cgacgagtac gtgaccagga ccaacatcta ctaccacgcc 120
ggcagcgcca ggctgctgac cgtgggccac ccctactaca gcatccccaa gagcgacaac 180
cccaagaaga tcgtggtgcc caaggtgagc ggcctgcagt acagggtgtt cagggtgagg 240
ctgcccgacc ccaacaagtt cggcttcccc gacaccagct tctacaaccc cgagacccag 300
aggctggtgt gggcctgcgt gggcctggag gtgggcaggg gccagcccct gggcgtgggc 360
atcagcggcc accccctgct gaacaagttc gacgacaccg agaacagcaa caggtacgcc 420
ggcggccccg gcaccgacaa cagggagtgc atcagcatgg actacaagca gacccagctg 480
tgcctgctgg gctgcaagcc ccccatcggc gagcactggg gcaagggcag cccctgcagc 540
aacaacgcca tcacccccgg cgactgcccc cccctggagc tgaagaacag cgtgatccag 600
gacggcgaca tggtggacac cggcttcggc gccatggact tcaccgccct gcaggacacc 660
aagagcaacg tgcccctgga catctgcaac agcatctgca agtaccccga ctacctgaag 720
atggtggccg agccctacgg cgacaccctg ttcttctacc tgaggaggga gcagatgttc 780
gtgaggcact tcttcaacag gagcggcacc gtgggcgaga gcgtgcccac cgacctgtac 840
atcaagggca gcggcagcac cgccaccctg gccaacagca cctacttccc cacccccagc 900
ggcagcatgg tgaccagcga cgcccagatc ttcaacaagc cctactggat gcagagggcc 960
cagggccaca acaacggcat ctgctggggc aaccagctgt tcgtgaccgt ggtggacacc 1020
accaggagca ccaacatgag cgtgtgcgcc gccatcgcca acagcgacac caccttcaag 1080
agcagcaact tcaaggagta cctgaggcac ggcgaggagt tcgacctgca gttcatcttc 1140
cagctgtgca agatcaccct gagcgccgac atcatgacct acatccacag catgaacccc 1200
gccatcctgg aggactggaa cttcggcctg accaccccc ccagcggcag cctggaggac 1260
acctacaggt tcgtgaccag ccaggccatc acctgccaga agtccgcccc ccagaagccc 1320
aaggaggacc ccttcaagga ctacgtgttc tgggaggtga acctgaagga gaagttcagc 1380
gccgacctgg accagttccc cctgggcagg aagttcctgc tgcaggccgg ctacagggcc 1440
aggcccaagt tcaaggccgg caagaggagc gcccccagcg ccagcaccac cacccccgcc 1500
aagaggaaga agaccaagaa gtaaactcga gctc 1534

<210> SEQ ID NO 58
<211> LENGTH: 1519
<212> TYPE: DNA
<213> ORGANISM: Artificial sequence
<220> FEATURE:
<223> OTHER INFORMATION: 3106 Synthetic HPV33 L1 gene

<400> SEQUENCE: 58
ctgggtacca tgagtgtgtg gagaccatct gaggctacag tctacctgcc tcctgtgcct 60
gtgagcaagg tggtgagcac agatgaatat gtgagcagga ccagcatcta ctactatgct 120
ggctccagca gactgctggc tgtgggacac ccatacttca gcatcaagaa cccaaccaat 180
gccaagaaac tgctggtgcc aaaggtgtct ggactccaat acagggtgtt cagggtgaga 240
ctgcctgacc caaacaagtt tggctttcct gacacctcct tctacaaccc tgacacccag 300
agactggtgt gggcttgtgt gggattggag attggcaggg gacaaccact gggagtgggc 360
atctctggac acccactgct gaacaagttt gatgacacag agacaggcaa caaataccct 420

-continued

```
ggacaacctg gagcagacaa cagggagtgt ctgagtatgg actacaagca gacccaactt    480

tgtctgctgg gctgtaagcc tccaacagga gaacactggg gcaagggagt ggcttgtacc    540

aatgctgccc ctgccaatga ctgtcctcca ttggaactga taaacaccat cattgaggat    600

ggagatatgg tggacacagg ctttggctgt atggacttca agaccctcca agccaacaag    660

tctgatgtgc caattgacat ctgtggcagc acttgtaaat accctgacta cctgaaaatg    720

acctctgaac catatggaga ctccctgttc ttcttcctga ggagggaaca gatgtttgtg    780

agacacttct tcaacagggc tggcaccctg ggagaggctg tgcctgatga cctctacatc    840

aagggctctg gcaccacagc cagcatccag tcctctgcct tctttccaac accatctggc    900

agtatggtga cctctgagag ccaacttttc aacaagccat actggctcca aagggctcaa    960

ggacacaaca atggcatctg ttggggcaac caggtgtttg tgacagtggt ggacaccacc   1020

aggagcacca atatgaccct gtgtacccag gtgacctctg acagcaccta caagaatgag   1080

aacttcaagg aatacatcag gcatgtggag gaatatgacc tccaatttgt gttccaactt   1140

tgtaaggtga ccctgacagc agaggtgatg acctacatcc atgctatgaa ccctgacatc   1200

ttggaggact ggcagtttgg actgacacct cctccatctg cctccctcca agacacctac   1260

aggtttgtga ccagccaggc tatcacttgt cagaagacag tgcctccaaa ggagaaggag   1320

gacccactgg gcaaatacac cttctgggag gtggacctga aagagaagtt ctctgctgac   1380

ctggaccagt ttccactggg caggaagttc ctgctccaag caggactgaa agccaagcca   1440

aaactgaaaa gggctgcccc aaccagcacc aggacctcct ctgccaagag gaagaaggtg   1500

aagaagtaaa ctcgagctc                                                1519
```

<210> SEQ ID NO 59
<211> LENGTH: 33
<212> TYPE: DNA
<213> ORGANISM: Artificial sequence
<220> FEATURE:
<223> OTHER INFORMATION: 3107 HPV31L1 F1

<400> SEQUENCE: 59

```
cttggtacca tgagcctgtg gaggcccagc gag                                  33
```

<210> SEQ ID NO 60
<211> LENGTH: 38
<212> TYPE: DNA
<213> ORGANISM: Artificial sequence
<220> FEATURE:
<223> OTHER INFORMATION: 3108 HPV31L1 R1

<400> SEQUENCE: 60

```
gcttggcttt gtagccggcc tgcagcagga acttcctg                             38
```

<210> SEQ ID NO 61
<211> LENGTH: 1444
<212> TYPE: DNA
<213> ORGANISM: Artificial sequence
<220> FEATURE:
<223> OTHER INFORMATION: 3109 HPV31L1 amplified sequence 1

<400> SEQUENCE: 61

```
cttggtacca tgagcctgtg gaggcccagc gaggccaccg tgtacctgcc ccccgtgccc     60

gtgagcaagg tggtgagcac cgacgagtac gtgaccagga ccaacatcta ctaccacgcc    120

ggcagcgcca ggctgctgac cgtgggccac ccctactaca gcatccccaa gagcgacaac    180

cccaagaaga tcgtggtgcc caaggtgagc ggcctgcagt acagggtgtt cagggtgagg    240
```

```
ctgcccgacc ccaacaagtt cggcttcccc gacaccagct tctacaaccc cgagacccag    300

aggctggtgt gggcctgcgt gggcctggag gtgggcaggg gccagcccct gggcgtgggc    360

atcagcggcc accccctgct gaacaagttc gacgacaccg agaacagcaa caggtacgcc    420

ggcggccccg gcaccgacaa cagggagtgc atcagcatgg actacaagca gacccagctg    480

tgcctgctgg gctgcaagcc ccccatcggc gagcactggg gcaagggcag cccctgcagc    540

aacaacgcca tcacccccgg cgactgcccc cccctggagc tgaagaacag cgtgatccag    600

gacggcgaca tggtggacac cggcttcggc gccatggact tcaccgccct gcaggacacc    660

aagagcaacg tgcccctgga catctgcaac agcatctgca agtaccccga ctacctgaag    720

atggtggccg agccctacgg cgacaccctg ttcttctacc tgaggaggga gcagatgttc    780

gtgaggcact tcttcaacag gagcggcacc gtgggcgaga gcgtgcccac cgacctgtac    840

atcaagggca gcggcagcac cgccaccctg gccaacagca cctacttccc cacccccagc    900

ggcagcatgg tgaccagcga cgcccagatc ttcaacaagc cctactggat gcagagggcc    960

cagggccaca acaacggcat ctgctggggc aaccagctgt tcgtgaccgt ggtggacacc   1020

accaggagca ccaacatgag cgtgtgcgcc gccatcgcca acagcgacac caccttcaag   1080

agcagcaact tcaaggagta cctgaggcac ggcgaggagt tcgacctgca gttcatcttc   1140

cagctgtgca agatcaccct gagcgccgac atcatgacct acatccacag catgaacccc   1200

gccatcctgg aggactggaa cttcggcctg accaccccc  ccagcggcag cctggaggac   1260

acctacaggt tcgtgaccag ccaggccatc acctgccaga agtccgcccc ccagaagccc   1320

aaggaggacc ccttcaagga ctacgtgttc tgggaggtga acctgaagga gaagttcagc   1380

gccgacctgg accagttccc cctgggcagg aagttcctgc tgcaggccgg ctacaaagcc   1440

aagc                                                                1444
```

<210> SEQ ID NO 62
<211> LENGTH: 35
<212> TYPE: DNA
<213> ORGANISM: Artificial sequence
<220> FEATURE:
<223> OTHER INFORMATION: 3110 HPV31L1 F2

<400> SEQUENCE: 62

```
ggccggctac aaagccaagc caaaactgaa aaggg                                35
```

<210> SEQ ID NO 63
<211> LENGTH: 41
<212> TYPE: DNA
<213> ORGANISM: Artificial sequence
<220> FEATURE:
<223> OTHER INFORMATION: 3111 HPV31L1 R2

<400> SEQUENCE: 63

```
ctgtctagat ttacttcttc accttcttcc tcttggcaga g                         41
```

<210> SEQ ID NO 64
<211> LENGTH: 101
<212> TYPE: DNA
<213> ORGANISM: Artificial sequence
<220> FEATURE:
<223> OTHER INFORMATION: 3112 HPV31L1 amplified sequence 2

<400> SEQUENCE: 64

```
ggccggctac aaagccaagc caaaactgaa aagggctgcc ccaaccagca ccaggacctc     60
```

```
ctctgccaag aggaagaagg tgaagaagta aatctagaca g                    101


<210> SEQ ID NO 65
<211> LENGTH: 38
<212> TYPE: PRT
<213> ORGANISM: Homo sapiens
<220> FEATURE:
<221> NAME/KEY: misc_feature
<223> OTHER INFORMATION: 3113 Amino acid sequence of HPV type 59 L1
      protein aa 471-508

<400> SEQUENCE: 65

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35


<210> SEQ ID NO 66
<211> LENGTH: 499
<212> TYPE: PRT
<213> ORGANISM: Homo sapiens
<220> FEATURE:
<221> NAME/KEY: misc_feature
<223> OTHER INFORMATION: 3301 Amino acid sequence of HPV type 33 L1
      protein

<400> SEQUENCE: 66

Met Ser Val Trp Arg Pro Ser Glu Ala Thr Val Tyr Leu Pro Pro Val
1               5                   10                  15

Pro Val Ser Lys Val Val Ser Thr Asp Glu Tyr Val Ser Arg Thr Ser
            20                  25                  30

Ile Tyr Tyr Tyr Ala Gly Ser Ser Arg Leu Leu Ala Val Gly His Pro
        35                  40                  45

Tyr Phe Ser Ile Lys Asn Pro Thr Asn Ala Lys Lys Leu Leu Val Pro
    50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Asp Thr
                85                  90                  95

Gln Arg Leu Val Trp Ala Cys Val Gly Leu Glu Ile Gly Arg Gly Gln
            100                 105                 110

Pro Leu Gly Val Gly Ile Ser Gly His Pro Leu Leu Asn Lys Phe Asp
        115                 120                 125

Asp Thr Glu Thr Gly Asn Lys Tyr Pro Gly Gln Pro Gly Ala Asp Asn
    130                 135                 140

Arg Glu Cys Leu Ser Met Asp Tyr Lys Gln Thr Gln Leu Cys Leu Leu
145                 150                 155                 160

Gly Cys Lys Pro Pro Thr Gly Glu His Trp Gly Lys Gly Val Ala Cys
                165                 170                 175

Thr Asn Ala Ala Pro Ala Asn Asp Cys Pro Pro Leu Glu Leu Ile Asn
            180                 185                 190

Thr Ile Ile Glu Asp Gly Asp Met Val Asp Thr Gly Phe Gly Cys Met
        195                 200                 205

Asp Phe Lys Thr Leu Gln Ala Asn Lys Ser Asp Val Pro Ile Asp Ile
    210                 215                 220

Cys Gly Ser Thr Cys Lys Tyr Pro Asp Tyr Leu Lys Met Thr Ser Glu
225                 230                 235                 240
```

```
Pro Tyr Gly Asp Ser Leu Phe Phe Phe Leu Arg Arg Glu Gln Met Phe
                245                 250                 255

Val Arg His Phe Phe Asn Arg Ala Gly Thr Leu Gly Glu Ala Val Pro
            260                 265                 270

Asp Asp Leu Tyr Ile Lys Gly Ser Gly Thr Thr Ala Ser Ile Gln Ser
        275                 280                 285

Ser Ala Phe Phe Pro Thr Pro Ser Gly Ser Met Val Thr Ser Glu Ser
    290                 295                 300

Gln Leu Phe Asn Lys Pro Tyr Trp Leu Gln Arg Ala Gln Gly His Asn
305                 310                 315                 320

Asn Gly Ile Cys Trp Gly Asn Gln Val Phe Val Thr Val Val Asp Thr
                325                 330                 335

Thr Arg Ser Thr Asn Met Thr Leu Cys Thr Gln Val Thr Ser Asp Ser
            340                 345                 350

Thr Tyr Lys Asn Glu Asn Phe Lys Glu Tyr Ile Arg His Val Glu Glu
        355                 360                 365

Tyr Asp Leu Gln Phe Val Phe Gln Leu Cys Lys Val Thr Leu Thr Ala
    370                 375                 380

Glu Val Met Thr Tyr Ile His Ala Met Asn Pro Asp Ile Leu Glu Asp
385                 390                 395                 400

Trp Gln Phe Gly Leu Thr Pro Pro Pro Ser Ala Ser Leu Gln Asp Thr
                405                 410                 415

Tyr Arg Phe Val Thr Ser Gln Ala Ile Thr Cys Gln Lys Thr Val Pro
            420                 425                 430

Pro Lys Glu Lys Glu Asp Pro Leu Gly Lys Tyr Thr Phe Trp Glu Val
        435                 440                 445

Asp Leu Lys Glu Lys Phe Ser Ala Asp Leu Asp Gln Phe Pro Leu Gly
    450                 455                 460

Arg Lys Phe Leu Leu Gln Ala Gly Leu Lys Ala Lys Pro Lys Leu Lys
465                 470                 475                 480

Arg Ala Ala Pro Thr Ser Thr Arg Thr Ser Ser Ala Lys Arg Lys Lys
                485                 490                 495

Val Lys Lys
```

```
<210> SEQ ID NO 67
<211> LENGTH: 1501
<212> TYPE: DNA
<213> ORGANISM: Homo sapiens
<220> FEATURE:
<221> NAME/KEY: misc_feature
<223> OTHER INFORMATION: 3302 Nucleotide sequence of HPV type 33 L1
      protein

<400> SEQUENCE: 67

atgagtgtgt ggagaccatc tgaggctaca gtctacctgc ctcctgtgcc tgtgagcaag      60

gtggtgagca cagatgaata tgtgagcagg accagcatct actactatgc tggctccagc     120

agactgctgg ctgtgggaca cccatacttc agcatcaaga acccaaccaa tgccaagaaa     180

ctgctggtgc caaaggtgtc tggactccaa tacagggtgt tcagggtgag actgcctgac     240

ccaaacaagt ttggctttcc tgacacctcc ttctacaacc ctgacaccca gagactggtg     300

tgggcttgtg tgggattgga gattggcagg ggacaaccac tgggagtggg catctctgga     360

cacccactgc tgaacaagtt tgatgacaca gagacaggca acaaataccc tggacaacct     420

ggagcagaca acagggagtg tctgagtatg gactacaagc agacccaact ttgtctgctg     480
```

-continued

```
ggctgtaagc ctccaacagg agaacactgg ggcaagggag tggcttgtac caatgctgcc    540
cctgccaatg actgtcctcc attggaactg ataaacacca tcattgagga tggagatatg    600
gtggacacag gctttggctg tatggacttc aagaccctcc aagccaacaa gtctgatgtg    660
ccaattgaca tctgtggcag cacttgtaaa taccctgact acctgaaaat gacctctgaa    720
ccatatggag actccctgtt cttcttcctg aggagggaac agatgtttgt gagacacttc    780
ttcaacaggg ctggcaccct gggagaggct gtgcctgatg acctctacat caagggctct    840
ggcaccacag ccagcatcca gtcctctgcc ttctttccaa caccatctgg cagtatggtg    900
acctctgaga gccaactttt caacaagcca tactggctcc aaagggctca aggacacaac    960
aatggcatct gttggggcaa ccaggtgttt gtgacagtgg tggacaccac caggagcacc   1020
aatatgaccc tgtgtaccca ggtgacctct gacagcacct acaagaatga gaacttcaag   1080
gaatacatca ggcatgtgga ggaatatgac ctccaatttg tgttccaact ttgtaaggtg   1140
accctgacag cagaggtgat gacctacatc catgctatga accctgacat cttggaggac   1200
tggcagtttg gactgacacc tcctccatct gcctccctcc aagacaccta caggtttgtg   1260
accagccagg ctatcacttg tcagaagaca gtgcctccaa aggagaagga ggacccactg   1320
ggcaaataca ccttctggga ggtggacctg aaagagaagt tctctgctga cctggaccag   1380
tttccactgg gcaggaagtt cctgctccaa gcaggactga aagccaagcc aaaactgaaa   1440
agggctgccc caaccagcac caggacctcc tctgccaaga ggaagaaggt gaagaagtaa   1500
a                                                                   1501
```

<210> SEQ ID NO 68
<211> LENGTH: 1519
<212> TYPE: DNA
<213> ORGANISM: Artificial sequence
<220> FEATURE:
<223> OTHER INFORMATION: 3303 Synthetic HPV33 L1 gene

<400> SEQUENCE: 68

```
ctgggtacca tgagtgtgtg gagaccatct gaggctacag tctacctgcc tcctgtgcct     60
gtgagcaagg tggtgagcac agatgaatat gtgagcagga ccagcatcta ctactatgct    120
ggctccagca gactgctggc tgtgggacac ccatacttca gcatcaagaa cccaaccaat    180
gccaagaaac tgctggtgcc aaaggtgtct ggactccaat acagggtgtt cagggtgaga    240
ctgcctgacc caaacaagtt tggctttcct gacacctcct tctacaaccc tgacacccag    300
agactggtgt gggcttgtgt gggattggag attggcaggg gacaaccact gggagtgggc    360
atctctggac acccactgct gaacaagttt gatgacacag agacaggcaa caaataccct    420
ggacaacctg gagcagacaa cagggagtgt ctgagtatgg actacaagca gacccaactt    480
tgtctgctgg gctgtaagcc tccaacagga gaacactggg gcaagggagt ggcttgtacc    540
aatgctgccc ctgccaatga ctgtcctcca ttggaactga taaacaccat cattgaggat    600
ggagatatgg tggacacagg ctttggctgt atggacttca agaccctcca agccaacaag    660
tctgatgtgc caattgacat ctgtggcagc acttgtaaat accctgacta cctgaaaatg    720
acctctgaac catatggaga ctccctgttc ttcttcctga ggagggaaca gatgtttgtg    780
agacacttct tcaacagggc tggcaccctg ggagaggctg tgcctgatga cctctacatc    840
aagggctctg gcaccacagc cagcatccag tcctctgcct tctttccaac accatctggc    900
agtatggtga cctctgagag ccaacttttc aacaagccat actggctcca aagggctcaa    960
ggacacaaca atggcatctg ttggggcaac caggtgtttg tgacagtggt ggacaccacc   1020
```

```
aggagcacca atatgaccct gtgtacccag gtgacctctg acagcaccta caagaatgag   1080

aacttcaagg aatacatcag gcatgtggag gaatatgacc tccaatttgt gttccaactt   1140

tgtaaggtga ccctgacagc agaggtgatg acctacatcc atgctatgaa ccctgacatc   1200

ttggaggact ggcagtttgg actgacacct cctccatctg cctccctcca agacacctac   1260

aggtttgtga ccagccaggc tatcacttgt cagaagacag tgcctccaaa ggagaaggag   1320

gacccactgg gcaaatacac cttctgggag gtggacctga aagagaagtt ctctgctgac   1380

ctggaccagt ttccactggg caggaagttc ctgctccaag caggactgaa agccaagcca   1440

aaactgaaaa gggctgcccc aaccagcacc aggacctcct ctgccaagag gaagaaggtg   1500

aagaagtaaa ctcgagctc                                                 1519
```

```
<210> SEQ ID NO 69
<211> LENGTH: 472
<212> TYPE: PRT
<213> ORGANISM: Homo sapiens
<220> FEATURE:
<221> NAME/KEY: misc_feature
<223> OTHER INFORMATION: 3501 Amino acid sequence of HPV type 35 L1
      protein aa 1-472

<400> SEQUENCE: 69

Met Ser Leu Trp Arg Ser Asn Glu Ala Thr Val Tyr Leu Pro Pro Val
1               5                   10                  15

Ser Val Ser Lys Val Val Ser Thr Asp Glu Tyr Val Thr Arg Thr Asn
            20                  25                  30

Ile Tyr Tyr His Ala Gly Ser Ser Arg Leu Leu Ala Val Gly His Pro
        35                  40                  45

Tyr Tyr Ala Ile Lys Lys Gln Asp Ser Asn Lys Ile Ala Val Pro Lys
    50                  55                  60

Val Ser Gly Leu Gln Tyr Arg Val Phe Arg Val Lys Leu Pro Asp Pro
65                  70                  75                  80

Asn Lys Phe Gly Phe Pro Asp Thr Ser Phe Tyr Asp Pro Ala Ser Gln
                85                  90                  95

Arg Leu Val Trp Ala Cys Thr Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ser Asn Lys Tyr Val Gly Asn Ser Gly Thr Asp Asn Arg
    130                 135                 140

Glu Cys Ile Ser Met Asp Tyr Lys Gln Thr Gln Leu Cys Leu Ile Gly
145                 150                 155                 160

Cys Arg Pro Pro Ile Gly Glu His Trp Gly Lys Gly Thr Pro Cys Asn
                165                 170                 175

Ala Asn Gln Val Lys Ala Gly Glu Cys Pro Pro Leu Glu Leu Leu Asn
            180                 185                 190

Thr Val Leu Gln Asp Gly Asp Met Val Asp Thr Gly Phe Gly Ala Met
        195                 200                 205

Asp Phe Thr Thr Leu Gln Ala Asn Lys Ser Asp Val Pro Leu Asp Ile
    210                 215                 220

Cys Ser Ser Ile Cys Lys Tyr Pro Asp Tyr Leu Lys Met Val Ser Glu
225                 230                 235                 240

Pro Tyr Gly Asp Met Leu Phe Phe Tyr Leu Arg Arg Glu Gln Met Phe
                245                 250                 255
```

```
Val Arg His Leu Phe Asn Arg Ala Gly Thr Val Gly Glu Thr Val Pro
            260                 265                 270

Ala Asp Leu Tyr Ile Lys Gly Thr Thr Gly Thr Leu Pro Ser Thr Ser
        275                 280                 285

Tyr Phe Pro Thr Pro Ser Gly Ser Met Val Thr Ser Asp Ala Gln Ile
    290                 295                 300

Phe Asn Lys Pro Tyr Trp Leu Gln Arg Ala Gln Gly His Asn Asn Gly
305                 310                 315                 320

Ile Cys Trp Ser Asn Gln Leu Phe Val Thr Val Val Asp Thr Thr Arg
                325                 330                 335

Ser Thr Asn Met Ser Val Cys Ser Ala Val Ser Ser Ser Asp Ser Thr
            340                 345                 350

Tyr Lys Asn Asp Asn Phe Lys Glu Tyr Leu Arg His Gly Glu Glu Tyr
        355                 360                 365

Asp Leu Gln Phe Ile Phe Gln Leu Cys Lys Ile Thr Leu Thr Ala Asp
    370                 375                 380

Val Met Thr Tyr Ile His Ser Met Asn Pro Ser Ile Leu Glu Asp Trp
385                 390                 395                 400

Asn Phe Gly Leu Thr Pro Pro Pro Ser Gly Thr Leu Glu Asp Thr Tyr
                405                 410                 415

Arg Tyr Val Thr Ser Gln Ala Val Thr Cys Gln Lys Pro Ser Ala Pro
            420                 425                 430

Lys Pro Lys Asp Asp Pro Leu Lys Asn Tyr Thr Phe Trp Glu Val Asp
        435                 440                 445

Leu Lys Glu Lys Phe Ser Ala Asp Leu Asp Gln Phe Pro Leu Gly Arg
    450                 455                 460

Lys Phe Leu Leu Gln Ala Gly Leu
465                 470


<210> SEQ ID NO 70
<211> LENGTH: 26
<212> TYPE: PRT
<213> ORGANISM: Homo sapiens
<220> FEATURE:
<221> NAME/KEY: misc_feature
<223> OTHER INFORMATION: 3502 Amino acid sequence of HPV type 33 L1
      protein aa 474-499

<400> SEQUENCE: 70

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25


<210> SEQ ID NO 71
<211> LENGTH: 498
<212> TYPE: PRT
<213> ORGANISM: Artificial sequence
<220> FEATURE:
<223> OTHER INFORMATION: 3503 Amino acid sequence of chimeric HPV type
      35 L1 protein

<400> SEQUENCE: 71

Met Ser Leu Trp Arg Ser Asn Glu Ala Thr Val Tyr Leu Pro Pro Val
1               5                   10                  15

Ser Val Ser Lys Val Val Ser Thr Asp Glu Tyr Val Thr Arg Thr Asn
            20                  25                  30

Ile Tyr Tyr His Ala Gly Ser Ser Arg Leu Leu Ala Val Gly His Pro
        35                  40                  45
```

-continued

```
Tyr Tyr Ala Ile Lys Lys Gln Asp Ser Asn Lys Ile Ala Val Pro Lys
    50                  55                  60

Val Ser Gly Leu Gln Tyr Arg Val Phe Arg Val Lys Leu Pro Asp Pro
65                  70                  75                  80

Asn Lys Phe Gly Phe Pro Asp Thr Ser Phe Tyr Asp Pro Ala Ser Gln
                85                  90                  95

Arg Leu Val Trp Ala Cys Thr Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ser Asn Lys Tyr Val Gly Asn Ser Gly Thr Asp Asn Arg
    130                 135                 140

Glu Cys Ile Ser Met Asp Tyr Lys Gln Thr Gln Leu Cys Leu Ile Gly
145                 150                 155                 160

Cys Arg Pro Pro Ile Gly Glu His Trp Gly Lys Gly Thr Pro Cys Asn
                165                 170                 175

Ala Asn Gln Val Lys Ala Gly Glu Cys Pro Pro Leu Glu Leu Leu Asn
            180                 185                 190

Thr Val Leu Gln Asp Gly Asp Met Val Asp Thr Gly Phe Gly Ala Met
        195                 200                 205

Asp Phe Thr Thr Leu Gln Ala Asn Lys Ser Asp Val Pro Leu Asp Ile
    210                 215                 220

Cys Ser Ser Ile Cys Lys Tyr Pro Asp Tyr Leu Lys Met Val Ser Glu
225                 230                 235                 240

Pro Tyr Gly Asp Met Leu Phe Phe Tyr Leu Arg Arg Glu Gln Met Phe
                245                 250                 255

Val Arg His Leu Phe Asn Arg Ala Gly Thr Val Gly Glu Thr Val Pro
            260                 265                 270

Ala Asp Leu Tyr Ile Lys Gly Thr Thr Gly Thr Leu Pro Ser Thr Ser
        275                 280                 285

Tyr Phe Pro Thr Pro Ser Gly Ser Met Val Thr Ser Asp Ala Gln Ile
    290                 295                 300

Phe Asn Lys Pro Tyr Trp Leu Gln Arg Ala Gln Gly His Asn Asn Gly
305                 310                 315                 320

Ile Cys Trp Ser Asn Gln Leu Phe Val Thr Val Val Asp Thr Thr Arg
                325                 330                 335

Ser Thr Asn Met Ser Val Cys Ser Ala Val Ser Ser Ser Asp Ser Thr
            340                 345                 350

Tyr Lys Asn Asp Asn Phe Lys Glu Tyr Leu Arg His Gly Glu Glu Tyr
        355                 360                 365

Asp Leu Gln Phe Ile Phe Gln Leu Cys Lys Ile Thr Leu Thr Ala Asp
    370                 375                 380

Val Met Thr Tyr Ile His Ser Met Asn Pro Ser Ile Leu Glu Asp Trp
385                 390                 395                 400

Asn Phe Gly Leu Thr Pro Pro Pro Ser Gly Thr Leu Glu Asp Thr Tyr
                405                 410                 415

Arg Tyr Val Thr Ser Gln Ala Val Thr Cys Gln Lys Pro Ser Ala Pro
            420                 425                 430

Lys Pro Lys Asp Asp Pro Leu Lys Asn Tyr Thr Phe Trp Glu Val Asp
        435                 440                 445

Leu Lys Glu Lys Phe Ser Ala Asp Leu Asp Gln Phe Pro Leu Gly Arg
    450                 455                 460
```

Lys Phe Leu Leu Gln Ala Gly Leu Lys Ala Lys Pro Lys Leu Lys Arg
465 470 475 480

Ala Ala Pro Thr Ser Thr Arg Thr Ser Ser Ala Lys Arg Lys Lys Val
485 490 495

Lys Lys

<210> SEQ ID NO 72
<211> LENGTH: 1498
<212> TYPE: DNA
<213> ORGANISM: Artificial sequence
<220> FEATURE:
<223> OTHER INFORMATION: 3504 Nucleotide sequence of chimeric HPV type 35 L1 protein

<400> SEQUENCE: 72

```
atgagtctgt ggaggagcaa tgaggctaca gtctacctgc ctcctgtgtc tgtgagcaag     60
gtggtgagca cagatgaata tgtgaccagg accaacatct actaccatgc tggctccagc    120
agactgctgg ctgtgggaca cccatactat gccatcaaga agcaggacag caacaagatt    180
gctgtgccaa aggtgtctgg actccaatac agggtgttca gggtgaaact gcctgaccca    240
aacaagtttg gctttcctga cacctccttc tatgaccctg ccagccagag actggtgtgg    300
gcttgtactg gagtggaggt gggcagggga caaccactgg gagtgggcat ctctggacac    360
ccactgctga acaaactgga tgacacagag aacagcaaca aatatgtggg caactctggc    420
acagacaaca gggagtgtat cagtatggac tacaagcaga cccaactttg tctgattggc    480
tgtagacctc caattggaga acactggggc aagggcacac catgtaatgc caaccaggtg    540
aaggctggag agtgtcctcc attggaactg ctgaacacag tgctccaaga tggagatatg    600
gtggacacag gctttggagc tatggacttc accaccctcc aagccaacaa gtctgatgtg    660
ccactggaca tctgttccag catctgtaaa taccctgact acctgaaaat ggtgtctgaa    720
ccatatggag atatgctgtt cttctacctg aggagggaac agatgtttgt gagacacctg    780
ttcaacaggg ctggcacagt gggagagaca gtgcctgctg acctctacat caagggcacc    840
acaggcaccc tgccaagcac ctcctacttt ccaacaccat ctggcagtat ggtgacctct    900
gatgcccaga ttttcaacaa gccatactgg ctccaaaggg ctcaaggaca caacaatggc    960
atctgttgga gcaaccaact ttttgtgaca gtggtggaca ccaccaggag caccaatatg   1020
agtgtgtgtt ctgctgtgtc ctcctctgac agcacctaca agaatgacaa cttcaaggaa   1080
tacctgagac atggagagga atatgacctc caattcatct tccaactttg taagattacc   1140
ctgacagcag atgtgatgac ctacatccac agtatgaacc caagcatctt ggaggactgg   1200
aactttggac tgacacctcc tccatctggc accttggagg acacctacag atatgtgacc   1260
agccaggctg tgacttgtca gaagccatct gccccaaagc caaaggatga cccactgaaa   1320
aactacacct tctgggaggt ggacctgaaa gagaagttct ctgctgacct ggaccagttt   1380
ccactgggca ggaagttcct gctccaagca ggactgaaag ccaagccaaa actgaaaagg   1440
gctgccccaa ccagcaccag gacctcctct gccaagagga agaaggtgaa gaagtaaa     1498
```

<210> SEQ ID NO 73
<211> LENGTH: 1528
<212> TYPE: DNA
<213> ORGANISM: Artificial sequence
<220> FEATURE:
<223> OTHER INFORMATION: 3505 Synthetic HPV35 L1 gene

<400> SEQUENCE: 73

-continued

```
ctgggtacca tgagtctgtg gaggagcaat gaggctacag tctacctgcc tcctgtgtct     60

gtgagcaagg tggtgagcac agatgaatat gtgaccagga ccaacatcta ctaccatgct    120

ggctccagca gactgctggc tgtgggacac ccatactatg ccatcaagaa gcaggacagc    180

aacaagattg ctgtgccaaa ggtgtctgga ctccaataca gggtgttcag ggtgaaactg    240

cctgacccaa acaagtttgg ctttcctgac acctccttct atgaccctgc cagccagaga    300

ctggtgtggg cttgtactgg agtggaggtg ggcaggggac aaccactggg agtgggcatc    360

tctggacacc cactgctgaa caaactggat gacacagaga acagcaacaa atatgtgggc    420

aactctggca cagacaacag ggagtgtatc agtatggact acaagcagac ccaactttgt    480

ctgattggct gtagacctcc aattggagaa cactggggca agggcacacc atgtaatgcc    540

aaccaggtga aggctggaga gtgtcctcca ttggaactgc tgaacacagt gctccaagat    600

ggagatatgg tggacacagg ctttggagct atggacttca ccaccctcca agccaacaag    660

tctgatgtgc cactggacat ctgttccagc atctgtaaat accctgacta cctgaaaatg    720

gtgtctgaac catatggaga tatgctgttc ttctacctga ggagggaaca gatgtttgtg    780

agacacctgt tcaacagggc tggcacagtg ggagagacag tgcctgctga cctctacatc    840

aagggcacca caggcaccct gccaagcacc tcctactttc caacaccatc tggcagtatg    900

gtgacctctg atgcccagat tttcaacaag ccatactggc tccaaagggc tcaaggacac    960

aacaatggca tctgttggag caaccaactt tttgtgacag tggtggacac caccaggagc   1020

accaatatga gtgtgtgttc tgctgtgtcc tcctctgaca gcacctacaa gaatgacaac   1080

ttcaaggaat acctgagaca tggagaggaa tatgacctcc aattcatctt ccaactttgt   1140

aagattaccc tgacagcaga tgtgatgacc tacatccaca gtatgaaccc aagcatcttg   1200

gaggactgga actttggact gacacctcct ccatctggca ccttggagga cacctacaga   1260

tatgtgacca gccaggctgt gacttgtcag aagccatctg ccccaaagcc aaaggatgac   1320

ccactgaaaa actacacctt ctgggaggtg gacctgaaag agaagttctc tgctgacctg   1380

gaccagtttc cactgggcag gaagttcctg ctccaagcag gactgaaagc cagaccaaac   1440

ttcagactgg gcaagagggc tgcccctgcc agcaccagca agaagtccag caccaagagg   1500

aggaaggtga agagctaaac tcgagctc                                      1528
```

<210> SEQ ID NO 74
<211> LENGTH: 1519
<212> TYPE: DNA
<213> ORGANISM: Artificial sequence
<220> FEATURE:
<223> OTHER INFORMATION: 3506 Synthetic HPV33 L1 gene

<400> SEQUENCE: 74

```
ctgggtacca tgagtgtgtg gagaccatct gaggctacag tctacctgcc tcctgtgcct     60

gtgagcaagg tggtgagcac agatgaatat gtgagcagga ccagcatcta ctactatgct    120

ggctccagca gactgctggc tgtgggacac ccatacttca gcatcaagaa cccaaccaat    180

gccaagaaac tgctggtgcc aaaggtgtct ggactccaat acagggtgtt cagggtgaga    240

ctgcctgacc caaacaagtt tggctttcct gacacctcct tctacaaccc tgacacccag    300

agactggtgt gggcttgtgt gggattggag attggcaggg gacaaccact gggagtgggc    360

atctctggac acccactgct gaacaagttt gatgacacag agacaggcaa caaataccct    420

ggacaacctg gagcagacaa cagggagtgt ctgagtatgg actacaagca gacccaactt    480

tgtctgctgg gctgtaagcc tccaacagga gaacactggg gcaagggagt ggcttgtacc    540
```

aatgctgccc ctgccaatga ctgtcctcca ttggaactga taaacaccat cattgaggat 600
ggagatatgg tggacacagg ctttggctgt atggacttca agaccctcca agccaacaag 660
tctgatgtgc caattgacat ctgtggcagc acttgtaaat accctgacta cctgaaaatg 720
acctctgaac catatggaga ctccctgttc ttcttcctga ggagggaaca gatgtttgtg 780
agacacttct tcaacagggc tggcaccctg ggagaggctg tgcctgatga cctctacatc 840
aagggctctg gcaccacagc cagcatccag tcctctgcct tctttccaac accatctggc 900
agtatggtga cctctgagag ccaacttttc aacaagccat actggctcca aagggctcaa 960
ggacacaaca atggcatctg ttggggcaac caggtgtttg tgacagtggt ggacaccacc 1020
aggagcacca atatgaccct gtgtacccag gtgacctctg acagcaccta caagaatgag 1080
aacttcaagg aatacatcag gcatgtggag gaatatgacc tccaatttgt gttccaactt 1140
tgtaaggtga ccctgacagc agaggtgatg acctacatcc atgctatgaa ccctgacatc 1200
ttggaggact ggcagtttgg actgacacct cctccatctg cctccctcca agacacctac 1260
aggtttgtga ccagccaggc tatcacttgt cagaagacag tgcctccaaa ggagaaggag 1320
gacccactgg gcaaatacac cttctgggag gtggacctga aagagaagtt ctctgctgac 1380
ctggaccagt ttccactggg caggaagttc ctgctccaag caggactgaa agccaagcca 1440
aaactgaaaa gggctgcccc aaccagcacc aggacctcct ctgccaagag gaagaaggtg 1500
aagaagtaaa ctcgagctc 1519

<210> SEQ ID NO 75
<211> LENGTH: 34
<212> TYPE: DNA
<213> ORGANISM: Artificial sequence
<220> FEATURE:
<223> OTHER INFORMATION: 3507 HPV35L1 F1

<400> SEQUENCE: 75
cttggtacca tgagtctgtg gaggagcaat gagg 34

<210> SEQ ID NO 76
<211> LENGTH: 36
<212> TYPE: DNA
<213> ORGANISM: Artificial sequence
<220> FEATURE:
<223> OTHER INFORMATION: 3508 HPV35L1 R1

<400> SEQUENCE: 76
gcttggcttt cagtcctgct tggagcagga acttcc 36

<210> SEQ ID NO 77
<211> LENGTH: 1435
<212> TYPE: DNA
<213> ORGANISM: Artificial sequence
<220> FEATURE:
<223> OTHER INFORMATION: 3509 HPV35L1 amplified sequence 1

<400> SEQUENCE: 77
cttggtacca tgagtctgtg gaggagcaat gaggctacag tctacctgcc tcctgtgtct 60
gtgagcaagg tggtgagcac agatgaatat gtgaccagga ccaacatcta ctaccatgct 120
ggctccagca gactgctggc tgtgggacac ccatactatg ccatcaagaa gcaggacagc 180
aacaagattg ctgtgccaaa ggtgtctgga ctccaataca gggtgttcag ggtgaaactg 240
cctgacccaa acaagtttgg ctttcctgac acctccttct atgaccctgc cagccagaga 300
ctggtgtggg cttgtactgg agtggaggtg ggcaggggac aaccactggg agtgggcatc 360
tctggacacc cactgctgaa caaactggat gacacagaga acagcaacaa atatgtgggc 420
aactctggca cagacaacag ggagtgtatc agtatggact acaagcagac ccaactttgt 480
ctgattggct gtagacctcc aattggagaa cactggggca agggcacacc atgtaatgcc 540
aaccaggtga aggctggaga gtgtcctcca ttggaactgc tgaacacagt gctccaagat 600
ggagatatgg tggacacagg ctttggagct atggacttca ccaccctcca agccaacaag 660
tctgatgtgc cactggacat ctgttccagc atctgtaaat accctgacta cctgaaaatg 720
gtgtctgaac catatggaga tatgctgttc ttctacctga ggagggaaca gatgtttgtg 780
agacacctgt tcaacagggc tggcacagtg ggagagacag tgcctgctga cctctacatc 840
aagggcacca caggcaccct gccaagcacc tcctactttc caacaccatc tggcagtatg 900
gtgacctctg atgcccagat tttcaacaag ccatactggc tccaaagggc tcaaggacac 960
aacaatggca tctgttggag caaccaactt tttgtgacag tggtggacac caccaggagc 1020
accaatatga gtgtgtgttc tgctgtgtcc tcctctgaca gcacctacaa gaatgacaac 1080
ttcaaggaat acctgagaca tggagaggaa tatgacctcc aattcatctt ccaactttgt 1140
aagattaccc tgacagcaga tgtgatgacc tacatccaca gtatgaaccc aagcatcttg 1200
gaggactgga actttggact gacacctcct ccatctggca ccttggagga cacctacaga 1260
tatgtgacca gccaggctgt gacttgtcag aagccatctg ccccaaagcc aaaggatgac 1320
ccactgaaaa actacacctt ctgggaggtg gacctgaaag agaagttctc tgctgacctg 1380
gaccagtttc cactgggcag gaagttcctg ctccaagcag gactgaaagc caagc 1435

<210> SEQ ID NO 78
<211> LENGTH: 35
<212> TYPE: DNA
<213> ORGANISM: Artificial sequence
<220> FEATURE:
<223> OTHER INFORMATION: 3510 HPV35L1 F2

<400> SEQUENCE: 78
agcaggactg aaagccaagc caaaactgaa aaggg 35

<210> SEQ ID NO 79
<211> LENGTH: 36
<212> TYPE: DNA
<213> ORGANISM: Artificial sequence
<220> FEATURE:
<223> OTHER INFORMATION: 3511 HPV35L1 R2

<400> SEQUENCE: 79
ctgtctagat ttacttcttc accttcttcc tcttgg 36

<210> SEQ ID NO 80
<211> LENGTH: 101
<212> TYPE: DNA
<213> ORGANISM: Artificial sequence
<220> FEATURE:
<223> OTHER INFORMATION: 3512 HPV35L1 amplified sequence 2

<400> SEQUENCE: 80
agcaggactg aaagccaagc caaaactgaa aagggctgcc ccaaccagca ccaggacctc 60
ctctgccaag aggaagaagg tgaagaagta aatctagaca g 101

<210> SEQ ID NO 81
<211> LENGTH: 38

<212> TYPE: PRT
<213> ORGANISM: Homo sapiens
<220> FEATURE:
<221> NAME/KEY: misc_feature
<223> OTHER INFORMATION: 3513 Amino acid sequence of HPV type 59 L1
protein aa 471-508

<400> SEQUENCE: 81

```
Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35
```

<210> SEQ ID NO 82
<211> LENGTH: 469
<212> TYPE: PRT
<213> ORGANISM: Homo sapiens
<220> FEATURE:
<221> NAME/KEY: misc_feature
<223> OTHER INFORMATION: 3901 Amino acid sequence of HPV type 39 L1
protein aa 1-469

<400> SEQUENCE: 82

```
Met Ala Met Trp Arg Ser Ser Asp Ser Met Val Tyr Leu Pro Pro Pro
1               5                   10                  15

Ser Val Ala Lys Val Val Asn Thr Asp Asp Tyr Val Thr Arg Thr Gly
            20                  25                  30

Ile Tyr Tyr Tyr Ala Gly Ser Ser Arg Leu Leu Thr Val Gly His Pro
        35                  40                  45

Tyr Phe Lys Val Gly Met Asn Gly Gly Arg Lys Gln Asp Ile Pro Lys
    50                  55                  60

Val Ser Ala Tyr Gln Tyr Arg Val Phe Arg Val Thr Leu Pro Asp Pro
65                  70                  75                  80

Asn Lys Phe Ser Ile Pro Asp Ala Ser Leu Tyr Asn Pro Glu Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Tyr Asn Arg Gln Asp Asp
        115                 120                 125

Thr Glu Asn Ser Pro Phe Ser Ser Thr Thr Asn Lys Asp Ser Arg Asp
    130                 135                 140

Asn Val Ser Val Asp Tyr Lys Gln Thr Gln Leu Cys Ile Ile Gly Cys
145                 150                 155                 160

Val Pro Ala Ile Gly Glu His Trp Gly Lys Gly Lys Ala Cys Lys Pro
                165                 170                 175

Asn Asn Val Ser Thr Gly Asp Cys Pro Pro Leu Glu Leu Val Asn Thr
            180                 185                 190

Pro Ile Glu Asp Gly Asp Met Ile Asp Thr Gly Tyr Gly Ala Met Asp
        195                 200                 205

Phe Gly Ala Leu Gln Glu Thr Lys Ser Glu Val Pro Leu Asp Ile Cys
    210                 215                 220

Gln Ser Ile Cys Lys Tyr Pro Asp Tyr Leu Gln Met Ser Ala Asp Val
225                 230                 235                 240

Tyr Gly Asp Ser Met Phe Phe Cys Leu Arg Arg Glu Gln Leu Phe Ala
                245                 250                 255

Arg His Phe Trp Asn Arg Gly Gly Met Val Gly Asp Ala Ile Pro Ala
```

```
            260                 265                 270

Gln Leu Tyr Ile Lys Gly Thr Asp Ile Arg Ala Asn Pro Gly Ser Ser
        275                 280                 285

Val Tyr Cys Pro Ser Pro Ser Gly Ser Met Val Thr Ser Asp Ser Gln
    290                 295                 300

Leu Phe Asn Lys Pro Tyr Trp Leu His Lys Ala Gln Gly His Asn Asn
305                 310                 315                 320

Gly Ile Cys Trp His Asn Gln Leu Phe Leu Thr Val Val Asp Thr Thr
                325                 330                 335

Arg Ser Thr Asn Phe Thr Leu Ser Thr Ser Ile Glu Ser Ser Ile Pro
            340                 345                 350

Ser Thr Tyr Asp Pro Ser Lys Phe Lys Glu Tyr Thr Arg His Val Glu
        355                 360                 365

Glu Tyr Asp Leu Gln Phe Ile Phe Gln Leu Cys Thr Val Thr Leu Thr
    370                 375                 380

Thr Asp Val Met Ser Tyr Ile His Thr Met Asn Ser Ser Ile Leu Asp
385                 390                 395                 400

Asn Trp Asn Phe Ala Val Ala Pro Pro Pro Ser Ala Ser Leu Val Asp
                405                 410                 415

Thr Tyr Arg Tyr Leu Gln Ser Ala Ala Ile Thr Cys Gln Lys Asp Ala
            420                 425                 430

Pro Ala Pro Glu Lys Lys Asp Pro Tyr Asp Gly Leu Lys Phe Trp Asn
        435                 440                 445

Val Asp Leu Arg Glu Lys Phe Ser Leu Glu Leu Asp Gln Phe Pro Leu
    450                 455                 460

Gly Arg Lys Phe Leu
465


<210> SEQ ID NO 83
<211> LENGTH: 38
<212> TYPE: PRT
<213> ORGANISM: Homo sapiens
<220> FEATURE:
<221> NAME/KEY: misc_feature
<223> OTHER INFORMATION: 3902 Amino acid sequence of HPV type 59 L1
      protein aa 471-508

<400> SEQUENCE: 83

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35


<210> SEQ ID NO 84
<211> LENGTH: 507
<212> TYPE: PRT
<213> ORGANISM: Artificial sequence
<220> FEATURE:
<223> OTHER INFORMATION: 3903 Amino acid sequence of chimeric HPV type
      39 L1 protein

<400> SEQUENCE: 84

Met Ala Met Trp Arg Ser Ser Asp Ser Met Val Tyr Leu Pro Pro Pro
1               5                   10                  15

Ser Val Ala Lys Val Val Asn Thr Asp Asp Tyr Val Thr Arg Thr Gly
            20                  25                  30
```

-continued

```
Ile Tyr Tyr Tyr Ala Gly Ser Ser Arg Leu Leu Thr Val Gly His Pro
        35                  40                  45

Tyr Phe Lys Val Gly Met Asn Gly Gly Arg Lys Gln Asp Ile Pro Lys
    50                  55                  60

Val Ser Ala Tyr Gln Tyr Arg Val Phe Arg Val Thr Leu Pro Asp Pro
65                  70                  75                  80

Asn Lys Phe Ser Ile Pro Asp Ala Ser Leu Tyr Asn Pro Glu Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Tyr Asn Arg Gln Asp Asp
        115                 120                 125

Thr Glu Asn Ser Pro Phe Ser Ser Thr Thr Asn Lys Asp Ser Arg Asp
    130                 135                 140

Asn Val Ser Val Asp Tyr Lys Gln Thr Gln Leu Cys Ile Ile Gly Cys
145                 150                 155                 160

Val Pro Ala Ile Gly Glu His Trp Gly Lys Gly Lys Ala Cys Lys Pro
                165                 170                 175

Asn Asn Val Ser Thr Gly Asp Cys Pro Pro Leu Glu Leu Val Asn Thr
            180                 185                 190

Pro Ile Glu Asp Gly Asp Met Ile Asp Thr Gly Tyr Gly Ala Met Asp
        195                 200                 205

Phe Gly Ala Leu Gln Glu Thr Lys Ser Glu Val Pro Leu Asp Ile Cys
    210                 215                 220

Gln Ser Ile Cys Lys Tyr Pro Asp Tyr Leu Gln Met Ser Ala Asp Val
225                 230                 235                 240

Tyr Gly Asp Ser Met Phe Phe Cys Leu Arg Arg Glu Gln Leu Phe Ala
                245                 250                 255

Arg His Phe Trp Asn Arg Gly Gly Met Val Gly Asp Ala Ile Pro Ala
            260                 265                 270

Gln Leu Tyr Ile Lys Gly Thr Asp Ile Arg Ala Asn Pro Gly Ser Ser
        275                 280                 285

Val Tyr Cys Pro Ser Pro Ser Gly Ser Met Val Thr Ser Asp Ser Gln
    290                 295                 300

Leu Phe Asn Lys Pro Tyr Trp Leu His Lys Ala Gln Gly His Asn Asn
305                 310                 315                 320

Gly Ile Cys Trp His Asn Gln Leu Phe Leu Thr Val Val Asp Thr Thr
                325                 330                 335

Arg Ser Thr Asn Phe Thr Leu Ser Thr Ser Ile Glu Ser Ser Ile Pro
            340                 345                 350

Ser Thr Tyr Asp Pro Ser Lys Phe Lys Glu Tyr Thr Arg His Val Glu
        355                 360                 365

Glu Tyr Asp Leu Gln Phe Ile Phe Gln Leu Cys Thr Val Thr Leu Thr
    370                 375                 380

Thr Asp Val Met Ser Tyr Ile His Thr Met Asn Ser Ser Ile Leu Asp
385                 390                 395                 400

Asn Trp Asn Phe Ala Val Ala Pro Pro Pro Ser Ala Ser Leu Val Asp
                405                 410                 415

Thr Tyr Arg Tyr Leu Gln Ser Ala Ala Ile Thr Cys Gln Lys Asp Ala
            420                 425                 430

Pro Ala Pro Glu Lys Lys Asp Pro Tyr Asp Gly Leu Lys Phe Trp Asn
        435                 440                 445

Val Asp Leu Arg Glu Lys Phe Ser Leu Glu Leu Asp Gln Phe Pro Leu
```

```
    450                 455                 460

Gly Arg Lys Phe Leu Leu Gln Leu Gly Ala Arg Pro Lys Pro Thr Ile
465                 470                 475                 480

Gly Pro Arg Lys Arg Ala Ala Pro Ala Pro Thr Ser Thr Pro Ser Pro
                485                 490                 495

Lys Arg Val Lys Arg Arg Lys Ser Ser Arg Lys
            500                 505


<210> SEQ ID NO 85
<211> LENGTH: 1525
<212> TYPE: DNA
<213> ORGANISM: Artificial sequence
<220> FEATURE:
<223> OTHER INFORMATION: 3904 Nucleotide sequence of chimeric HPV type
      39 L1 protein

<400> SEQUENCE: 85

atggctatgt ggaggtcctc tgacagtatg gtctacctgc ctcctccatc tgtggctaag     60

gtggtgaaca cagatgacta tgtgaccagg acaggcatct actactatgc tggctccagc    120

agactgctga cagtgggaca cccatacttc aaggtgggga tgaatggagg caggaagcag    180

gacatcccaa aggtgtctgc ctaccaatac agggtgttca gggtgaccct gcctgaccca    240

aacaagttca gcatccctga tgcctccctc tacaaccctg agacccagag actggtgtgg    300

gcttgtgtgg gagtggaggt gggcagggga caaccactgg gagtgggcat ctctggacac    360

ccactctaca acagacagga tgacacagag aacagcccat tctccagcac caccaacaag    420

gacagcaggg acaatgtgtc tgtggactac aagcagaccc aactttgtat cattggctgt    480

gtgcctgcca ttggagaaca ctggggcaag ggcaaggctt gtaagccaaa caatgtgagc    540

acaggagact gtcctccatt ggaactggtg aacacaccaa ttgaggatgg agatatgatt    600

gacacaggct atggagctat ggactttgga gccctccaag agaccaagtc tgaggtgcca    660

ctggacatct gtcagagcat ctgtaaatac cctgactacc tccaaatgag tgctgatgtc    720

tatggagaca gtatgttctt ctgtctgagg agggaacaac tttttgccag acacttctgg    780

aacaggggag ggatggtggg agatgccatc cctgcccaac tctacatcaa gggcacagac    840

atcagggcta accctggctc ctctgtctac tgtccaagcc catctggcag tatggtgacc    900

tctgacagcc aacttttcaa caagccatac tggctgcaca aggctcaagg acacaacaat    960

ggcatctgtt ggcacaacca acttttcctg acagtggtgg acaccaccag gagcaccaac   1020

ttcaccctga gcaccagcat tgagtccagc atcccaagca cctatgaccc aagcaagttc   1080

aaggaataca ccaggcatgt ggaggaatat gacctccaat tcatcttcca actttgtact   1140

gtgaccctga ccacagatgt gatgagttac atccacacaa tgaactccag catcctggac   1200

aactggaact ttgctgtggc tcctcctcca tctgcctccc tggtggacac ctacagatac   1260

ctccaatctg ctgccatcac ttgtcagaag gatgcccctg cccctgagaa gaaggaccca   1320

tatgatggac tgaagttctg gaatgtggac ctgagggaga agttctcctt ggaactggac   1380

cagtttccac tgggcaggaa gttcctgctc caacttggag ccagaccaaa gccaaccatt   1440

ggaccaagga agagggctgc ccctgcccca accagcacac caagcccaaa gagggtgaag   1500

aggaggaagt ccagcaggaa gtaaa                                         1525


<210> SEQ ID NO 86
<211> LENGTH: 1537
<212> TYPE: DNA
<213> ORGANISM: Artificial sequence
```

<220> FEATURE:
<223> OTHER INFORMATION: 3905 Synthetic HPV39 L1 gene

<400> SEQUENCE: 86
ctgggtacca tggctatgtg gaggtcctct gacagtatgg tctacctgcc tcctccatct 60
gtggctaagg tggtgaacac agatgactat gtgaccagga caggcatcta ctactatgct 120
ggctccagca gactgctgac agtgggacac ccatacttca aggtggggat gaatggaggc 180
aggaagcagg acatcccaaa ggtgtctgcc taccaataca gggtgttcag ggtgaccctg 240
cctgacccaa acaagttcag catccctgat gcctccctct acaaccctga gacccagaga 300
ctggtgtggg cttgtgtggg agtggaggtg ggcaggggac aaccactggg agtgggcatc 360
tctggacacc cactctacaa cagacaggat gacacagaga acagcccatt ctccagcacc 420
accaacaagg acagcaggga caatgtgtct gtggactaca agcagaccca actttgtatc 480
attggctgtg tgcctgccat tggagaacac tggggcaagg gcaaggcttg taagccaaac 540
aatgtgagca caggagactg tcctccattg gaactggtga acacaccaat tgaggatgga 600
gatatgattg acacaggcta tggagctatg gactttggag ccctccaaga gaccaagtct 660
gaggtgccac tggacatctg tcagagcatc tgtaaatacc ctgactacct ccaaatgagt 720
gctgatgtct atggagacag tatgttcttc tgtctgagga gggaacaact tttgccaga 780
cacttctgga acaggggagg gatggtggga gatgccatcc ctgcccaact ctacatcaag 840
ggcacagaca tcagggctaa ccctggctcc tctgtctact gtccaagccc atctggcagt 900
atggtgacct ctgacagcca acttttcaac aagccatact ggctgcacaa ggctcaagga 960
cacaacaatg gcatctgttg gcacaaccaa cttttcctga cagtggtgga caccaccagg 1020
agcaccaact tcaccctgag caccagcatt gagtccagca tcccaagcac ctatgaccca 1080
agcaagttca aggaatacac caggcatgtg gaggaatatg acctccaatt catcttccaa 1140
ctttgtactg tgaccctgac cacagatgtg atgagttaca tccacacaat gaactccagc 1200
atcctggaca actggaactt tgctgtggct cctcctccat ctgcctccct ggtggacacc 1260
tacagatacc tccaatctgc tgccatcact tgtcagaagg atgcccctgc ccctgagaag 1320
aaggacccat atgatggact gaagttctgg aatgtggacc tgagggagaa gttctccttg 1380
gaactggacc agtttccact gggcaggaag ttcctgctcc aagccagggt gaggaggaga 1440
ccaaccattg gaccaaggaa gagacctgct gccagcacct cctcctcctc tgccaccaaa 1500
cacaagagga agagggtgag caagtaaact cgagctc 1537

<210> SEQ ID NO 87
<211> LENGTH: 1546
<212> TYPE: DNA
<213> ORGANISM: Artificial sequence
<220> FEATURE:
<223> OTHER INFORMATION: 3906 Synthetic HPV59 L1 gene

<400> SEQUENCE: 87
ctgggtacca tggctctgtg gaggtcctct gacaacaagg tctacctgcc tcctccatct 60
gtggctaagg tggtgagcac agatgaatat gtgaccagga ccagcatctt ctaccatgct 120
ggctccagca gactgctgac agtgggacac ccatacttca aggtgccaaa gggaggcaat 180
ggcagacagg atgtgccaaa ggtgtctgcc taccaataca gggtgttcag ggtgaaactg 240
cctgacccaa acaagtttgg actgcctgac aacacagtct atgacccaaa cagccagaga 300
ctggtgtggg cttgtgtggg agtggagatt ggcaggggac aaccactggg agtgggactg 360

```
tctggacacc cactctacaa caaactggat gacacagaga actctcatgt ggcatctgct    420

gtggacacca aggacaccag ggacaatgtg tctgtggact acaagcagac ccaactttgt    480

atcattggct gtgtgcctgc cattggagaa cactggacca agggcacagc ctgtaagcca    540

accacagtgg tccagggaga ctgtcctcca ttggaactga taaacacacc aattgaggat    600

ggagatatgg tggacacagg ctatggagct atggacttca aactgctcca agacaacaag    660

tctgaggtgc cactggacat ctgtcagagc atctgtaaat accctgacta cctccaaatg    720

agtgctgatg cctatggaga cagtatgttc ttctgtctga ggagggaaca ggtgtttgcc    780

agacacttct ggaacaggtc tggcacaatg ggagaccaac ttcctgagtc cctctacatc    840

aagggcacag acatcagggc taaccctggc tcctacctct acagcccaag cccatctggc    900

tctgtggtga cctctgacag ccaacttttc aacaagccat actggctgca caaggctcaa    960

ggactgaaca atggcatctg ttggcacaac caacttttcc tgacagtggt ggacaccacc   1020

aggagcacca acctgtctgt gtgtgccagc accacctcca gcatcccaaa tgtctacaca   1080

ccaacctcct tcaaggaata tgccaggcat gtggaggagt ttgacctcca attcatcttc   1140

caactttgta agattaccct gaccacagag gtgatgagtt acatccacaa tatgaacacc   1200

accatcttgg aggactggaa ctttggagtg acacctcctc caacagcctc cctggtggac   1260

acctacaggt ttgtccagtc tgctgctgtg acttgtcaga aggacacagc ccctcctgtg   1320

aagcaggacc catatgacaa actgaagttc tggcctgtgg acctgaaaga gaggttctct   1380

gctgacctgg accagtttcc actgggcagg aagttcctgc tccaacttgg agccagacca   1440

aagccaacca ttggaccaag gaagagggct gcccctgccc caaccagcac accaagccca   1500

aagagggtga agaggaggaa gtccagcagg aagtaaactc gagctc                  1546
```

<210> SEQ ID NO 88
<211> LENGTH: 38
<212> TYPE: DNA
<213> ORGANISM: Artificial sequence
<220> FEATURE:
<223> OTHER INFORMATION: 3907 HPV39L1 F1

<400> SEQUENCE: 88

```
cttggtacca tggctatgtg gaggtcctct gacagtat                             38
```

<210> SEQ ID NO 89
<211> LENGTH: 38
<212> TYPE: DNA
<213> ORGANISM: Artificial sequence
<220> FEATURE:
<223> OTHER INFORMATION: 3908 HPV39L1 R1

<400> SEQUENCE: 89

```
tccaagttgg agcaggaact tcctgcccag tggaaact                             38
```

<210> SEQ ID NO 90
<211> LENGTH: 1428
<212> TYPE: DNA
<213> ORGANISM: Artificial sequence
<220> FEATURE:
<223> OTHER INFORMATION: 3909 HPV39L1 amplified sequence 1

<400> SEQUENCE: 90

```
cttggtacca tggctatgtg gaggtcctct gacagtatgg tctacctgcc tcctccatct     60

gtggctaagg tggtgaacac agatgactat gtgaccagga caggcatcta ctactatgct    120

ggctccagca gactgctgac agtgggacac ccatacttca aggtggggat gaatggaggc    180
```

-continued

```
aggaagcagg acatcccaaa ggtgtctgcc taccaataca gggtgttcag ggtgaccctg    240

cctgacccaa acaagttcag catccctgat gcctccctct acaaccctga gacccagaga    300

ctggtgtggg cttgtgtggg agtggaggtg ggcaggggac aaccactggg agtgggcatc    360

tctggacacc cactctacaa cagacaggat gacacagaga acagcccatt ctccagcacc    420

accaacaagg acagcaggga caatgtgtct gtggactaca agcagaccca actttgtatc    480

attggctgtg tgcctgccat tggagaacac tggggcaagg gcaaggcttg taagccaaac    540

aatgtgagca caggagactg tcctccattg gaactggtga acacaccaat tgaggatgga    600

gatatgattg acacaggcta tggagctatg gactttggag ccctccaaga gaccaagtct    660

gaggtgccac tggacatctg tcagagcatc tgtaaatacc ctgactacct ccaaatgagt    720

gctgatgtct atggagacag tatgttcttc tgtctgagga gggaacaact ttttgccaga    780

cacttctgga acaggggagg gatggtggga gatgccatcc ctgcccaact ctacatcaag    840

ggcacagaca tcagggctaa ccctggctcc tctgtctact gtccaagccc atctggcagt    900

atggtgacct ctgacagcca acttttcaac aagccatact ggctgcacaa ggctcaagga    960

cacaacaatg gcatctgttg gcacaaccaa cttttcctga cagtggtgga caccaccagg   1020

agcaccaact tcaccctgag caccagcatt gagtccagca tcccaagcac ctatgaccca   1080

agcaagttca aggaatacac caggcatgtg gaggaatatg acctccaatt catcttccaa   1140

ctttgtactg tgaccctgac cacagatgtg atgagttaca tccacacaat gaactccagc   1200

atcctggaca actggaactt tgctgtggct cctcctccat ctgcctccct ggtggacacc   1260

tacagatacc tccaatctgc tgccatcact tgtcagaagg atgcccctgc ccctgagaag   1320

aaggacccat atgatggact gaagttctgg aatgtggacc tgagggagaa gttctccttg   1380

gaactggacc agtttccact gggcaggaag ttcctgctcc aacttgga                1428
```

<210> SEQ ID NO 91
<211> LENGTH: 37
<212> TYPE: DNA
<213> ORGANISM: Artificial sequence
<220> FEATURE:
<223> OTHER INFORMATION: 3910 HPV39L1 F2

<400> SEQUENCE: 91

```
aggaagttcc tgctccaact tggagccaga ccaaagc                              37
```

<210> SEQ ID NO 92
<211> LENGTH: 40
<212> TYPE: DNA
<213> ORGANISM: Artificial sequence
<220> FEATURE:
<223> OTHER INFORMATION: 3911 HPV39L1 R2

<400> SEQUENCE: 92

```
ctgtctagat ttacttcctg ctggacttcc tcctcttcac                           40
```

<210> SEQ ID NO 93
<211> LENGTH: 139
<212> TYPE: DNA
<213> ORGANISM: Artificial sequence
<220> FEATURE:
<223> OTHER INFORMATION: 3912 HPV39L1 amplified sequence 2

<400> SEQUENCE: 93

```
aggaagttcc tgctccaact tggagccaga ccaaagccaa ccattggacc aaggaagagg     60
```

gctgcccctg ccccaaccag cacaccaagc ccaaagaggg tgaagaggag gaagtccagc 120
aggaagtaaa tctagacag 139

<210> SEQ ID NO 94
<211> LENGTH: 26
<212> TYPE: PRT
<213> ORGANISM: Homo sapiens
<220> FEATURE:
<221> NAME/KEY: misc_feature
<223> OTHER INFORMATION: 3913 Amino acid sequence of HPV type 33 L1
protein aa 474-499

<400> SEQUENCE: 94

Lys Ala Lys Pro Lys Leu Lys Arg Ala Ala Pro Thr Ser Thr Arg Thr
1 5 10 15

Ser Ser Ala Lys Arg Lys Lys Val Lys Lys
20 25

<210> SEQ ID NO 95
<211> LENGTH: 478
<212> TYPE: PRT
<213> ORGANISM: Homo sapiens
<220> FEATURE:
<221> NAME/KEY: misc_feature
<223> OTHER INFORMATION: 4501 Amino acid sequence of HPV type 45 L1
protein aa 1-478

<400> SEQUENCE: 95

Met Ala Leu Trp Arg Pro Ser Asp Ser Thr Val Tyr Leu Pro Pro Pro
1 5 10 15

Ser Val Ala Arg Val Val Asn Thr Asp Asp Tyr Val Ser Arg Thr Ser
20 25 30

Ile Phe Tyr His Ala Gly Ser Ser Arg Leu Leu Thr Val Gly Asn Pro
35 40 45

Tyr Phe Arg Val Val Pro Ser Gly Ala Gly Asn Lys Gln Ala Val Pro
50 55 60

Lys Val Ser Ala Tyr Gln Tyr Arg Val Phe Arg Val Ala Leu Pro Asp
65 70 75 80

Pro Asn Lys Phe Gly Leu Pro Asp Ser Thr Ile Tyr Asn Pro Glu Thr
85 90 95

Gln Arg Leu Val Trp Ala Cys Val Gly Met Glu Ile Gly Arg Gly Gln
100 105 110

Pro Leu Gly Ile Gly Leu Ser Gly His Pro Phe Tyr Asn Lys Leu Asp
115 120 125

Asp Thr Glu Ser Ala His Ala Ala Thr Ala Val Ile Thr Gln Asp Val
130 135 140

Arg Asp Asn Val Ser Val Asp Tyr Lys Gln Thr Gln Leu Cys Ile Leu
145 150 155 160

Gly Cys Val Pro Ala Ile Gly Glu His Trp Ala Lys Gly Thr Leu Cys
165 170 175

Lys Pro Ala Gln Leu Gln Pro Gly Asp Cys Pro Pro Leu Glu Leu Lys
180 185 190

Asn Thr Ile Ile Glu Asp Gly Asp Met Val Asp Thr Gly Tyr Gly Ala
195 200 205

Met Asp Phe Ser Thr Leu Gln Asp Thr Lys Cys Glu Val Pro Leu Asp
210 215 220

Ile Cys Gln Ser Ile Cys Lys Tyr Pro Asp Tyr Leu Gln Met Ser Ala
225 230 235 240

```
Asp Pro Tyr Gly Asp Ser Met Phe Phe Cys Leu Arg Arg Glu Gln Leu
                245                 250                 255

Phe Ala Arg His Phe Trp Asn Arg Ala Gly Val Met Gly Asp Thr Val
            260                 265                 270

Pro Thr Asp Leu Tyr Ile Lys Gly Thr Ser Ala Asn Met Arg Glu Thr
        275                 280                 285

Pro Gly Ser Cys Val Tyr Ser Pro Ser Pro Ser Gly Ser Ile Thr Thr
    290                 295                 300

Ser Asp Ser Gln Leu Phe Asn Lys Pro Tyr Trp Leu His Lys Ala Gln
305                 310                 315                 320

Gly His Asn Asn Gly Ile Cys Trp His Asn Gln Leu Phe Val Thr Val
                325                 330                 335

Val Asp Thr Thr Arg Ser Thr Asn Leu Thr Leu Cys Ala Ser Thr Gln
            340                 345                 350

Asn Pro Val Pro Asn Thr Tyr Asp Pro Thr Lys Phe Lys His Tyr Ser
        355                 360                 365

Arg His Val Glu Glu Tyr Asp Leu Gln Phe Ile Phe Gln Leu Cys Thr
    370                 375                 380

Ile Thr Leu Thr Ala Glu Val Met Ser Tyr Ile His Ser Met Asn Ser
385                 390                 395                 400

Ser Ile Leu Glu Asn Trp Asn Phe Gly Val Pro Pro Pro Pro Thr Thr
                405                 410                 415

Ser Leu Val Asp Thr Tyr Arg Phe Val Gln Ser Val Ala Val Thr Cys
            420                 425                 430

Gln Lys Asp Thr Thr Pro Pro Glu Lys Gln Asp Pro Tyr Asp Lys Leu
        435                 440                 445

Lys Phe Trp Thr Val Asp Leu Lys Glu Lys Phe Ser Ser Asp Leu Asp
    450                 455                 460

Gln Tyr Pro Leu Gly Arg Lys Phe Leu Val Gln Ala Gly Leu
465                 470                 475
```

```
<210> SEQ ID NO 96
<211> LENGTH: 26
<212> TYPE: PRT
<213> ORGANISM: Homo sapiens
<220> FEATURE:
<221> NAME/KEY: misc_feature
<223> OTHER INFORMATION: 4502 Amino acid sequence of HPV type 33 L1
      protein aa 474-499

<400> SEQUENCE: 96

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25
```

```
<210> SEQ ID NO 97
<211> LENGTH: 504
<212> TYPE: PRT
<213> ORGANISM: Artificial sequence
<220> FEATURE:
<223> OTHER INFORMATION: 4503 Amino acid sequence of chimeric HPV type
      45 L1 protein

<400> SEQUENCE: 97

Met Ala Leu Trp Arg Pro Ser Asp Ser Thr Val Tyr Leu Pro Pro Pro
1               5                   10                  15

Ser Val Ala Arg Val Val Asn Thr Asp Asp Tyr Val Ser Arg Thr Ser
            20                  25                  30
```

-continued

```
Ile Phe Tyr His Ala Gly Ser Ser Arg Leu Leu Thr Val Gly Asn Pro
        35                  40                  45

Tyr Phe Arg Val Val Pro Ser Gly Ala Gly Asn Lys Gln Ala Val Pro
    50                  55                  60

Lys Val Ser Ala Tyr Gln Tyr Arg Val Phe Arg Val Ala Leu Pro Asp
65                  70                  75                  80

Pro Asn Lys Phe Gly Leu Pro Asp Ser Thr Ile Tyr Asn Pro Glu Thr
                85                  90                  95

Gln Arg Leu Val Trp Ala Cys Val Gly Met Glu Ile Gly Arg Gly Gln
            100                 105                 110

Pro Leu Gly Ile Gly Leu Ser Gly His Pro Phe Tyr Asn Lys Leu Asp
        115                 120                 125

Asp Thr Glu Ser Ala His Ala Ala Thr Ala Val Ile Thr Gln Asp Val
    130                 135                 140

Arg Asp Asn Val Ser Val Asp Tyr Lys Gln Thr Gln Leu Cys Ile Leu
145                 150                 155                 160

Gly Cys Val Pro Ala Ile Gly Glu His Trp Ala Lys Gly Thr Leu Cys
                165                 170                 175

Lys Pro Ala Gln Leu Gln Pro Gly Asp Cys Pro Pro Leu Glu Leu Lys
            180                 185                 190

Asn Thr Ile Ile Glu Asp Gly Asp Met Val Asp Thr Gly Tyr Gly Ala
        195                 200                 205

Met Asp Phe Ser Thr Leu Gln Asp Thr Lys Cys Glu Val Pro Leu Asp
    210                 215                 220

Ile Cys Gln Ser Ile Cys Lys Tyr Pro Asp Tyr Leu Gln Met Ser Ala
225                 230                 235                 240

Asp Pro Tyr Gly Asp Ser Met Phe Phe Cys Leu Arg Arg Glu Gln Leu
                245                 250                 255

Phe Ala Arg His Phe Trp Asn Arg Ala Gly Val Met Gly Asp Thr Val
            260                 265                 270

Pro Thr Asp Leu Tyr Ile Lys Gly Thr Ser Ala Asn Met Arg Glu Thr
        275                 280                 285

Pro Gly Ser Cys Val Tyr Ser Pro Ser Pro Ser Gly Ser Ile Thr Thr
    290                 295                 300

Ser Asp Ser Gln Leu Phe Asn Lys Pro Tyr Trp Leu His Lys Ala Gln
305                 310                 315                 320

Gly His Asn Asn Gly Ile Cys Trp His Asn Gln Leu Phe Val Thr Val
                325                 330                 335

Val Asp Thr Thr Arg Ser Thr Asn Leu Thr Leu Cys Ala Ser Thr Gln
            340                 345                 350

Asn Pro Val Pro Asn Thr Tyr Asp Pro Thr Lys Phe Lys His Tyr Ser
        355                 360                 365

Arg His Val Glu Glu Tyr Asp Leu Gln Phe Ile Phe Gln Leu Cys Thr
    370                 375                 380

Ile Thr Leu Thr Ala Glu Val Met Ser Tyr Ile His Ser Met Asn Ser
385                 390                 395                 400

Ser Ile Leu Glu Asn Trp Asn Phe Gly Val Pro Pro Pro Pro Thr Thr
                405                 410                 415

Ser Leu Val Asp Thr Tyr Arg Phe Val Gln Ser Val Ala Val Thr Cys
            420                 425                 430

Gln Lys Asp Thr Thr Pro Pro Glu Lys Gln Asp Pro Tyr Asp Lys Leu
        435                 440                 445
```

-continued

```
Lys Phe Trp Thr Val Asp Leu Lys Glu Lys Phe Ser Ser Asp Leu Asp
    450                 455                 460

Gln Tyr Pro Leu Gly Arg Lys Phe Leu Val Gln Ala Gly Leu Lys Ala
465                 470                 475                 480

Lys Pro Lys Leu Lys Arg Ala Ala Pro Thr Ser Thr Arg Thr Ser Ser
                485                 490                 495

Ala Lys Arg Lys Lys Val Lys Lys
            500
```

<210> SEQ ID NO 98
<211> LENGTH: 1516
<212> TYPE: DNA
<213> ORGANISM: Artificial sequence
<220> FEATURE:
<223> OTHER INFORMATION: 4504 Nucleotide sequence of chimeric HPV type 45 L1 protein

<400> SEQUENCE: 98

```
atggctctgt ggagaccatc tgacagcaca gtctacctgc ctcctccatc tgtggcaagg     60

gtggtgaaca cagatgacta tgtgagcagg accagcatct tctaccatgc tggctccagc    120

agactgctga cagtgggcaa cccatacttc agggtggtgc caagtggagc aggcaacaag    180

caggctgtgc caaaggtgtc tgcctaccaa tacagggtgt tcagggtggc tctgcctgac    240

ccaaacaagt ttggactgcc tgacagcacc atctacaacc ctgagaccca gagactggtg    300

tgggcttgtg tggggatgga gattggcagg ggacaaccac tgggcattgg actgtctgga    360

cacccattct acaacaaact ggatgacaca gagtctgccc atgctgccac agcagtgatt    420

acccaggatg tgagggacaa tgtgtctgtg gactacaagc agacccaact ttgtatcctg    480

ggctgtgtgc ctgccattgg agaacactgg gctaagggca ccctgtgtaa gcctgcccaa    540

ctccaacctg gagactgtcc tccattggaa ctgaaaaaca ccatcattga ggatggagat    600

atggtggaca caggctatgg agctatggac ttcagcaccc tccaagacac caagtgtgag    660

gtgccactgg acatctgtca gagcatctgt aaataccctg actacctcca aatgagtgct    720

gacccatatg gagacagtat gttcttctgt ctgaggaggg aacaactttt tgccagacac    780

ttctggaaca gggctggagt gatgggagac acagtgccaa cagacctcta catcaagggc    840

acctctgcca atatgaggga gacacctggc tcctgtgtct acagcccaag cccatctggc    900

agcatcacca cctctgacag ccaacttttc aacaagccat actggctgca caaggctcaa    960

ggacacaaca atggcatctg ttggcacaac caactttttg tgacagtggt ggacaccacc   1020

aggagcacca acctgaccct gtgtgccagc acccagaacc ctgtgccaaa cacctatgac   1080

ccaaccaagt tcaagcacta cagcaggcat gtggaggaat atgacctcca attcatcttc   1140

caactttgta ccatcaccct gacagcagag gtgatgagtt acatccacag tatgaactcc   1200

agcatcttgg agaactggaa ctttggagtg cctcctcctc caaccacctc cctggtggac   1260

acctacaggt ttgtccagtc tgtggctgtg acttgtcaga aggacaccac acctcctgag   1320

aagcaggacc catatgacaa actgaagttc tggacagtgg acctgaaaga gaagttctcc   1380

tctgacctgg accaataccc actgggcagg aagttcctgg tccaggctgg actgaaagcc   1440

aagccaaaac tgaaaagggc tgccccaacc agcaccagga cctcctctgc caagaggaag   1500

aaggtgaaga agtaaa                                                   1516
```

<210> SEQ ID NO 99
<211> LENGTH: 1552
<212> TYPE: DNA

<213> ORGANISM: Artificial sequence
<220> FEATURE:
<223> OTHER INFORMATION: 4505 Synthetic HPV45 L1 gene

<400> SEQUENCE: 99
ctgggtacca tggctctgtg gagaccatct gacagcacag tctacctgcc tcctccatct 60
gtggcaaggg tggtgaacac agatgactat gtgagcagga ccagcatctt ctaccatgct 120
ggctccagca gactgctgac agtgggcaac ccatacttca gggtggtgcc aagtggagca 180
ggcaacaagc aggctgtgcc aaaggtgtct gcctaccaat acagggtgtt cagggtggct 240
ctgcctgacc caaacaagtt tggactgcct gacagcacca tctacaaccc tgagacccag 300
agactggtgt gggcttgtgt ggggatggag attggcaggg gacaaccact gggcattgga 360
ctgtctggac acccattcta caacaaactg gatgacacag agtctgccca tgctgccaca 420
gcagtgatta cccaggatgt gagggacaat gtgtctgtgg actacaagca gacccaactt 480
tgtatcctgg gctgtgtgcc tgccattgga gaacactggg ctaagggcac cctgtgtaag 540
cctgcccaac tccaacctgg agactgtcct ccattggaac tgaaaaacac catcattgag 600
gatggagata tggtggacac aggctatgga gctatggact tcagcaccct ccaagacacc 660
aagtgtgagg tgccactgga catctgtcag agcatctgta aataccctga ctacctccaa 720
atgagtgctg acccatatgg agacagtatg ttcttctgtc tgaggaggga acaacttttt 780
gccagacact tctggaacag ggctggagtg atgggagaca cagtgccaac agacctctac 840
atcaagggca cctctgccaa tatgagggag acacctggct cctgtgtcta cagcccaagc 900
ccatctggca gcatcaccac ctctgacagc caacttttca acaagccata ctggctgcac 960
aaggctcaag gacacaacaa tggcatctgt tggcacaacc aactttttgt gacagtggtg 1020
gacaccacca ggagcaccaa cctgaccctg tgtgccagca cccagaaccc tgtgccaaac 1080
acctatgacc caaccaagtt caagcactac agcaggcatg tggaggaata tgacctccaa 1140
ttcatcttcc aactttgtac catcaccctg acagcagagg tgatgagtta catccacagt 1200
atgaactcca gcatcttgga gaactggaac tttggagtgc ctcctcctcc aaccacctcc 1260
ctggtggaca cctacaggtt tgtccagtct gtggctgtga cttgtcagaa ggacaccaca 1320
cctcctgaga agcaggaccc atatgacaaa ctgaagttct ggacagtgga cctgaaagag 1380
aagttctcct ctgacctgga ccaataccca ctgggcagga agttcctggt ccaggctgga 1440
ctgaggagga gaccaaccat tggaccaagg aagagacctg ctgccagcac cagcacagcc 1500
agcagacctg ccaagagggt gaggattagg agcaagaagt aaactcgagc tc 1552

<210> SEQ ID NO 100
<211> LENGTH: 1519
<212> TYPE: DNA
<213> ORGANISM: Artificial sequence
<220> FEATURE:
<223> OTHER INFORMATION: 4506 Synthetic HPV33 L1 gene

<400> SEQUENCE: 100
ctgggtacca tgagtgtgtg gagaccatct gaggctacag tctacctgcc tcctgtgcct 60
gtgagcaagg tggtgagcac agatgaatat gtgagcagga ccagcatcta ctactatgct 120
ggctccagca gactgctggc tgtgggacac ccatacttca gcatcaagaa cccaaccaat 180
gccaagaaac tgctggtgcc aaaggtgtct ggactccaat acagggtgtt cagggtgaga 240
ctgcctgacc caaacaagtt tggctttcct gacacctcct tctacaaccc tgacacccag 300
agactggtgt gggcttgtgt gggattggag attggcaggg gacaaccact gggagtgggc 360

```
atctctggac acccactgct gaacaagttt gatgacacag agacaggcaa caaataccct    420

ggacaacctg gagcagacaa cagggagtgt ctgagtatgg actacaagca gacccaactt    480

tgtctgctgg gctgtaagcc tccaacagga gaacactggg gcaagggagt ggcttgtacc    540

aatgctgccc ctgccaatga ctgtcctcca ttggaactga taaacaccat cattgaggat    600

ggagatatgg tggacacagg ctttggctgt atggacttca agaccctcca agccaacaag    660

tctgatgtgc caattgacat ctgtggcagc acttgtaaat accctgacta cctgaaaatg    720

acctctgaac catatggaga ctccctgttc ttcttcctga ggagggaaca gatgtttgtg    780

agacacttct tcaacagggc tggcaccctg ggagaggctg tgcctgatga cctctacatc    840

aagggctctg gcaccacagc cagcatccag tcctctgcct tctttccaac accatctggc    900

agtatggtga cctctgagag ccaacttttc aacaagccat actggctcca aagggctcaa    960

ggacacaaca atggcatctg ttggggcaac caggtgtttg tgacagtggt ggacaccacc   1020

aggagcacca atatgaccct gtgtacccag gtgacctctg acagcaccta caagaatgag   1080

aacttcaagg aatacatcag gcatgtggag gaatatgacc tccaatttgt gttccaactt   1140

tgtaaggtga ccctgacagc agaggtgatg acctacatcc atgctatgaa ccctgacatc   1200

ttggaggact ggcagtttgg actgacacct cctccatctg cctccctcca agacacctac   1260

aggtttgtga ccagccaggc tatcacttgt cagaagacag tgcctccaaa ggagaaggag   1320

gacccactgg gcaaatacac cttctgggag gtggacctga aagagaagtt ctctgctgac   1380

ctggaccagt ttccactggg caggaagttc ctgctccaag caggactgaa agccaagcca   1440

aaactgaaaa gggctgcccc aaccagcacc aggacctcct ctgccaagag gaagaaggtg   1500

aagaagtaaa ctcgagctc                                                1519
```

<210> SEQ ID NO 101
<211> LENGTH: 33
<212> TYPE: DNA
<213> ORGANISM: Artificial sequence
<220> FEATURE:
<223> OTHER INFORMATION: 4507 HPV45L1 F1

<400> SEQUENCE: 101

```
cttggtacca tggctctgtg gagaccatct gac                                  33
```

<210> SEQ ID NO 102
<211> LENGTH: 32
<212> TYPE: DNA
<213> ORGANISM: Artificial sequence
<220> FEATURE:
<223> OTHER INFORMATION: 4508 HPV45L1 R1

<400> SEQUENCE: 102

```
gcttggcttt cagtccagcc tggaccagga ac                                   32
```

<210> SEQ ID NO 103
<211> LENGTH: 1453
<212> TYPE: DNA
<213> ORGANISM: Artificial sequence
<220> FEATURE:
<223> OTHER INFORMATION: 4509 HPV45L1 amplified sequence 1

<400> SEQUENCE: 103

```
cttggtacca tggctctgtg gagaccatct gacagcacag tctacctgcc tcctccatct     60

gtggcaaggg tggtgaacac agatgactat gtgagcagga ccagcatctt ctaccatgct    120
```

-continued

```
ggctccagca gactgctgac agtgggcaac ccatacttca gggtggtgcc aagtggagca    180

ggcaacaagc aggctgtgcc aaaggtgtct gcctaccaat acagggtgtt cagggtggct    240

ctgcctgacc caaacaagtt tggactgcct gacagcacca tctacaaccc tgagacccag    300

agactggtgt gggcttgtgt ggggatggag attggcaggg gacaaccact gggcattgga    360

ctgtctggac acccattcta caacaaactg gatgacacag agtctgccca tgctgccaca    420

gcagtgatta cccaggatgt gagggacaat gtgtctgtgg actacaagca gacccaactt    480

tgtatcctgg gctgtgtgcc tgccattgga gaacactggg ctaagggcac cctgtgtaag    540

cctgcccaac tccaacctgg agactgtcct ccattggaac tgaaaaacac catcattgag    600

gatggagata tggtggacac aggctatgga gctatggact tcagcaccct ccaagacacc    660

aagtgtgagg tgccactgga catctgtcag agcatctgta aataccctga ctacctccaa    720

atgagtgctg acccatatgg agacagtatg ttcttctgtc tgaggaggga acaacttttt    780

gccagacact tctggaacag ggctggagtg atgggagaca cagtgccaac agacctctac    840

atcaagggca cctctgccaa tatgagggag acacctggct cctgtgtcta cagcccaagc    900

ccatctggca gcatcaccac ctctgacagc caacttttca acaagccata ctggctgcac    960

aaggctcaag gacacaacaa tggcatctgt tggcacaacc aactttttgt gacagtggtg   1020

gacaccacca ggagcaccaa cctgaccctg tgtgccagca cccagaaccc tgtgccaaac   1080

acctatgacc caaccaagtt caagcactac agcaggcatg tggaggaata tgacctccaa   1140

ttcatcttcc aactttgtac catcaccctg acagcagagg tgatgagtta catccacagt   1200

atgaactcca gcatcttgga gaactggaac tttggagtgc ctcctcctcc aaccacctcc   1260

ctggtggaca cctacaggtt tgtccagtct gtggctgtga cttgtcagaa ggacaccaca   1320

cctcctgaga agcaggaccc atatgacaaa ctgaagttct ggacagtgga cctgaaagag   1380

aagttctcct ctgacctgga ccaataccca ctgggcagga agttcctggt ccaggctgga   1440

ctgaaagcca agc                                                      1453
```

<210> SEQ ID NO 104
<211> LENGTH: 35
<212> TYPE: DNA
<213> ORGANISM: Artificial sequence
<220> FEATURE:
<223> OTHER INFORMATION: 4510 HPV45L1 F2

<400> SEQUENCE: 104

```
ggctggactg aaagccaagc caaaactgaa aaggg                                35
```

<210> SEQ ID NO 105
<211> LENGTH: 37
<212> TYPE: DNA
<213> ORGANISM: Artificial sequence
<220> FEATURE:
<223> OTHER INFORMATION: 4511 HPV45L1 R2

<400> SEQUENCE: 105

```
ctgtctagat ttacttcttc accttcttcc tcttggc                              37
```

<210> SEQ ID NO 106
<211> LENGTH: 101
<212> TYPE: DNA
<213> ORGANISM: Artificial sequence
<220> FEATURE:
<223> OTHER INFORMATION: 4512 HPV45L1 amplified sequence 2

<400> SEQUENCE: 106

```
ggctggactg aaagccaagc caaaactgaa aagggctgcc ccaaccagca ccaggacctc     60

ctctgccaag aggaagaagg tgaagaagta aatctagaca g                        101


<210> SEQ ID NO 107
<211> LENGTH: 38
<212> TYPE: PRT
<213> ORGANISM: Homo sapiens
<220> FEATURE:
<221> NAME/KEY: misc_feature
<223> OTHER INFORMATION: 4513 Amino acid sequence of HPV type 59 L1
      protein aa 471-508

<400> SEQUENCE: 107

Leu Gln Leu Gly Ala Arg Pro Lys Pro Thr Ile Gly Pro Arg Lys Arg
1               5                   10                  15

Ala Ala Pro Ala Pro Thr Ser Thr Pro Ser Pro Lys Arg Val Lys Arg
            20                  25                  30

Arg Lys Ser Ser Arg Lys
        35


<210> SEQ ID NO 108
<211> LENGTH: 474
<212> TYPE: PRT
<213> ORGANISM: Homo sapiens
<220> FEATURE:
<221> NAME/KEY: misc_feature
<223> OTHER INFORMATION: 5101 Amino acid sequence of HPV type 51 L1
      protein aa 1-474

<400> SEQUENCE: 108

Met Ala Leu Trp Arg Thr Asn Asp Ser Lys Val Tyr Leu Pro Pro Ala
1               5                   10                  15

Pro Val Ser Arg Ile Val Asn Thr Glu Glu Tyr Ile Thr Arg Thr Gly
            20                  25                  30

Ile Tyr Tyr Tyr Ala Gly Ser Ser Arg Leu Ile Thr Leu Gly His Pro
        35                  40                  45

Tyr Phe Pro Ile Pro Lys Thr Ser Thr Arg Ala Ala Ile Pro Lys Val
    50                  55                  60

Ser Ala Phe Gln Tyr Arg Val Phe Arg Val Gln Leu Pro Asp Pro Asn
65                  70                  75                  80

Lys Phe Gly Leu Pro Asp Pro Asn Leu Tyr Asn Pro Asp Thr Asp Arg
                85                  90                  95

Leu Val Trp Gly Cys Val Gly Val Glu Val Gly Arg Gly Gln Pro Leu
            100                 105                 110

Gly Val Gly Leu Ser Gly His Pro Leu Phe Asn Lys Tyr Asp Asp Thr
        115                 120                 125

Glu Asn Ser Arg Ile Ala Asn Gly Asn Ala Gln Gln Asp Val Arg Asp
    130                 135                 140

Asn Thr Ser Val Asp Asn Lys Gln Thr Gln Leu Cys Ile Ile Gly Cys
145                 150                 155                 160

Ala Pro Pro Ile Gly Glu His Trp Gly Ile Gly Thr Thr Cys Lys Asn
                165                 170                 175

Thr Pro Val Pro Pro Gly Asp Cys Pro Pro Leu Glu Leu Val Ser Ser
            180                 185                 190

Val Ile Gln Asp Gly Asp Met Ile Asp Thr Gly Phe Gly Ala Met Asp
        195                 200                 205

Phe Ala Ala Leu Gln Ala Thr Lys Ser Asp Val Pro Leu Asp Ile Ser
    210                 215                 220
```

```
Gln Ser Val Cys Lys Tyr Pro Asp Tyr Leu Lys Met Ser Ala Asp Thr
225                 230                 235                 240

Tyr Gly Asn Ser Met Phe Phe His Leu Arg Arg Glu Gln Ile Phe Ala
                245                 250                 255

Arg His Tyr Tyr Asn Lys Leu Val Gly Val Gly Glu Asp Ile Pro Asn
            260                 265                 270

Asp Tyr Tyr Ile Lys Gly Ser Gly Asn Gly Arg Asp Pro Ile Glu Ser
        275                 280                 285

Tyr Ile Tyr Ser Ala Thr Pro Ser Gly Ser Met Ile Thr Ser Asp Ser
    290                 295                 300

Gln Ile Phe Asn Lys Pro Tyr Trp Leu His Arg Ala Gln Gly His Asn
305                 310                 315                 320

Asn Gly Ile Cys Trp Asn Asn Gln Leu Phe Ile Thr Cys Val Asp Thr
                325                 330                 335

Thr Arg Ser Thr Asn Leu Thr Ile Ser Thr Ala Thr Ala Ala Val Ser
            340                 345                 350

Pro Thr Phe Thr Pro Ser Asn Phe Lys Gln Tyr Ile Arg His Gly Glu
        355                 360                 365

Glu Tyr Glu Leu Gln Phe Ile Phe Gln Leu Cys Lys Ile Thr Leu Thr
    370                 375                 380

Thr Glu Val Met Ala Tyr Leu His Thr Met Asp Pro Thr Ile Leu Glu
385                 390                 395                 400

Gln Trp Asn Phe Gly Leu Thr Leu Pro Pro Ser Ala Ser Leu Glu Asp
                405                 410                 415

Ala Tyr Arg Phe Val Arg Asn Ala Ala Thr Ser Cys Gln Lys Asp Thr
            420                 425                 430

Pro Pro Gln Ala Lys Pro Asp Pro Leu Ala Lys Tyr Lys Phe Trp Asp
        435                 440                 445

Val Asp Leu Lys Glu Arg Phe Ser Leu Asp Leu Asp Gln Phe Ala Leu
    450                 455                 460

Gly Arg Lys Phe Leu Leu Gln Val Gly Val
465                 470
```

<210> SEQ ID NO 109
<211> LENGTH: 26
<212> TYPE: PRT
<213> ORGANISM: Homo sapiens
<220> FEATURE:
<221> NAME/KEY: misc_feature
<223> OTHER INFORMATION: 5102 Amino acid sequence of HPV type 33 L1 protein aa 474-499

<400> SEQUENCE: 109

```
Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25
```

<210> SEQ ID NO 110
<211> LENGTH: 500
<212> TYPE: PRT
<213> ORGANISM: Artificial sequence
<220> FEATURE:
<223> OTHER INFORMATION: 5103 Amino acid sequence of chimeric HPV type 51 L1 protein

<400> SEQUENCE: 110

```
Met Ala Leu Trp Arg Thr Asn Asp Ser Lys Val Tyr Leu Pro Pro Ala
```

-continued

```
1               5                   10                  15

Pro Val Ser Arg Ile Val Asn Thr Glu Glu Tyr Ile Thr Arg Thr Gly
            20                  25                  30

Ile Tyr Tyr Tyr Ala Gly Ser Ser Arg Leu Ile Thr Leu Gly His Pro
        35                  40                  45

Tyr Phe Pro Ile Pro Lys Thr Ser Thr Arg Ala Ala Ile Pro Lys Val
    50                  55                  60

Ser Ala Phe Gln Tyr Arg Val Phe Arg Val Gln Leu Pro Asp Pro Asn
65                  70                  75                  80

Lys Phe Gly Leu Pro Asp Pro Asn Leu Tyr Asn Pro Asp Thr Asp Arg
                85                  90                  95

Leu Val Trp Gly Cys Val Gly Val Glu Val Gly Arg Gly Gln Pro Leu
            100                 105                 110

Gly Val Gly Leu Ser Gly His Pro Leu Phe Asn Lys Tyr Asp Asp Thr
        115                 120                 125

Glu Asn Ser Arg Ile Ala Asn Gly Asn Ala Gln Gln Asp Val Arg Asp
    130                 135                 140

Asn Thr Ser Val Asp Asn Lys Gln Thr Gln Leu Cys Ile Ile Gly Cys
145                 150                 155                 160

Ala Pro Pro Ile Gly Glu His Trp Gly Ile Gly Thr Thr Cys Lys Asn
                165                 170                 175

Thr Pro Val Pro Pro Gly Asp Cys Pro Pro Leu Glu Leu Val Ser Ser
            180                 185                 190

Val Ile Gln Asp Gly Asp Met Ile Asp Thr Gly Phe Gly Ala Met Asp
        195                 200                 205

Phe Ala Ala Leu Gln Ala Thr Lys Ser Asp Val Pro Leu Asp Ile Ser
    210                 215                 220

Gln Ser Val Cys Lys Tyr Pro Asp Tyr Leu Lys Met Ser Ala Asp Thr
225                 230                 235                 240

Tyr Gly Asn Ser Met Phe Phe His Leu Arg Arg Glu Gln Ile Phe Ala
                245                 250                 255

Arg His Tyr Tyr Asn Lys Leu Val Gly Val Gly Glu Asp Ile Pro Asn
            260                 265                 270

Asp Tyr Tyr Ile Lys Gly Ser Gly Asn Gly Arg Asp Pro Ile Glu Ser
        275                 280                 285

Tyr Ile Tyr Ser Ala Thr Pro Ser Gly Ser Met Ile Thr Ser Asp Ser
    290                 295                 300

Gln Ile Phe Asn Lys Pro Tyr Trp Leu His Arg Ala Gln Gly His Asn
305                 310                 315                 320

Asn Gly Ile Cys Trp Asn Asn Gln Leu Phe Ile Thr Cys Val Asp Thr
                325                 330                 335

Thr Arg Ser Thr Asn Leu Thr Ile Ser Thr Ala Thr Ala Ala Val Ser
            340                 345                 350

Pro Thr Phe Thr Pro Ser Asn Phe Lys Gln Tyr Ile Arg His Gly Glu
        355                 360                 365

Glu Tyr Glu Leu Gln Phe Ile Phe Gln Leu Cys Lys Ile Thr Leu Thr
    370                 375                 380

Thr Glu Val Met Ala Tyr Leu His Thr Met Asp Pro Thr Ile Leu Glu
385                 390                 395                 400

Gln Trp Asn Phe Gly Leu Thr Leu Pro Pro Ser Ala Ser Leu Glu Asp
                405                 410                 415

Ala Tyr Arg Phe Val Arg Asn Ala Ala Thr Ser Cys Gln Lys Asp Thr
            420                 425                 430
```

```
Pro Pro Gln Ala Lys Pro Asp Pro Leu Ala Lys Tyr Lys Phe Trp Asp
        435                 440                 445

Val Asp Leu Lys Glu Arg Phe Ser Leu Asp Leu Asp Gln Phe Ala Leu
    450                 455                 460

Gly Arg Lys Phe Leu Leu Gln Val Gly Val Lys Ala Lys Pro Lys Leu
465                 470                 475                 480

Lys Arg Ala Ala Pro Thr Ser Thr Arg Thr Ser Ser Ala Lys Arg Lys
                485                 490                 495

Lys Val Lys Lys
            500


<210> SEQ ID NO 111
<211> LENGTH: 1504
<212> TYPE: DNA
<213> ORGANISM: Artificial sequence
<220> FEATURE:
<223> OTHER INFORMATION: 5104 Nucleotide sequence of chimeric HPV type
      51 L1 protein

<400> SEQUENCE: 111

atggctctgt ggaggaccaa tgacagcaag gtctacctgc ctcctgcccc tgtgagcagg     60

attgtgaaca cagaggaata catcaccagg acaggcatct actactatgc tggctccagc    120

agactgatta ccctgggaca cccatacttt ccaatcccaa agaccagcac cagggctgcc    180

atcccaaagg tgtctgcctt ccaatacagg gtgttcaggg tccaacttcc tgacccaaac    240

aagtttggac tgcctgaccc aaacctctac aaccctgaca cagacagact ggtgtggggc    300

tgtgtgggag tggaggtggg caggggacaa ccactgggag tgggactgtc tggacaccca    360

ctgttcaaca aatatgatga cacagagaac agcaggattg ccaatggcaa tgcccaacag    420

gatgtgaggg acaacacctc tgtggacaac aagcagaccc aactttgtat cattggctgt    480

gcccctccaa ttggagaaca ctggggcatt ggcaccactt gtaagaacac acctgtgcct    540

cctggagact gtcctccatt ggaactggtg tcctctgtga ttcaggatgg agatatgatt    600

gacacaggct ttggagctat ggactttgct gccctccaag ccaccaagtc tgatgtgcca    660

ctggacatca gccagtctgt gtgtaaatac cctgactacc tgaaaatgag tgctgacacc    720

tatggcaaca gtatgttctt ccacctgagg agggaacaga tttttgccag acactactac    780

aacaaactgg tgggagtggg agaggacatc ccaaatgact actacatcaa gggctctggc    840

aatggcaggg acccaattga gtcctacatc tactctgcca caccatctgg cagtatgatt    900

acctctgaca gccagatttt caacaagcca tactggctgc acagggctca aggacacaac    960

aatggcatct gttggaacaa ccaacttttc atcacttgtg tggacaccac caggagcacc   1020

aacctgacca tcagcacagc cacagcagca gtgagcccaa ccttcacacc aagcaacttc   1080

aagcaataca tcagacatgg agaggaatat gaactccaat tcatcttcca actttgtaag   1140

attaccctga ccacagaggt gatggcttac ctgcacacaa tggacccaac catcttggaa   1200

cagtggaact ttggactgac cctgcctcca tctgcctcct tggaggatgc ctacaggttt   1260

gtgaggaatg ctgccacctc ctgtcagaag gacacacctc cacaggctaa gcctgaccca   1320

ctggctaaat acaagttctg ggatgtggac ctgaaagaga ggttctccct ggacctggac   1380

cagtttgccc tgggcaggaa gttcctgctc caagtgggag tcaaagccaa gccaaaactg   1440

aaaagggctg ccccaaccag caccaggacc tcctctgcca agaggaagaa ggtgaagaag   1500

taaa                                                                1504
```

<210> SEQ ID NO 112
<211> LENGTH: 1534
<212> TYPE: DNA
<213> ORGANISM: Artificial sequence
<220> FEATURE:
<223> OTHER INFORMATION: 5105 Synthetic HPV51 L1 gene

<400> SEQUENCE: 112

```
ctgggtacca tggctctgtg gaggaccaat gacagcaagg tctacctgcc tcctgcccct      60

gtgagcagga ttgtgaacac agaggaatac atcaccagga caggcatcta ctactatgct     120

ggctccagca gactgattac cctgggacac ccatactttc caatcccaaa gaccagcacc     180

agggctgcca tcccaaaggt gtctgccttc caatacaggg tgttcagggt ccaacttcct     240

gacccaaaca agtttggact gcctgaccca aacctctaca accctgacac agacagactg     300

gtgtggggct gtgtgggagt ggaggtgggc aggggacaac cactgggagt gggactgtct     360

ggacacccac tgttcaacaa atatgatgac acagagaaca gcaggattgc caatggcaat     420

gcccaacagg atgtgaggga caacacctct gtggacaaca agcagaccca actttgtatc     480

attggctgtg cccctccaat tggagaacac tggggcattg gcaccacttg taagaacaca     540

cctgtgcctc ctggagactg tcctccattg gaactggtgt cctctgtgat tcaggatgga     600

gatatgattg acacaggctt tggagctatg gactttgctg ccctccaagc caccaagtct     660

gatgtgccac tggacatcag ccagtctgtg tgtaaatacc ctgactacct gaaaatgagt     720

gctgacacct atggcaacag tatgttcttc cacctgagga gggaacagat ttttgccaga     780

cactactaca acaaactggt gggagtggga gaggacatcc caaatgacta ctacatcaag     840

ggctctggca atggcaggga cccaattgag tcctacatct actctgccac accatctggc     900

agtatgatta cctctgacag ccagattttc aacaagccat actggctgca cagggctcaa     960

ggacacaaca atggcatctg ttggaacaac caactttca tcacttgtgt ggacaccacc    1020

aggagcacca acctgaccat cagcacagcc acagcagcag tgagcccaac cttcacacca    1080

agcaacttca agcaatacat cagacatgga gaggaatatg aactccaatt catcttccaa    1140

ctttgtaaga ttaccctgac cacagaggtg atggcttacc tgcacacaat ggacccaacc    1200

atcttggaac agtggaactt tggactgacc ctgcctccat ctgcctcctt ggaggatgcc    1260

tacaggtttg tgaggaatgc tgccacctcc tgtcagaagg acacacctcc acaggctaag    1320

cctgacccac tggctaaata caagttctgg gatgtggacc tgaaagagag gttctccctg    1380

gacctggacc agtttgccct gggcaggaag ttcctgctcc aagtgggagt ccagaggaag    1440

ccaagacctg gactgaaaag acctgcctcc tctgcctcct cctcctcctc ctcctctgcc    1500

aagaggaaga gggtgaagaa gtaaactcga gctc                               1534
```

<210> SEQ ID NO 113
<211> LENGTH: 1519
<212> TYPE: DNA
<213> ORGANISM: Artificial sequence
<220> FEATURE:
<223> OTHER INFORMATION: 5106 Synthetic HPV33 L1 gene

<400> SEQUENCE: 113

```
ctgggtacca tgagtgtgtg gagaccatct gaggctacag tctacctgcc tcctgtgcct      60

gtgagcaagg tggtgagcac agatgaatat gtgagcagga ccagcatcta ctactatgct     120

ggctccagca gactgctggc tgtgggacac ccatacttca gcatcaagaa cccaaccaat     180

gccaagaaac tgctggtgcc aaaggtgtct ggactccaat acagggtgtt cagggtgaga     240
```

```
ctgcctgacc caaacaagtt tggctttcct gacacctcct tctacaaccc tgacacccag    300

agactggtgt gggcttgtgt gggattggag attggcaggg gacaaccact gggagtgggc    360

atctctggac acccactgct gaacaagttt gatgacacag agacaggcaa caaataccct    420

ggacaacctg gagcagacaa cagggagtgt ctgagtatgg actacaagca gacccaactt    480

tgtctgctgg gctgtaagcc tccaacagga gaacactggg gcaagggagt ggcttgtacc    540

aatgctgccc ctgccaatga ctgtcctcca ttggaactga taaacaccat cattgaggat    600

ggagatatgg tggacacagg ctttggctgt atggacttca agaccctcca agccaacaag    660

tctgatgtgc caattgacat ctgtggcagc acttgtaaat accctgacta cctgaaaatg    720

acctctgaac catatggaga ctccctgttc ttcttcctga ggagggaaca gatgtttgtg    780

agacacttct tcaacagggc tggcaccctg ggagaggctg tgcctgatga cctctacatc    840

aagggctctg gcaccacagc cagcatccag tcctctgcct tctttccaac accatctggc    900

agtatggtga cctctgagag ccaacttttc aacaagccat actggctcca aagggctcaa    960

ggacacaaca atggcatctg ttggggcaac caggtgtttg tgacagtggt ggacaccacc   1020

aggagcacca atatgaccct gtgtacccag gtgacctctg acagcaccta caagaatgag   1080

aacttcaagg aatacatcag gcatgtggag gaatatgacc tccaatttgt gttccaactt   1140

tgtaaggtga ccctgacagc agaggtgatg acctacatcc atgctatgaa ccctgacatc   1200

ttggaggact ggcagtttgg actgacacct cctccatctg cctccctcca agacacctac   1260

aggtttgtga ccagccaggc tatcacttgt cagaagacag tgcctccaaa ggagaaggag   1320

gacccactgg gcaaatacac cttctgggag gtggacctga aagagaagtt ctctgctgac   1380

ctggaccagt ttccactggg caggaagttc ctgctccaag caggactgaa agccaagcca   1440

aaactgaaaa gggctgcccc aaccagcacc aggacctcct ctgccaagag gaagaaggtg   1500

aagaagtaaa ctcgagctc                                                1519
```

<210> SEQ ID NO 114
<211> LENGTH: 34
<212> TYPE: DNA
<213> ORGANISM: Artificial sequence
<220> FEATURE:
<223> OTHER INFORMATION: 5107 HPV51L1 F1

<400> SEQUENCE: 114

```
cttggtacca tggctctgtg gaggaccaat gaca                                 34
```

<210> SEQ ID NO 115
<211> LENGTH: 32
<212> TYPE: DNA
<213> ORGANISM: Artificial sequence
<220> FEATURE:
<223> OTHER INFORMATION: 5108 HPV51L1 R1

<400> SEQUENCE: 115

```
gcttggcttt gactcccact tggagcagga ac                                   32
```

<210> SEQ ID NO 116
<211> LENGTH: 1441
<212> TYPE: DNA
<213> ORGANISM: Artificial sequence
<220> FEATURE:
<223> OTHER INFORMATION: 5109 HPV51L1 amplified sequence 1

<400> SEQUENCE: 116

-continued

```
cttggtacca tggctctgtg gaggaccaat gacagcaagg tctacctgcc tcctgcccct     60

gtgagcagga ttgtgaacac agaggaatac atcaccagga caggcatcta ctactatgct    120

ggctccagca gactgattac cctgggacac ccatactttc caatcccaaa gaccagcacc    180

agggctgcca tcccaaaggt gtctgccttc caatacaggg tgttcagggt ccaacttcct    240

gacccaaaca agtttggact gcctgaccca aacctctaca accctgacac agacagactg    300

gtgtggggct gtgtgggagt ggaggtgggc aggggacaac cactgggagt gggactgtct    360

ggacacccac tgttcaacaa atatgatgac acagagaaca gcaggattgc caatggcaat    420

gcccaacagg atgtgaggga caacacctct gtggacaaca agcagaccca actttgtatc    480

attggctgtg cccctccaat tggagaacac tggggcattg gcaccacttg taagaacaca    540

cctgtgcctc ctggagactg tcctccattg gaactggtgt cctctgtgat tcaggatgga    600

gatatgattg acacaggctt tggagctatg gactttgctg ccctccaagc caccaagtct    660

gatgtgccac tggacatcag ccagtctgtg tgtaaatacc ctgactacct gaaaatgagt    720

gctgacacct atggcaacag tatgttcttc cacctgagga gggaacagat tttgccaga     780

cactactaca acaaactggt gggagtggga gaggacatcc caaatgacta ctacatcaag    840

ggctctggca atggcaggga cccaattgag tcctacatct actctgccac accatctggc    900

agtatgatta cctctgacag ccagattttc aacaagccat actggctgca cagggctcaa    960

ggacacaaca atggcatctg ttggaacaac caacttttca tcacttgtgt ggacaccacc   1020

aggagcacca acctgaccat cagcacagcc acagcagcag tgagcccaac cttcacacca   1080

agcaacttca agcaatacat cagacatgga gaggaatatg aactccaatt catcttccaa   1140

ctttgtaaga ttaccctgac cacagaggtg atggcttacc tgcacacaat ggacccaacc   1200

atcttggaac agtggaactt tggactgacc ctgcctccat ctgcctcctt ggaggatgcc   1260

tacaggtttg tgaggaatgc tgccacctcc tgtcagaagg acacacctcc acaggctaag   1320

cctgacccac tggctaaata caagttctgg gatgtggacc tgaaagagag gttctccctg   1380

gacctggacc agtttgccct gggcaggaag ttcctgctcc aagtgggagt caaagccaag   1440

c                                                                   1441
```

<210> SEQ ID NO 117
<211> LENGTH: 35
<212> TYPE: DNA
<213> ORGANISM: Artificial sequence
<220> FEATURE:
<223> OTHER INFORMATION: 5110 HPV51L1 F2

<400> SEQUENCE: 117

```
agtgggagtc aaagccaagc caaaactgaa aaggg                                35
```

<210> SEQ ID NO 118
<211> LENGTH: 36
<212> TYPE: DNA
<213> ORGANISM: Artificial sequence
<220> FEATURE:
<223> OTHER INFORMATION: 5111 HPV51L1 R2

<400> SEQUENCE: 118

```
ctgtctagat ttacttcttc accttcttcc tcttgg                               36
```

<210> SEQ ID NO 119
<211> LENGTH: 101
<212> TYPE: DNA
<213> ORGANISM: Artificial sequence
<220> FEATURE:
<223> OTHER INFORMATION: 5112 HPV51L1 amplified sequence 2

<400> SEQUENCE: 119
agtgggagtc aaagccaagc caaaactgaa aagggctgcc ccaaccagca ccaggacctc 60
ctctgccaag aggaagaagg tgaagaagta aatctagaca g 101

<210> SEQ ID NO 120
<211> LENGTH: 38
<212> TYPE: PRT
<213> ORGANISM: Homo sapiens
<220> FEATURE:
<221> NAME/KEY: misc_feature
<223> OTHER INFORMATION: 5113 Amino acid sequence of HPV type 59 L1
protein aa 471-508

<400> SEQUENCE: 120

Leu Gln Leu Gly Ala Arg Pro Lys Pro Thr Ile Gly Pro Arg Lys Arg
1 5 10 15

Ala Ala Pro Ala Pro Thr Ser Thr Pro Ser Pro Lys Arg Val Lys Arg
20 25 30

Arg Lys Ser Ser Arg Lys
35

<210> SEQ ID NO 121
<211> LENGTH: 478
<212> TYPE: PRT
<213> ORGANISM: Homo sapiens
<220> FEATURE:
<221> NAME/KEY: misc_feature
<223> OTHER INFORMATION: 5201 Amino acid sequence of HPV type 52 L1
protein aa 1-478

<400> SEQUENCE: 121

Met Ser Val Trp Arg Pro Ser Glu Ala Thr Val Tyr Leu Pro Pro Val
1 5 10 15

Pro Val Ser Lys Val Val Ser Thr Asp Glu Tyr Val Ser Arg Thr Ser
20 25 30

Ile Tyr Tyr Tyr Ala Gly Ser Ser Arg Leu Leu Thr Val Gly His Pro
35 40 45

Tyr Phe Ser Ile Lys Asn Thr Ser Ser Gly Asn Gly Lys Lys Val Leu
50 55 60

Val Pro Lys Val Ser Gly Leu Gln Tyr Arg Val Phe Arg Ile Lys Leu
65 70 75 80

Pro Asp Pro Asn Lys Phe Gly Phe Pro Asp Thr Ser Phe Tyr Asn Pro
85 90 95

Glu Thr Gln Arg Leu Val Trp Ala Cys Thr Gly Leu Glu Ile Gly Arg
100 105 110

Gly Gln Pro Leu Gly Val Gly Ile Ser Gly His Pro Leu Leu Asn Lys
115 120 125

Phe Asp Asp Thr Glu Thr Ser Asn Lys Tyr Ala Gly Lys Pro Gly Ile
130 135 140

Asp Asn Arg Glu Cys Leu Ser Met Asp Tyr Lys Gln Thr Gln Leu Cys
145 150 155 160

Ile Leu Gly Cys Lys Pro Pro Ile Gly Glu His Trp Gly Lys Gly Thr
165 170 175

Pro Cys Asn Asn Asn Ser Gly Asn Pro Gly Asp Cys Pro Pro Leu Gln
180 185 190

Leu Ile Asn Ser Val Ile Gln Asp Gly Asp Met Val Asp Thr Gly Phe

```
        195                 200                 205

Gly Cys Met Asp Phe Asn Thr Leu Gln Ala Ser Lys Ser Asp Val Pro
    210                 215                 220

Ile Asp Ile Cys Ser Ser Val Cys Lys Tyr Pro Asp Tyr Leu Gln Met
225                 230                 235                 240

Ala Ser Glu Pro Tyr Gly Asp Ser Leu Phe Phe Phe Leu Arg Arg Glu
                245                 250                 255

Gln Met Phe Val Arg His Phe Phe Asn Arg Ala Gly Thr Leu Gly Asp
            260                 265                 270

Pro Val Pro Gly Asp Leu Tyr Ile Gln Gly Ser Asn Ser Gly Asn Thr
        275                 280                 285

Ala Thr Val Gln Ser Ser Ala Phe Phe Pro Thr Pro Ser Gly Ser Met
    290                 295                 300

Val Thr Ser Glu Ser Gln Leu Phe Asn Lys Pro Tyr Trp Leu Gln Arg
305                 310                 315                 320

Ala Gln Gly His Asn Asn Gly Ile Cys Trp Gly Asn Gln Leu Phe Val
                325                 330                 335

Thr Val Val Asp Thr Thr Arg Ser Thr Asn Met Thr Leu Cys Ala Glu
            340                 345                 350

Val Lys Lys Glu Ser Thr Tyr Lys Asn Glu Asn Phe Lys Glu Tyr Leu
        355                 360                 365

Arg His Gly Glu Glu Phe Asp Leu Gln Phe Ile Phe Gln Leu Cys Lys
    370                 375                 380

Ile Thr Leu Thr Ala Asp Val Met Thr Tyr Ile His Lys Met Asp Ala
385                 390                 395                 400

Thr Ile Leu Glu Asp Trp Gln Phe Gly Leu Thr Pro Pro Pro Ser Ala
                405                 410                 415

Ser Leu Glu Asp Thr Tyr Arg Phe Val Thr Ser Thr Ala Ile Thr Cys
            420                 425                 430

Gln Lys Asn Thr Pro Pro Lys Gly Lys Glu Asp Pro Leu Lys Asp Tyr
        435                 440                 445

Met Phe Trp Glu Val Asp Leu Lys Glu Lys Phe Ser Ala Asp Leu Asp
    450                 455                 460

Gln Phe Pro Leu Gly Arg Lys Phe Leu Leu Gln Ala Gly Leu
465                 470                 475
```

<210> SEQ ID NO 122
<211> LENGTH: 26
<212> TYPE: PRT
<213> ORGANISM: Homo sapiens
<220> FEATURE:
<221> NAME/KEY: misc_feature
<223> OTHER INFORMATION: 5202 Amino acid sequence of HPV type 33 L1 protein aa 474-499

<400> SEQUENCE: 122

```
Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25
```

<210> SEQ ID NO 123
<211> LENGTH: 504
<212> TYPE: PRT
<213> ORGANISM: Artificial sequence
<220> FEATURE:
<223> OTHER INFORMATION: 5203 Amino acid sequence of chimeric HPV type 52 L1 protein

<400> SEQUENCE: 123

Met Ser Val Trp Arg Pro Ser Glu Ala Thr Val Tyr Leu Pro Pro Val
1 5 10 15

Pro Val Ser Lys Val Val Ser Thr Asp Glu Tyr Val Ser Arg Thr Ser
20 25 30

Ile Tyr Tyr Tyr Ala Gly Ser Ser Arg Leu Leu Thr Val Gly His Pro
35 40 45

Tyr Phe Ser Ile Lys Asn Thr Ser Ser Gly Asn Gly Lys Lys Val Leu
50 55 60

Val Pro Lys Val Ser Gly Leu Gln Tyr Arg Val Phe Arg Ile Lys Leu
65 70 75 80

Pro Asp Pro Asn Lys Phe Gly Phe Pro Asp Thr Ser Phe Tyr Asn Pro
85 90 95

Glu Thr Gln Arg Leu Val Trp Ala Cys Thr Gly Leu Glu Ile Gly Arg
100 105 110

Gly Gln Pro Leu Gly Val Gly Ile Ser Gly His Pro Leu Leu Asn Lys
115 120 125

Phe Asp Asp Thr Glu Thr Ser Asn Lys Tyr Ala Gly Lys Pro Gly Ile
130 135 140

Asp Asn Arg Glu Cys Leu Ser Met Asp Tyr Lys Gln Thr Gln Leu Cys
145 150 155 160

Ile Leu Gly Cys Lys Pro Pro Ile Gly Glu His Trp Gly Lys Gly Thr
165 170 175

Pro Cys Asn Asn Asn Ser Gly Asn Pro Gly Asp Cys Pro Pro Leu Gln
180 185 190

Leu Ile Asn Ser Val Ile Gln Asp Gly Asp Met Val Asp Thr Gly Phe
195 200 205

Gly Cys Met Asp Phe Asn Thr Leu Gln Ala Ser Lys Ser Asp Val Pro
210 215 220

Ile Asp Ile Cys Ser Ser Val Cys Lys Tyr Pro Asp Tyr Leu Gln Met
225 230 235 240

Ala Ser Glu Pro Tyr Gly Asp Ser Leu Phe Phe Phe Leu Arg Arg Glu
245 250 255

Gln Met Phe Val Arg His Phe Phe Asn Arg Ala Gly Thr Leu Gly Asp
260 265 270

Pro Val Pro Gly Asp Leu Tyr Ile Gln Gly Ser Asn Ser Gly Asn Thr
275 280 285

Ala Thr Val Gln Ser Ser Ala Phe Phe Pro Thr Pro Ser Gly Ser Met
290 295 300

Val Thr Ser Glu Ser Gln Leu Phe Asn Lys Pro Tyr Trp Leu Gln Arg
305 310 315 320

Ala Gln Gly His Asn Asn Gly Ile Cys Trp Gly Asn Gln Leu Phe Val
325 330 335

Thr Val Val Asp Thr Thr Arg Ser Thr Asn Met Thr Leu Cys Ala Glu
340 345 350

Val Lys Lys Glu Ser Thr Tyr Lys Asn Glu Asn Phe Lys Glu Tyr Leu
355 360 365

Arg His Gly Glu Glu Phe Asp Leu Gln Phe Ile Phe Gln Leu Cys Lys
370 375 380

Ile Thr Leu Thr Ala Asp Val Met Thr Tyr Ile His Lys Met Asp Ala
385 390 395 400

Thr Ile Leu Glu Asp Trp Gln Phe Gly Leu Thr Pro Pro Pro Ser Ala

-continued

```
                405                 410                 415

Ser Leu Glu Asp Thr Tyr Arg Phe Val Thr Ser Thr Ala Ile Thr Cys
            420                 425                 430

Gln Lys Asn Thr Pro Pro Lys Gly Lys Glu Asp Pro Leu Lys Asp Tyr
        435                 440                 445

Met Phe Trp Glu Val Asp Leu Lys Glu Lys Phe Ser Ala Asp Leu Asp
    450                 455                 460

Gln Phe Pro Leu Gly Arg Lys Phe Leu Leu Gln Ala Gly Leu Lys Ala
465                 470                 475                 480

Lys Pro Lys Leu Lys Arg Ala Ala Pro Thr Ser Thr Arg Thr Ser Ser
                485                 490                 495

Ala Lys Arg Lys Lys Val Lys Lys
            500
```

<210> SEQ ID NO 124
<211> LENGTH: 1516
<212> TYPE: DNA
<213> ORGANISM: Artificial sequence
<220> FEATURE:
<223> OTHER INFORMATION: 5204 Nucleotide sequence of chimeric HPV type 52 L1 protein

<400> SEQUENCE: 124

```
atgagcgtgt ggaggcccag cgaggccacc gtgtacctgc cccccgtgcc cgtgagcaag     60

gtggtgagca ccgacgagta cgtgagcagg accagcatct actactacgc cggcagcagc    120

aggctgctga ccgtgggcca cccctacttc agcatcaaga acaccagcag cggcaacggc    180

aagaaggtgc tggtgcccaa ggtgagcggc ctgcagtaca gggtgttcag gatcaagctg    240

cccgacccca acaagttcgg cttccccgac accagcttct acaaccccga gacccagagg    300

ctggtgtggg cctgcaccgg cctggagatc ggcaggggcc agcccctggg cgtgggcatc    360

agcggccacc ccctgctgaa caagttcgac gacaccgaga ccagcaacaa gtacgccggc    420

aagcccggca tcgacaacag ggagtgcctg agcatggact acaagcagac ccagctgtgc    480

atcctgggct gcaagccccc catcggcgag cactggggca agggcacccc ctgcaacaac    540

aacagcggca accccggcga ctgccccccc ctgcagctga tcaacagcgt gatccaggac    600

ggcgacatgg tggacaccgg cttcggctgc atggacttca acaccctgca ggccagcaag    660

agcgacgtgc ccatcgacat ctgcagcagc gtgtgcaagt accccgacta cctgcagatg    720

gccagcgagc cctacggcga cagcctgttc ttcttcctga ggagggagca gatgttcgtg    780

aggcacttct tcaacagggc cggcaccctg ggcgaccccg tgcccggcga cctgtacatc    840

cagggcagca acagcggcaa caccgccacc gtgcagagca gcgccttctt ccccaccccc    900

agcggcagca tggtgaccag cgagagccag ctgttcaaca agccctactg gctgcagagg    960

gcccagggcc acaacaacgg catctgctgg ggcaaccagc tgttcgtgac cgtggtggac   1020

accaccagga gcaccaacat gaccctgtgc gccgaggtga agaaggagag cacctacaag   1080

aacgagaact tcaaggagta cctgaggcac ggcgaggagt tcgacctgca gttcatcttc   1140

cagctgtgca agatcaccct gaccgccgac gtgatgacct acatccacaa gatggacgcc   1200

accatcctgg aggactggca gttcggcctg accccccccc ccagcgccag cctggaggac   1260

acctacaggt tcgtgaccag caccgccatc acctgccaga agaacacccc ccccaagggc   1320

aaggaggacc ccctgaagga ctacatgttc tgggaggtgg acctgaagga gaagttcagc   1380

gccgacctgg accagttccc cctgggcagg aagttcctgc tgcaggccgg cctgaaagcc   1440
```

aagccaaaac tgaaaagggc tgccccaacc agcaccagga cctcctctgc caagaggaag 1500
aaggtgaaga agtaaa 1516

<210> SEQ ID NO 125
<211> LENGTH: 1531
<212> TYPE: DNA
<213> ORGANISM: Artificial sequence
<220> FEATURE:
<223> OTHER INFORMATION: 5205 Synthetic HPV52 L1 gene

<400> SEQUENCE: 125
ctgggtacca tgagcgtgtg gaggcccagc gaggccaccg tgtacctgcc ccccgtgccc 60
gtgagcaagg tggtgagcac cgacgagtac gtgagcagga ccagcatcta ctactacgcc 120
ggcagcagca ggctgctgac cgtgggccac ccctacttca gcatcaagaa caccagcagc 180
ggcaacggca agaaggtgct ggtgcccaag gtgagcggcc tgcagtacag ggtgttcagg 240
atcaagctgc ccgaccccaa caagttcggc ttccccgaca ccagcttcta caaccccgag 300
acccagaggc tggtgtgggc ctgcaccggc ctggagatcg gcaggggcca gcccctgggc 360
gtgggcatca gcggccaccc cctgctgaac aagttcgacg acaccgagac cagcaacaag 420
tacgccggca agcccggcat cgacaacagg gagtgcctga gcatggacta caagcagacc 480
cagctgtgca tcctgggctg caagcccccc atcggcgagc actggggcaa gggcaccccc 540
tgcaacaaca acagcggcaa ccccggcgac tgcccccccc tgcagctgat caacagcgtg 600
atccaggacg gcgacatggt ggacaccggc ttcggctgca tggacttcaa caccctgcag 660
gccagcaaga gcgacgtgcc catcgacatc tgcagcagcg tgtgcaagta ccccgactac 720
ctgcagatgg ccagcgagcc ctacggcgac agcctgttct tcttcctgag gagggagcag 780
atgttcgtga ggcacttctt caacagggcc ggcaccctgg gcgaccccgt gcccggcgac 840
ctgtacatcc agggcagcaa cagcggcaac accgccaccg tgcagagcag cgccttcttc 900 cccacccccca gcggcagcat ggtgaccagc gagagccagc tgttcaacaa gccctactgg 960
ctgcagaggg cccagggcca caacaacggc atctgctggg gcaaccagct gttcgtgacc 1020
gtggtggaca ccaccaggag caccaacatg accctgtgcg ccgaggtgaa gaaggagagc 1080
acctacaaga acgagaactt caaggagtac ctgaggcacg gcgaggagtt cgacctgcag 1140
ttcatcttcc agctgtgcaa gatcaccctg accgccgacg tgatgaccta catccacaag 1200
atggacgcca ccatcctgga ggactggcag ttcggcctga cccccccccc cagcgccagc 1260
ctggaggaca cctacaggtt cgtgaccagc accgccatca cctgccagaa gaacaccccc 1320
cccaagggca aggaggaccc cctgaaggac tacatgttct gggaggtgga cctgaaggag 1380
aagttcagcg ccgacctgga ccagttcccc ctgggcagga agttcctgct gcaggccggc 1440
ctgcaggcca ggcccaagct gaagaggccc gccagcagcg cccccaggac cagcaccaag 1500
aagaagaagg tgaagaggta aactcgagct c 1531

<210> SEQ ID NO 126
<211> LENGTH: 1519
<212> TYPE: DNA
<213> ORGANISM: Artificial sequence
<220> FEATURE:
<223> OTHER INFORMATION: 5206 Synthetic HPV33 L1 gene

<400> SEQUENCE: 126
ctgggtacca tgagtgtgtg gagaccatct gaggctacag tctacctgcc tcctgtgcct 60
gtgagcaagg tggtgagcac agatgaatat gtgagcagga ccagcatcta ctactatgct 120
ggctccagca gactgctggc tgtgggacac ccatacttca gcatcaagaa cccaaccaat 180
gccaagaaac tgctggtgcc aaaggtgtct ggactccaat acagggtgtt cagggtgaga 240
ctgcctgacc caaacaagtt tggctttcct gacacctcct tctacaaccc tgacacccag 300
agactggtgt gggcttgtgt gggattggag attggcaggg gacaaccact gggagtgggc 360
atctctggac acccactgct gaacaagttt gatgacacag agacaggcaa caaataccct 420
ggacaacctg gagcagacaa cagggagtgt ctgagtatgg actacaagca gacccaactt 480
tgtctgctgg gctgtaagcc tccaacagga gaacactggg gcaagggagt ggcttgtacc 540
aatgctgccc ctgccaatga ctgtcctcca ttggaactga taaacaccat cattgaggat 600
ggagatatgg tggacacagg ctttggctgt atggacttca agaccctcca agccaacaag 660
tctgatgtgc caattgacat ctgtggcagc acttgtaaat accctgacta cctgaaaatg 720
acctctgaac catatggaga ctccctgttc ttcttcctga ggagggaaca gatgtttgtg 780
agacacttct tcaacagggc tggcaccctg ggagaggctg tgcctgatga cctctacatc 840
aagggctctg gcaccacagc cagcatccag tcctctgcct tctttccaac accatctggc 900
agtatggtga cctctgagag ccaacttttc aacaagccat actggctcca aagggctcaa 960
ggacacaaca atggcatctg ttggggcaac caggtgtttg tgacagtggt ggacaccacc 1020
aggagcacca atatgaccct gtgtacccag gtgacctctg acagcaccta caagaatgag 1080
aacttcaagg aatacatcag gcatgtggag gaatatgacc tccaatttgt gttccaactt 1140
tgtaaggtga ccctgacagc agaggtgatg acctacatcc atgctatgaa ccctgacatc 1200
ttggaggact ggcagtttgg actgacacct cctccatctg cctccctcca agacacctac 1260
aggtttgtga ccagccaggc tatcacttgt cagaagacag tgcctccaaa ggagaaggag 1320
gacccactgg gcaaatacac cttctgggag gtggacctga aagagaagtt ctctgctgac 1380
ctggaccagt ttccactggg caggaagttc ctgctccaag caggactgaa agccaagcca 1440
aaactgaaaa gggctgcccc aaccagcacc aggacctcct ctgccaagag gaagaaggtg 1500
aagaagtaaa ctcgagctc 1519

<210> SEQ ID NO 127
<211> LENGTH: 34
<212> TYPE: DNA
<213> ORGANISM: Artificial sequence
<220> FEATURE:
<223> OTHER INFORMATION: 5207 HPV52L1 F1

<400> SEQUENCE: 127
cttggtacca tgagcgtgtg gaggcccagc gagg 34

<210> SEQ ID NO 128
<211> LENGTH: 35
<212> TYPE: DNA
<213> ORGANISM: Artificial sequence
<220> FEATURE:
<223> OTHER INFORMATION: 5208 HPV52L1 R1

<400> SEQUENCE: 128
gcttggcttt caggccggcc tgcagcagga acttc 35

<210> SEQ ID NO 129
<211> LENGTH: 1453
<212> TYPE: DNA
<213> ORGANISM: Artificial sequence
<220> FEATURE:

<223> OTHER INFORMATION: 5209 HPV52L1 amplified sequence 1

<400> SEQUENCE: 129
cttggtacca tgagcgtgtg gaggcccagc gaggccaccg tgtacctgcc ccccgtgccc 60
gtgagcaagg tggtgagcac cgacgagtac gtgagcagga ccagcatcta ctactacgcc 120
ggcagcagca ggctgctgac cgtgggccac ccctacttca gcatcaagaa caccagcagc 180
ggcaacggca agaaggtgct ggtgcccaag gtgagcggcc tgcagtacag ggtgttcagg 240
atcaagctgc ccgaccccaa caagttcggc ttccccgaca ccagcttcta caaccccgag 300
acccagaggc tggtgtgggc ctgcaccggc ctggagatcg gcaggggcca gcccctgggc 360
gtgggcatca gcggccaccc cctgctgaac aagttcgacg acaccgagac cagcaacaag 420
tacgccggca agcccggcat cgacaacagg gagtgcctga gcatggacta caagcagacc 480
cagctgtgca tcctgggctg caagcccccc atcggcgagc actggggcaa gggcaccccc 540
tgcaacaaca acagcggcaa ccccggcgac tgcccccccc tgcagctgat caacagcgtg 600
atccaggacg gcgacatggt ggacaccggc ttcggctgca tggacttcaa caccctgcag 660
gccagcaaga gcgacgtgcc catcgacatc tgcagcagcg tgtgcaagta ccccgactac 720
ctgcagatgg ccagcgagcc ctacggcgac agcctgttct tcttcctgag gagggagcag 780
atgttcgtga ggcacttctt caacagggcc ggcaccctgg gcgaccccgt gcccggcgac 840
ctgtacatcc agggcagcaa cagcggcaac accgccaccg tgcagagcag cgccttcttc 900
cccaccccca gcggcagcat ggtgaccagc gagagccagc tgttcaacaa gccctactgg 960
ctgcagaggg cccagggcca caacaacggc atctgctggg gcaaccagct gttcgtgacc 1020
gtggtggaca ccaccaggag caccaacatg accctgtgcg ccgaggtgaa gaaggagagc 1080
acctacaaga acgagaactt caaggagtac ctgaggcacg gcgaggagtt cgacctgcag 1140
ttcatcttcc agctgtgcaa gatcaccctg accgccgacg tgatgaccta catccacaag 1200
atggacgcca ccatcctgga ggactggcag ttcggcctga cccccccccc cagcgccagc 1260
ctggaggaca cctacaggtt cgtgaccagc accgccatca cctgccagaa gaacaccccc 1320
cccaagggca aggaggaccc cctgaaggac tacatgttct gggaggtgga cctgaaggag 1380
aagttcagcg ccgacctgga ccagttcccc ctgggcagga agttcctgct gcaggccggc 1440
ctgaaagcca agc 1453

<210> SEQ ID NO 130
<211> LENGTH: 35
<212> TYPE: DNA
<213> ORGANISM: Artificial sequence
<220> FEATURE:
<223> OTHER INFORMATION: 5210 HPV52L1 F2

<400> SEQUENCE: 130
ggccggcctg aaagccaagc caaaactgaa aaggg 35

<210> SEQ ID NO 131
<211> LENGTH: 36
<212> TYPE: DNA
<213> ORGANISM: Artificial sequence
<220> FEATURE:
<223> OTHER INFORMATION: 5211 HPV52L1 R2

<400> SEQUENCE: 131
ctgtctagat ttacttcttc accttcttcc tcttgg 36

<210> SEQ ID NO 132
<211> LENGTH: 101
<212> TYPE: DNA
<213> ORGANISM: Artificial sequence
<220> FEATURE:
<223> OTHER INFORMATION: 5212 HPV52L1 amplified sequence 2

<400> SEQUENCE: 132
ggccggcctg aaagccaagc caaaactgaa aagggctgcc ccaaccagca ccaggacctc 60
ctctgccaag aggaagaagg tgaagaagta aatctagaca g 101

<210> SEQ ID NO 133
<211> LENGTH: 38
<212> TYPE: PRT
<213> ORGANISM: Homo sapiens
<220> FEATURE:
<221> NAME/KEY: misc_feature
<223> OTHER INFORMATION: 5213 Amino acid sequence of HPV type 59 L1 protein aa 471-508

<400> SEQUENCE: 133

Leu Gln Leu Gly Ala Arg Pro Lys Pro Thr Ile Gly Pro Arg Lys Arg
1 5 10 15

Ala Ala Pro Ala Pro Thr Ser Thr Pro Ser Pro Lys Arg Val Lys Arg
20 25 30

Arg Lys Ser Ser Arg Lys
35

<210> SEQ ID NO 134
<211> LENGTH: 467
<212> TYPE: PRT
<213> ORGANISM: Homo sapiens
<220> FEATURE:
<221> NAME/KEY: misc_feature
<223> OTHER INFORMATION: 5601 Amino acid sequence of HPV type 56 L1 protein aa 1-467

<400> SEQUENCE: 134

Met Ala Thr Trp Arg Pro Ser Glu Asn Lys Val Tyr Leu Pro Pro Thr
1 5 10 15

Pro Val Ser Lys Val Val Ala Thr Asp Ser Tyr Val Lys Arg Thr Ser
20 25 30

Ile Phe Tyr His Ala Gly Ser Ser Arg Leu Leu Ala Val Gly His Pro
35 40 45

Tyr Tyr Ser Val Thr Lys Asp Asn Thr Lys Thr Asn Ile Pro Lys Val
50 55 60

Ser Ala Tyr Gln Tyr Arg Val Phe Arg Val Arg Leu Pro Asp Pro Asn
65 70 75 80

Lys Phe Gly Leu Pro Asp Thr Asn Ile Tyr Asn Pro Asp Gln Glu Arg
85 90 95

Leu Val Trp Ala Cys Val Gly Leu Glu Val Gly Arg Gly Gln Pro Leu
100 105 110

Gly Ala Gly Leu Ser Gly His Pro Leu Phe Asn Arg Leu Asp Asp Thr
115 120 125

Glu Ser Ser Asn Leu Ala Asn Asn Asn Val Ile Glu Asp Ser Arg Asp
130 135 140

Asn Ile Ser Val Asp Gly Lys Gln Thr Gln Leu Cys Ile Val Gly Cys
145 150 155 160

Thr Pro Ala Met Gly Glu His Trp Thr Lys Gly Ala Val Cys Lys Ser
165 170 175

-continued

```
Thr Gln Val Thr Thr Gly Asp Cys Pro Pro Leu Ala Leu Ile Asn Thr
            180                 185                 190

Pro Ile Glu Asp Gly Asp Met Ile Asp Thr Gly Phe Gly Ala Met Asp
        195                 200                 205

Phe Lys Val Leu Gln Glu Ser Lys Ala Glu Val Pro Leu Asp Ile Val
    210                 215                 220

Gln Ser Thr Cys Lys Tyr Pro Asp Tyr Leu Lys Met Ser Ala Asp Ala
225                 230                 235                 240

Tyr Gly Asp Ser Met Trp Phe Tyr Leu Arg Arg Glu Gln Leu Phe Ala
                245                 250                 255

Arg His Tyr Phe Asn Arg Ala Gly Lys Val Gly Glu Thr Ile Pro Ala
            260                 265                 270

Glu Leu Tyr Leu Lys Gly Ser Asn Gly Arg Glu Pro Pro Pro Ser Ser
        275                 280                 285

Val Tyr Val Ala Thr Pro Ser Gly Ser Met Ile Thr Ser Glu Ala Gln
    290                 295                 300

Leu Phe Asn Lys Pro Tyr Trp Leu Gln Arg Ala Gln Gly His Asn Asn
305                 310                 315                 320

Gly Ile Cys Trp Gly Asn Gln Leu Phe Val Thr Val Val Asp Thr Thr
                325                 330                 335

Arg Ser Thr Asn Met Thr Ile Ser Thr Ala Thr Glu Gln Leu Ser Lys
            340                 345                 350

Tyr Asp Ala Arg Lys Ile Asn Gln Tyr Leu Arg His Val Glu Glu Tyr
        355                 360                 365

Glu Leu Gln Phe Val Phe Gln Leu Cys Lys Ile Thr Leu Ser Ala Glu
    370                 375                 380

Val Met Ala Tyr Leu His Asn Met Asn Ala Asn Leu Leu Glu Asp Trp
385                 390                 395                 400

Asn Ile Gly Leu Ser Pro Pro Val Ala Thr Ser Leu Glu Asp Lys Tyr
                405                 410                 415

Arg Tyr Val Arg Ser Thr Ala Ile Thr Cys Gln Arg Glu Gln Pro Pro
            420                 425                 430

Thr Glu Lys Gln Asp Pro Leu Ala Lys Tyr Lys Phe Trp Asp Val Asn
        435                 440                 445

Leu Gln Asp Ser Phe Ser Thr Asp Leu Asp Gln Phe Pro Leu Gly Arg
    450                 455                 460

Lys Phe Leu
465


<210> SEQ ID NO 135
<211> LENGTH: 31
<212> TYPE: PRT
<213> ORGANISM: Homo sapiens
<220> FEATURE:
<221> NAME/KEY: misc_feature
<223> OTHER INFORMATION: 5602 Amino acid sequence of HPV type 33 L1
      protein aa 469-499

<400> SEQUENCE: 135

Leu Gln Ala Gly Leu Lys Ala Lys Pro Lys Leu Lys Arg Ala Ala Pro
1               5                   10                  15

Thr Ser Thr Arg Thr Ser Ser Ala Lys Arg Lys Lys Val Lys Lys
            20                  25                  30


<210> SEQ ID NO 136
<211> LENGTH: 498
<212> TYPE: PRT
```

```
<213> ORGANISM: Artificial sequence
<220> FEATURE:
<223> OTHER INFORMATION: 5603 Amino acid sequence of chimeric HPV type
      56 L1 protein

<400> SEQUENCE: 136

Met Ala Thr Trp Arg Pro Ser Glu Asn Lys Val Tyr Leu Pro Pro Thr
1               5                   10                  15

Pro Val Ser Lys Val Val Ala Thr Asp Ser Tyr Val Lys Arg Thr Ser
            20                  25                  30

Ile Phe Tyr His Ala Gly Ser Ser Arg Leu Leu Ala Val Gly His Pro
        35                  40                  45

Tyr Tyr Ser Val Thr Lys Asp Asn Thr Lys Thr Asn Ile Pro Lys Val
    50                  55                  60

Ser Ala Tyr Gln Tyr Arg Val Phe Arg Val Arg Leu Pro Asp Pro Asn
65                  70                  75                  80

Lys Phe Gly Leu Pro Asp Thr Asn Ile Tyr Asn Pro Asp Gln Glu Arg
                85                  90                  95

Leu Val Trp Ala Cys Val Gly Leu Glu Val Gly Arg Gly Gln Pro Leu
            100                 105                 110

Gly Ala Gly Leu Ser Gly His Pro Leu Phe Asn Arg Leu Asp Asp Thr
        115                 120                 125

Glu Ser Ser Asn Leu Ala Asn Asn Asn Val Ile Glu Asp Ser Arg Asp
    130                 135                 140

Asn Ile Ser Val Asp Gly Lys Gln Thr Gln Leu Cys Ile Val Gly Cys
145                 150                 155                 160

Thr Pro Ala Met Gly Glu His Trp Thr Lys Gly Ala Val Cys Lys Ser
                165                 170                 175

Thr Gln Val Thr Thr Gly Asp Cys Pro Pro Leu Ala Leu Ile Asn Thr
            180                 185                 190

Pro Ile Glu Asp Gly Asp Met Ile Asp Thr Gly Phe Gly Ala Met Asp
        195                 200                 205

Phe Lys Val Leu Gln Glu Ser Lys Ala Glu Val Pro Leu Asp Ile Val
    210                 215                 220

Gln Ser Thr Cys Lys Tyr Pro Asp Tyr Leu Lys Met Ser Ala Asp Ala
225                 230                 235                 240

Tyr Gly Asp Ser Met Trp Phe Tyr Leu Arg Arg Glu Gln Leu Phe Ala
                245                 250                 255

Arg His Tyr Phe Asn Arg Ala Gly Lys Val Gly Glu Thr Ile Pro Ala
            260                 265                 270

Glu Leu Tyr Leu Lys Gly Ser Asn Gly Arg Glu Pro Pro Pro Ser Ser
        275                 280                 285

Val Tyr Val Ala Thr Pro Ser Gly Ser Met Ile Thr Ser Glu Ala Gln
    290                 295                 300

Leu Phe Asn Lys Pro Tyr Trp Leu Gln Arg Ala Gln Gly His Asn Asn
305                 310                 315                 320

Gly Ile Cys Trp Gly Asn Gln Leu Phe Val Thr Val Val Asp Thr Thr
                325                 330                 335

Arg Ser Thr Asn Met Thr Ile Ser Thr Ala Thr Glu Gln Leu Ser Lys
            340                 345                 350

Tyr Asp Ala Arg Lys Ile Asn Gln Tyr Leu Arg His Val Glu Glu Tyr
        355                 360                 365

Glu Leu Gln Phe Val Phe Gln Leu Cys Lys Ile Thr Leu Ser Ala Glu
    370                 375                 380
```

```
Val Met Ala Tyr Leu His Asn Met Asn Ala Asn Leu Leu Glu Asp Trp
385                 390                 395                 400

Asn Ile Gly Leu Ser Pro Pro Val Ala Thr Ser Leu Glu Asp Lys Tyr
                405                 410                 415

Arg Tyr Val Arg Ser Thr Ala Ile Thr Cys Gln Arg Glu Gln Pro Pro
            420                 425                 430

Thr Glu Lys Gln Asp Pro Leu Ala Lys Tyr Lys Phe Trp Asp Val Asn
        435                 440                 445

Leu Gln Asp Ser Phe Ser Thr Asp Leu Asp Gln Phe Pro Leu Gly Arg
    450                 455                 460

Lys Phe Leu Leu Gln Ala Gly Leu Lys Ala Lys Pro Lys Leu Lys Arg
465                 470                 475                 480

Ala Ala Pro Thr Ser Thr Arg Thr Ser Ser Ala Lys Arg Lys Lys Val
                485                 490                 495

Lys Lys


<210> SEQ ID NO 137
<211> LENGTH: 1498
<212> TYPE: DNA
<213> ORGANISM: Artificial sequence
<220> FEATURE:
<223> OTHER INFORMATION: 5604 Nucleotide sequence of chimeric HPV type
      56 L1 protein

<400> SEQUENCE: 137

atggctacct ggagaccatc tgagaacaag gtctacctgc ctccaacacc tgtgagcaag      60

gtggtggcta cagactccta tgtgaagagg accagcatct tctaccatgc tggctccagc     120

agactgctgg ctgtgggaca cccatactac tctgtgacca aggacaacac caagaccaac     180

atcccaaagg tgtctgccta ccaatacagg gtgttcaggg tgagactgcc tgacccaaac     240

aagtttggac tgcctgacac caacatctac aaccctgacc aggagagact ggtgtgggct     300

tgtgtgggat tggaggtggg caggggacaa ccactgggag caggactgtc tggacaccca     360

ctgttcaaca gactggatga cacagagtcc agcaacctgg ctaacaacaa tgtgattgag     420

gacagcaggg acaacatctc tgtggatggc aagcagaccc aactttgtat tgtgggctgt     480

actcctgcta tgggagaaca ctggaccaag ggagcagtgt gtaagagcac ccaggtgacc     540

acaggagact gtcctccact ggctctgata aacacaccaa ttgaggatgg agatatgatt     600

gacacaggct ttggagctat ggacttcaag gtgctccaag agagcaaggc tgaggtgcca     660

ctggacattg tccagagcac ttgtaaatac cctgactacc tgaaaatgag tgctgatgcc     720

tatggagaca gtatgtggtt ctacctgagg agggaacaac tttttgccag acactacttc     780

aacagggctg gcaaggtggg agagaccatc cctgctgaac tctacctgaa aggcagcaat     840

ggcagggaac ctcctccatc ctctgtctat gtggctacac catctggcag tatgattacc     900

tctgaggctc aacttttcaa caagccatac tggctccaaa gggctcaagg acacaacaat     960

ggcatctgtt ggggcaacca actttttgtg acagtggtgg acaccaccag gagcaccaat    1020

atgaccatca gcacagccac agaacaactt agcaaatatg atgccaggaa gataaaccaa    1080

tacctgaggc atgtggagga atatgaactc caatttgtgt tccaactttg taagattacc    1140

ctgtctgctg aggtgatggc ttacctgcac aatatgaatg ccaacctgtt ggaggactgg    1200

aacattggac tgagccctcc tgtggctacc tccttggagg acaaatacag atatgtgagg    1260

agcacagcca tcacttgtca gagggaacaa cctccaacag agaagcagga cccactggct    1320

aaatacaagt tctgggatgt gaacctccaa gactccttca gcacagacct ggaccagttt    1380
```

ccactgggca ggaagttcct gctccaagca ggactgaaag ccaagccaaa actgaaaagg 1440
gctgccccaa ccagcaccag gacctcctct gccaagagga agaaggtgaa gaagtaaa 1498

<210> SEQ ID NO 138
<211> LENGTH: 1519
<212> TYPE: DNA
<213> ORGANISM: Artificial sequence
<220> FEATURE:
<223> OTHER INFORMATION: 5605 Synthetic HPV56 L1 gene

<400> SEQUENCE: 138
ctgggtacca tggctacctg gagaccatct gagaacaagg tctacctgcc tccaacacct 60
gtgagcaagg tggtggctac agactcctat gtgaagagga ccagcatctt ctaccatgct 120
ggctccagca gactgctggc tgtgggacac ccatactact ctgtgaccaa ggacaacacc 180
aagaccaaca tcccaaaggt gtctgcctac caatacaggg tgttcagggt gagactgcct 240
gacccaaaca agtttggact gcctgacacc aacatctaca accctgacca ggagagactg 300
gtgtgggctt gtgtgggatt ggaggtgggc aggggacaac cactgggagc aggactgtct 360
ggacacccac tgttcaacag actggatgac acagagtcca gcaacctggc taacaacaat 420
gtgattgagg acagcaggga caacatctct gtggatggca agcagaccca actttgtatt 480
gtgggctgta ctcctgctat gggagaacac tggaccaagg gagcagtgtg taagagcacc 540
caggtgacca caggagactg tcctccactg gctctgataa acacaccaat tgaggatgga 600
gatatgattg acacaggctt tggagctatg gacttcaagg tgctccaaga gagcaaggct 660
gaggtgccac tggacattgt ccagagcact tgtaaatacc ctgactacct gaaaatgagt 720
gctgatgcct atggagacag tatgtggttc tacctgagga gggaacaact ttttgccaga 780
cactacttca acagggctgg caaggtggga gagaccatcc ctgctgaact ctacctgaaa 840
ggcagcaatg gcagggaacc tcctccatcc tctgtctatg tggctacacc atctggcagt 900
atgattacct ctgaggctca acttttcaac aagccatact ggctccaaag ggctcaagga 960
cacaacaatg gcatctgttg ggcaaccaa ctttttgtga cagtggtgga caccaccagg 1020
agcaccaata tgaccatcag cacagccaca gaacaactta gcaaatatga tgccaggaag 1080
ataaaccaat acctgaggca tgtggaggaa tatgaactcc aatttgtgtt ccaactttgt 1140
aagattaccc tgtctgctga ggtgatggct tacctgcaca atatgaatgc caacctgttg 1200
gaggactgga acattggact gagccctcct gtggctacct ccttggagga caaatacaga 1260
tatgtgagga gcacagccat cacttgtcag agggaacaac ctccaacaga gaagcaggac 1320
ccactggcta aatacaagtt ctgggatgtg aacctccaag actccttcag cacagacctg 1380
gaccagtttc cactgggcag gaagttcctg atgcaacttg gcaccaggag caagcctgct 1440
gtggctacca gcaagaagag gtctgcccca accagcacca gcacacctgc caagaggaag 1500
aggaggtaaa ctcgagctc 1519

<210> SEQ ID NO 139
<211> LENGTH: 1519
<212> TYPE: DNA
<213> ORGANISM: Artificial sequence
<220> FEATURE:
<223> OTHER INFORMATION: 5606 Synthetic HPV33 L1 gene

<400> SEQUENCE: 139
ctgggtacca tgagtgtgtg gagaccatct gaggctacag tctacctgcc tcctgtgcct 60

```
gtgagcaagg tggtgagcac agatgaatat gtgagcagga ccagcatcta ctactatgct    120

ggctccagca gactgctggc tgtgggacac ccatacttca gcatcaagaa cccaaccaat    180

gccaagaaac tgctggtgcc aaaggtgtct ggactccaat acagggtgtt cagggtgaga    240

ctgcctgacc caaacaagtt tggctttcct gacacctcct tctacaaccc tgacacccag    300

agactggtgt gggcttgtgt gggattggag attggcaggg gacaaccact gggagtgggc    360

atctctggac acccactgct gaacaagttt gatgacacag agacaggcaa caaataccct    420

ggacaacctg gagcagacaa cagggagtgt ctgagtatgg actacaagca gacccaactt    480

tgtctgctgg gctgtaagcc tccaacagga gaacactggg gcaagggagt ggcttgtacc    540

aatgctgccc ctgccaatga ctgtcctcca ttggaactga taaacaccat cattgaggat    600

ggagatatgg tggacacagg ctttggctgt atggacttca agaccctcca agccaacaag    660

tctgatgtgc caattgacat ctgtggcagc acttgtaaat accctgacta cctgaaaatg    720

acctctgaac catatggaga ctccctgttc ttcttcctga ggagggaaca gatgtttgtg    780

agacacttct tcaacagggc tggcaccctg ggagaggctg tgcctgatga cctctacatc    840

aagggctctg gcaccacagc cagcatccag tcctctgcct tctttccaac accatctggc    900

agtatggtga cctctgagag ccaacttttc aacaagccat actggctcca aagggctcaa    960

ggacacaaca atggcatctg ttggggcaac caggtgtttg tgacagtggt ggacaccacc   1020

aggagcacca atatgaccct gtgtacccag gtgacctctg acagcaccta caagaatgag   1080

aacttcaagg aatacatcag gcatgtggag gaatatgacc tccaatttgt gttccaactt   1140

tgtaaggtga ccctgacagc agaggtgatg acctacatcc atgctatgaa ccctgacatc   1200

ttggaggact ggcagtttgg actgacacct cctccatctg cctccctcca agacacctac   1260

aggtttgtga ccagccaggc tatcacttgt cagaagacag tgcctccaaa ggagaaggag   1320

gacccactgg gcaaatacac cttctgggag gtggacctga aagagaagtt ctctgctgac   1380

ctggaccagt ttccactggg caggaagttc ctgctccaag caggactgaa agccaagcca   1440

aaactgaaaa gggctgcccc aaccagcacc aggacctcct ctgccaagag gaagaaggtg   1500

aagaagtaaa ctcgagctc                                                1519
```

```
<210> SEQ ID NO 140
<211> LENGTH: 33
<212> TYPE: DNA
<213> ORGANISM: Artificial sequence
<220> FEATURE:
<223> OTHER INFORMATION: 5607 HPV56L1 F1

<400> SEQUENCE: 140

cttggtacca tggctacctg gagaccatct gag                                  33


<210> SEQ ID NO 141
<211> LENGTH: 31
<212> TYPE: DNA
<213> ORGANISM: Artificial sequence
<220> FEATURE:
<223> OTHER INFORMATION: 5608 HPV56L1 R1

<400> SEQUENCE: 141

ctgcttggag caggaacttc ctgcccagtg g                                    31


<210> SEQ ID NO 142
<211> LENGTH: 1420
<212> TYPE: DNA
<213> ORGANISM: Artificial sequence
```

-continued

<220> FEATURE:
<223> OTHER INFORMATION: 5609 HPV56L1 amplified sequence 1

<400> SEQUENCE: 142
cttggtacca tggctacctg gagaccatct gagaacaagg tctacctgcc tccaacacct 60
gtgagcaagg tggtggctac agactcctat gtgaagagga ccagcatctt ctaccatgct 120
ggctccagca gactgctggc tgtgggacac ccatactact ctgtgaccaa ggacaacacc 180
aagaccaaca tcccaaaggt gtctgcctac caatacaggg tgttcagggt gagactgcct 240
gacccaaaca agtttggact gcctgacacc aacatctaca accctgacca ggagagactg 300
gtgtgggctt gtgtgggatt ggaggtgggc aggggacaac cactgggagc aggactgtct 360
ggacacccac tgttcaacag actggatgac acagagtcca gcaacctggc taacaacaat 420
gtgattgagg acagcaggga caacatctct gtggatggca agcagaccca actttgtatt 480
gtgggctgta ctcctgctat gggagaacac tggaccaagg gagcagtgtg taagagcacc 540
caggtgacca caggagactg tcctccactg gctctgataa acacaccaat tgaggatgga 600
gatatgattg acacaggctt tggagctatg gacttcaagg tgctccaaga gagcaaggct 660
gaggtgccac tggacattgt ccagagcact tgtaaatacc ctgactacct gaaaatgagt 720
gctgatgcct atggagacag tatgtggttc tacctgagga gggaacaact ttttgccaga 780
cactacttca acagggctgg caaggtggga gagaccatcc ctgctgaact ctacctgaaa 840
ggcagcaatg gcagggaacc tcctccatcc tctgtctatg tggctacacc atctggcagt 900
atgattacct ctgaggctca acttttcaac aagccatact ggctccaaag ggctcaagga 960
cacaacaatg gcatctgttg gggcaaccaa ctttttgtga cagtggtgga caccaccagg 1020
agcaccaata tgaccatcag cacagccaca gaacaactta gcaaatatga tgccaggaag 1080
ataaaccaat acctgaggca tgtggaggaa tatgaactcc aatttgtgtt ccaactttgt 1140
aagattaccc tgtctgctga ggtgatggct tacctgcaca atatgaatgc caacctgttg 1200
gaggactgga acattggact gagccctcct gtggctacct ccttggagga caaatacaga 1260
tatgtgagga gcacagccat cacttgtcag agggaacaac ctccaacaga gaagcaggac 1320
ccactggcta aatacaagtt ctgggatgtg aacctccaag actccttcag cacagacctg 1380
gaccagtttc cactgggcag gaagttcctg ctccaagcag 1420

<210> SEQ ID NO 143
<211> LENGTH: 36
<212> TYPE: DNA
<213> ORGANISM: Artificial sequence
<220> FEATURE:
<223> OTHER INFORMATION: 5610 HPV56L1 F2

<400> SEQUENCE: 143
gaagttcctg ctccaagcag gactgaaagc caagcc 36

<210> SEQ ID NO 144
<211> LENGTH: 36
<212> TYPE: DNA
<213> ORGANISM: Artificial sequence
<220> FEATURE:
<223> OTHER INFORMATION: 5611 HPV56L1 R2

<400> SEQUENCE: 144
ctgtctagat ttacttcttc accttcttcc tcttgg 36

<210> SEQ ID NO 145

<211> LENGTH: 116
<212> TYPE: DNA
<213> ORGANISM: Artificial sequence
<220> FEATURE:
<223> OTHER INFORMATION: 5612 HPV56L1 amplified sequence 2

<400> SEQUENCE: 145
gaagttcctg ctccaagcag gactgaaagc caagccaaaa ctgaaaaggg ctgccccaac 60
cagcaccagg acctcctctg ccaagaggaa gaaggtgaag aagtaaatct agacag 116

<210> SEQ ID NO 146
<211> LENGTH: 38
<212> TYPE: PRT
<213> ORGANISM: Homo sapiens
<220> FEATURE:
<221> NAME/KEY: misc_feature
<223> OTHER INFORMATION: 5613 Amino acid sequence of HPV type 59 L1
protein aa 471-508

<400> SEQUENCE: 146

Leu Gln Leu Gly Ala Arg Pro Lys Pro Thr Ile Gly Pro Arg Lys Arg
1 5 10 15

Ala Ala Pro Ala Pro Thr Ser Thr Pro Ser Pro Lys Arg Val Lys Arg
20 25 30

Arg Lys Ser Ser Arg Lys
35

<210> SEQ ID NO 147
<211> LENGTH: 473
<212> TYPE: PRT
<213> ORGANISM: Homo sapiens
<220> FEATURE:
<221> NAME/KEY: misc_feature
<223> OTHER INFORMATION: 5801 Amino acid sequence of HPV type 58 L1
protein aa 1-473

<400> SEQUENCE: 147

Met Ser Val Trp Arg Pro Ser Glu Ala Thr Val Tyr Leu Pro Pro Val
1 5 10 15

Pro Val Ser Lys Val Val Ser Thr Asp Glu Tyr Val Ser Arg Thr Ser
20 25 30

Ile Tyr Tyr Tyr Ala Gly Ser Ser Arg Leu Leu Ala Val Gly Asn Pro
35 40 45

Tyr Phe Ser Ile Lys Ser Pro Asn Asn Asn Lys Lys Val Leu Val Pro
50 55 60

Lys Val Ser Gly Leu Gln Tyr Arg Val Phe Arg Val Arg Leu Pro Asp
65 70 75 80

Pro Asn Lys Phe Gly Phe Pro Asp Thr Ser Phe Tyr Asn Pro Asp Thr
85 90 95

Gln Arg Leu Val Trp Ala Cys Val Gly Leu Glu Ile Gly Arg Gly Gln
100 105 110

Pro Leu Gly Val Gly Val Ser Gly His Pro Tyr Leu Asn Lys Phe Asp
115 120 125

Asp Thr Glu Thr Ser Asn Arg Tyr Pro Ala Gln Pro Gly Ser Asp Asn
130 135 140

Arg Glu Cys Leu Ser Met Asp Tyr Lys Gln Thr Gln Leu Cys Leu Ile
145 150 155 160

Gly Cys Lys Pro Pro Thr Gly Glu His Trp Gly Lys Gly Val Ala Cys
165 170 175

Asn Asn Asn Ala Ala Ala Thr Asp Cys Pro Pro Leu Glu Leu Phe Asn

-continued

```
            180                 185                 190

Ser Ile Ile Glu Asp Gly Asp Met Val Asp Thr Gly Phe Gly Cys Met
        195                 200                 205

Asp Phe Gly Thr Leu Gln Ala Asn Lys Ser Asp Val Pro Ile Asp Ile
    210                 215                 220

Cys Asn Ser Thr Cys Lys Tyr Pro Asp Tyr Leu Lys Met Ala Ser Glu
225                 230                 235                 240

Pro Tyr Gly Asp Ser Leu Phe Phe Phe Leu Arg Arg Glu Gln Met Phe
                245                 250                 255

Val Arg His Phe Phe Asn Arg Ala Gly Lys Leu Gly Glu Ala Val Pro
            260                 265                 270

Asp Asp Leu Tyr Ile Lys Gly Ser Gly Asn Thr Ala Val Ile Gln Ser
        275                 280                 285

Ser Ala Phe Phe Pro Thr Pro Ser Gly Ser Ile Val Thr Ser Glu Ser
    290                 295                 300

Gln Leu Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Thr Leu Cys Thr Glu Val Thr Lys Glu Gly
            340                 345                 350

Thr Tyr Lys Asn Asp Asn Phe Lys Glu Tyr Val Arg His Val Glu Glu
        355                 360                 365

Tyr Asp Leu Gln Phe Val Phe Gln Leu Cys Lys Ile Thr Leu Thr Ala
    370                 375                 380

Glu Ile Met Thr Tyr Ile His Thr Met Asp Ser Asn Ile Leu Glu Asp
385                 390                 395                 400

Trp Gln Phe Gly Leu Thr Pro Pro Pro Ser Ala Ser Leu Gln Asp Thr
                405                 410                 415

Tyr Arg Phe Val Thr Ser Gln Ala Ile Thr Cys Gln Lys Thr Ala Pro
            420                 425                 430

Pro Lys Glu Lys Glu Asp Pro Leu Asn Lys Tyr Thr Phe Trp Glu Val
        435                 440                 445

Asn Leu Lys Glu Lys Phe Ser Ala Asp Leu Asp Gln Phe Pro Leu Gly
    450                 455                 460

Arg Lys Phe Leu Leu Gln Ser Gly Leu
465                 470


<210> SEQ ID NO 148
<211> LENGTH: 26
<212> TYPE: PRT
<213> ORGANISM: Homo sapiens
<220> FEATURE:
<221> NAME/KEY: misc_feature
<223> OTHER INFORMATION: 5802 Amino acid sequence of HPV type 33 L1
      protein aa 474-499

<400> SEQUENCE: 148

Lys Ala Lys Pro Lys Leu Lys Arg Ala Ala Pro Thr Ser Thr Arg Thr
1               5                   10                  15

Ser Ser Ala Lys Arg Lys Lys Val Lys Lys
            20                  25


<210> SEQ ID NO 149
<211> LENGTH: 499
<212> TYPE: PRT
<213> ORGANISM: Artificial sequence
```

<220> FEATURE:
<223> OTHER INFORMATION: 5803 Amino acid sequence of chimeric HPV type
58 L1 protein

<400> SEQUENCE: 149

Met Ser Val Trp Arg Pro Ser Glu Ala Thr Val Tyr Leu Pro Pro Val
1 5 10 15

Pro Val Ser Lys Val Val Ser Thr Asp Glu Tyr Val Ser Arg Thr Ser
20 25 30

Ile Tyr Tyr Tyr Ala Gly Ser Ser Arg Leu Leu Ala Val Gly Asn Pro
35 40 45

Tyr Phe Ser Ile Lys Ser Pro Asn Asn Asn Lys Lys Val Leu Val Pro
50 55 60

Lys Val Ser Gly Leu Gln Tyr Arg Val Phe Arg Val Arg Leu Pro Asp
65 70 75 80

Pro Asn Lys Phe Gly Phe Pro Asp Thr Ser Phe Tyr Asn Pro Asp Thr
85 90 95

Gln Arg Leu Val Trp Ala Cys Val Gly Leu Glu Ile Gly Arg Gly Gln
100 105 110

Pro Leu Gly Val Gly Val Ser Gly His Pro Tyr Leu Asn Lys Phe Asp
115 120 125

Asp Thr Glu Thr Ser Asn Arg Tyr Pro Ala Gln Pro Gly Ser Asp Asn
130 135 140

Arg Glu Cys Leu Ser Met Asp Tyr Lys Gln Thr Gln Leu Cys Leu Ile
145 150 155 160

Gly Cys Lys Pro Pro Thr Gly Glu His Trp Gly Lys Gly Val Ala Cys
165 170 175

Asn Asn Asn Ala Ala Ala Thr Asp Cys Pro Pro Leu Glu Leu Phe Asn
180 185 190

Ser Ile Ile Glu Asp Gly Asp Met Val Asp Thr Gly Phe Gly Cys Met
195 200 205

Asp Phe Gly Thr Leu Gln Ala Asn Lys Ser Asp Val Pro Ile Asp Ile
210 215 220

Cys Asn Ser Thr Cys Lys Tyr Pro Asp Tyr Leu Lys Met Ala Ser Glu
225 230 235 240

Pro Tyr Gly Asp Ser Leu Phe Phe Phe Leu Arg Arg Glu Gln Met Phe
245 250 255

Val Arg His Phe Phe Asn Arg Ala Gly Lys Leu Gly Glu Ala Val Pro
260 265 270

Asp Asp Leu Tyr Ile Lys Gly Ser Gly Asn Thr Ala Val Ile Gln Ser
275 280 285

Ser Ala Phe Phe Pro Thr Pro Ser Gly Ser Ile Val Thr Ser Glu Ser
290 295 300

Gln Leu Phe Asn Lys Pro Tyr Trp Leu Gln Arg Ala Gln Gly His Asn
305 310 315 320

Asn Gly Ile Cys Trp Gly Asn Gln Leu Phe Val Thr Val Val Asp Thr
325 330 335

Thr Arg Ser Thr Asn Met Thr Leu Cys Thr Glu Val Thr Lys Glu Gly
340 345 350

Thr Tyr Lys Asn Asp Asn Phe Lys Glu Tyr Val Arg His Val Glu Glu
355 360 365

Tyr Asp Leu Gln Phe Val Phe Gln Leu Cys Lys Ile Thr Leu Thr Ala
370 375 380

Glu Ile Met Thr Tyr Ile His Thr Met Asp Ser Asn Ile Leu Glu Asp

```
385                 390                 395                 400

Trp Gln Phe Gly Leu Thr Pro Pro Pro Ser Ala Ser Leu Gln Asp Thr
                405                 410                 415

Tyr Arg Phe Val Thr Ser Gln Ala Ile Thr Cys Gln Lys Thr Ala Pro
            420                 425                 430

Pro Lys Glu Lys Glu Asp Pro Leu Asn Lys Tyr Thr Phe Trp Glu Val
        435                 440                 445

Asn Leu Lys Glu Lys Phe Ser Ala Asp Leu Asp Gln Phe Pro Leu Gly
    450                 455                 460

Arg Lys Phe Leu Leu Gln Ser Gly Leu Lys Ala Lys Pro Lys Leu Lys
465                 470                 475                 480

Arg Ala Ala Pro Thr Ser Thr Arg Thr Ser Ser Ala Lys Arg Lys Lys
                485                 490                 495

Val Lys Lys


<210> SEQ ID NO 150
<211> LENGTH: 1501
<212> TYPE: DNA
<213> ORGANISM: Artificial sequence
<220> FEATURE:
<223> OTHER INFORMATION: 5804 Nucleotide sequence of chimeric HPV type
      58 L1 protein

<400> SEQUENCE: 150

atgagcgtgt ggaggcccag cgaggccacc gtgtacctgc cccccgtgcc cgtgagcaag     60

gtggtgagca ccgacgagta cgtgagcagg accagcatct actactacgc cggcagcagc    120

aggctgctgg ccgtgggcaa cccctacttc agcatcaaga gccccaacaa caacaagaag    180

gtgctggtgc ccaaggtgag cggcctgcag tacagggtgt tcagggtgag gctgcccgac    240

cccaacaagt tcggcttccc cgacaccagc ttctacaacc ccgacaccca gaggctggtg    300

tgggcctgcg tgggcctgga gatcggcagg ggccagcccc tgggcgtggg cgtgagcggc    360

cacccctacc tgaacaagtt cgacgacacc gagaccagca acaggtaccc cgcccagccc    420

ggcagcgaca acagggagtg cctgagcatg gactacaagc agacccagct gtgcctgatc    480

ggctgcaagc cccccaccgg cgagcactgg ggcaagggcg tggcctgcaa caacaacgcc    540

gccgccaccg actgcccccc cctggagctg ttcaacagca tcatcgagga cggcgacatg    600

gtggacaccg gcttcggctg catggacttc ggcaccctgc aggccaacaa gagcgacgtg    660

cccatcgaca tctgcaacag cacctgcaag taccccgact acctgaagat ggccagcgag    720

ccctacggcg acagcctgtt cttcttcctg aggagggagc agatgttcgt gaggcacttc    780

ttcaacaggg ccggcaagct gggcgaggcc gtgcccgacg acctgtacat caagggcagc    840

ggcaacaccg ccgtgatcca gagcagcgcc ttcttcccca cccccagcgg cagcatcgtg    900

accagcgaga gccagctgtt caacaagccc tactggctgc agagggccca gggccacaac    960

aacggcatct gctggggcaa ccagctgttc gtgaccgtgg tggacaccac caggagcacc   1020

aacatgaccc tgtgcaccga ggtgaccaag gagggcacct acaagaacga caacttcaag   1080

gagtacgtga ggcacgtgga ggagtacgac ctgcagttcg tgttccagct gtgcaagatc   1140

accctgaccg ccgagatcat gacctacatc cacaccatgg acagcaacat cctggaggac   1200

tggcagttcg gcctgacccc cccccccagc gccagcctgc aggacaccta caggttcgtg   1260

accagccagg ccatcacctg ccagaagacc gcccccccca aggagaagga ggacccccctg   1320

aacaagtaca ccttctggga ggtgaacctg aaggagaagt tcagcgccga cctggaccag   1380
```

```
ttccccctgg gcaggaagtt cctgctgcag agcggcctga aagccaagcc aaaactgaaa   1440

agggctgccc caaccagcac caggacctcc tctgccaaga ggaagaaggt gaagaagtaa   1500

a                                                                   1501
```

<210> SEQ ID NO 151
<211> LENGTH: 1516
<212> TYPE: DNA
<213> ORGANISM: Artificial sequence
<220> FEATURE:
<223> OTHER INFORMATION: 5805 Synthetic HPV58 L1 gene

<400> SEQUENCE: 151

```
ctgggtacca tgagcgtgtg gaggcccagc gaggccaccg tgtacctgcc ccccgtgccc     60

gtgagcaagg tggtgagcac cgacgagtac gtgagcagga ccagcatcta ctactacgcc    120

ggcagcagca ggctgctggc cgtgggcaac ccctacttca gcatcaagag ccccaacaac    180

aacaagaagg tgctggtgcc caaggtgagc ggcctgcagt acagggtgtt cagggtgagg    240

ctgcccgacc ccaacaagtt cggcttcccc gacaccagct tctacaaccc cgacacccag    300

aggctggtgt gggcctgcgt gggcctggag atcggcaggg gccagcccct gggcgtgggc    360

gtgagcggcc accccctacct gaacaagttc gacgacaccg agaccagcaa caggtacccc    420

gcccagcccg gcagcgacaa cagggagtgc ctgagcatgg actacaagca gacccagctg    480

tgcctgatcg gctgcaagcc ccccaccggc gagcactggg gcaagggcgt ggcctgcaac    540

aacaacgccg ccgccaccga ctgccccccc ctggagctgt tcaacagcat catcgaggac    600

ggcgacatgg tggacaccgg cttcggctgc atggacttcg gcaccctgca ggccaacaag    660

agcgacgtgc ccatcgacat ctgcaacagc acctgcaagt accccgacta cctgaagatg    720

gccagcgagc cctacggcga cagcctgttc ttcttcctga ggagggagca gatgttcgtg    780

aggcacttct tcaacagggc cggcaagctg ggcgaggccg tgcccgacga cctgtacatc    840

aagggcagcg gcaacaccgc cgtgatccag agcagcgcct tcttccccac ccccagcggc    900

agcatcgtga ccagcgagag ccagctgttc aacaagccct actggctgca gagggcccag    960

ggccacaaca acggcatctg ctggggcaac cagctgttcg tgaccgtggt ggacaccacc   1020

aggagcacca acatgaccct gtgcaccgag gtgaccaagg agggcaccta caagaacgac   1080

aacttcaagg agtacgtgag gcacgtggag gagtacgacc tgcagttcgt gttccagctg   1140

tgcaagatca ccctgaccgc cgagatcatg acctacatcc acaccatgga cagcaacatc   1200

ctggaggact ggcagttcgg cctgaccccc ccccccagcg ccagcctgca ggacacctac   1260

aggttcgtga ccagccaggc catcacctgc cagaagaccg ccccccccaa ggagaaggag   1320

gacccccctga acaagtacac cttctgggag gtgaacctga aggagaagtt cagcgccgac   1380

ctggaccagt tcccccctggg caggaagttc ctgctgcaga gcggcctgaa ggccaagccc   1440

aggctgaaga ggagcgcccc caccaccagg gcccccagca ccaagaggaa gaaggtgaag   1500

aagtaaactc gagctc                                                   1516
```

<210> SEQ ID NO 152
<211> LENGTH: 1519
<212> TYPE: DNA
<213> ORGANISM: Artificial sequence
<220> FEATURE:
<223> OTHER INFORMATION: 5806 Synthetic HPV33 L1 gene

<400> SEQUENCE: 152

```
ctgggtacca tgagtgtgtg gagaccatct gaggctacag tctacctgcc tcctgtgcct     60
```

gtgagcaagg tggtgagcac agatgaatat gtgagcagga ccagcatcta ctactatgct 120
ggctccagca gactgctggc tgtgggacac ccatacttca gcatcaagaa cccaaccaat 180
gccaagaaac tgctggtgcc aaaggtgtct ggactccaat acagggtgtt cagggtgaga 240
ctgcctgacc caaacaagtt tggctttcct gacacctcct tctacaaccc tgacacccag 300
agactggtgt gggcttgtgt gggattggag attggcaggg gacaaccact gggagtgggc 360
atctctggac acccactgct gaacaagttt gatgacacag agacaggcaa caaataccct 420
ggacaacctg gagcagacaa cagggagtgt ctgagtatgg actacaagca gacccaactt 480
tgtctgctgg gctgtaagcc tccaacagga gaacactggg gcaagggagt ggcttgtacc 540
aatgctgccc ctgccaatga ctgtcctcca ttggaactga taaacaccat cattgaggat 600
ggagatatgg tggacacagg ctttggctgt atggacttca agaccctcca agccaacaag 660
tctgatgtgc caattgacat ctgtggcagc acttgtaaat accctgacta cctgaaaatg 720
acctctgaac catatggaga ctccctgttc ttcttcctga ggagggaaca gatgtttgtg 780
agacacttct tcaacagggc tggcaccctg ggagaggctg tgcctgatga cctctacatc 840
aagggctctg gcaccacagc cagcatccag tcctctgcct tctttccaac accatctggc 900
agtatggtga cctctgagag ccaacttttc aacaagccat actggctcca aagggctcaa 960
ggacacaaca atggcatctg ttggggcaac caggtgtttg tgacagtggt ggacaccacc 1020
aggagcacca atatgaccct gtgtacccag gtgacctctg acagcaccta caagaatgag 1080
aacttcaagg aatacatcag gcatgtggag gaatatgacc tccaatttgt gttccaactt 1140
tgtaaggtga ccctgacagc agaggtgatg acctacatcc atgctatgaa ccctgacatc 1200
ttggaggact ggcagtttgg actgacacct cctccatctg cctccctcca agacacctac 1260
aggtttgtga ccagccaggc tatcacttgt cagaagacag tgcctccaaa ggagaaggag 1320
gacccactgg gcaaatacac cttctgggag gtggacctga aagagaagtt ctctgctgac 1380
ctggaccagt ttccactggg caggaagttc ctgctccaag caggactgaa agccaagcca 1440
aaactgaaaa gggctgcccc aaccagcacc aggacctcct ctgccaagag gaagaaggtg 1500
aagaagtaaa ctcgagctc 1519

<210> SEQ ID NO 153
<211> LENGTH: 34
<212> TYPE: DNA
<213> ORGANISM: Artificial sequence
<220> FEATURE:
<223> OTHER INFORMATION: 5807 HPV58L1 F1

<400> SEQUENCE: 153
cttggtacca tgagcgtgtg gaggcccagc gagg 34

<210> SEQ ID NO 154
<211> LENGTH: 36
<212> TYPE: DNA
<213> ORGANISM: Artificial sequence
<220> FEATURE:
<223> OTHER INFORMATION: 5808 HPV58L1 R1

<400> SEQUENCE: 154
gcttggcttt caggccgctc tgcagcagga acttcc 36

<210> SEQ ID NO 155
<211> LENGTH: 1438
<212> TYPE: DNA

<213> ORGANISM: Artificial sequence
<220> FEATURE:
<223> OTHER INFORMATION: 5809 HPV58L1 amplified sequence 1

<400> SEQUENCE: 155
cttggtacca tgagcgtgtg gaggcccagc gaggccaccg tgtacctgcc ccccgtgccc 60
gtgagcaagg tggtgagcac cgacgagtac gtgagcagga ccagcatcta ctactacgcc 120
ggcagcagca ggctgctggc cgtgggcaac ccctacttca gcatcaagag ccccaacaac 180
aacaagaagg tgctggtgcc caaggtgagc ggcctgcagt acagggtgtt cagggtgagg 240
ctgcccgacc ccaacaagtt cggcttcccc gacaccagct tctacaaccc cgacacccag 300
aggctggtgt gggcctgcgt gggcctggag atcggcaggg gccagcccct gggcgtgggc 360
gtgagcggcc acccctacct gaacaagttc gacgacaccg agaccagcaa caggtacccc 420
gcccagcccg gcagcgacaa cagggagtgc ctgagcatgg actacaagca gacccagctg 480
tgcctgatcg gctgcaagcc ccccaccggc gagcactggg gcaagggcgt ggcctgcaac 540
aacaacgccg ccgccaccga ctgccccccc ctggagctgt tcaacagcat catcgaggac 600
ggcgacatgg tggacaccgg cttcggctgc atggacttcg gcaccctgca ggccaacaag 660
agcgacgtgc ccatcgacat ctgcaacagc acctgcaagt accccgacta cctgaagatg 720
gccagcgagc cctacggcga cagcctgttc ttcttcctga ggagggagca gatgttcgtg 780
aggcacttct tcaacagggc cggcaagctg ggcgaggccg tgcccgacga cctgtacatc 840
aagggcagcg gcaacaccgc cgtgatccag agcagcgcct tcttccccac ccccagcggc 900
agcatcgtga ccagcgagag ccagctgttc aacaagccct actggctgca gagggcccag 960
ggccacaaca acggcatctg ctggggcaac cagctgttcg tgaccgtggt ggacaccacc 1020
aggagcacca acatgaccct gtgcaccgag gtgaccaagg agggcaccta caagaacgac 1080
aacttcaagg agtacgtgag gcacgtggag gagtacgacc tgcagttcgt gttccagctg 1140
tgcaagatca ccctgaccgc cgagatcatg acctacatcc acaccatgga cagcaacatc 1200
ctggaggact ggcagttcgg cctgaccccc ccccccagcg ccagcctgca ggacacctac 1260
aggttcgtga ccagccaggc catcacctgc cagaagaccg cccccccaa ggagaaggag 1320
gacccccctga acaagtacac cttctgggag gtgaacctga aggagaagtt cagcgccgac 1380
ctggaccagt tcccccctggg caggaagttc ctgctgcaga gcggcctgaa agccaagc 1438

<210> SEQ ID NO 156
<211> LENGTH: 35
<212> TYPE: DNA
<213> ORGANISM: Artificial sequence
<220> FEATURE:
<223> OTHER INFORMATION: 5810 HPV58L1 F2

<400> SEQUENCE: 156
gagcggcctg aaagccaagc caaaactgaa aaggg 35

<210> SEQ ID NO 157
<211> LENGTH: 36
<212> TYPE: DNA
<213> ORGANISM: Artificial sequence
<220> FEATURE:
<223> OTHER INFORMATION: 5811 HPV58L1 R2

<400> SEQUENCE: 157
ctgtctagat ttacttcttc accttcttcc tcttgg 36

<210> SEQ ID NO 158
<211> LENGTH: 101
<212> TYPE: DNA
<213> ORGANISM: Artificial sequence
<220> FEATURE:
<223> OTHER INFORMATION: 5812 HPV58L1 amplified sequence 2

<400> SEQUENCE: 158
gagcggcctg aaagccaagc caaaactgaa aagggctgcc ccaaccagca ccaggacctc 60
ctctgccaag aggaagaagg tgaagaagta aatctagaca g 101

<210> SEQ ID NO 159
<211> LENGTH: 38
<212> TYPE: PRT
<213> ORGANISM: Homo sapiens
<220> FEATURE:
<221> NAME/KEY: misc_feature
<223> OTHER INFORMATION: 5813 Amino acid sequence of HPV type 59 L1 protein aa 471-508

<400> SEQUENCE: 159

Leu Gln Leu Gly Ala Arg Pro Lys Pro Thr Ile Gly Pro Arg Lys Arg
1 5 10 15

Ala Ala Pro Ala Pro Thr Ser Thr Pro Ser Pro Lys Arg Val Lys Arg
20 25 30

Arg Lys Ser Ser Arg Lys
35

<210> SEQ ID NO 160
<211> LENGTH: 508
<212> TYPE: PRT
<213> ORGANISM: Homo sapiens
<220> FEATURE:
<221> NAME/KEY: misc_feature
<223> OTHER INFORMATION: 5901 Amino acid sequence of HPV type 59 L1 protein

<400> SEQUENCE: 160

Met Ala Leu Trp Arg Ser Ser Asp Asn Lys Val Tyr Leu Pro Pro Pro
1 5 10 15

Ser Val Ala Lys Val Val Ser Thr Asp Glu Tyr Val Thr Arg Thr Ser
20 25 30

Ile Phe Tyr His Ala Gly Ser Ser Arg Leu Leu Thr Val Gly His Pro
35 40 45

Tyr Phe Lys Val Pro Lys Gly Gly Asn Gly Arg Gln Asp Val Pro Lys
50 55 60

Val Ser Ala Tyr Gln Tyr Arg Val Phe Arg Val Lys Leu Pro Asp Pro
65 70 75 80

Asn Lys Phe Gly Leu Pro Asp Asn Thr Val Tyr Asp Pro Asn Ser Gln
85 90 95

Arg Leu Val Trp Ala Cys Val Gly Val Glu Ile Gly Arg Gly Gln Pro
100 105 110

Leu Gly Val Gly Leu Ser Gly His Pro Leu Tyr Asn Lys Leu Asp Asp
115 120 125

Thr Glu Asn Ser His Val Ala Ser Ala Val Asp Thr Lys Asp Thr Arg
130 135 140

Asp Asn Val Ser Val Asp Tyr Lys Gln Thr Gln Leu Cys Ile Ile Gly
145 150 155 160

Cys Val Pro Ala Ile Gly Glu His Trp Thr Lys Gly Thr Ala Cys Lys
165 170 175

-continued

```
Pro Thr Thr Val Val Gln Gly Asp Cys Pro Pro Leu Glu Leu Ile Asn
            180                 185                 190

Thr Pro Ile Glu Asp Gly Asp Met Val Asp Thr Gly Tyr Gly Ala Met
        195                 200                 205

Asp Phe Lys Leu Leu Gln Asp Asn Lys Ser Glu Val Pro Leu Asp Ile
    210                 215                 220

Cys Gln Ser Ile Cys Lys Tyr Pro Asp Tyr Leu Gln Met Ser Ala Asp
225                 230                 235                 240

Ala Tyr Gly Asp Ser Met Phe Phe Cys Leu Arg Arg Glu Gln Val Phe
                245                 250                 255

Ala Arg His Phe Trp Asn Arg Ser Gly Thr Met Gly Asp Gln Leu Pro
            260                 265                 270

Glu Ser Leu Tyr Ile Lys Gly Thr Asp Ile Arg Ala Asn Pro Gly Ser
        275                 280                 285

Tyr Leu Tyr Ser Pro Ser Pro Ser Gly Ser Val Val Thr Ser Asp Ser
    290                 295                 300

Gln Leu Phe Asn Lys Pro Tyr Trp Leu His Lys Ala Gln Gly Leu Asn
305                 310                 315                 320

Asn Gly Ile Cys Trp His Asn Gln Leu Phe Leu Thr Val Val Asp Thr
                325                 330                 335

Thr Arg Ser Thr Asn Leu Ser Val Cys Ala Ser Thr Thr Ser Ser Ile
            340                 345                 350

Pro Asn Val Tyr Thr Pro Thr Ser Phe Lys Glu Tyr Ala Arg His Val
        355                 360                 365

Glu Glu Phe Asp Leu Gln Phe Ile Phe Gln Leu Cys Lys Ile Thr Leu
    370                 375                 380

Thr Thr Glu Val Met Ser Tyr Ile His Asn Met Asn Thr Thr Ile Leu
385                 390                 395                 400

Glu Asp Trp Asn Phe Gly Val Thr Pro Pro Pro Thr Ala Ser Leu Val
                405                 410                 415

Asp Thr Tyr Arg Phe Val Gln Ser Ala Ala Val Thr Cys Gln Lys Asp
            420                 425                 430

Thr Ala Pro Pro Val Lys Gln Asp Pro Tyr Asp Lys Leu Lys Phe Trp
        435                 440                 445

Pro Val Asp Leu Lys Glu Arg Phe Ser Ala Asp Leu Asp Gln Phe Pro
    450                 455                 460

Leu Gly Arg Lys Phe Leu Leu Gln Leu Gly Ala Arg Pro Lys Pro Thr
465                 470                 475                 480

Ile Gly Pro Arg Lys Arg Ala Ala Pro Ala Pro Thr Ser Thr Pro Ser
                485                 490                 495

Pro Lys Arg Val Lys Arg Arg Lys Ser Ser Arg Lys
            500                 505
```

```
<210> SEQ ID NO 161
<211> LENGTH: 1528
<212> TYPE: DNA
<213> ORGANISM: Homo sapiens
<220> FEATURE:
<221> NAME/KEY: misc_feature
<223> OTHER INFORMATION: 5902 Nucleotide sequence of HPV type 59 L1
      protein

<400> SEQUENCE: 161

atggctctgt ggaggtcctc tgacaacaag gtctacctgc ctcctccatc tgtggctaag      60

gtggtgagca cagatgaata tgtgaccagg accagcatct tctaccatgc tggctccagc     120
```

agactgctga cagtgggaca cccatacttc aaggtgccaa agggaggcaa tggcagacag 180
gatgtgccaa aggtgtctgc ctaccaatac agggtgttca gggtgaaact gcctgaccca 240
aacaagtttg gactgcctga caacacagtc tatgacccaa acagccagag actggtgtgg 300
gcttgtgtgg gagtggagat tggcagggga caaccactgg gagtgggact gtctggacac 360
ccactctaca acaaactgga tgacacagag aactctcatg tggcatctgc tgtggacacc 420
aaggacacca gggacaatgt gtctgtggac tacaagcaga cccaactttg tatcattggc 480
tgtgtgcctg ccattggaga acactggacc aagggcacag cctgtaagcc aaccacagtg 540
gtccagggag actgtcctcc attggaactg ataaacacac caattgagga tggagatatg 600
gtggacacag gctatggagc tatggacttc aaactgctcc aagacaacaa gtctgaggtg 660
ccactggaca tctgtcagag catctgtaaa taccctgact acctccaaat gagtgctgat 720
gcctatggag acagtatgtt cttctgtctg aggagggaac aggtgtttgc cagacacttc 780
tggaacaggt ctggcacaat gggagaccaa cttcctgagt ccctctacat caagggcaca 840
gacatcaggg ctaaccctgg ctcctacctc tacagcccaa gcccatctgg ctctgtggtg 900
acctctgaca gccaactttt caacaagcca tactggctgc acaaggctca aggactgaac 960
aatggcatct gttggcacaa ccaacttttc ctgacagtgg tggacaccac caggagcacc 1020
aacctgtctg tgtgtgccag caccacctcc agcatcccaa atgtctacac accaacctcc 1080
ttcaaggaat atgccaggca tgtggaggag tttgacctcc aattcatctt ccaactttgt 1140
aagattaccc tgaccacaga ggtgatgagt tacatccaca atatgaacac caccatcttg 1200
gaggactgga actttggagt gacacctcct ccaacagcct ccctggtgga cacctacagg 1260
tttgtccagt ctgctgctgt gacttgtcag aaggacacag cccctcctgt gaagcaggac 1320
ccatatgaca aactgaagtt ctggcctgtg gacctgaaag agaggttctc tgctgacctg 1380
gaccagtttc cactgggcag gaagttcctg ctccaacttg gagccagacc aaagccaacc 1440
attggaccaa ggaagagggc tgcccctgcc ccaaccagca caccaagccc aaagagggtg 1500
aagaggagga agtccagcag gaagtaaa 1528

<210> SEQ ID NO 162
<211> LENGTH: 1546
<212> TYPE: DNA
<213> ORGANISM: Artificial sequence
<220> FEATURE:
<223> OTHER INFORMATION: 5903 Synthetic HPV59 L1 gene

<400> SEQUENCE: 162
ctgggtacca tggctctgtg gaggtcctct gacaacaagg tctacctgcc tcctccatct 60
gtggctaagg tggtgagcac agatgaatat gtgaccagga ccagcatctt ctaccatgct 120
ggctccagca gactgctgac agtgggacac ccatacttca aggtgccaaa gggaggcaat 180
ggcagacagg atgtgccaaa ggtgtctgcc taccaataca gggtgttcag ggtgaaactg 240
cctgacccaa acaagtttgg actgcctgac aacacagtct atgacccaaa cagccagaga 300
ctggtgtggg cttgtgtggg agtggagatt ggcaggggac aaccactggg agtgggactg 360
tctggacacc cactctacaa caaactggat gacacagaga actctcatgt ggcatctgct 420
gtggacacca aggacaccag ggacaatgtg tctgtggact acaagcagac ccaactttgt 480
atcattggct gtgtgcctgc cattggagaa cactggacca agggcacagc ctgtaagcca 540
accacagtgg tccagggaga ctgtcctcca ttggaactga taaacacacc aattgaggat 600
ggagatatgg tggacacagg ctatggagct atggacttca aactgctcca agacaacaag 660

```
tctgaggtgc cactggacat ctgtcagagc atctgtaaat accctgacta cctccaaatg    720

agtgctgatg cctatggaga cagtatgttc ttctgtctga ggagggaaca ggtgtttgcc    780

agacacttct ggaacaggtc tggcacaatg ggagaccaac ttcctgagtc cctctacatc    840

aagggcacag acatcagggc taaccctggc tcctacctct acagcccaag cccatctggc    900

tctgtggtga cctctgacag ccaacttttc aacaagccat actggctgca caaggctcaa    960

ggactgaaca atggcatctg ttggcacaac caacttttcc tgacagtggt ggacaccacc   1020

aggagcacca acctgtctgt gtgtgccagc accacctcca gcatcccaaa tgtctacaca   1080

ccaacctcct tcaaggaata tgccaggcat gtggaggagt ttgacctcca attcatcttc   1140

caactttgta agattaccct gaccacagag gtgatgagtt acatccacaa tatgaacacc   1200

accatcttgg aggactggaa ctttggagtg acacctcctc caacagcctc cctggtggac   1260

acctacaggt ttgtccagtc tgctgctgtg acttgtcaga aggacacagc ccctcctgtg   1320

aagcaggacc catatgacaa actgaagttc tggcctgtgg acctgaaaga gaggttctct   1380

gctgacctgg accagtttcc actgggcagg aagttcctgc tccaacttgg agccagacca   1440

aagccaacca ttggaccaag gaagagggct gcccctgccc caaccagcac accaagccca   1500

aagagggtga agaggaggaa gtccagcagg aagtaaactc gagctc                  1546
```

<210> SEQ ID NO 163
<211> LENGTH: 4
<212> TYPE: PRT
<213> ORGANISM: Human Papillomavirus
<220> FEATURE:
<221> NAME/KEY: misc_feature
<222> LOCATION: (1)..(4)
<223> OTHER INFORMATION: Tetrapeptide in L1 protein of each HPV type

<400> SEQUENCE: 163

```
Arg Lys Phe Leu
1
```

<210> SEQ ID NO 164
<211> LENGTH: 6
<212> TYPE: PRT
<213> ORGANISM: Human Papillomavirus
<220> FEATURE:
<221> NAME/KEY: misc_feature
<222> LOCATION: (1)..(6)
<223> OTHER INFORMATION: Hexapeptide in L1 protein of each HPV type

<400> SEQUENCE: 164

```
Leu Gly Arg Lys Phe Leu
1               5
```

<210> SEQ ID NO 165
<211> LENGTH: 18
<212> TYPE: PRT
<213> ORGANISM: Human Papillomavirus
<220> FEATURE:
<221> NAME/KEY: misc_feature
<222> LOCATION: (1)..(18)
<223> OTHER INFORMATION: Epitope of the L1 protein

<400> SEQUENCE: 165

```
Glu Glu Tyr Asp Leu Gln Phe Ile Phe Gln Leu Cys Lys Ile Thr Leu
1               5                   10                  15

Thr Ala
```

<210> SEQ ID NO 166
<211> LENGTH: 21
<212> TYPE: PRT
<213> ORGANISM: Human Papillomavirus
<220> FEATURE:
<221> NAME/KEY: misc_feature
<222> LOCATION: (1)..(21)
<223> OTHER INFORMATION: Epitope of the L1 protein

<400> SEQUENCE: 166

Arg His Gly Glu Glu Tyr Asp Leu Gln Phe Ile Phe Gln Leu Cys Lys
1 5 10 15

Ile Thr Leu Thr Ala
20

<210> SEQ ID NO 167
<211> LENGTH: 7
<212> TYPE: PRT
<213> ORGANISM: Human Papillomavirus
<220> FEATURE:
<221> NAME/KEY: misc_feature
<222> LOCATION: (1)..(7)
<223> OTHER INFORMATION: Epitope of the L1 protein

<400> SEQUENCE: 167

Leu Pro Asp Pro Asn Lys Phe
1 5

<210> SEQ ID NO 168
<211> LENGTH: 10
<212> TYPE: PRT
<213> ORGANISM: Human Papillomavirus
<220> FEATURE:
<221> NAME/KEY: misc_feature
<222> LOCATION: (1)..(10)
<223> OTHER INFORMATION: Epitope of the L1 protein

<400> SEQUENCE: 168

Pro Glu Thr Gln Arg Leu Val Trp Ala Cys
1 5 10

<210> SEQ ID NO 169
<211> LENGTH: 8
<212> TYPE: PRT
<213> ORGANISM: Human Papillomavirus
<220> FEATURE:
<221> NAME/KEY: misc_feature
<222> LOCATION: (1)..(8)
<223> OTHER INFORMATION: Epitope of the L1 protein

<400> SEQUENCE: 169

Pro Val Pro Gly Gln Tyr Asp Ala
1 5

<210> SEQ ID NO 170
<211> LENGTH: 12
<212> TYPE: PRT
<213> ORGANISM: Human Papillomavirus
<220> FEATURE:
<221> NAME/KEY: misc_feature
<222> LOCATION: (1)..(12)
<223> OTHER INFORMATION: Epitope of the L1 protein

<400> SEQUENCE: 170

Tyr Asn Pro Glu Thr Gln Arg Leu Val Trp Ala Cys
1 5 10

<210> SEQ ID NO 171

```
<211> LENGTH: 8
<212> TYPE: PRT
<213> ORGANISM: Human Papillomavirus
<220> FEATURE:
<221> NAME/KEY: misc_feature
<222> LOCATION: (1)..(8)
<223> OTHER INFORMATION: Epitope of the L1 protein

<400> SEQUENCE: 171

Asp Thr Gly Tyr Gly Ala Met Asp
1               5


<210> SEQ ID NO 172
<211> LENGTH: 10
<212> TYPE: PRT
<213> ORGANISM: Human Papillomavirus
<220> FEATURE:
<221> NAME/KEY: misc_feature
<222> LOCATION: (1)..(10)
<223> OTHER INFORMATION: Epitope of the L1 protein

<400> SEQUENCE: 172

Pro Val Pro Gly Gln Tyr Asp Ala Thr Lys
1               5                   10


<210> SEQ ID NO 173
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: Epitope of the L1 protein

<400> SEQUENCE: 173

Lys Gln Asp Ile Pro Lys Val Ser Ala Tyr Gln Tyr Arg Val Phe Arg
1               5                   10                  15

Val


<210> SEQ ID NO 174
<211> LENGTH: 15
<212> TYPE: PRT
<213> ORGANISM: Human Papillomavirus
<220> FEATURE:
<221> NAME/KEY: misc_feature
<222> LOCATION: (1)..(15)
<223> OTHER INFORMATION: Epitope of the L1 protein

<400> SEQUENCE: 174

Arg Asp Asn Val Ser Val Asp Tyr Lys Gln Thr Gln Leu Cys Ile
1               5                   10                  15


<210> SEQ ID NO 175
<211> LENGTH: 14
<212> TYPE: PRT
<213> ORGANISM: Human Papillomavirus
<220> FEATURE:
<221> NAME/KEY: misc_feature
<222> LOCATION: (1)..(14)
<223> OTHER INFORMATION: Epitope of the L1 protein

<400> SEQUENCE: 175

Tyr Ser Arg His Val Glu Glu Tyr Asp Leu Gln Phe Ile Phe
1               5                   10


<210> SEQ ID NO 176
<211> LENGTH: 505
<212> TYPE: PRT
```

<213> ORGANISM: Human Papillomavirus
<220> FEATURE:
<221> NAME/KEY: misc_feature
<222> LOCATION: (1)..(505)
<223> OTHER INFORMATION: Amino Acid Sequence of Native HPV16L1

<400> SEQUENCE: 176

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380
```

```
Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
                405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505


<210> SEQ ID NO 177
<211> LENGTH: 502
<212> TYPE: PRT
<213> ORGANISM: Human Papillomavirus
<220> FEATURE:
<221> NAME/KEY: misc_feature
<222> LOCATION: (1)..(502)
<223> OTHER INFORMATION: Amino Acid Sequence of Native HPV35L1

<400> SEQUENCE: 177

Met Ser Leu Trp Arg Ser Asn Glu Ala Thr Val Tyr Leu Pro Pro Val
1               5                   10                  15

Ser Val Ser Lys Val Val Ser Thr Asp Glu Tyr Val Thr Arg Thr Asn
            20                  25                  30

Ile Tyr Tyr His Ala Gly Ser Ser Arg Leu Leu Ala Val Gly His Pro
        35                  40                  45

Tyr Tyr Ala Ile Lys Lys Gln Asp Ser Asn Lys Ile Ala Val Pro Lys
    50                  55                  60

Val Ser Gly Leu Gln Tyr Arg Val Phe Arg Val Lys Leu Pro Asp Pro
65                  70                  75                  80

Asn Lys Phe Gly Phe Pro Asp Thr Ser Phe Tyr Asp Pro Ala Ser Gln
                85                  90                  95

Arg Leu Val Trp Ala Cys Thr Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ser Asn Lys Tyr Val Gly Asn Ser Gly Thr Asp Asn Arg
    130                 135                 140

Glu Cys Ile Ser Met Asp Tyr Lys Gln Thr Gln Leu Cys Leu Ile Gly
145                 150                 155                 160

Cys Arg Pro Pro Ile Gly Glu His Trp Gly Lys Gly Thr Pro Cys Asn
                165                 170                 175

Ala Asn Gln Val Lys Ala Gly Glu Cys Pro Pro Leu Glu Leu Leu Asn
            180                 185                 190

Thr Val Leu Gln Asp Gly Asp Met Val Asp Thr Gly Phe Gly Ala Met
        195                 200                 205

Asp Phe Thr Thr Leu Gln Ala Asn Lys Ser Asp Val Pro Leu Asp Ile
    210                 215                 220
```

```
Cys Ser Ser Ile Cys Lys Tyr Pro Asp Tyr Leu Lys Met Val Ser Glu
225                 230                 235                 240

Pro Tyr Gly Asp Met Leu Phe Phe Tyr Leu Arg Arg Glu Gln Met Phe
                245                 250                 255

Val Arg His Leu Phe Asn Arg Ala Gly Thr Val Gly Glu Thr Val Pro
            260                 265                 270

Ala Asp Leu Tyr Ile Lys Gly Thr Thr Gly Thr Leu Pro Ser Thr Ser
        275                 280                 285

Tyr Phe Pro Thr Pro Ser Gly Ser Met Val Thr Ser Asp Ala Gln Ile
    290                 295                 300

Phe Asn Lys Pro Tyr Trp Leu Gln Arg Ala Gln Gly His Asn Asn Gly
305                 310                 315                 320

Ile Cys Trp Ser Asn Gln Leu Phe Val Thr Val Val Asp Thr Thr Arg
                325                 330                 335

Ser Thr Asn Met Ser Val Cys Ser Ala Val Ser Ser Ser Asp Ser Thr
            340                 345                 350

Tyr Lys Asn Asp Asn Phe Lys Glu Tyr Leu Arg His Gly Glu Glu Tyr
        355                 360                 365

Asp Leu Gln Phe Ile Phe Gln Leu Cys Lys Ile Thr Leu Thr Ala Asp
    370                 375                 380

Val Met Thr Tyr Ile His Ser Met Asn Pro Ser Ile Leu Glu Asp Trp
385                 390                 395                 400

Asn Phe Gly Leu Thr Pro Pro Pro Ser Gly Thr Leu Glu Asp Thr Tyr
                405                 410                 415

Arg Tyr Val Thr Ser Gln Ala Val Thr Cys Gln Lys Pro Ser Ala Pro
            420                 425                 430

Lys Pro Lys Asp Asp Pro Leu Lys Asn Tyr Thr Phe Trp Glu Val Asp
        435                 440                 445

Leu Lys Glu Lys Phe Ser Ala Asp Leu Asp Gln Phe Pro Leu Gly Arg
    450                 455                 460

Lys Phe Leu Leu Gln Ala Gly Leu Lys Ala Arg Pro Asn Phe Arg Leu
465                 470                 475                 480

Gly Lys Arg Ala Ala Pro Ala Ser Thr Ser Lys Lys Ser Ser Thr Lys
                485                 490                 495

Arg Arg Lys Val Lys Ser
            500
```

<210> SEQ ID NO 178
<211> LENGTH: 501
<212> TYPE: PRT
<213> ORGANISM: Human Papillomavirus
<220> FEATURE:
<221> NAME/KEY: misc_feature
<222> LOCATION: (1)..(501)
<223> OTHER INFORMATION: Amino Acid Sequence of Native HPV11L1

<400> SEQUENCE: 178

```
Met Trp Arg Pro Ser Asp Ser Thr Val Tyr Val Pro Pro Pro Asn Pro
1               5                   10                  15

Val Ser Lys Val Val Ala Thr Asp Ala Tyr Val Lys Arg Thr Asn Ile
            20                  25                  30

Phe Tyr His Ala Ser Ser Ser Arg Leu Leu Ala Val Gly His Pro Tyr
        35                  40                  45

Tyr Ser Ile Lys Lys Val Asn Lys Thr Val Val Pro Lys Val Ser Gly
    50                  55                  60

Tyr Gln Tyr Arg Val Phe Lys Val Val Leu Pro Asp Pro Asn Lys Phe
```

-continued

```
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
        115                 120                 125

Ser Gly Gly Tyr Gly Gly Asn Pro Gly Gln Asp Asn Arg Val Asn Val
    130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
        195                 200                 205

Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu
            260                 265                 270

Leu Val Lys Gly Gly Asn Asn Arg Ser Ser Val Ala Ser Ser Ile Tyr
        275                 280                 285

Val His Thr Pro Ser Gly Ser Leu Val Ser Ser Glu Ala Gln Leu Phe
    290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Val Asp Thr Thr Arg Ser
                325                 330                 335

Thr Asn Met Thr Leu Cys Ala Ser Val Ser Lys Ser Ala Thr Tyr Thr
            340                 345                 350

Asn Ser Asp Tyr Lys Glu Tyr Met Arg His Val Glu Glu Phe Asp Leu
        355                 360                 365

Gln Phe Ile Phe Gln Leu Cys Ser Ile Thr Leu Ser Ala Glu Val Met
    370                 375                 380

Ala Tyr Ile His Thr Met Asn Pro Ser Val Leu Glu Asp Trp Asn Phe
385                 390                 395                 400

Gly Leu Ser Pro Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
        435                 440                 445

Glu Lys Phe Ser Ser Glu Leu Asp Gln Phe Pro Leu Gly Arg Lys Phe
    450                 455                 460

Leu Leu Gln Ser Gly Tyr Arg Gly Arg Thr Ser Ala Arg Thr Gly Ile
465                 470                 475                 480

Lys Arg Pro Ala Val Ser Lys Pro Ser Thr Ala Pro Lys Arg Lys Arg
                485                 490                 495
```

```
Thr Lys Thr Lys Lys
            500


<210> SEQ ID NO 179
<211> LENGTH: 507
<212> TYPE: PRT
<213> ORGANISM: Human Papillomavirus
<220> FEATURE:
<221> NAME/KEY: misc_feature
<222> LOCATION: (1)..(507)
<223> OTHER INFORMATION: Amino Acid Sequence of Native HPV18L1

<400> SEQUENCE: 179

Met Ala Leu Trp Arg Pro Ser Asp Asn Thr Val Tyr Leu Pro Pro Pro
1               5                   10                  15

Ser Val Ala Arg Val Val Asn Thr Asp Asp Tyr Val Thr Arg Thr Ser
            20                  25                  30

Ile Phe Tyr His Ala Gly Ser Ser Arg Leu Leu Thr Val Gly Asn Pro
        35                  40                  45

Tyr Phe Arg Val Pro Ala Gly Gly Gly Asn Lys Gln Asp Ile Pro Lys
    50                  55                  60

Val Ser Ala Tyr Gln Tyr Arg Val Phe Arg Val Gln Leu Pro Asp Pro
65                  70                  75                  80

Asn Lys Phe Gly Leu Pro Asp Thr Ser Ile Tyr Asn Pro Glu Thr Gln
                85                  90                  95

Arg Leu Val Trp Ala Cys Ala Gly Val Glu Ile Gly Arg Gly Gln Pro
            100                 105                 110

Leu Gly Val Gly Leu Ser Gly His Pro Phe Tyr Asn Lys Leu Asp Asp
        115                 120                 125

Thr Glu Ser Ser His Ala Ala Thr Ser Asn Val Ser Glu Asp Val Arg
    130                 135                 140

Asp Asn Val Ser Val Asp Tyr Lys Gln Thr Gln Leu Cys Ile Leu Gly
145                 150                 155                 160

Cys Ala Pro Ala Ile Gly Glu His Trp Ala Lys Gly Thr Ala Cys Lys
                165                 170                 175

Ser Arg Pro Leu Ser Gln Gly Asp Cys Pro Pro Leu Glu Leu Lys Asn
            180                 185                 190

Thr Val Leu Glu Asp Gly Asp Met Val Asp Thr Gly Tyr Gly Ala Met
        195                 200                 205

Asp Phe Ser Thr Leu Gln Asp Thr Lys Cys Glu Val Pro Leu Asp Ile
    210                 215                 220

Cys Gln Ser Ile Cys Lys Tyr Pro Asp Tyr Leu Gln Met Ser Ala Asp
225                 230                 235                 240

Pro Tyr Gly Asp Ser Met Phe Phe Cys Leu Arg Arg Glu Gln Leu Phe
                245                 250                 255

Ala Arg His Phe Trp Asn Arg Ala Gly Thr Met Gly Asp Thr Val Pro
            260                 265                 270

Gln Ser Leu Tyr Ile Lys Gly Thr Gly Met Arg Ala Ser Pro Gly Ser
        275                 280                 285

Cys Val Tyr Ser Pro Ser Pro Ser Gly Ser Ile Val Thr Ser Asp Ser
    290                 295                 300

Gln Leu Phe Asn Lys Pro Tyr Trp Leu His Lys Ala Gln Gly His Asn
305                 310                 315                 320

Asn Gly Val Cys Trp His Asn Gln Leu Phe Val Thr Val Val Asp Thr
                325                 330                 335
```

-continued

Thr Arg Ser Thr Asn Leu Thr Ile Cys Ala Ser Thr Gln Ser Pro Val
340 345 350

Pro Gly Gln Tyr Asp Ala Thr Lys Phe Lys Gln Tyr Ser Arg His Val
355 360 365

Glu Glu Tyr Asp Leu Gln Phe Ile Phe Gln Leu Cys Thr Ile Thr Leu
370 375 380

Thr Ala Asp Val Met Ser Tyr Ile His Ser Met Asn Ser Ser Ile Leu
385 390 395 400

Glu Asp Trp Asn Phe Gly Val Pro Pro Pro Pro Thr Thr Ser Leu Val
405 410 415

Asp Thr Tyr Arg Phe Val Gln Ser Val Ala Ile Thr Cys Gln Lys Asp
420 425 430

Ala Ala Pro Ala Glu Asn Lys Asp Pro Tyr Asp Lys Leu Lys Phe Trp
435 440 445

Asn Val Asp Leu Lys Glu Lys Phe Ser Leu Asp Leu Asp Gln Tyr Pro
450 455 460

Leu Gly Arg Lys Phe Leu Val Gln Ala Gly Leu Arg Arg Lys Pro Thr
465 470 475 480

Ile Gly Pro Arg Lys Arg Ser Ala Pro Ser Ala Thr Thr Ser Ser Lys
485 490 495

Pro Ala Lys Arg Val Arg Val Arg Ala Arg Lys
500 505

<210> SEQ ID NO 180
<211> LENGTH: 500
<212> TYPE: PRT
<213> ORGANISM: Human Papillomavirus
<220> FEATURE:
<221> NAME/KEY: misc_feature
<222> LOCATION: (1)..(500)
<223> OTHER INFORMATION: Amino Acid Sequence of Native HPV6L1

<400> SEQUENCE: 180

Met Trp Arg Pro Ser Asp Ser Thr Val Tyr Val Pro Pro Pro Asn Pro
1 5 10 15

Val Ser Lys Val Val Ala Thr Asp Ala Tyr Val Thr Arg Thr Asn Ile
20 25 30

Phe Tyr His Ala Ser Ser Ser Arg Leu Leu Ala Val Gly His Pro Tyr
35 40 45

Phe Ser Ile Lys Arg Ala Asn Lys Thr Val Val Pro Lys Val Ser Gly
50 55 60

Tyr Gln Tyr Arg Val Phe Lys Val Val Leu Pro Asp Pro Asn Lys Phe
65 70 75 80

Ala Leu Pro Asp Ser Ser Leu Phe Asp Pro Thr Thr Gln Arg Leu Val
85 90 95

Trp Ala Cys Thr Gly Leu Glu Val Gly Arg Gly Gln Pro Leu Gly Val
100 105 110

Gly Val Ser Gly His Pro Phe Leu Asn Lys Tyr Asp Asp Val Glu Asn
115 120 125

Ser Gly Ser Gly Gly Asn Pro Gly Gln Asp Asn Arg Val Asn Val Gly
130 135 140

Met Asp Tyr Lys Gln Thr Gln Leu Cys Met Val Gly Cys Ala Pro Pro
145 150 155 160

Leu Gly Glu His Trp Gly Lys Gly Lys Gln Cys Thr Asn Thr Pro Val
165 170 175

Gln Ala Gly Asp Cys Pro Pro Leu Glu Leu Ile Thr Ser Val Ile Gln

```
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser Gly Tyr Arg Gly Arg Ser Ser Ile Arg Thr Gly Val Lys
465                 470                 475                 480

Arg Pro Ala Val Ser Lys Ala Ser Ala Ala Pro Lys Arg Lys Arg Ala
                485                 490                 495

Lys Thr Lys Arg
            500


<210> SEQ ID NO 181
<211> LENGTH: 503
<212> TYPE: PRT
<213> ORGANISM: Human Papillomavirus
<220> FEATURE:
<221> NAME/KEY: misc_feature
<222> LOCATION: (1)..(503)
<223> OTHER INFORMATION: Amino Acid Sequence of Native HPV52L1

<400> SEQUENCE: 181

Met Ser Val Trp Arg Pro Ser Glu Ala Thr Val Tyr Leu Pro Pro Val
1               5                   10                  15

Pro Val Ser Lys Val Val Ser Thr Asp Glu Tyr Val Ser Arg Thr Ser
            20                  25                  30
```

-continued

```
Ile Tyr Tyr Tyr Ala Gly Ser Ser Arg Leu Leu Thr Val Gly His Pro
        35                  40                  45

Tyr Phe Ser Ile Lys Asn Thr Ser Ser Gly Asn Gly Lys Lys Val Leu
    50                  55                  60

Val Pro Lys Val Ser Gly Leu Gln Tyr Arg Val Phe Arg Ile Lys Leu
65                  70                  75                  80

Pro Asp Pro Asn Lys Phe Gly Phe Pro Asp Thr Ser Phe Tyr Asn Pro
                85                  90                  95

Glu Thr Gln Arg Leu Val Trp Ala Cys Thr Gly Leu Glu Ile Gly Arg
            100                 105                 110

Gly Gln Pro Leu Gly Val Gly Ile Ser Gly His Pro Leu Leu Asn Lys
        115                 120                 125

Phe Asp Asp Thr Glu Thr Ser Asn Lys Tyr Ala Gly Lys Pro Gly Ile
    130                 135                 140

Asp Asn Arg Glu Cys Leu Ser Met Asp Tyr Lys Gln Thr Gln Leu Cys
145                 150                 155                 160

Ile Leu Gly Cys Lys Pro Pro Ile Gly Glu His Trp Gly Lys Gly Thr
                165                 170                 175

Pro Cys Asn Asn Asn Ser Gly Asn Pro Gly Asp Cys Pro Pro Leu Gln
            180                 185                 190

Leu Ile Asn Ser Val Ile Gln Asp Gly Asp Met Val Asp Thr Gly Phe
        195                 200                 205

Gly Cys Met Asp Phe Asn Thr Leu Gln Ala Ser Lys Ser Asp Val Pro
    210                 215                 220

Ile Asp Ile Cys Ser Ser Val Cys Lys Tyr Pro Asp Tyr Leu Gln Met
225                 230                 235                 240

Ala Ser Glu Pro Tyr Gly Asp Ser Leu Phe Phe Phe Leu Arg Arg Glu
                245                 250                 255

Gln Met Phe Val Arg His Phe Phe Asn Arg Ala Gly Thr Leu Gly Asp
            260                 265                 270

Pro Val Pro Gly Asp Leu Tyr Ile Gln Gly Ser Asn Ser Gly Asn Thr
        275                 280                 285

Ala Thr Val Gln Ser Ser Ala Phe Phe Pro Thr Pro Ser Gly Ser Met
    290                 295                 300

Val Thr Ser Glu Ser Gln Leu Phe Asn Lys Pro Tyr Trp Leu Gln Arg
305                 310                 315                 320

Ala Gln Gly His Asn Asn Gly Ile Cys Trp Gly Asn Gln Leu Phe Val
                325                 330                 335

Thr Val Val Asp Thr Thr Arg Ser Thr Asn Met Thr Leu Cys Ala Glu
            340                 345                 350

Val Lys Lys Glu Ser Thr Tyr Lys Asn Glu Asn Phe Lys Glu Tyr Leu
        355                 360                 365

Arg His Gly Glu Glu Phe Asp Leu Gln Phe Ile Phe Gln Leu Cys Lys
    370                 375                 380

Ile Thr Leu Thr Ala Asp Val Met Thr Tyr Ile His Lys Met Asp Ala
385                 390                 395                 400

Thr Ile Leu Glu Asp Trp Gln Phe Gly Leu Thr Pro Pro Pro Ser Ala
                405                 410                 415

Ser Leu Glu Asp Thr Tyr Arg Phe Val Thr Ser Thr Ala Ile Thr Cys
            420                 425                 430

Gln Lys Asn Thr Pro Pro Lys Gly Lys Glu Asp Pro Leu Lys Asp Tyr
        435                 440                 445
```

```
Met Phe Trp Glu Val Asp Leu Lys Glu Lys Phe Ser Ala Asp Leu Asp
    450                 455                 460

Gln Phe Pro Leu Gly Arg Lys Phe Leu Leu Gln Ala Gly Leu Gln Ala
465                 470                 475                 480

Arg Pro Lys Leu Lys Arg Pro Ala Ser Ser Ala Pro Arg Thr Ser Thr
                485                 490                 495

Lys Lys Lys Lys Val Lys Arg
            500


<210> SEQ ID NO 182
<211> LENGTH: 498
<212> TYPE: PRT
<213> ORGANISM: Human Papillomavirus
<220> FEATURE:
<221> NAME/KEY: misc_feature
<222> LOCATION: (1)..(498)
<223> OTHER INFORMATION: Amino Acid Sequence of Native HPV58L1

<400> SEQUENCE: 182

Met Ser Val Trp Arg Pro Ser Glu Ala Thr Val Tyr Leu Pro Pro Val
1               5                   10                  15

Pro Val Ser Lys Val Val Ser Thr Asp Glu Tyr Val Ser Arg Thr Ser
            20                  25                  30

Ile Tyr Tyr Tyr Ala Gly Ser Ser Arg Leu Leu Ala Val Gly Asn Pro
        35                  40                  45

Tyr Phe Ser Ile Lys Ser Pro Asn Asn Asn Lys Lys Val Leu Val Pro
    50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Asp Thr
                85                  90                  95

Gln Arg Leu Val Trp Ala Cys Val Gly Leu Glu Ile Gly Arg Gly Gln
            100                 105                 110

Pro Leu Gly Val Gly Val Ser Gly His Pro Tyr Leu Asn Lys Phe Asp
        115                 120                 125

Asp Thr Glu Thr Ser Asn Arg Tyr Pro Ala Gln Pro Gly Ser Asp Asn
    130                 135                 140

Arg Glu Cys Leu Ser Met Asp Tyr Lys Gln Thr Gln Leu Cys Leu Ile
145                 150                 155                 160

Gly Cys Lys Pro Pro Thr Gly Glu His Trp Gly Lys Gly Val Ala Cys
                165                 170                 175

Asn Asn Asn Ala Ala Ala Thr Asp Cys Pro Pro Leu Glu Leu Phe Asn
            180                 185                 190

Ser Ile Ile Glu Asp Gly Asp Met Val Asp Thr Gly Phe Gly Cys Met
        195                 200                 205

Asp Phe Gly Thr Leu Gln Ala Asn Lys Ser Asp Val Pro Ile Asp Ile
    210                 215                 220

Cys Asn Ser Thr Cys Lys Tyr Pro Asp Tyr Leu Lys Met Ala Ser Glu
225                 230                 235                 240

Pro Tyr Gly Asp Ser Leu Phe Phe Phe Leu Arg Arg Glu Gln Met Phe
                245                 250                 255

Val Arg His Phe Phe Asn Arg Ala Gly Lys Leu Gly Glu Ala Val Pro
            260                 265                 270

Asp Asp Leu Tyr Ile Lys Gly Ser Gly Asn Thr Ala Val Ile Gln Ser
        275                 280                 285

Ser Ala Phe Phe Pro Thr Pro Ser Gly Ser Ile Val Thr Ser Glu Ser
```

```
    290                 295                 300

Gln Leu Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Thr Leu Cys Thr Glu Val Thr Lys Glu Gly
            340                 345                 350

Thr Tyr Lys Asn Asp Asn Phe Lys Glu Tyr Val Arg His Val Glu Glu
        355                 360                 365

Tyr Asp Leu Gln Phe Val Phe Gln Leu Cys Lys Ile Thr Leu Thr Ala
    370                 375                 380

Glu Ile Met Thr Tyr Ile His Thr Met Asp Ser Asn Ile Leu Glu Asp
385                 390                 395                 400

Trp Gln Phe Gly Leu Thr Pro Pro Pro Ser Ala Ser Leu Gln Asp Thr
                405                 410                 415

Tyr Arg Phe Val Thr Ser Gln Ala Ile Thr Cys Gln Lys Thr Ala Pro
            420                 425                 430

Pro Lys Glu Lys Glu Asp Pro Leu Asn Lys Tyr Thr Phe Trp Glu Val
        435                 440                 445

Asn Leu Lys Glu Lys Phe Ser Ala Asp Leu Asp Gln Phe Pro Leu Gly
    450                 455                 460

Arg Lys Phe Leu Leu Gln Ser Gly Leu Lys Ala Lys Pro Arg Leu Lys
465                 470                 475                 480

Arg Ser Ala Pro Thr Thr Arg Ala Pro Ser Thr Lys Arg Lys Lys Val
                485                 490                 495

Lys Lys


<210> SEQ ID NO 183
<211> LENGTH: 499
<212> TYPE: PRT
<213> ORGANISM: Human Papillomavirus
<220> FEATURE:
<221> NAME/KEY: misc_feature
<222> LOCATION: (1)..(499)
<223> OTHER INFORMATION: Amino Acid Sequence of Native HPV33L1

<400> SEQUENCE: 183

Met Ser Val Trp Arg Pro Ser Glu Ala Thr Val Tyr Leu Pro Pro Val
1               5                   10                  15

Pro Val Ser Lys Val Val Ser Thr Asp Glu Tyr Val Ser Arg Thr Ser
            20                  25                  30

Ile Tyr Tyr Tyr Ala Gly Ser Ser Arg Leu Leu Ala Val Gly His Pro
        35                  40                  45

Tyr Phe Ser Ile Lys Asn Pro Thr Asn Ala Lys Lys Leu Leu Val Pro
    50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Asp Thr
                85                  90                  95

Gln Arg Leu Val Trp Ala Cys Val Gly Leu Glu Ile Gly Arg Gly Gln
            100                 105                 110

Pro Leu Gly Val Gly Ile Ser Gly His Pro Leu Leu Asn Lys Phe Asp
        115                 120                 125

Asp Thr Glu Thr Gly Asn Lys Tyr Pro Gly Gln Pro Gly Ala Asp Asn
    130                 135                 140
```

Arg Glu Cys Leu Ser Met Asp Tyr Lys Gln Thr Gln Leu Cys Leu Leu
145 150 155 160

Gly Cys Lys Pro Pro Thr Gly Glu His Trp Gly Lys Gly Val Ala Cys
165 170 175

Thr Asn Ala Ala Pro Ala Asn Asp Cys Pro Pro Leu Glu Leu Ile Asn
180 185 190

Thr Ile Ile Glu Asp Gly Asp Met Val Asp Thr Gly Phe Gly Cys Met
195 200 205

Asp Phe Lys Thr Leu Gln Ala Asn Lys Ser Asp Val Pro Ile Asp Ile
210 215 220

Cys Gly Ser Thr Cys Lys Tyr Pro Asp Tyr Leu Lys Met Thr Ser Glu
225 230 235 240

Pro Tyr Gly Asp Ser Leu Phe Phe Phe Leu Arg Arg Glu Gln Met Phe
245 250 255

Val Arg His Phe Phe Asn Arg Ala Gly Thr Leu Gly Glu Ala Val Pro
260 265 270

Asp Asp Leu Tyr Ile Lys Gly Ser Gly Thr Thr Ala Ser Ile Gln Ser
275 280 285

Ser Ala Phe Phe Pro Thr Pro Ser Gly Ser Met Val Thr Ser Glu Ser
290 295 300

Gln Leu Phe Asn Lys Pro Tyr Trp Leu Gln Arg Ala Gln Gly His Asn
305 310 315 320

Asn Gly Ile Cys Trp Gly Asn Gln Val Phe Val Thr Val Val Asp Thr
325 330 335

Thr Arg Ser Thr Asn Met Thr Leu Cys Thr Gln Val Thr Ser Asp Ser
340 345 350

Thr Tyr Lys Asn Glu Asn Phe Lys Glu Tyr Ile Arg His Val Glu Glu
355 360 365

Tyr Asp Leu Gln Phe Val Phe Gln Leu Cys Lys Val Thr Leu Thr Ala
370 375 380

Glu Val Met Thr Tyr Ile His Ala Met Asn Pro Asp Ile Leu Glu Asp
385 390 395 400

Trp Gln Phe Gly Leu Thr Pro Pro Pro Ser Ala Ser Leu Gln Asp Thr
405 410 415

Tyr Arg Phe Val Thr Ser Gln Ala Ile Thr Cys Gln Lys Thr Val Pro
420 425 430

Pro Lys Glu Lys Glu Asp Pro Leu Gly Lys Tyr Thr Phe Trp Glu Val
435 440 445

Asp Leu Lys Glu Lys Phe Ser Ala Asp Leu Asp Gln Phe Pro Leu Gly
450 455 460

Arg Lys Phe Leu Leu Gln Ala Gly Leu Lys Ala Lys Pro Lys Leu Lys
465 470 475 480

Arg Ala Ala Pro Thr Ser Thr Arg Thr Ser Ser Ala Lys Arg Lys Lys
485 490 495

Val Lys Lys

<210> SEQ ID NO 184
<211> LENGTH: 504
<212> TYPE: PRT
<213> ORGANISM: Human Papillomavirus
<220> FEATURE:
<221> NAME/KEY: misc_feature
<222> LOCATION: (1)..(504)
<223> OTHER INFORMATION: Amino Acid Sequence of Native HPV31L1

<400> SEQUENCE: 184

-continued

```
Met Ser Leu Trp Arg Pro Ser Glu Ala Thr Val Tyr Leu Pro Pro Val
1               5                   10                  15

Pro Val Ser Lys Val Val Ser Thr Asp Glu Tyr Val Thr Arg Thr Asn
            20                  25                  30

Ile Tyr Tyr His Ala Gly Ser Ala Arg Leu Leu Thr Val Gly His Pro
        35                  40                  45

Tyr Tyr Ser Ile Pro Lys Ser Asp Asn Pro Lys Lys Ile Val Val Pro
    50                  55                  60

Lys Val Ser Gly Leu Gln Tyr Arg Val Phe Arg Val Arg Leu Pro Asp
65                  70                  75                  80

Pro Asn Lys Phe Gly Phe Pro Asp Thr Ser Phe Tyr Asn Pro Glu Thr
                85                  90                  95

Gln Arg Leu Val Trp Ala Cys Val Gly Leu Glu Val Gly Arg Gly Gln
            100                 105                 110

Pro Leu Gly Val Gly Ile Ser Gly His Pro Leu Leu Asn Lys Phe Asp
        115                 120                 125

Asp Thr Glu Asn Ser Asn Arg Tyr Ala Gly Gly Pro Gly Thr Asp Asn
    130                 135                 140

Arg Glu Cys Ile Ser Met Asp Tyr Lys Gln Thr Gln Leu Cys Leu Leu
145                 150                 155                 160

Gly Cys Lys Pro Pro Ile Gly Glu His Trp Gly Lys Gly Ser Pro Cys
                165                 170                 175

Ser Asn Asn Ala Ile Thr Pro Gly Asp Cys Pro Pro Leu Glu Leu Lys
            180                 185                 190

Asn Ser Val Ile Gln Asp Gly Asp Met Val Asp Thr Gly Phe Gly Ala
        195                 200                 205

Met Asp Phe Thr Ala Leu Gln Asp Thr Lys Ser Asn Val Pro Leu Asp
    210                 215                 220

Ile Cys Asn Ser Ile Cys Lys Tyr Pro Asp Tyr Leu Lys Met Val Ala
225                 230                 235                 240

Glu Pro Tyr Gly Asp Thr Leu Phe Phe Tyr Leu Arg Arg Glu Gln Met
                245                 250                 255

Phe Val Arg His Phe Phe Asn Arg Ser Gly Thr Val Gly Glu Ser Val
            260                 265                 270

Pro Thr Asp Leu Tyr Ile Lys Gly Ser Gly Ser Thr Ala Thr Leu Ala
        275                 280                 285

Asn Ser Thr Tyr Phe Pro Thr Pro Ser Gly Ser Met Val Thr Ser Asp
    290                 295                 300

Ala Gln Ile Phe Asn Lys Pro Tyr Trp Met Gln Arg Ala Gln Gly His
305                 310                 315                 320

Asn Asn Gly Ile Cys Trp Gly Asn Gln Leu Phe Val Thr Val Val Asp
                325                 330                 335

Thr Thr Arg Ser Thr Asn Met Ser Val Cys Ala Ala Ile Ala Asn Ser
            340                 345                 350

Asp Thr Thr Phe Lys Ser Ser Asn Phe Lys Glu Tyr Leu Arg His Gly
        355                 360                 365

Glu Glu Phe Asp Leu Gln Phe Ile Phe Gln Leu Cys Lys Ile Thr Leu
    370                 375                 380

Ser Ala Asp Ile Met Thr Tyr Ile His Ser Met Asn Pro Ala Ile Leu
385                 390                 395                 400

Glu Asp Trp Asn Phe Gly Leu Thr Thr Pro Pro Ser Gly Ser Leu Glu
                405                 410                 415
```

```
Asp Thr Tyr Arg Phe Val Thr Ser Gln Ala Ile Thr Cys Gln Lys Ser
            420                 425                 430

Ala Pro Gln Lys Pro Lys Glu Asp Pro Phe Lys Asp Tyr Val Phe Trp
        435                 440                 445

Glu Val Asn Leu Lys Glu Lys Phe Ser Ala Asp Leu Asp Gln Phe Pro
    450                 455                 460

Leu Gly Arg Lys Phe Leu Leu Gln Ala Gly Tyr Arg Ala Arg Pro Lys
465                 470                 475                 480

Phe Lys Ala Gly Lys Arg Ser Ala Pro Ser Ala Ser Thr Thr Thr Pro
                485                 490                 495

Ala Lys Arg Lys Lys Thr Lys Lys
            500


<210> SEQ ID NO 185
<211> LENGTH: 504
<212> TYPE: PRT
<213> ORGANISM: Human Papillomavirus
<220> FEATURE:
<221> NAME/KEY: misc_feature
<222> LOCATION: (1)..(504)
<223> OTHER INFORMATION: Amino Acid Sequence of Native HPV51L1

<400> SEQUENCE: 185

Met Ala Leu Trp Arg Thr Asn Asp Ser Lys Val Tyr Leu Pro Pro Ala
1               5                   10                  15

Pro Val Ser Arg Ile Val Asn Thr Glu Glu Tyr Ile Thr Arg Thr Gly
            20                  25                  30

Ile Tyr Tyr Tyr Ala Gly Ser Ser Arg Leu Ile Thr Leu Gly His Pro
        35                  40                  45

Tyr Phe Pro Ile Pro Lys Thr Ser Thr Arg Ala Ala Ile Pro Lys Val
    50                  55                  60

Ser Ala Phe Gln Tyr Arg Val Phe Arg Val Gln Leu Pro Asp Pro Asn
65                  70                  75                  80

Lys Phe Gly Leu Pro Asp Pro Asn Leu Tyr Asn Pro Asp Thr Asp Arg
                85                  90                  95

Leu Val Trp Gly Cys Val Gly Val Glu Val Gly Arg Gly Gln Pro Leu
            100                 105                 110

Gly Val Gly Leu Ser Gly His Pro Leu Phe Asn Lys Tyr Asp Asp Thr
        115                 120                 125

Glu Asn Ser Arg Ile Ala Asn Gly Asn Ala Gln Gln Asp Val Arg Asp
    130                 135                 140

Asn Thr Ser Val Asp Asn Lys Gln Thr Gln Leu Cys Ile Ile Gly Cys
145                 150                 155                 160

Ala Pro Pro Ile Gly Glu His Trp Gly Ile Gly Thr Thr Cys Lys Asn
                165                 170                 175

Thr Pro Val Pro Pro Gly Asp Cys Pro Pro Leu Glu Leu Val Ser Ser
            180                 185                 190

Val Ile Gln Asp Gly Asp Met Ile Asp Thr Gly Phe Gly Ala Met Asp
        195                 200                 205

Phe Ala Ala Leu Gln Ala Thr Lys Ser Asp Val Pro Leu Asp Ile Ser
    210                 215                 220

Gln Ser Val Cys Lys Tyr Pro Asp Tyr Leu Lys Met Ser Ala Asp Thr
225                 230                 235                 240

Tyr Gly Asn Ser Met Phe Phe His Leu Arg Arg Glu Gln Ile Phe Ala
                245                 250                 255

Arg His Tyr Tyr Asn Lys Leu Val Gly Val Gly Glu Asp Ile Pro Asn
```

```
            260                 265                 270

Asp Tyr Tyr Ile Lys Gly Ser Gly Asn Gly Arg Asp Pro Ile Glu Ser
        275                 280                 285

Tyr Ile Tyr Ser Ala Thr Pro Ser Gly Ser Met Ile Thr Ser Asp Ser
    290                 295                 300

Gln Ile Phe Asn Lys Pro Tyr Trp Leu His Arg Ala Gln Gly His Asn
305                 310                 315                 320

Asn Gly Ile Cys Trp Asn Asn Gln Leu Phe Ile Thr Cys Val Asp Thr
                325                 330                 335

Thr Arg Ser Thr Asn Leu Thr Ile Ser Thr Ala Thr Ala Ala Val Ser
            340                 345                 350

Pro Thr Phe Thr Pro Ser Asn Phe Lys Gln Tyr Ile Arg His Gly Glu
        355                 360                 365

Glu Tyr Glu Leu Gln Phe Ile Phe Gln Leu Cys Lys Ile Thr Leu Thr
    370                 375                 380

Thr Glu Val Met Ala Tyr Leu His Thr Met Asp Pro Thr Ile Leu Glu
385                 390                 395                 400

Gln Trp Asn Phe Gly Leu Thr Leu Pro Pro Ser Ala Ser Leu Glu Asp
                405                 410                 415

Ala Tyr Arg Phe Val Arg Asn Ala Ala Thr Ser Cys Gln Lys Asp Thr
            420                 425                 430

Pro Pro Gln Ala Lys Pro Asp Pro Leu Ala Lys Tyr Lys Phe Trp Asp
        435                 440                 445

Val Asp Leu Lys Glu Arg Phe Ser Leu Asp Leu Asp Gln Phe Ala Leu
    450                 455                 460

Gly Arg Lys Phe Leu Leu Gln Val Gly Val Gln Arg Lys Pro Arg Pro
465                 470                 475                 480

Gly Leu Lys Arg Pro Ala Ser Ser Ala Ser Ser Ser Ser Ser Ser Ser
                485                 490                 495

Ala Lys Arg Lys Arg Val Lys Lys
            500


<210> SEQ ID NO 186
<211> LENGTH: 499
<212> TYPE: PRT
<213> ORGANISM: Human Papillomavirus
<220> FEATURE:
<221> NAME/KEY: misc_feature
<222> LOCATION: (1)..(499)
<223> OTHER INFORMATION: Amino Acid Sequence of Native HPV56L1

<400> SEQUENCE: 186

Met Ala Thr Trp Arg Pro Ser Glu Asn Lys Val Tyr Leu Pro Pro Thr
1               5                   10                  15

Pro Val Ser Lys Val Val Ala Thr Asp Ser Tyr Val Lys Arg Thr Ser
            20                  25                  30

Ile Phe Tyr His Ala Gly Ser Ser Arg Leu Leu Ala Val Gly His Pro
        35                  40                  45

Tyr Tyr Ser Val Thr Lys Asp Asn Thr Lys Thr Asn Ile Pro Lys Val
    50                  55                  60

Ser Ala Tyr Gln Tyr Arg Val Phe Arg Val Arg Leu Pro Asp Pro Asn
65                  70                  75                  80

Lys Phe Gly Leu Pro Asp Thr Asn Ile Tyr Asn Pro Asp Gln Glu Arg
                85                  90                  95

Leu Val Trp Ala Cys Val Gly Leu Glu Val Gly Arg Gly Gln Pro Leu
            100                 105                 110
```

```
Gly Ala Gly Leu Ser Gly His Pro Leu Phe Asn Arg Leu Asp Asp Thr
        115                 120                 125

Glu Ser Ser Asn Leu Ala Asn Asn Asn Val Ile Glu Asp Ser Arg Asp
    130                 135                 140

Asn Ile Ser Val Asp Gly Lys Gln Thr Gln Leu Cys Ile Val Gly Cys
145                 150                 155                 160

Thr Pro Ala Met Gly Glu His Trp Thr Lys Gly Ala Val Cys Lys Ser
                165                 170                 175

Thr Gln Val Thr Thr Gly Asp Cys Pro Pro Leu Ala Leu Ile Asn Thr
            180                 185                 190

Pro Ile Glu Asp Gly Asp Met Ile Asp Thr Gly Phe Gly Ala Met Asp
        195                 200                 205

Phe Lys Val Leu Gln Glu Ser Lys Ala Glu Val Pro Leu Asp Ile Val
    210                 215                 220

Gln Ser Thr Cys Lys Tyr Pro Asp Tyr Leu Lys Met Ser Ala Asp Ala
225                 230                 235                 240

Tyr Gly Asp Ser Met Trp Phe Tyr Leu Arg Arg Glu Gln Leu Phe Ala
                245                 250                 255

Arg His Tyr Phe Asn Arg Ala Gly Lys Val Gly Glu Thr Ile Pro Ala
            260                 265                 270

Glu Leu Tyr Leu Lys Gly Ser Asn Gly Arg Glu Pro Pro Pro Ser Ser
        275                 280                 285

Val Tyr Val Ala Thr Pro Ser Gly Ser Met Ile Thr Ser Glu Ala Gln
    290                 295                 300

Leu Phe Asn Lys Pro Tyr Trp Leu Gln Arg Ala Gln Gly His Asn Asn
305                 310                 315                 320

Gly Ile Cys Trp Gly Asn Gln Leu Phe Val Thr Val Val Asp Thr Thr
                325                 330                 335

Arg Ser Thr Asn Met Thr Ile Ser Thr Ala Thr Glu Gln Leu Ser Lys
            340                 345                 350

Tyr Asp Ala Arg Lys Ile Asn Gln Tyr Leu Arg His Val Glu Glu Tyr
        355                 360                 365

Glu Leu Gln Phe Val Phe Gln Leu Cys Lys Ile Thr Leu Ser Ala Glu
    370                 375                 380

Val Met Ala Tyr Leu His Asn Met Asn Ala Asn Leu Leu Glu Asp Trp
385                 390                 395                 400

Asn Ile Gly Leu Ser Pro Pro Val Ala Thr Ser Leu Glu Asp Lys Tyr
                405                 410                 415

Arg Tyr Val Arg Ser Thr Ala Ile Thr Cys Gln Arg Glu Gln Pro Pro
            420                 425                 430

Thr Glu Lys Gln Asp Pro Leu Ala Lys Tyr Lys Phe Trp Asp Val Asn
        435                 440                 445

Leu Gln Asp Ser Phe Ser Thr Asp Leu Asp Gln Phe Pro Leu Gly Arg
    450                 455                 460

Lys Phe Leu Met Gln Leu Gly Thr Arg Ser Lys Pro Ala Val Ala Thr
465                 470                 475                 480

Ser Lys Lys Arg Ser Ala Pro Thr Ser Thr Ser Thr Pro Ala Lys Arg
                485                 490                 495

Lys Arg Arg
```

<210> SEQ ID NO 187
<211> LENGTH: 505
<212> TYPE: PRT

<213> ORGANISM: Human Papillomavirus
<220> FEATURE:
<221> NAME/KEY: misc_feature
<222> LOCATION: (1)..(505)
<223> OTHER INFORMATION: Amino Acid Sequence of Native HPV39L1

<400> SEQUENCE: 187

```
Met Ala Met Trp Arg Ser Ser Asp Ser Met Val Tyr Leu Pro Pro Pro
1               5                   10                  15

Ser Val Ala Lys Val Val Asn Thr Asp Asp Tyr Val Thr Arg Thr Gly
            20                  25                  30

Ile Tyr Tyr Tyr Ala Gly Ser Ser Arg Leu Leu Thr Val Gly His Pro
        35                  40                  45

Tyr Phe Lys Val Gly Met Asn Gly Gly Arg Lys Gln Asp Ile Pro Lys
    50                  55                  60

Val Ser Ala Tyr Gln Tyr Arg Val Phe Arg Val Thr Leu Pro Asp Pro
65                  70                  75                  80

Asn Lys Phe Ser Ile Pro Asp Ala Ser Leu Tyr Asn Pro Glu Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Tyr Asn Arg Gln Asp Asp
        115                 120                 125

Thr Glu Asn Ser Pro Phe Ser Ser Thr Thr Asn Lys Asp Ser Arg Asp
    130                 135                 140

Asn Val Ser Val Asp Tyr Lys Gln Thr Gln Leu Cys Ile Ile Gly Cys
145                 150                 155                 160

Val Pro Ala Ile Gly Glu His Trp Gly Lys Gly Lys Ala Cys Lys Pro
                165                 170                 175

Asn Asn Val Ser Thr Gly Asp Cys Pro Pro Leu Glu Leu Val Asn Thr
            180                 185                 190

Pro Ile Glu Asp Gly Asp Met Ile Asp Thr Gly Tyr Gly Ala Met Asp
        195                 200                 205

Phe Gly Ala Leu Gln Glu Thr Lys Ser Glu Val Pro Leu Asp Ile Cys
    210                 215                 220

Gln Ser Ile Cys Lys Tyr Pro Asp Tyr Leu Gln Met Ser Ala Asp Val
225                 230                 235                 240

Tyr Gly Asp Ser Met Phe Phe Cys Leu Arg Arg Glu Gln Leu Phe Ala
                245                 250                 255

Arg His Phe Trp Asn Arg Gly Gly Met Val Gly Asp Ala Ile Pro Ala
            260                 265                 270

Gln Leu Tyr Ile Lys Gly Thr Asp Ile Arg Ala Asn Pro Gly Ser Ser
        275                 280                 285

Val Tyr Cys Pro Ser Pro Ser Gly Ser Met Val Thr Ser Asp Ser Gln
    290                 295                 300

Leu Phe Asn Lys Pro Tyr Trp Leu His Lys Ala Gln Gly His Asn Asn
305                 310                 315                 320

Gly Ile Cys Trp His Asn Gln Leu Phe Leu Thr Val Val Asp Thr Thr
                325                 330                 335

Arg Ser Thr Asn Phe Thr Leu Ser Thr Ser Ile Glu Ser Ser Ile Pro
            340                 345                 350

Ser Thr Tyr Asp Pro Ser Lys Phe Lys Glu Tyr Thr Arg His Val Glu
        355                 360                 365

Glu Tyr Asp Leu Gln Phe Ile Phe Gln Leu Cys Thr Val Thr Leu Thr
    370                 375                 380
```

Thr Asp Val Met Ser Tyr Ile His Thr Met Asn Ser Ser Ile Leu Asp
385 390 395 400

Asn Trp Asn Phe Ala Val Ala Pro Pro Pro Ser Ala Ser Leu Val Asp
405 410 415

Thr Tyr Arg Tyr Leu Gln Ser Ala Ala Ile Thr Cys Gln Lys Asp Ala
420 425 430

Pro Ala Pro Glu Lys Lys Asp Pro Tyr Asp Gly Leu Lys Phe Trp Asn
435 440 445

Val Asp Leu Arg Glu Lys Phe Ser Leu Glu Leu Asp Gln Phe Pro Leu
450 455 460

Gly Arg Lys Phe Leu Leu Gln Ala Arg Val Arg Arg Arg Pro Thr Ile
465 470 475 480

Gly Pro Arg Lys Arg Pro Ala Ala Ser Thr Ser Ser Ser Ser Ala Thr
485 490 495

Lys His Lys Arg Lys Arg Val Ser Lys
500 505

<210> SEQ ID NO 188
<211> LENGTH: 508
<212> TYPE: PRT
<213> ORGANISM: Human Papillomavirus
<220> FEATURE:
<221> NAME/KEY: misc_feature
<222> LOCATION: (1)..(508)
<223> OTHER INFORMATION: Amino Acid Sequence of Native HPV59L1

<400> SEQUENCE: 188

Met Ala Leu Trp Arg Ser Ser Asp Asn Lys Val Tyr Leu Pro Pro Pro
1 5 10 15

Ser Val Ala Lys Val Val Ser Thr Asp Glu Tyr Val Thr Arg Thr Ser
20 25 30

Ile Phe Tyr His Ala Gly Ser Ser Arg Leu Leu Thr Val Gly His Pro
35 40 45

Tyr Phe Lys Val Pro Lys Gly Gly Asn Gly Arg Gln Asp Val Pro Lys
50 55 60

Val Ser Ala Tyr Gln Tyr Arg Val Phe Arg Val Lys Leu Pro Asp Pro
65 70 75 80

Asn Lys Phe Gly Leu Pro Asp Asn Thr Val Tyr Asp Pro Asn Ser Gln
85 90 95

Arg Leu Val Trp Ala Cys Val Gly Val Glu Ile Gly Arg Gly Gln Pro
100 105 110

Leu Gly Val Gly Leu Ser Gly His Pro Leu Tyr Asn Lys Leu Asp Asp
115 120 125

Thr Glu Asn Ser His Val Ala Ser Ala Val Asp Thr Lys Asp Thr Arg
130 135 140

Asp Asn Val Ser Val Asp Tyr Lys Gln Thr Gln Leu Cys Ile Ile Gly
145 150 155 160

Cys Val Pro Ala Ile Gly Glu His Trp Thr Lys Gly Thr Ala Cys Lys
165 170 175

Pro Thr Thr Val Val Gln Gly Asp Cys Pro Pro Leu Glu Leu Ile Asn
180 185 190

Thr Pro Ile Glu Asp Gly Asp Met Val Asp Thr Gly Tyr Gly Ala Met
195 200 205

Asp Phe Lys Leu Leu Gln Asp Asn Lys Ser Glu Val Pro Leu Asp Ile
210 215 220

-continued

Cys Gln Ser Ile Cys Lys Tyr Pro Asp Tyr Leu Gln Met Ser Ala Asp
225 230 235 240

Ala Tyr Gly Asp Ser Met Phe Phe Cys Leu Arg Arg Glu Gln Val Phe
245 250 255

Ala Arg His Phe Trp Asn Arg Ser Gly Thr Met Gly Asp Gln Leu Pro
260 265 270

Glu Ser Leu Tyr Ile Lys Gly Thr Asp Ile Arg Ala Asn Pro Gly Ser
275 280 285

Tyr Leu Tyr Ser Pro Ser Pro Ser Gly Ser Val Val Thr Ser Asp Ser
290 295 300

Gln Leu Phe Asn Lys Pro Tyr Trp Leu His Lys Ala Gln Gly Leu Asn
305 310 315 320

Asn Gly Ile Cys Trp His Asn Gln Leu Phe Leu Thr Val Val Asp Thr
325 330 335

Thr Arg Ser Thr Asn Leu Ser Val Cys Ala Ser Thr Thr Ser Ser Ile
340 345 350

Pro Asn Val Tyr Thr Pro Thr Ser Phe Lys Glu Tyr Ala Arg His Val
355 360 365

Glu Glu Phe Asp Leu Gln Phe Ile Phe Gln Leu Cys Lys Ile Thr Leu
370 375 380

Thr Thr Glu Val Met Ser Tyr Ile His Asn Met Asn Thr Thr Ile Leu
385 390 395 400

Glu Asp Trp Asn Phe Gly Val Thr Pro Pro Pro Thr Ala Ser Leu Val
405 410 415

Asp Thr Tyr Arg Phe Val Gln Ser Ala Ala Val Thr Cys Gln Lys Asp
420 425 430

Thr Ala Pro Pro Val Lys Gln Asp Pro Tyr Asp Lys Leu Lys Phe Trp
435 440 445

Pro Val Asp Leu Lys Glu Arg Phe Ser Ala Asp Leu Asp Gln Phe Pro
450 455 460

Leu Gly Arg Lys Phe Leu Leu Gln Leu Gly Ala Arg Pro Lys Pro Thr
465 470 475 480

Ile Gly Pro Arg Lys Arg Ala Ala Pro Ala Pro Thr Ser Thr Pro Ser
485 490 495

Pro Lys Arg Val Lys Arg Arg Lys Ser Ser Arg Lys
500 505

<210> SEQ ID NO 189
<211> LENGTH: 510
<212> TYPE: PRT
<213> ORGANISM: Human Papillomavirus
<220> FEATURE:
<221> NAME/KEY: misc_feature
<222> LOCATION: (1)..(510)
<223> OTHER INFORMATION: Amino Acid Sequence of Native HPV45L1

<400> SEQUENCE: 189

Met Ala Leu Trp Arg Pro Ser Asp Ser Thr Val Tyr Leu Pro Pro Pro
1 5 10 15

Ser Val Ala Arg Val Val Asn Thr Asp Asp Tyr Val Ser Arg Thr Ser
20 25 30

Ile Phe Tyr His Ala Gly Ser Ser Arg Leu Leu Thr Val Gly Asn Pro
35 40 45

Tyr Phe Arg Val Val Pro Ser Gly Ala Gly Asn Lys Gln Ala Val Pro
50 55 60

Lys Val Ser Ala Tyr Gln Tyr Arg Val Phe Arg Val Ala Leu Pro Asp

-continued

```
65                  70                  75                  80

Pro Asn Lys Phe Gly Leu Pro Asp Ser Thr Ile Tyr Asn Pro Glu Thr
                85                  90                  95

Gln Arg Leu Val Trp Ala Cys Val Gly Met Glu Ile Gly Arg Gly Gln
            100                 105                 110

Pro Leu Gly Ile Gly Leu Ser Gly His Pro Phe Tyr Asn Lys Leu Asp
        115                 120                 125

Asp Thr Glu Ser Ala His Ala Ala Thr Ala Val Ile Thr Gln Asp Val
    130                 135                 140

Arg Asp Asn Val Ser Val Asp Tyr Lys Gln Thr Gln Leu Cys Ile Leu
145                 150                 155                 160

Gly Cys Val Pro Ala Ile Gly Glu His Trp Ala Lys Gly Thr Leu Cys
                165                 170                 175

Lys Pro Ala Gln Leu Gln Pro Gly Asp Cys Pro Pro Leu Glu Leu Lys
            180                 185                 190

Asn Thr Ile Ile Glu Asp Gly Asp Met Val Asp Thr Gly Tyr Gly Ala
        195                 200                 205

Met Asp Phe Ser Thr Leu Gln Asp Thr Lys Cys Glu Val Pro Leu Asp
    210                 215                 220

Ile Cys Gln Ser Ile Cys Lys Tyr Pro Asp Tyr Leu Gln Met Ser Ala
225                 230                 235                 240

Asp Pro Tyr Gly Asp Ser Met Phe Phe Cys Leu Arg Arg Glu Gln Leu
                245                 250                 255

Phe Ala Arg His Phe Trp Asn Arg Ala Gly Val Met Gly Asp Thr Val
            260                 265                 270

Pro Thr Asp Leu Tyr Ile Lys Gly Thr Ser Ala Asn Met Arg Glu Thr
        275                 280                 285

Pro Gly Ser Cys Val Tyr Ser Pro Ser Pro Ser Gly Ser Ile Thr Thr
    290                 295                 300

Ser Asp Ser Gln Leu Phe Asn Lys Pro Tyr Trp Leu His Lys Ala Gln
305                 310                 315                 320

Gly His Asn Asn Gly Ile Cys Trp His Asn Gln Leu Phe Val Thr Val
                325                 330                 335

Val Asp Thr Thr Arg Ser Thr Asn Leu Thr Leu Cys Ala Ser Thr Gln
            340                 345                 350

Asn Pro Val Pro Asn Thr Tyr Asp Pro Thr Lys Phe Lys His Tyr Ser
        355                 360                 365

Arg His Val Glu Glu Tyr Asp Leu Gln Phe Ile Phe Gln Leu Cys Thr
    370                 375                 380

Ile Thr Leu Thr Ala Glu Val Met Ser Tyr Ile His Ser Met Asn Ser
385                 390                 395                 400

Ser Ile Leu Glu Asn Trp Asn Phe Gly Val Pro Pro Pro Pro Thr Thr
                405                 410                 415

Ser Leu Val Asp Thr Tyr Arg Phe Val Gln Ser Val Ala Val Thr Cys
            420                 425                 430

Gln Lys Asp Thr Thr Pro Pro Glu Lys Gln Asp Pro Tyr Asp Lys Leu
        435                 440                 445

Lys Phe Trp Thr Val Asp Leu Lys Glu Lys Phe Ser Ser Asp Leu Asp
    450                 455                 460

Gln Tyr Pro Leu Gly Arg Lys Phe Leu Val Gln Ala Gly Leu Arg Arg
465                 470                 475                 480

Arg Pro Thr Ile Gly Pro Arg Lys Arg Pro Ala Ala Ser Thr Ser Thr
                485                 490                 495
```

Ala Ser Arg Pro Ala Lys Arg Val Arg Ile Arg Ser Lys Lys
500 505 510

<210> SEQ ID NO 190
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV6

<400> SEQUENCE: 190

Glu Leu Asp Gln Tyr Pro Leu Gly Arg Lys Phe Leu Leu Gln Ser Gly
1 5 10 15

Tyr

<210> SEQ ID NO 191
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV11

<400> SEQUENCE: 191

Glu Leu Asp Gln Phe Pro Leu Gly Arg Lys Phe Leu Leu Gln Ser Gly
1 5 10 15

Tyr

<210> SEQ ID NO 192
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV16

<400> SEQUENCE: 192

Asp Leu Asp Gln Phe Pro Leu Gly Arg Lys Phe Leu Leu Gln Ala Gly
1 5 10 15

Leu

<210> SEQ ID NO 193
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV18

<400> SEQUENCE: 193

Asp Leu Asp Gln Tyr Pro Leu Gly Arg Lys Phe Leu Val Gln Ala Gly
1 5 10 15

Leu

<210> SEQ ID NO 194
<211> LENGTH: 17
<212> TYPE: PRT
<213> ORGANISM: Human Papillomavirus
<220> FEATURE:
<221> NAME/KEY: misc_feature

<222> LOCATION: (1)..(17)
<223> OTHER INFORMATION: HPV31

<400> SEQUENCE: 194

Asp Leu Asp Gln Phe Pro Leu Gly Arg Lys Phe Leu Leu Gln Ala Gly
1 5 10 15

Tyr

<210> SEQ ID NO 195
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV35

<400> SEQUENCE: 195

Asp Leu Asp Gln Phe Pro Leu Gly Arg Lys Phe Leu Leu Gln Ala Gly
1 5 10 15

Leu

<210> SEQ ID NO 196
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV39

<400> SEQUENCE: 196

Glu Leu Asp Gln Phe Pro Leu Gly Arg Lys Phe Leu Leu Gln Ala Arg
1 5 10 15

Val

<210> SEQ ID NO 197
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV45

<400> SEQUENCE: 197

Asp Leu Asp Gln Tyr Pro Leu Gly Arg Lys Phe Leu Val Gln Ala Gly
1 5 10 15

Leu

<210> SEQ ID NO 198
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV51

<400> SEQUENCE: 198

Asp Leu Asp Gln Phe Ala Leu Gly Arg Lys Phe Leu Leu Gln Val Gly
1 5 10 15

Val

<210> SEQ ID NO 199
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV52

<400> SEQUENCE: 199

Asp Leu Asp Gln Phe Pro Leu Gly Arg Lys Phe Leu Leu Gln Ala Gly
1               5                   10                  15

Leu

<210> SEQ ID NO 200
<211> LENGTH: 19
<212> TYPE: PRT
<213> ORGANISM: Human Papillomavirus
<220> FEATURE:
<221> NAME/KEY: misc_feature
<222> LOCATION: (1)..(19)
<223> OTHER INFORMATION: HPV56

<400> SEQUENCE: 200

Asp Leu Asp Gln Phe Pro Leu Gly Arg Lys Phe Leu Met Gln Leu Gly
1               5                   10                  15

Thr Arg Ser

<210> SEQ ID NO 201
<211> LENGTH: 17
<212> TYPE: PRT
<213> ORGANISM: Human Papillomavirus
<220> FEATURE:
<221> NAME/KEY: misc_feature
<222> LOCATION: (1)..(17)
<223> OTHER INFORMATION: HPV58

<400> SEQUENCE: 201

Asp Leu Asp Gln Phe Pro Leu Gly Arg Lys Phe Leu Leu Gln Ser Gly
1               5                   10                  15

Leu

<210> SEQ ID NO 202
<211> LENGTH: 43
<212> TYPE: PRT
<213> ORGANISM: Human Papillomavirus
<220> FEATURE:
<221> NAME/KEY: misc_feature
<222> LOCATION: (1)..(43)
<223> OTHER INFORMATION: HPV33

<400> SEQUENCE: 202

Asp Leu Asp Gln Phe Pro Leu Gly Arg Lys Phe Leu Leu Gln Ala Gly
1               5                   10                  15

Leu Lys Ala Lys Pro Lys Leu Lys Arg Ala Ala Pro Thr Ser Thr Arg
            20                  25                  30

Thr Ser Ser Ala Lys Arg Lys Lys Val Lys Lys
        35                  40

<210> SEQ ID NO 203
<211> LENGTH: 4
<212> TYPE: PRT
<213> ORGANISM: Human Papillomavirus
<220> FEATURE:
<221> NAME/KEY: misc_feature
<222> LOCATION: (1)..(4)

-continued

<223> OTHER INFORMATION: nuclear localization sequence

<400> SEQUENCE: 203

Lys Arg Lys Lys
1

<210> SEQ ID NO 204
<211> LENGTH: 50
<212> TYPE: PRT
<213> ORGANISM: Human Papillomavirus
<220> FEATURE:
<221> NAME/KEY: misc_feature
<222> LOCATION: (1)..(50)
<223> OTHER INFORMATION: HPV59

<400> SEQUENCE: 204

```
Asp Leu Asp Gln Phe Pro Leu Gly Arg Lys Phe Leu Leu Gln Leu Gly
1               5                   10                  15

Ala Arg Pro Lys Pro Thr Ile Gly Pro Arg Lys Arg Ala Ala Pro Ala
            20                  25                  30

Pro Thr Ser Thr Pro Ser Pro Lys Arg Val Lys Arg Arg Lys Ser Ser
        35                  40                  45

Arg Lys
    50
```

<210> SEQ ID NO 205
<211> LENGTH: 7
<212> TYPE: PRT
<213> ORGANISM: Human Papillomavirus
<220> FEATURE:
<221> NAME/KEY: misc_feature
<222> LOCATION: (1)..(7)
<223> OTHER INFORMATION: nuclear localization sequence

<400> SEQUENCE: 205

```
Lys Arg Val Lys Arg Arg Lys
1               5
```

<210> SEQ ID NO 206
<211> LENGTH: 4
<212> TYPE: PRT
<213> ORGANISM: Human Papillomavirus
<220> FEATURE:
<221> NAME/KEY: misc_feature
<222> LOCATION: (1)..(4)
<223> OTHER INFORMATION: nuclear localization sequence

<400> SEQUENCE: 206

Lys Arg Lys Arg
1

<210> SEQ ID NO 207
<211> LENGTH: 5
<212> TYPE: PRT
<213> ORGANISM: Human Papillomavirus
<220> FEATURE:
<221> NAME/KEY: misc_feature
<222> LOCATION: (1)..(5)
<223> OTHER INFORMATION: nuclear localization sequence

<400> SEQUENCE: 207

```
Lys Arg Lys Arg Lys
1               5
```

<210> SEQ ID NO 208
<211> LENGTH: 6

-continued

```
<212> TYPE: PRT
<213> ORGANISM: Human Papillomavirus
<220> FEATURE:
<221> NAME/KEY: misc_feature
<222> LOCATION: (1)..(6)
<223> OTHER INFORMATION: nuclear localization sequence

<400> SEQUENCE: 208

Lys Arg Lys Lys Arg Lys
1               5
```